United States Patent
Kollar et al.

(10) Patent No.: US 11,446,037 B2
(45) Date of Patent: Sep. 20, 2022

(54) HANDHELD ELECTROMECHANICAL SURGICAL SYSTEM

(71) Applicant: Covidien LP, Mansfield, MA (US)

(72) Inventors: Charles R. Kollar, West Hartford, CT (US); David E. Valentine, Hamden, CT (US); Alexander Hart, Tolland, CT (US); James Delbo, Danville, PA (US); Jonathan M. Sandor, North Haven, CT (US); Haley Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/894,944

(22) Filed: Jun. 8, 2020

(65) Prior Publication Data

US 2020/0367891 A1    Nov. 26, 2020

Related U.S. Application Data

(63) Continuation-in-part of application No. PCT/US2019/040440, filed on Jul. 3, 2019.
(Continued)

(51) Int. Cl.
*A61B 17/00* (2006.01)
*A61B 17/115* (2006.01)
*A61B 17/34* (2006.01)

(52) U.S. Cl.
CPC .......... *A61B 17/1155* (2013.01); *A61B 17/34* (2013.01); *A61B 2017/00367* (2013.01)

(58) Field of Classification Search
CPC .............. A61B 17/1155; A61B 17/34; A61B 2017/00367; A61B 2090/0813;
(Continued)

(56) References Cited

U.S. PATENT DOCUMENTS

| 6,050,472 A * | 4/2000 | Shibata ............. A61B 17/115 227/175.2 |
| 7,226,458 B2 * | 6/2007 | Kaplan ............... A61B 17/10 606/139 |

(Continued)

FOREIGN PATENT DOCUMENTS

| EP | 2891462 A1 | 7/2015 |
| WO | 2016138059 A1 | 9/2016 |
| WO | 2020014056 A1 | 1/2020 |

OTHER PUBLICATIONS

International Search Report and Written Opinion of the International Searching Authority, dated Dec. 11, 2019, corresponding to counterpart International Application No. PCT/US2019/040440; 21 total pages.
(Continued)

*Primary Examiner* — Robert F Long

(57) ABSTRACT

A surgical device includes a handle assembly, an adapter assembly configured to selectively couple to the handle assembly, an annular reload configured to selectively couple to a distal portion of the adapter assembly, and a shipping cap coupled to the annular reload and configured to detach from the annular reload in response to a movement of a trocar of the adapter assembly. The annular reload has a memory having stored therein information about the reload. The handle assembly includes a controller configured to encode to the memory an occurrence of a detachment of the shipping cap from the reload.

6 Claims, 86 Drawing Sheets

Related U.S. Application Data

(60) Provisional application No. 62/695,369, filed on Jul. 9, 2018, provisional application No. 62/695,344, filed on Jul. 9, 2018, provisional application No. 62/695,365, filed on Jul. 9, 2018, provisional application No. 62/695,325, filed on Jul. 9, 2018.

(58) Field of Classification Search
CPC .......... A61B 50/30; A61B 2017/00119; A61B 2090/0803; A61B 2090/038; A61B 2090/08021; A61B 2090/0814; A61B 2017/00477; A61B 2217/007; A61B 90/98; A61B 2017/293; A61B 2050/3014; A61B 2090/0808; A61B 2090/0811; A61B 2090/064; A61B 2017/00725; A61B 2017/00017; A61B 2017/00398; A61B 2017/00734; A61B 2017/0046; A61B 2017/00473; G16H 20/40; G16H 40/40; G16H 40/63
USPC ...................... 227/175.1–182.1; 606/142–143
See application file for complete search history.

(56) References Cited

U.S. PATENT DOCUMENTS

| | | | |
|---|---|---|---|
| 7,918,377 B2 | 4/2011 | Measamer et al. | |
| 8,437,833 B2* | 5/2013 | Silverstein | A61B 34/20 600/427 |
| 8,746,532 B2* | 6/2014 | Nalagatla | A61B 17/1114 227/181.1 |
| 10,127,836 B2* | 11/2018 | Alexandersson | G09B 23/285 |
| 10,172,618 B2* | 1/2019 | Shelton, IV | A61L 24/046 |
| 2003/0216667 A1* | 11/2003 | Viola | A61B 10/0275 600/564 |
| 2006/0021891 A1* | 2/2006 | Franer | A61B 50/20 206/363 |
| 2011/0095070 A1* | 4/2011 | Patel | A61B 17/105 227/181.1 |
| 2011/0114700 A1* | 5/2011 | Baxter, III | A61B 17/1155 227/179.1 |
| 2011/0118761 A1* | 5/2011 | Baxter, III | A61B 17/1155 606/148 |
| 2012/0232339 A1* | 9/2012 | Csiky | A61B 1/00135 600/104 |
| 2013/0153633 A1* | 6/2013 | Casasanta, Jr | A61B 17/1155 227/176.1 |
| 2013/0181029 A1 | 7/2013 | Milliman | |
| 2013/0214024 A1* | 8/2013 | Takei | A61B 17/115 227/175.1 |
| 2013/0334282 A1* | 12/2013 | Filiciotto | A61B 17/0218 227/176.1 |
| 2014/0005681 A1 | 1/2014 | Gee et al. | |
| 2014/0191012 A1* | 7/2014 | Chen | A61B 17/115 227/176.1 |
| 2015/0173757 A1* | 6/2015 | Williams | A61B 17/072 227/180.1 |
| 2015/0351844 A1* | 12/2015 | Smith | A61B 50/30 24/531 |
| 2016/0100839 A1 | 4/2016 | Marczyk | |
| 2016/0106406 A1 | 4/2016 | Cabrera et al. | |
| 2016/0256184 A1* | 9/2016 | Shelton, IV | A61B 17/068 |
| 2016/0296234 A1* | 10/2016 | Richard | A61B 17/1155 |
| 2016/0310134 A1* | 10/2016 | Contini | A61B 17/0682 |
| 2016/0374667 A1 | 12/2016 | Miller | |
| 2016/0374668 A1 | 12/2016 | Measamer et al. | |
| 2016/0374672 A1 | 12/2016 | Bear et al. | |
| 2017/0245854 A1 | 8/2017 | Zemlok et al. | |
| 2017/0360445 A1 | 12/2017 | Milliman | |
| 2019/0059945 A1* | 2/2019 | Cabrera | A61B 17/3496 |
| 2019/0183494 A1* | 6/2019 | Shelton, IV | A61B 17/07207 |
| 2019/0201034 A1* | 7/2019 | Shelton, IV | A61B 18/00 |
| 2020/0405304 A1* | 12/2020 | Mozdzierz | A61B 17/072 |

OTHER PUBLICATIONS

European Search Report dated Oct. 28, 2021, issued in corresponding EP 21177654, 10 pages.
Supplementary European Search Report dated Mar. 17, 2022, issued in corresponding EP Appln. No. 19833219, 13 pages.
Extended European Search Report dated Jun. 20, 2022, issued in corresponding EP Appln. No. 19833219, 10 pages.

* cited by examiner

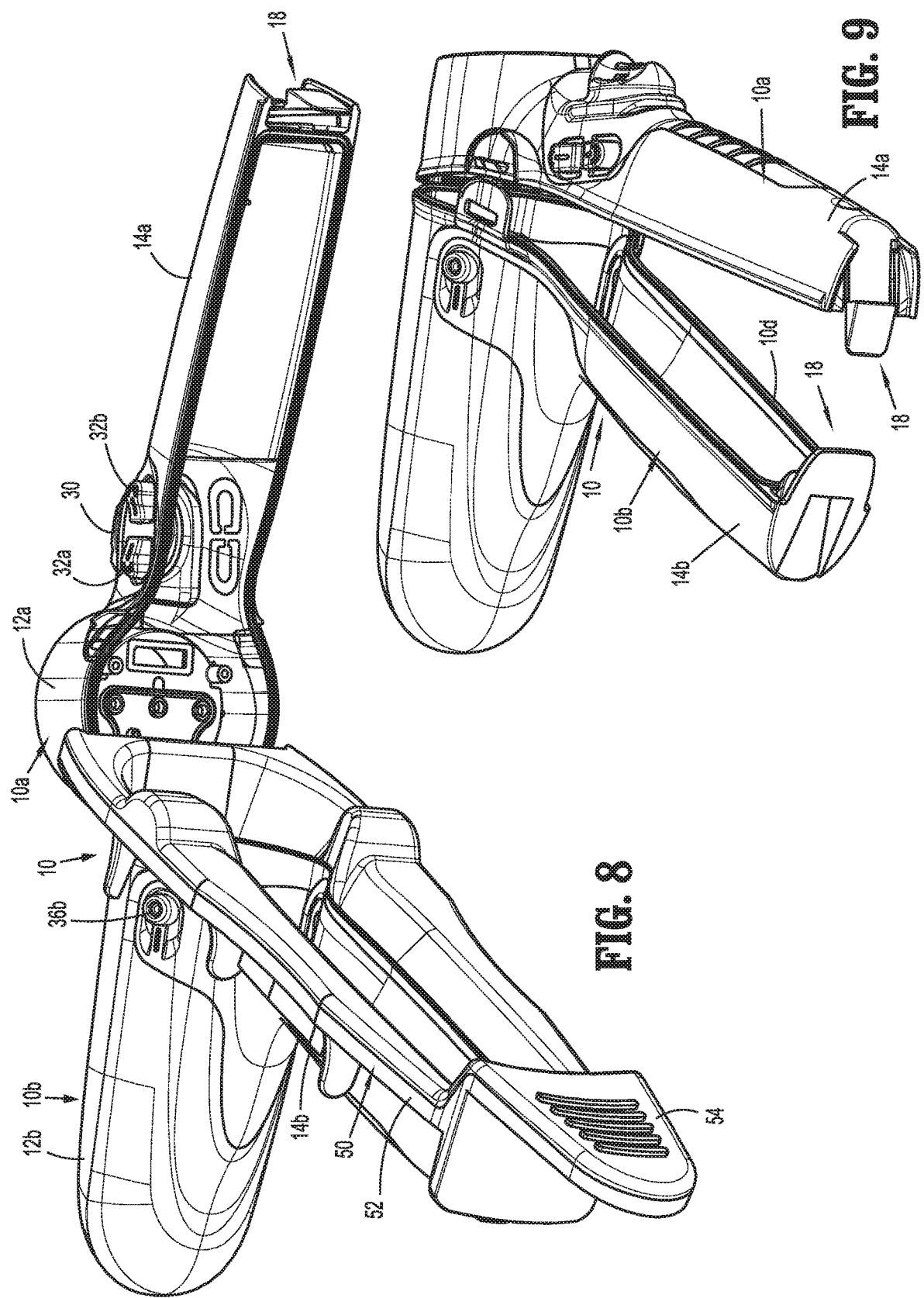

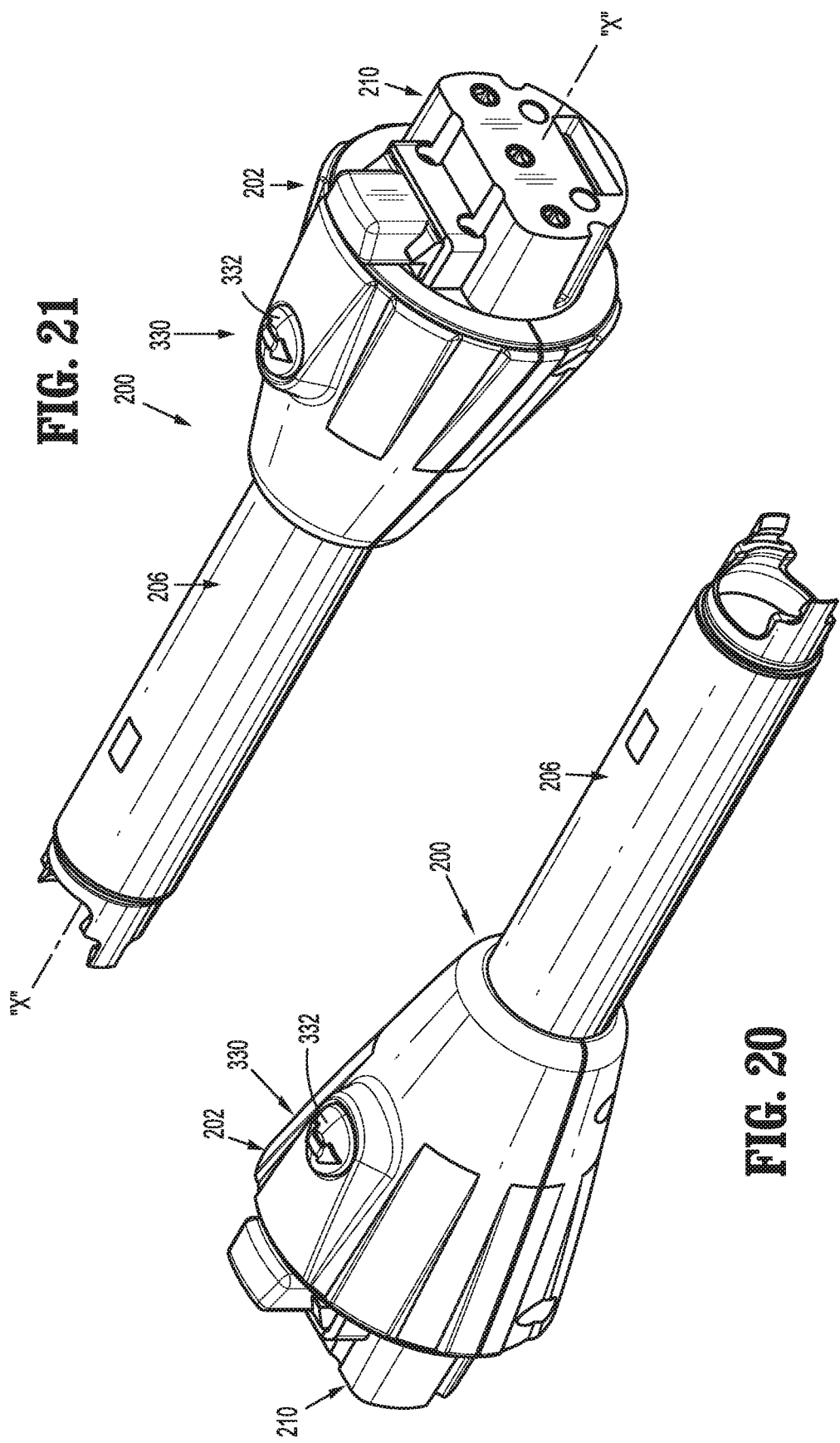

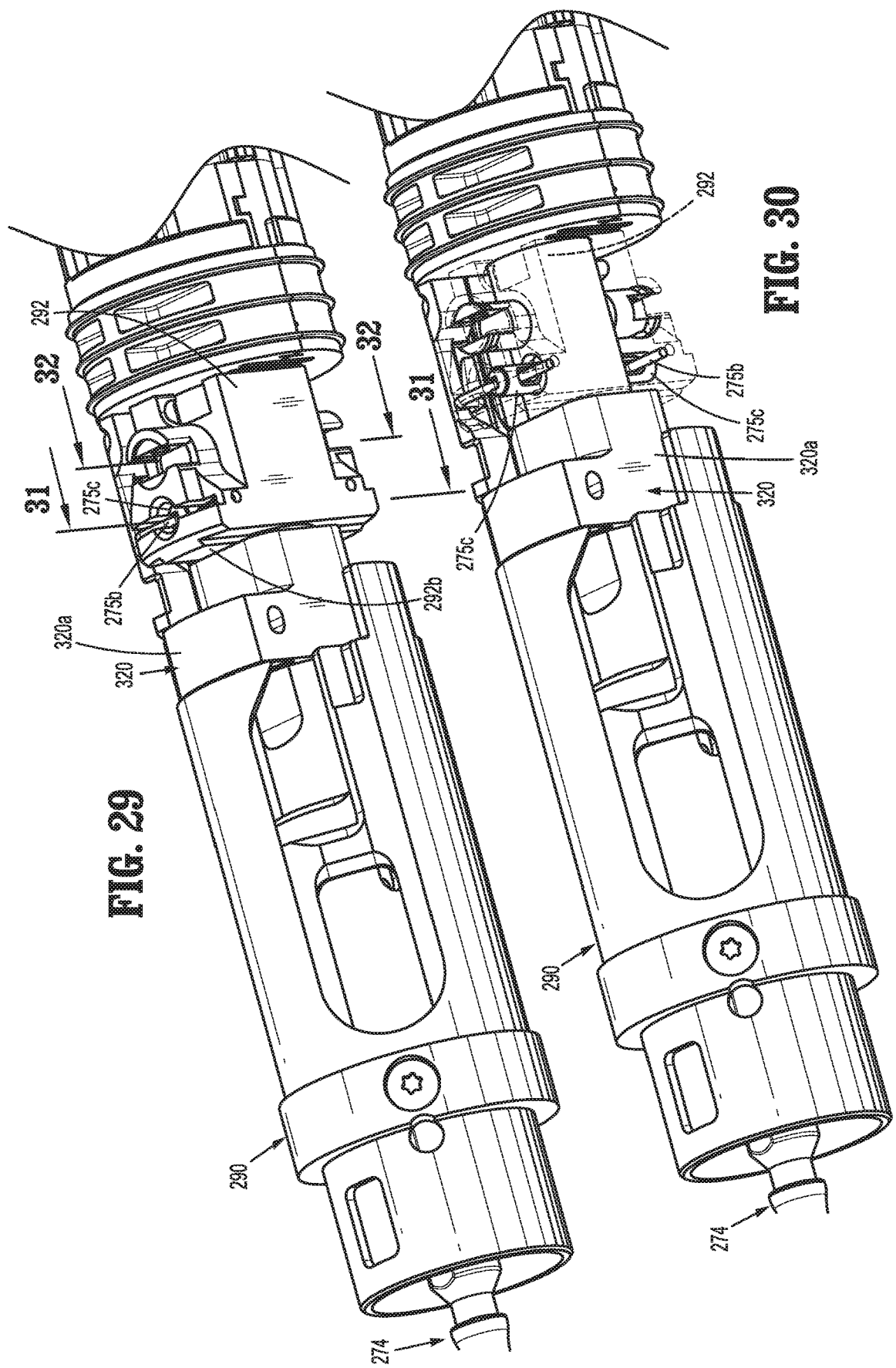

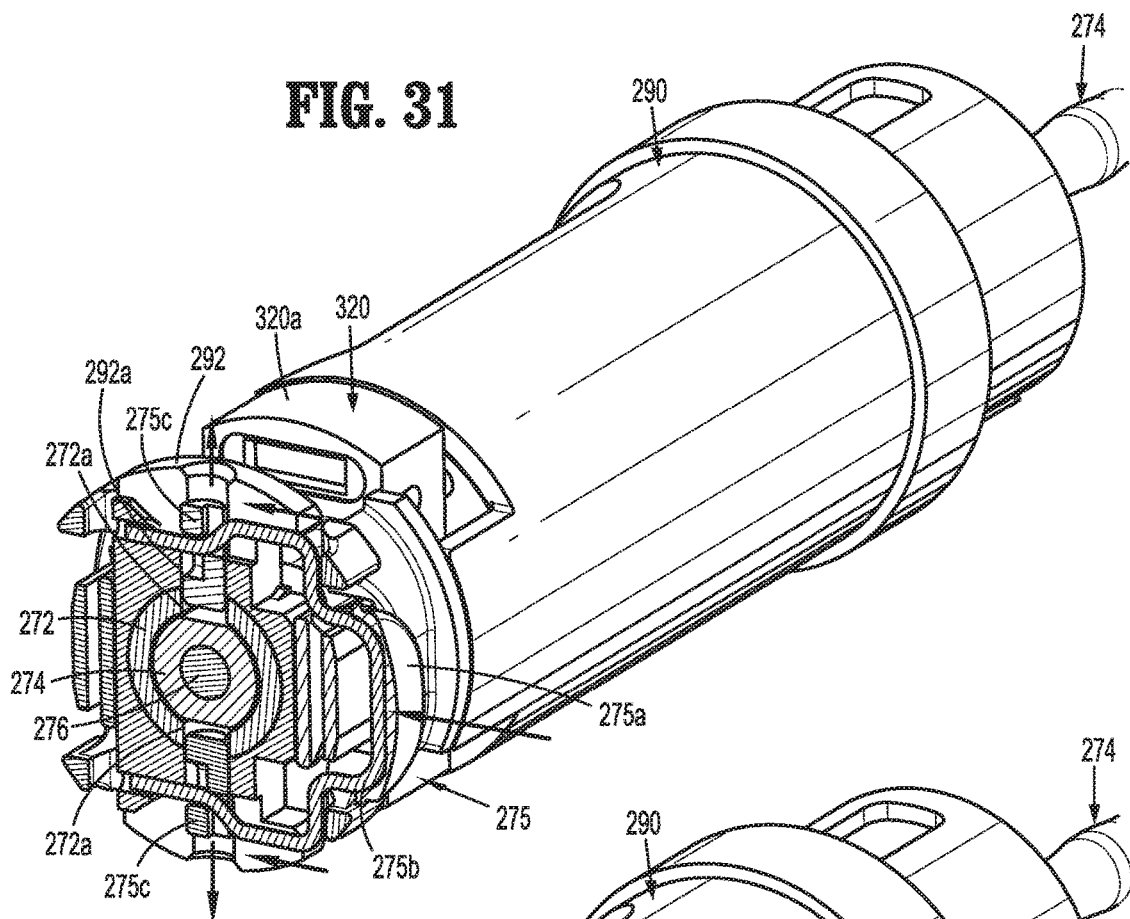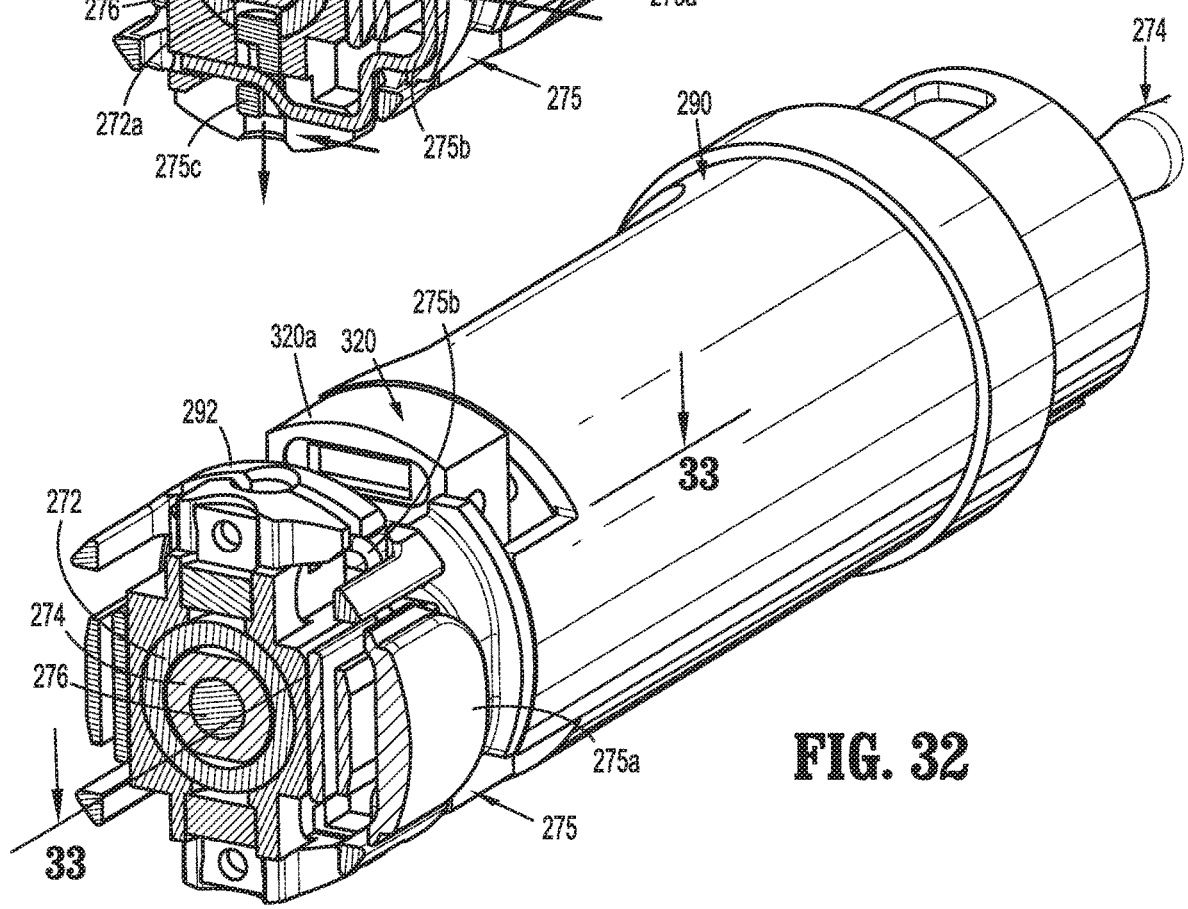

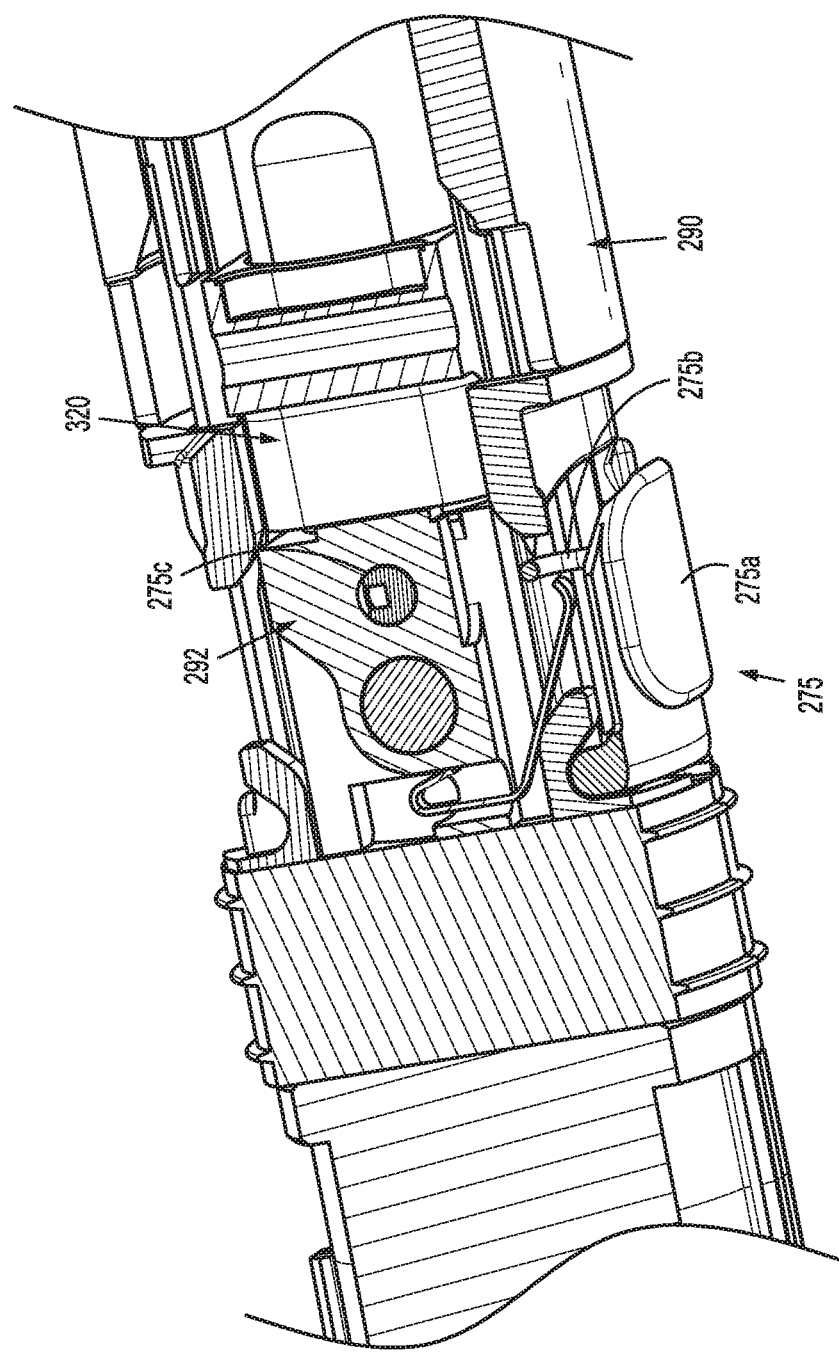

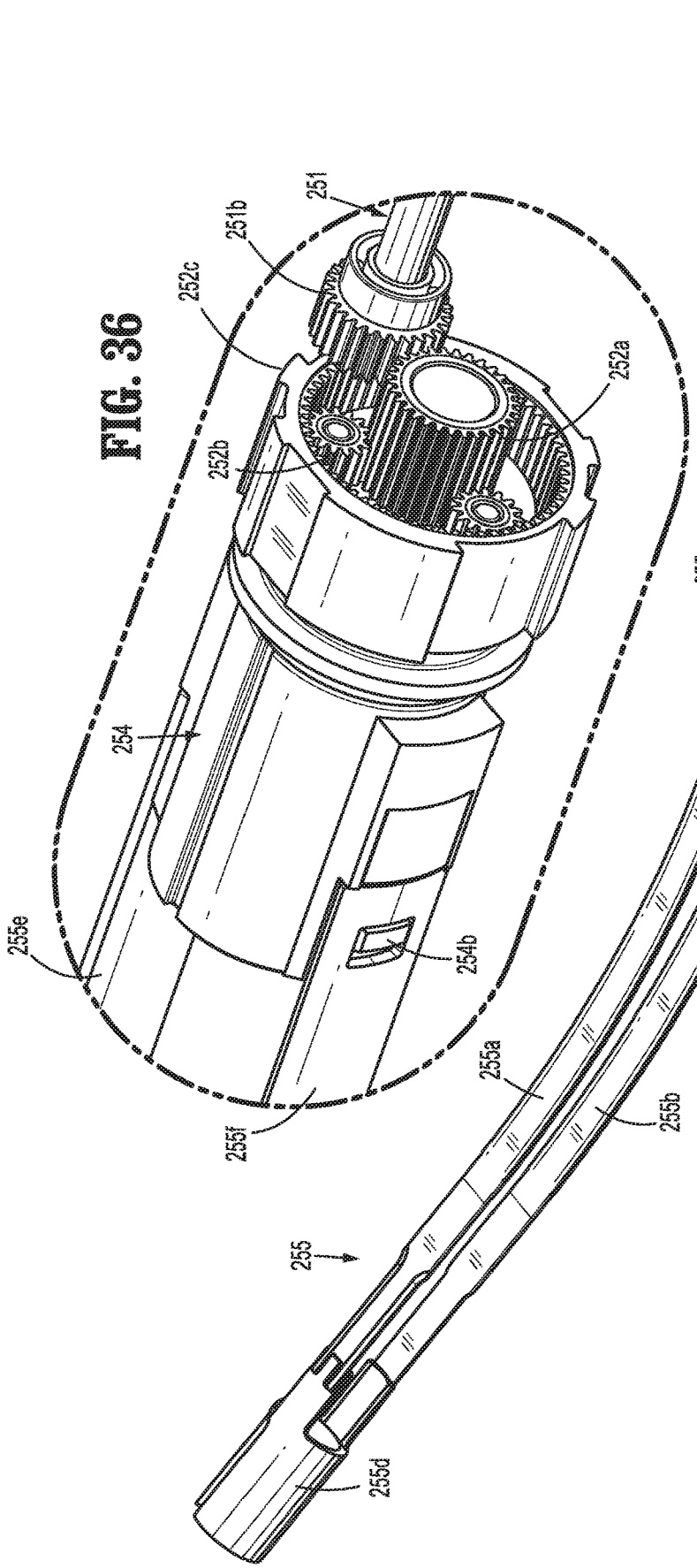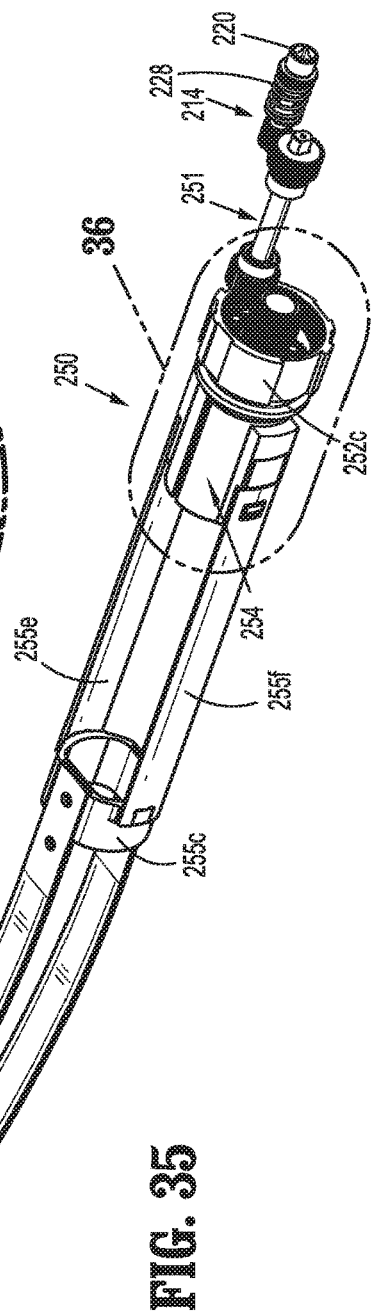

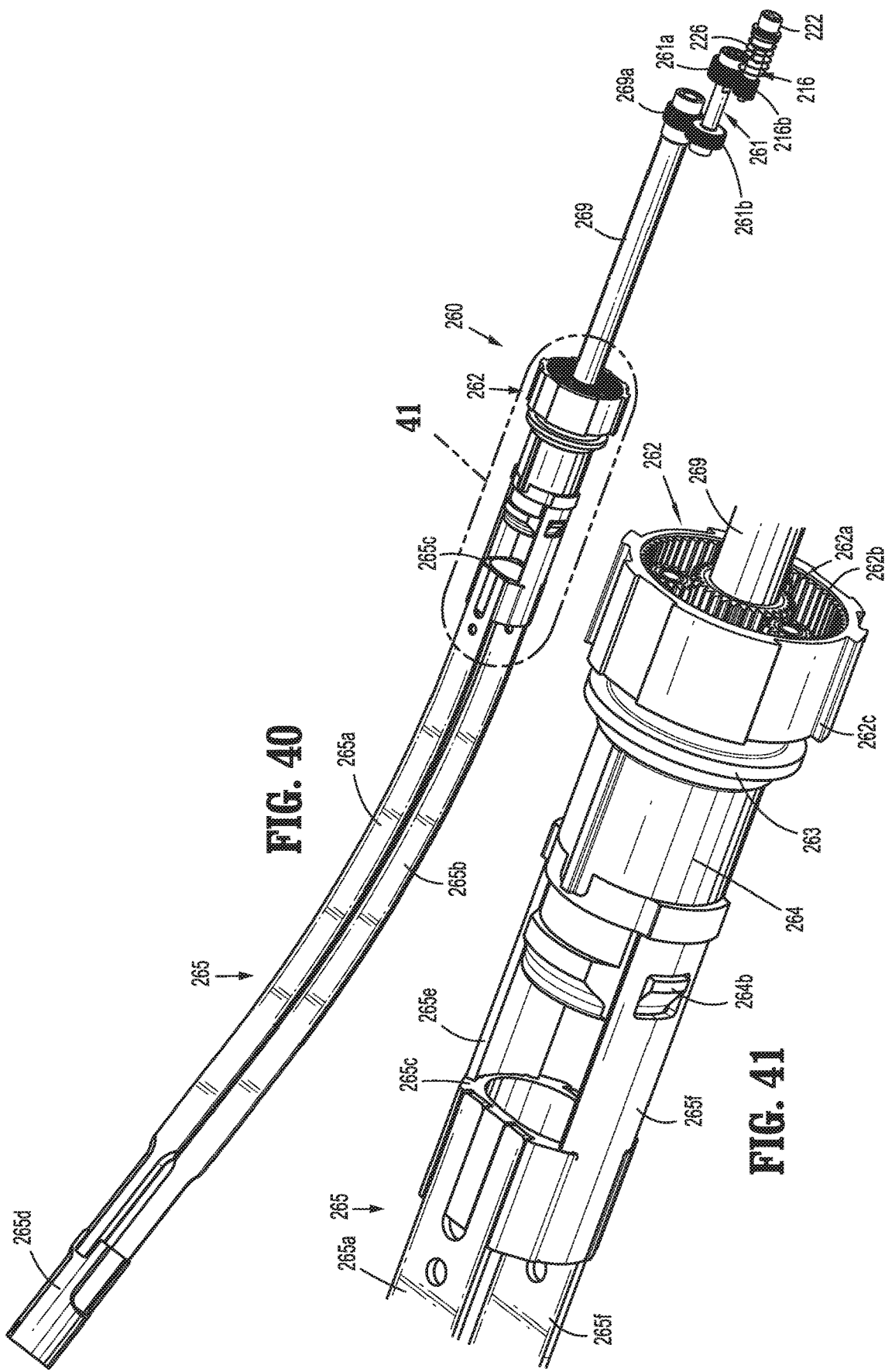

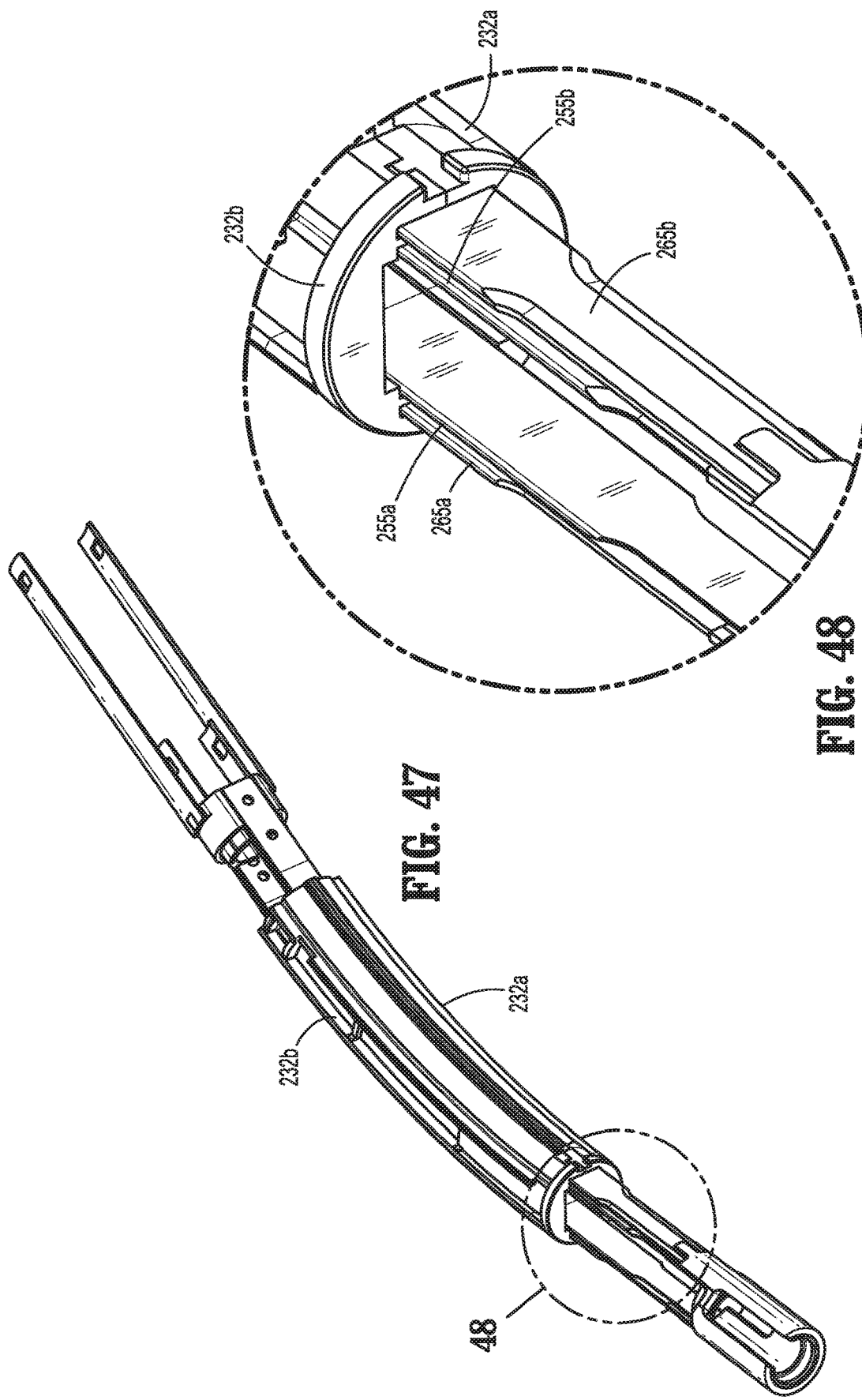

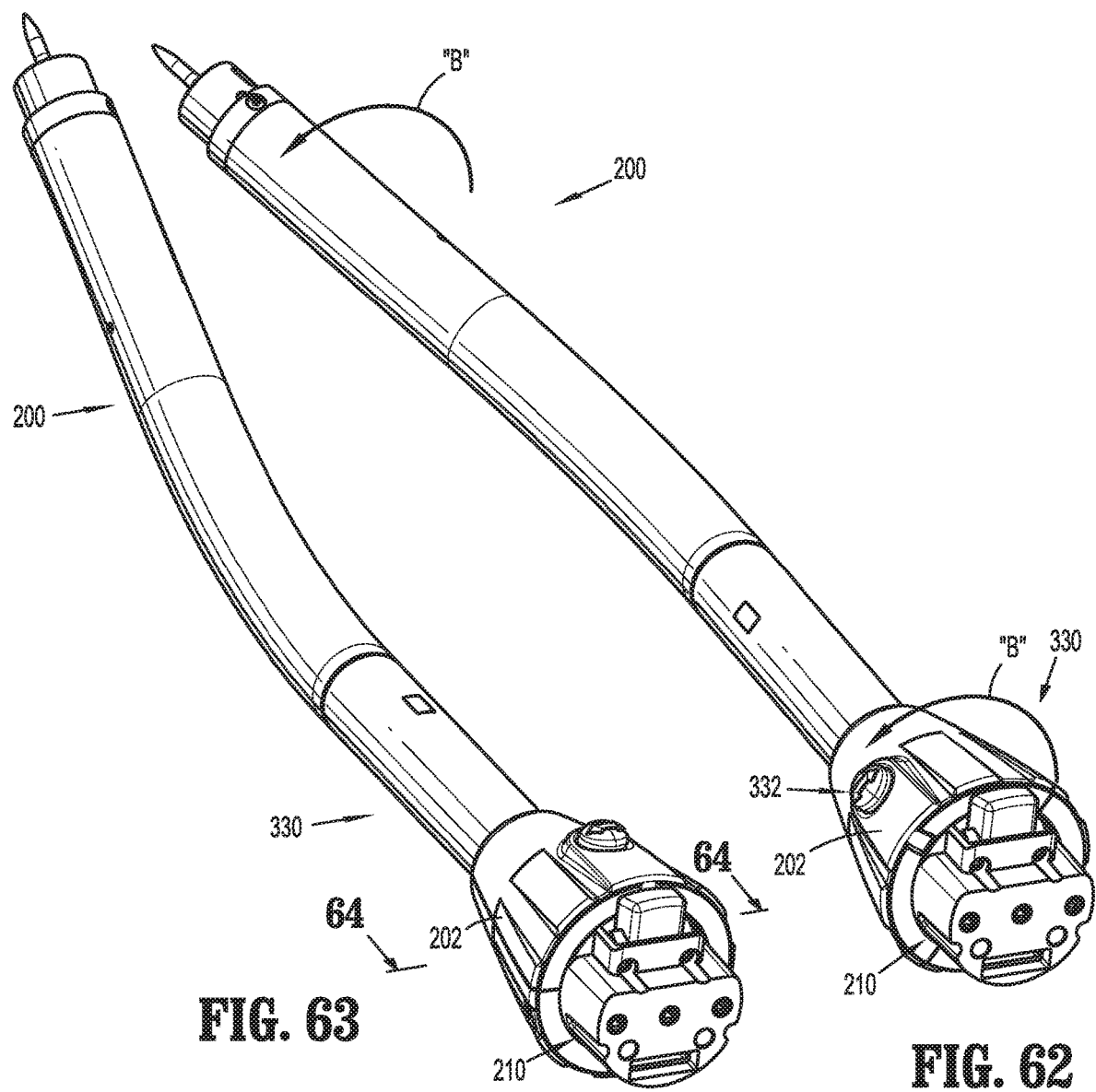

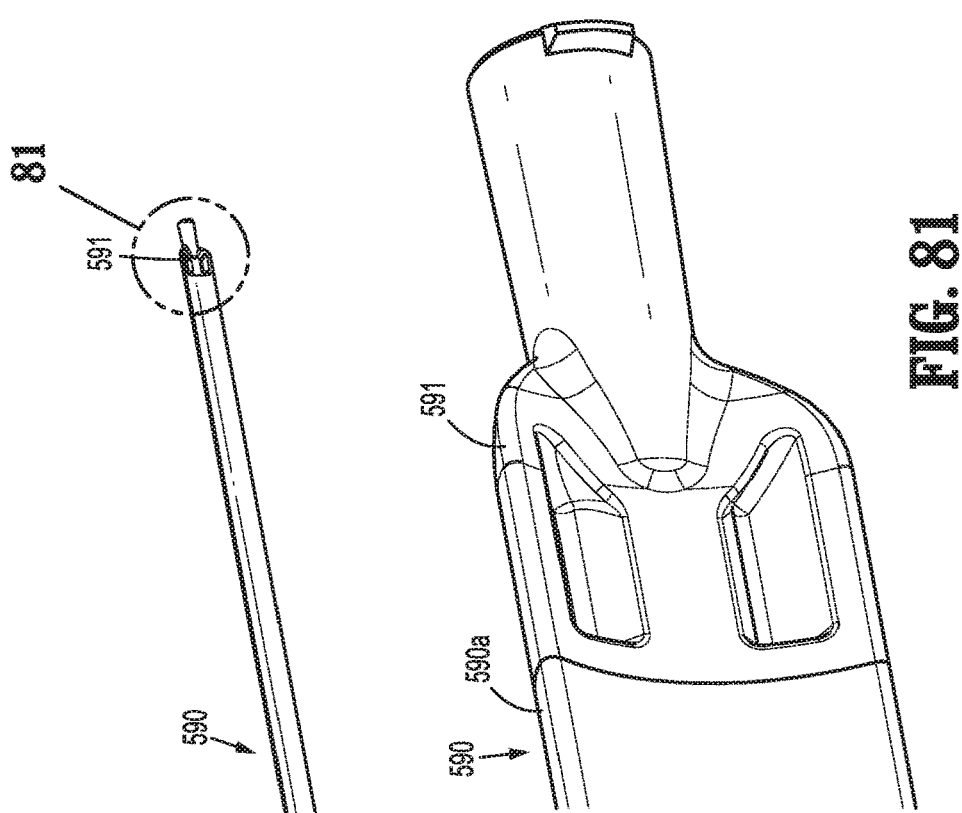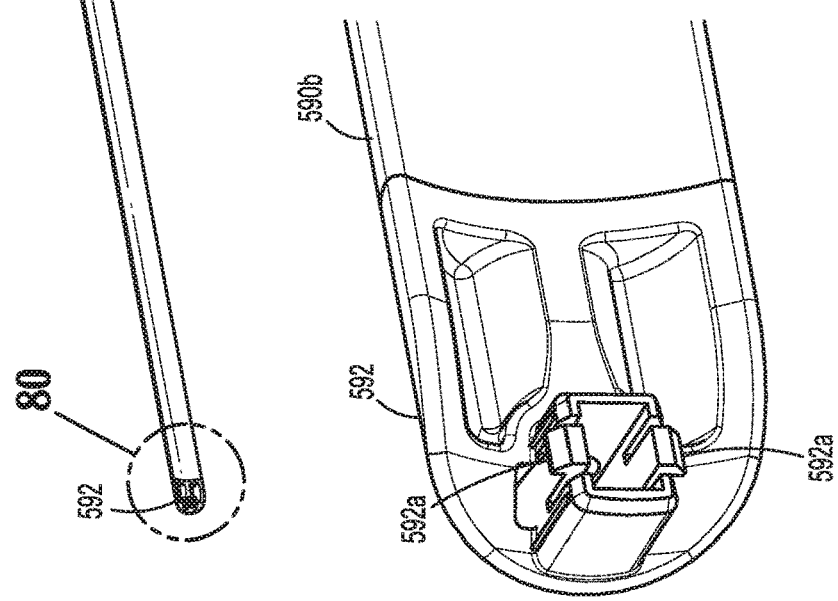

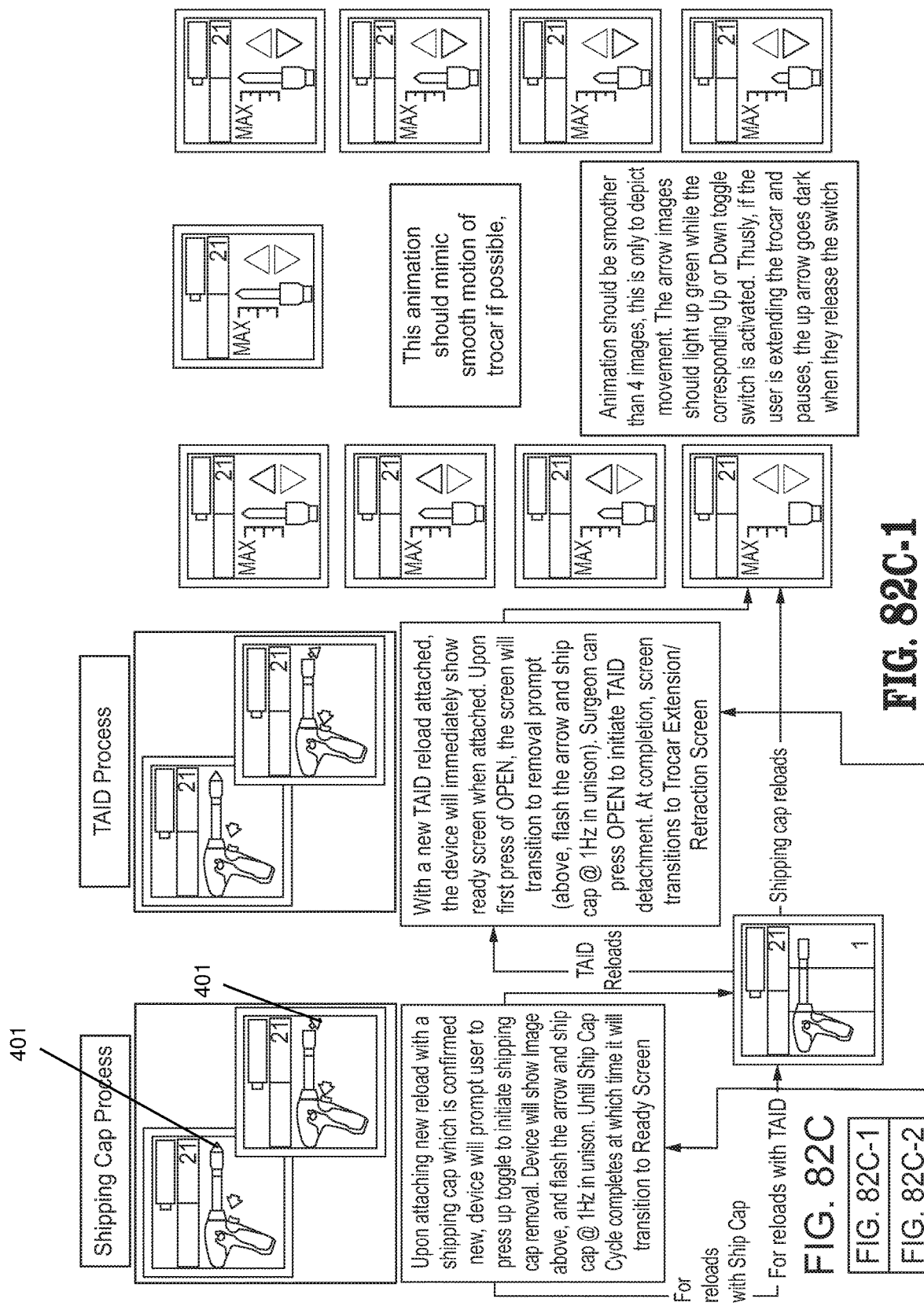

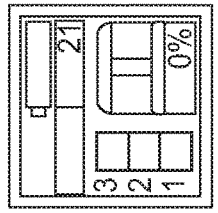
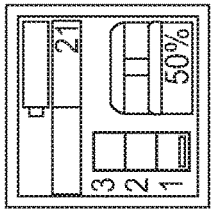
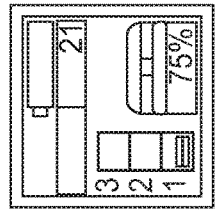
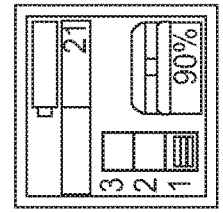
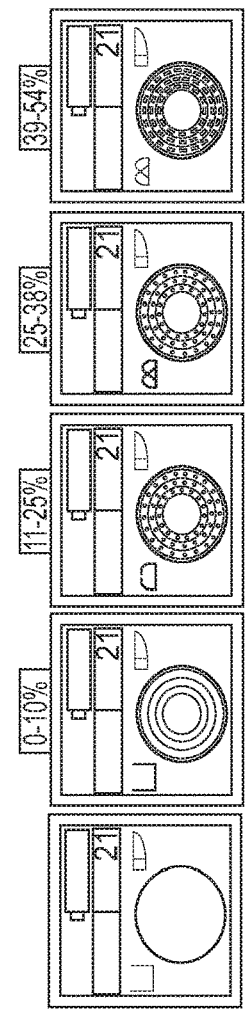
Zone 1 during clamping shows rising force from 0-50% clamp force limit. Zone 2 during clamping indicates 51-100% clamp force limit. Device will interrupt clamping at limit of zone 2(100%) after 30 seconds and indicate high force. The user can then re-clamp to initiate zone 3 which will proceed to the Maximum Force limit for clamping designated by R&D.
FIG. 82D
| FIG. 82D-1 |
| FIG. 82D-2 |

//

HANDHELD ELECTROMECHANICAL SURGICAL SYSTEM

CROSS-REFERENCE TO RELATED APPLICATIONS

The present application is a Continuation-in-part application of PCT/US2019/040440, filed on Jul. 3, 2019, which claims the benefit of and priority to each of U.S. Provisional Patent Application Ser. No. 62/695,325, filed on Jul. 9, 2018, U.S. Provisional Patent Application Ser. No. 62/695,344, filed on Jul. 9, 2018, U.S. Provisional Patent Application Ser. No. 62/695,365, filed on Jul. 9, 2018, and U.S. Provisional Patent Application Ser. No. 62/695,369, filed on Jul. 9, 2018, the entire content of each of which being incorporated herein by reference.

BACKGROUND

1. Technical Field

The present disclosure relates to surgical devices. More specifically, the present disclosure relates to handheld electromechanical surgical systems for performing surgical procedures.

2. Background of Related Art

One type of surgical device is a circular clamping, cutting and stapling device. Such a device may be employed in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis, and an annular knife is fired to core a portion of the clamped tissue portions. After the end-to-end anastomosis has been effected, the circular stapling apparatus is removed from the surgical site.

A number of surgical device manufacturers have developed product lines with proprietary powered drive systems for operating and/or manipulating the surgical device. In many instances the surgical devices include a powered handle assembly, which is reusable, and a disposable staple cartridge assembly, end effector or the like that is selectively connected to the powered handle assembly prior to use and then disconnected from the staple cartridge assembly or end effector following use in order to be disposed of or in some instances sterilized for re-use.

The use of powered electro and endomechanical surgical staplers, including intelligent battery power, has grown tremendously over the past few decades. Advanced technology and informatics within these intelligent battery-powered stapling devices provide the ability to gather clinical data and drive design improvements to ultimately improve patient outcomes. Accordingly, a need exists for improved powered electro and endomechanical surgical staplers that are capable of evaluating conditions that affect staple formation with the intention of building a more intelligent stapling algorithm.

SUMMARY

In accordance with an aspect of the disclosure, a surgical device is provided and includes a handle assembly including a controller, an adapter assembly configured to selectively couple to the handle assembly, an annular reload configured to selectively couple to a distal portion of the adapter assembly, and a shipping cap coupled to the annular reload and configured to detach from the annular reload in response to a movement of a trocar of the adapter assembly. The reload has a memory having stored therein information about the reload. The controller is configured to encode to the memory an occurrence of a detachment of the shipping cap from the reload.

In aspects, the memory may be an EEPROM chip.

In aspects, the controller may be configured to read the memory of the reload to determine whether the shipping cap is detached from the reload.

In aspects, reading the memory of the reload may include searching for a presence or absence of the encoding in the memory.

In aspects, the controller may be configured to initiate an operational sequence for detaching the shipping cap in response to determining that the shipping cap is attached to the reload. The controller may be further configured to not initiate the operational sequence for detaching the shipping cap in response to determining that the shipping cap is detached from the reload.

In aspects, the operational sequence for detaching the shipping cap may include activating a motor of the handle assembly to move the trocar to detach the shipping cap from the annular reload.

In aspects, the operational sequence for detaching the shipping cap may further include the controller prompting a user to actuate a toggle of the surgical device, thereby activating the motor.

In accordance with another aspect of the disclosure, a method of using a surgical device is provided. The method includes decoupling a first handle assembly from an adapter assembly, the adapter assembly supporting an annular reload having a memory; coupling a second handle assembly to the adapter assembly; and reading the memory of the annular reload to determine whether a shipping cap is detached from the annular reload.

In aspects, the method may further include detaching the shipping cap from the annular reload when the first handle assembly is coupled to the adapter assembly; and encoding to the memory that the shipping cap is detached from the annular reload in response to detaching the shipping cap from the annular reload.

In aspects, reading the memory may include a controller of the second handle assembly searching for the encoding in the memory.

In aspects, the controller of the second handle assembly may be configured to not initiate an operational sequence for detaching the shipping cap from the annular reload in response to finding the encoding in the memory.

In aspects, the method may further include initiating, by a controller of the second handle assembly, an operational sequence for detaching the shipping cap from the annular reload in response to determining that the shipping cap is attached to the annular reload.

In aspects, the operational sequence may include activating a motor of the second handle assembly to move a trocar of the adapter assembly to detach the shipping cap from the annular reload.

In aspects, the operational sequence may further include the controller prompting a user to actuate a toggle of the surgical device, thereby activating the motor.

According to one embodiment of the present disclosure, a surgical end effector is disclosed. The surgical end effector includes: an annular reload including a plurality of tissue fasteners and defining a central lumen therethrough; an anvil assembly including a center rod and a head coupled to the center rod, the head configured to deform the plurality of tissue fasteners, the anvil assembly being insertable into the central lumen; and one or more sensors configured to sense a presence of the center rod within the central lumen.

According to another embodiment of the present disclosure, a surgical device is disclosed. The surgical device includes: a handle assembly having: a power source; a motor coupled to the power source; and a controller configured to control the motor. The surgical device further includes: an adapter assembly configured to selectively couple to the handle assembly, the adapter assembly having a trocar; an anvil assembly including a center rod and a head coupled to the center rod, the center rod configured to couple to the trocar; and an annular reload configured to selectively couple to a distal portion of the adapter assembly. The annular reload includes a central lumen defined therethrough, a plurality of tissue fasteners deformable by the head; and at least one sensor configured to sense the center rod being coupled to the trocar.

According to one aspect of any of the above embodiments, the sensor is a limit switch. The limit switch includes a switching element and a leg coupled thereto, the leg extending into the central lumen, such that the center rod engages the leg upon insertion of the center rod into the central lumen. The switching element is configured to output a signal in response to the leg being engaged by the center rod.

According to another aspect of any of the above embodiments, the sensor is a magnetic sensor. The annular reload includes a magnet disposed therein. The magnet is disposed in a diameterically opposed configuration relative to magnetic sensor. The center rod includes a ferromagnetic material configured to modify a magnetic field of the magnet. The magnetic sensor is configured to measure the magnetic field and to output a signal corresponding to a change in the magnetic field by the ferromagnetic material due to insertion of the center rod into the central lumen.

According to a further aspect of the above embodiment, the controller is configured to control the at least one motor based on the signal from at least one of the limit switch or the magnetic sensor.

According to one embodiment of the present disclosure an annular reload is disclosed. The annular reload includes an outer cylindrical portion and an inner cylindrical portion coupled to the outer cylindrical portion and defining a central lumen therethrough. The annular reload also includes a staple cartridge disposed between the outer cylindrical portion and the inner cylindrical portion, the staple cartridge having a plurality of tissue fasteners; a chip assembly having an annular flange disposed about a proximal end portion of the inner cylindrical portion, the annular flange having a first tapered surface; and a bushing member including an annular ridge having a second tapered surface complementary to the first tapered surface, the bushing member disposed in contact with the annular flange and the inner cylindrical portion.

According to one aspect of the above embodiment, the chip assembly includes a housing defining a cavity enclosing a circuit board assembly having a chip and a pair of contact members coupled thereto. The cavity also includes a proximally-facing opening.

According to another aspect of the above embodiment, the first tapered surface slopes outward relative to a direction of insertion of the bushing member and the second tapered surface slopes inward relative to the direction of insertion of the bushing member.

According to another embodiment of the present disclosure, a method of using a surgical device is disclosed. The method includes: coupling an adapter assembly to a first handle assembly, the adapter assembly including a storage device and the first handle assembly including a motor, a memory, and a controller and executing an operational sequence by the controller to control the motor to actuate at least one component of the adapter assembly. The method also includes registering an error state associated with the operational sequence; writing a recovery code in the storage device; disconnecting the first handle assembly from the adapter assembly in response to the error state; coupling a second handle assembly to the adapter assembly; reading the recovery code from the storage device at the second handle assembly; and resuming the operational sequence based on the recovery code read from the storage device.

According to one aspect of the above embodiment, the method further includes: calibrating the second handle assembly while the second handle assembly is coupled to the adapter assembly; and storing calibration data collected during calibration of the second handle assembly in the memory. Resuming the operational sequence is based on the recovery code read from the storage device and the calibration data.

According to another aspect of the above embodiment, the method further includes: coupling an anastomosis reload to a distal end portion of the adapter assembly; inserting the adapter assembly with the anastomosis reload into a patient; and coupling an anvil assembly to the distal end portion of the adapter assembly. The error state may be registered while the adapter assembly is disposed within the patient. In addition, the first handle assembly may be disconnected from the adapter assembly while the adapter assembly is disposed within the patient.

According to a further embodiment of the present disclosure, a surgical device adapter is disclosed. The surgical device includes: a housing; an outer tube extending distally from the housing; and a rotation transmitting assembly disposed within the housing and the outer tube and configured to convert rotational motion into longitudinal motion. The surgical device also includes a trocar coupled to a distal end portion of the rotation transmitting assembly and at least partially extending from a distal end portion of the outer tube, the trocar configured to penetrate tissue and to couple to an anvil assembly. The surgical device further includes an electrical connector disposed at a proximal end portion of the housing and coupled to a ground connection; and a conductive pathway coupled to the trocar and to the electrical connector.

According to one aspect of the above embodiment, the conductive pathway is disposed within the outer tube.

According to another aspect of the above embodiment, the surgical device adapter further includes a wiring harness assembly, which includes a flexible circuit having the conductive pathway.

BRIEF DESCRIPTION OF THE DRAWINGS

Embodiments of the present disclosure are described herein with reference to the accompanying drawings, wherein:

FIG. 8 is a front, perspective view of the outer shell housing, shown in an open condition;

FIG. 9 is a front, perspective view of the outer shell housing, shown in a partially open condition, and with an insertion guide removed therefrom;

FIG. 20 is a front, perspective view of the adapter assembly of FIG. 1;

FIG. 21 is a rear, perspective view of the adapter assembly of FIGS. 1 and 20;

FIG. 29 is a perspective view, of a distal end portion of the first force/rotation transmitting/converting assembly of FIG. 25, illustrating a support block thereof;

FIG. 30 is a perspective view, of a distal end portion of the first force/rotation transmitting/converting assembly of FIG. 25, with the support block thereof shown in phantom;

FIG. 31 is a cross-sectional view as taken through 31-31 of FIG. 29;

FIG. 32 is a cross-sectional view as taken through 32-32 of FIG. 29;

FIG. 33 is a cross-sectional view as taken through 33-33 of FIG. 32;

FIG. 35 is a perspective view of the second force/rotation transmitting/converting assembly of FIG. 34;

FIG. 36 is an enlarged view of the indicated area of detail of FIG. 35;

FIG. 40 is a perspective view of the third force/rotation transmitting/converting assembly of FIG. 39;

FIG. 41 is an enlarged view of the indicated area of detail of FIG. 40;

FIG. 47 is a front, perspective view of the internal components of the distal end portion of the adapter assembly;

FIG. 48 is an enlarged view of the indicated area of detail of FIG. 47;

FIG. 62 is a rear, perspective view of the adapter assembly, illustrating a rotation of the rotation assembly and a shaft assembly relative to a drive coupling assembly thereof;

FIG. 63 is a rear, perspective view of the adapter assembly, illustrating the adapter assembly in a non-rotated position thereof;

FIG. 79 is a perspective view of the irrigation tube;

FIG. 80 is an enlarged view of the indicated area of detail of FIG. 79;

FIG. 81 is an enlarged view of the indicated area of detail of FIG. 79;

DETAILED DESCRIPTION OF EMBODIMENTS

Figure 1:
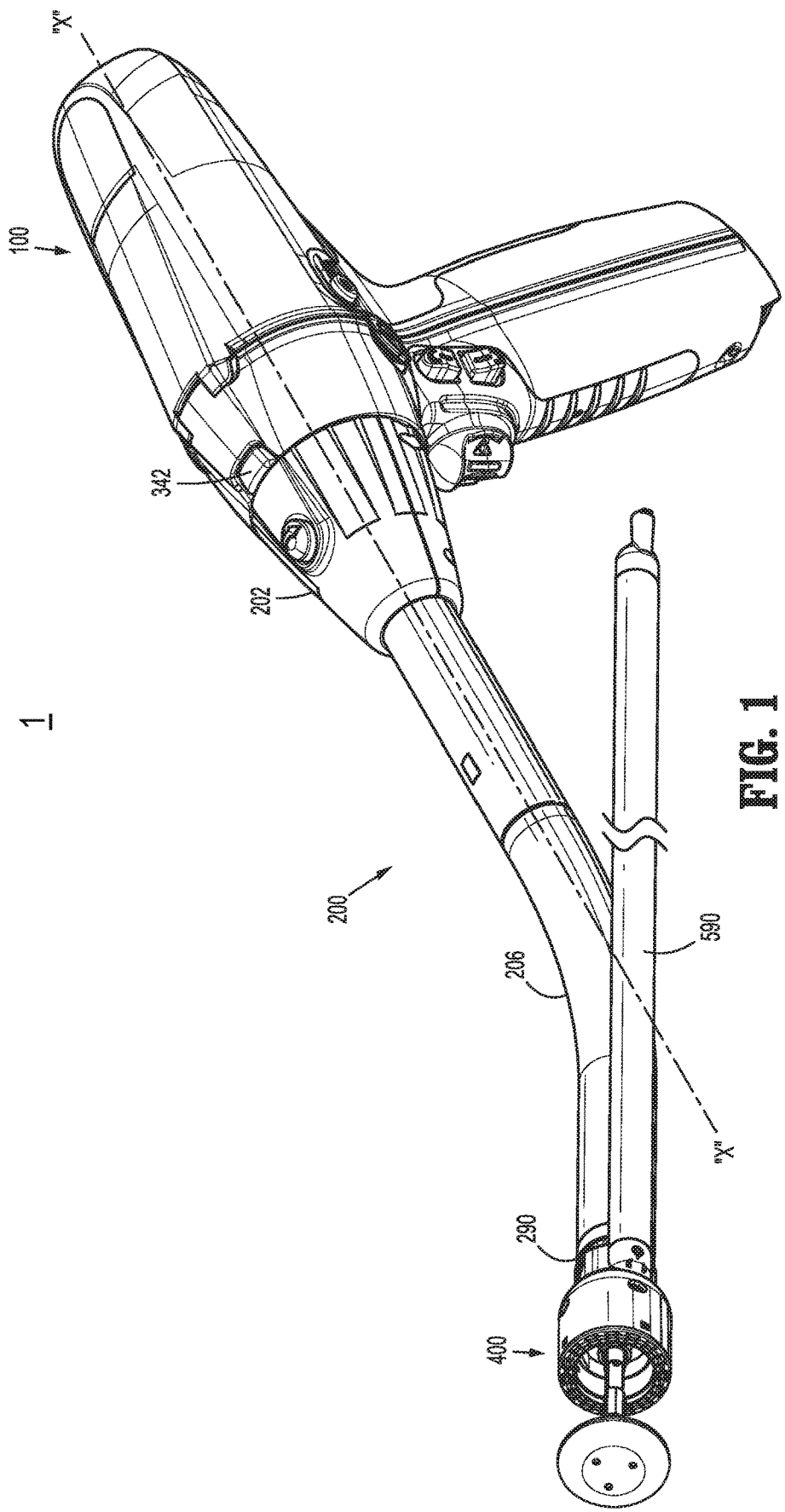
FIG. 1 is a perspective view of a handheld surgical device and adapter assembly, in accordance with an embodiment of the present disclosure, illustrating a connection thereof with an end effector or reload.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

An intelligent surgical instrument, such as a hand-held circular stapler, includes a handle assembly, an adapter assembly coupled to the handle assembly, and a surgical reload coupled to the adapter assembly. During a surgical procedure, if the handle assembly experiences any difficulty (e.g., a battery malfunction), the clinician may replace the handle assembly by disconnecting the handle assembly and replacing it with a new handle assembly. Since the new handle assembly is required to pick up where the last handle assembly left off within the procedure, software within the surgical instrument goes through a series of recovery steps so the clinician can continue with the procedure.

During normal use, a clinician may activate the stapler to eject a shipping cap from the surgical reload. Once the shipping cap gets ejected, the software stored within the stapler may mark an E-Prom Chip located within the surgical reload. In particular, the stapler marks that the shipping cap was already removed in case of a system fault and an ensuing entry into recovery mode.

During the recovery stage, the stapler may determine whether the shipping cap was ejected. If the software reads that the shipping cap is still present, the new handle assembly will prompt the user to eject the shipping cap as per normal operation. If the software determines that the shipping cap was removed, it will not activate shipping cap removal. Marking the E-Prom Chip that the shipping cap was ejected is important if the system enters the recovery mode while clamped on tissue. By doing so, the system knows that the shipping cap was removed and is prevented from extending and retracting the trocar, which is performed during removal of the shipping cap. This prevents possible tissue damage and other unexpected actions.

A surgical device, in accordance with an embodiment of the present disclosure, is a handheld surgical device in the form of a powered electromechanical handle assembly configured for selective attachment thereto of a plurality of different reloads, via a plurality of respective adapter assemblies, that are each configured for actuation and manipulation by the powered electromechanical handle assembly.

The surgical device includes a handle assembly 100 which is configured for selective connection with an adapter assembly 200, and, in turn, adapter assembly 200 is configured for selective connection with a selected reload 400 (of a plurality of reloads), which are configured to produce a surgical effect on tissue of a patient.

As illustrated in FIGS. 1-11, handle assembly 100 includes a power handle 101, and an outer shell housing 10 configured to selectively receive and encase power handle 101. Outer shell housing 10 includes a distal half-section 10a and a proximal half-section 10b pivotably connected to distal half-section 10a by a hinge 16 located along an upper edge of distal half-section 10a and proximal half-section 10b. When joined, distal and proximal half-sections 10a, 10b define a shell cavity 10c therein in which power handle 101 is selectively situated.

Distal and proximal half-sections 10a, 10b of shell housing 10 are divided along a plane that traverses a longitudinal axis "X" of adapter assembly 200.

Each of distal and proximal half-sections 10a, 10b of shell housing 10 includes a respective upper shell portion 12a, 12b, and a respective lower shell portion 14a, 14b. Lower shell portions 14a, 14b define a snap closure feature 18 for selectively securing lower shell portions 14a, 14b to one another and for maintaining shell housing 10 in a closed condition. Shell housing 10 includes right-side and left-side snap closure features 18a for further securing distal and proximal half-sections 10a, 10b of shell housing 10 to one another.

Distal half-section 10a of shell housing 10 defines a connecting portion 20 configured to accept a corresponding drive coupling assembly 210 of Adapter assembly 200. Specifically, distal half-section 10a of shell housing 10 has a recess 20 that receives a portion of drive coupling assembly 210 of Adapter assembly 200 when Adapter assembly 200 is mated to handle assembly 100.

Connecting portion 20 of distal half-section 10a defines a pair of axially extending guide rails 20a, 20b projecting radially inward from inner side surfaces thereof. Guide rails 20a, 20b assist in rotationally orienting Adapter assembly 200 relative to handle assembly 100 when Adapter assembly 200 is mated to handle assembly 100.

Connecting portion 20 of distal half-section 10a defines three apertures 22a, 22b, 22c formed in a distally facing surface thereof and which are arranged in a common plane or line with one another. Connecting portion 20 of distal half-section 10a also defines an elongate slot 24 (to contain connector 66, see FIG. 3) also formed in the distally facing surface thereof.

Connecting portion 20 of distal half-section 10a further defines a female connecting feature 26 (see FIG. 2) formed in a surface thereof. Female connecting feature 26 selectively engages with a male connecting feature of Adapter assembly 200, as will be described in greater detail below.

Distal half-section 10a of shell housing 10 supports a distal facing toggle control button 30. Toggle control button 30 is capable of being actuated in a left, right, up and down direction upon application of a corresponding force thereto or a depressive force thereto.

Figure 2:
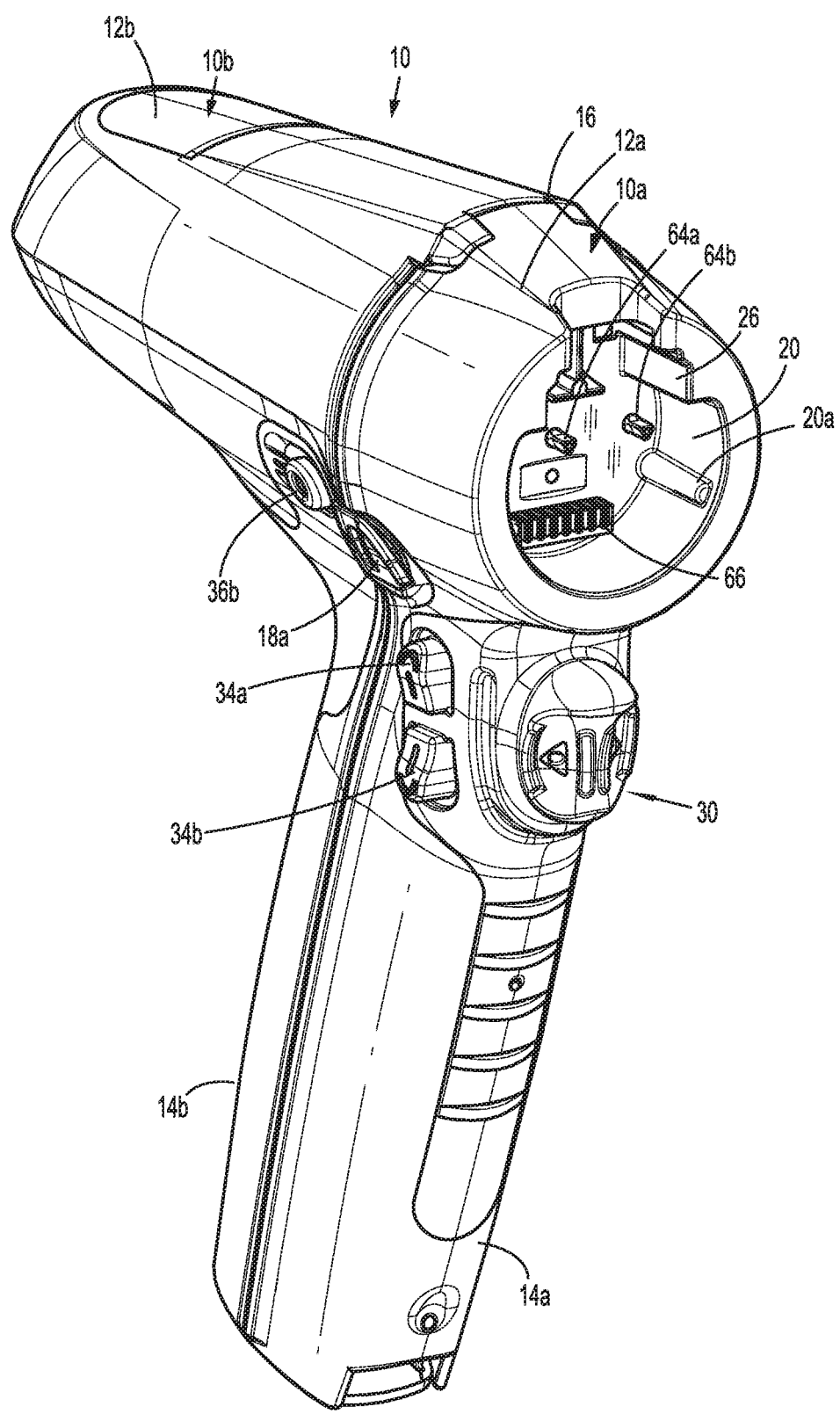
FIG. 2 is a front perspective view of a handle assembly of the surgical device of FIG. 1.

Distal half-section 10a of shell housing 10 supports a right-side pair of control buttons 32a, 32b (see FIG. 3); and a left-side pair of control button 34a, 34b (see FIG. 2). Right-side control buttons 32a, 32b and left-side control buttons 34a, 34b are capable of being actuated upon application of a corresponding force thereto or a depressive force thereto.

Proximal half-section 10b of shell housing 10 supports a right-side fire button 36a (see FIG. 3) and a left-side fire button 36b (see FIG. 2). Right-side fire button 36a and left-side fire button 36b are capable of being actuated upon application of a corresponding force thereto or a depressive force thereto.

Distal half-section 10a and proximal half-section 10b of shell housing 10 are fabricated from a polycarbonate, and are clear or transparent or may be overmolded.

With reference to FIGS. 5-11, handle assembly 100 includes an insertion guide 50 that is configured and shaped to seat on and entirely surround a distal facing edge 10d (FIGS. 3 and 9) of proximal half-section 10b. Insertion guide 50 includes a body portion 52 defining a central opening therein, and a hand/finger grip tab 54 extending from a bottom of body portion 52.

In use, when body portion 52 of insertion guide 50 is seated on distal facing edge 10d of proximal half-section 10b, the central opening of insertion guide 50 provides access to shell cavity 10c of shell housing 10 for insertion of a non-sterile power handle 101 of handle assembly 100 into proximal half-section 10b of sterile shell housing 10.

Figure 3:
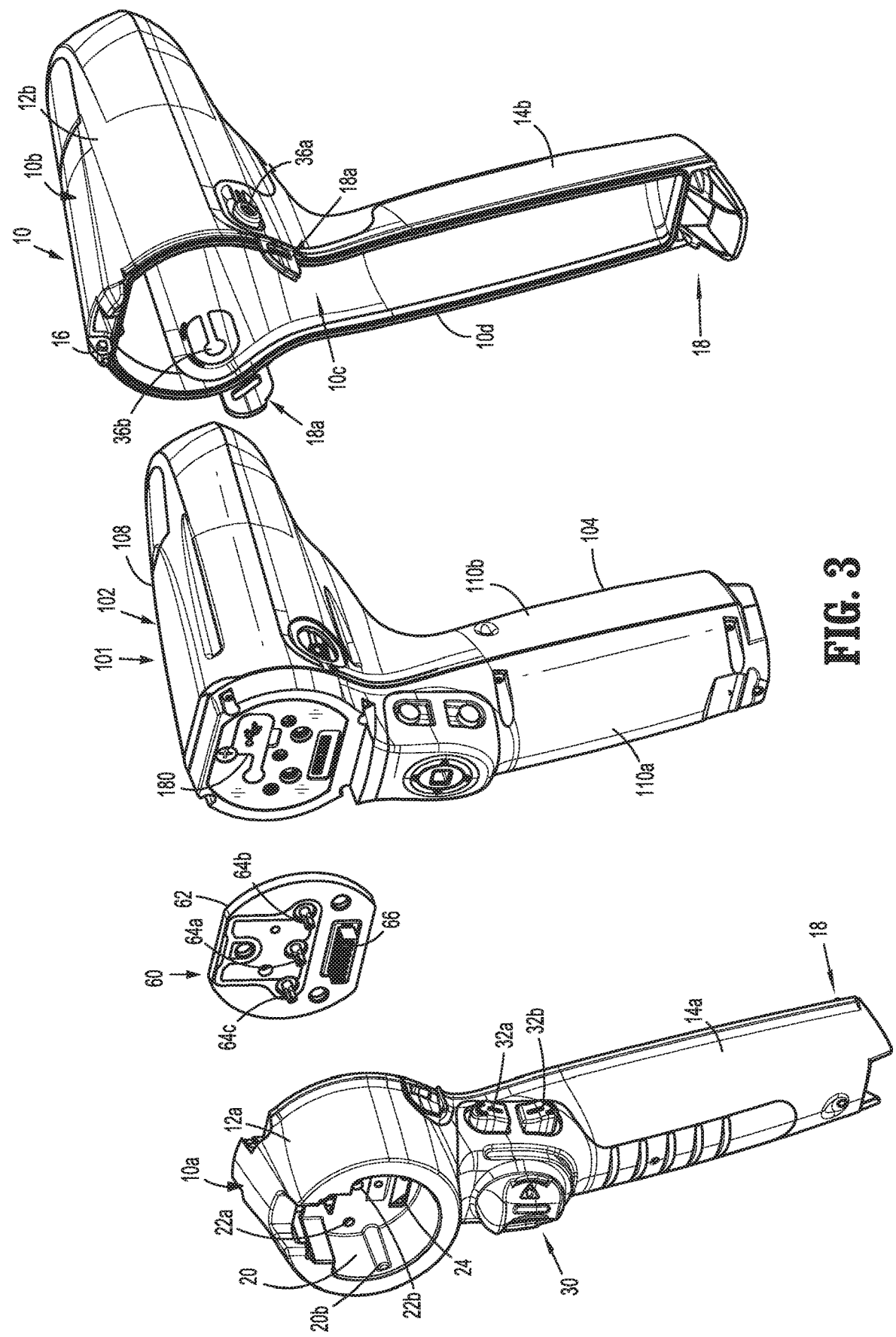
FIG. 3 is a front, perspective view, with parts separated, of the handle assembly of FIG. 2.
Figure 4:
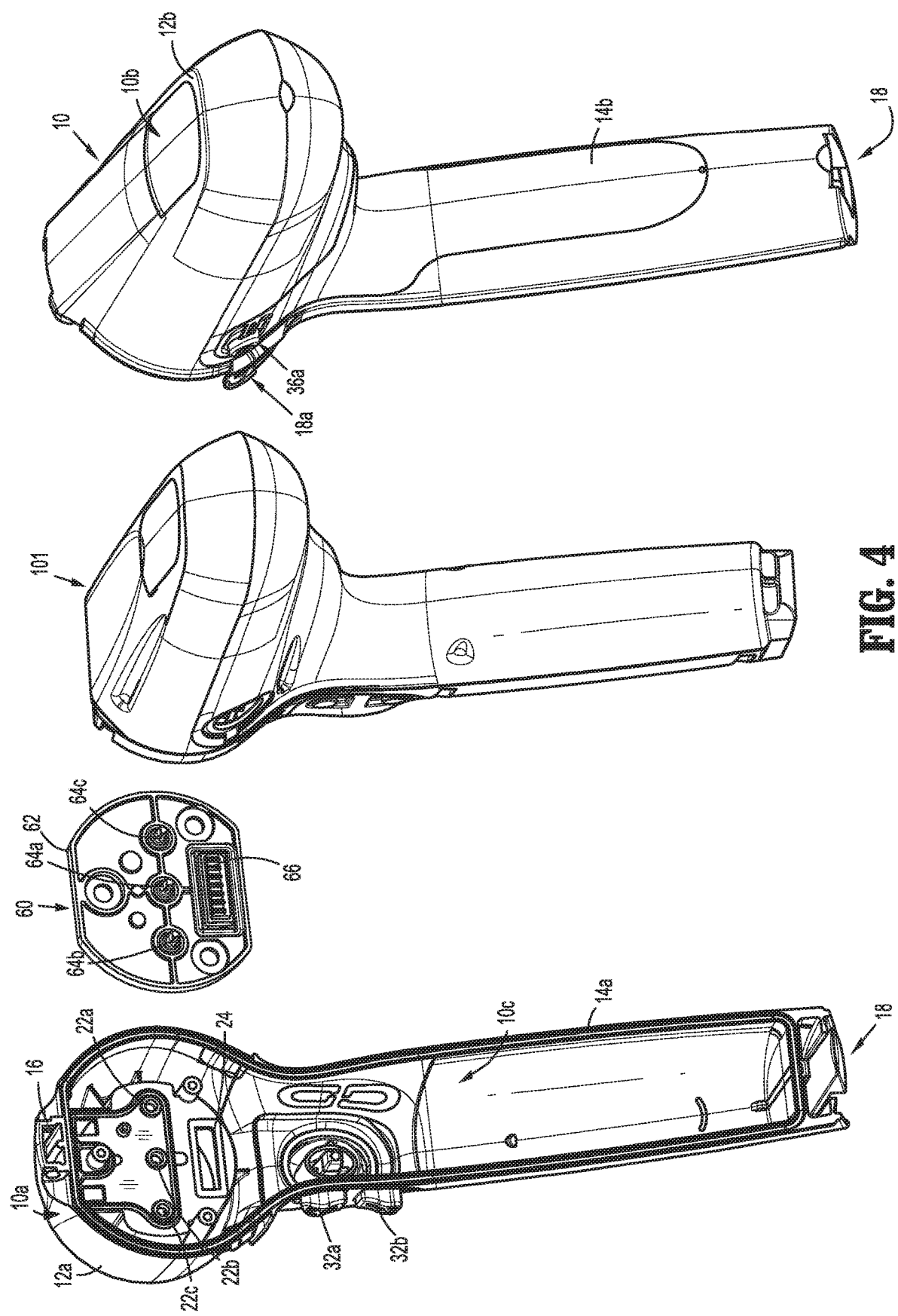
FIG. 4 is a rear, perspective view, with parts separated, of the handle assembly of FIG. 2.
Figure 6:
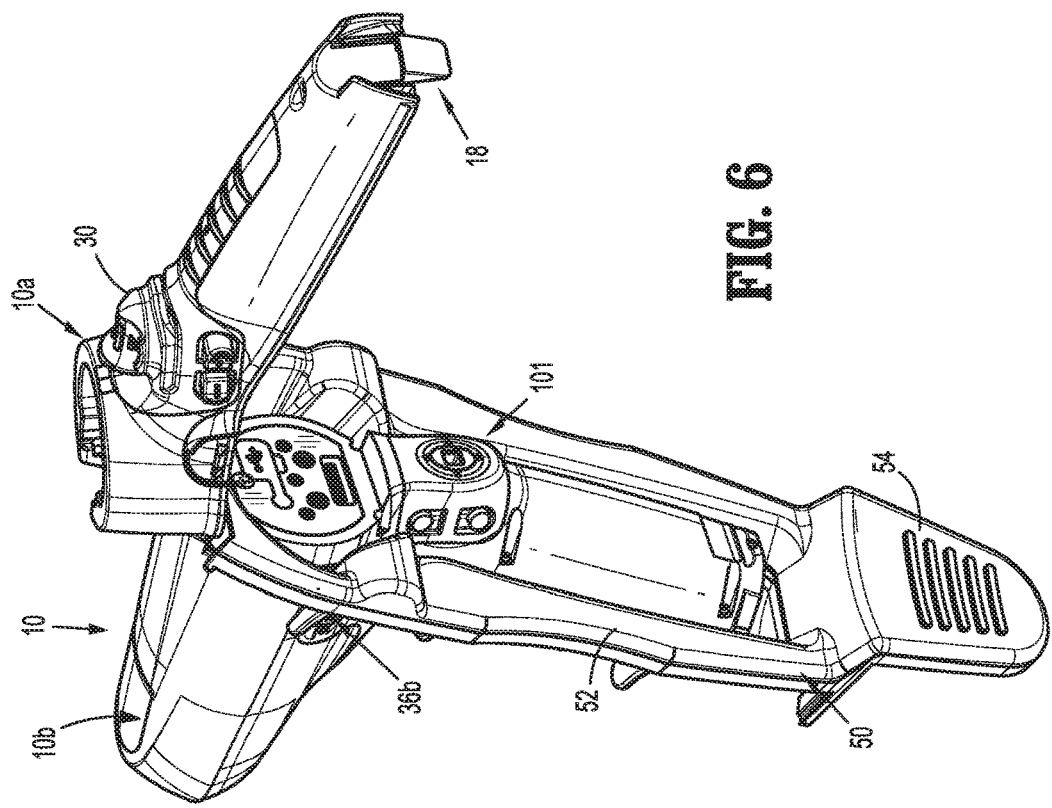
FIG. 6 is a perspective view illustrating the handle assembly inserted in a proximal half-section of the outer shell housing assembly, in accordance with the present disclosure.
Figure 5:
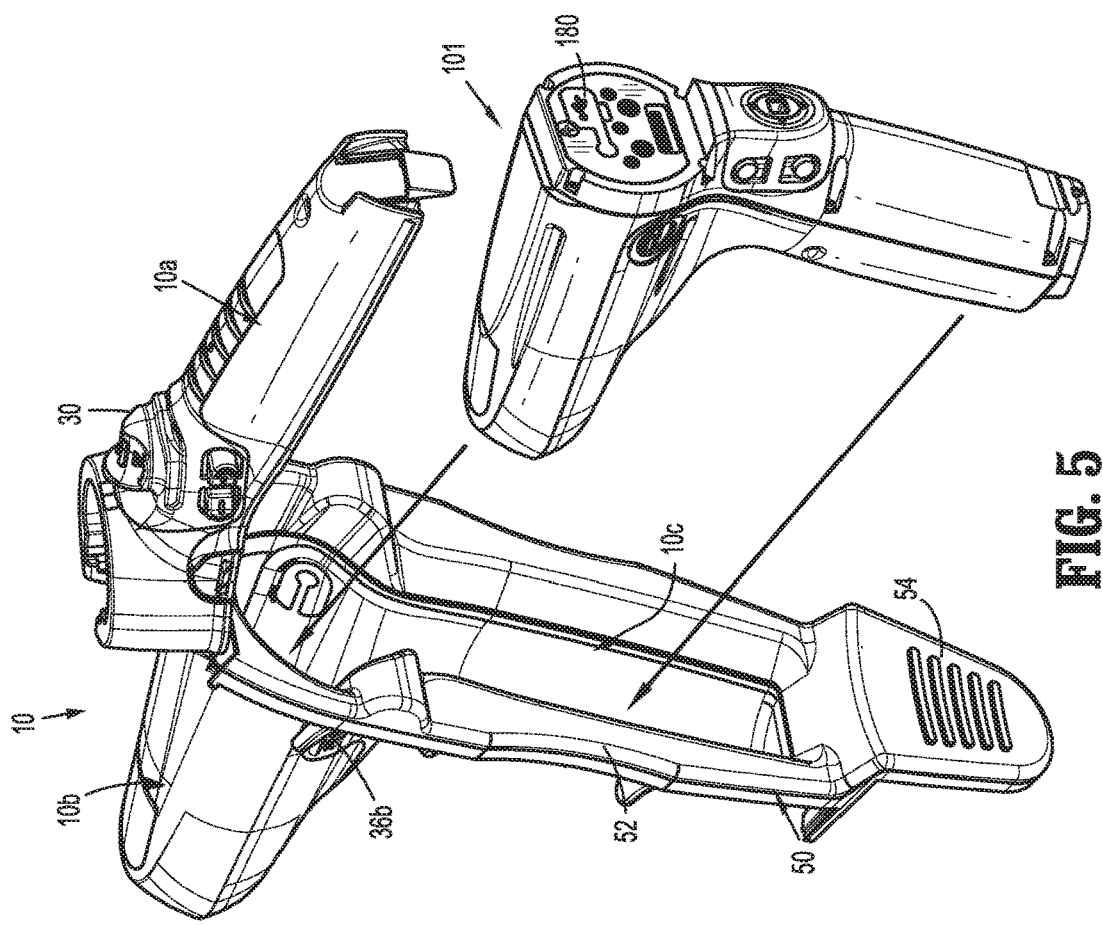
FIG. 5 is a perspective view illustrating an insertion of the handle assembly into an outer shell housing assembly, in accordance with the present disclosure.
Figure 7:
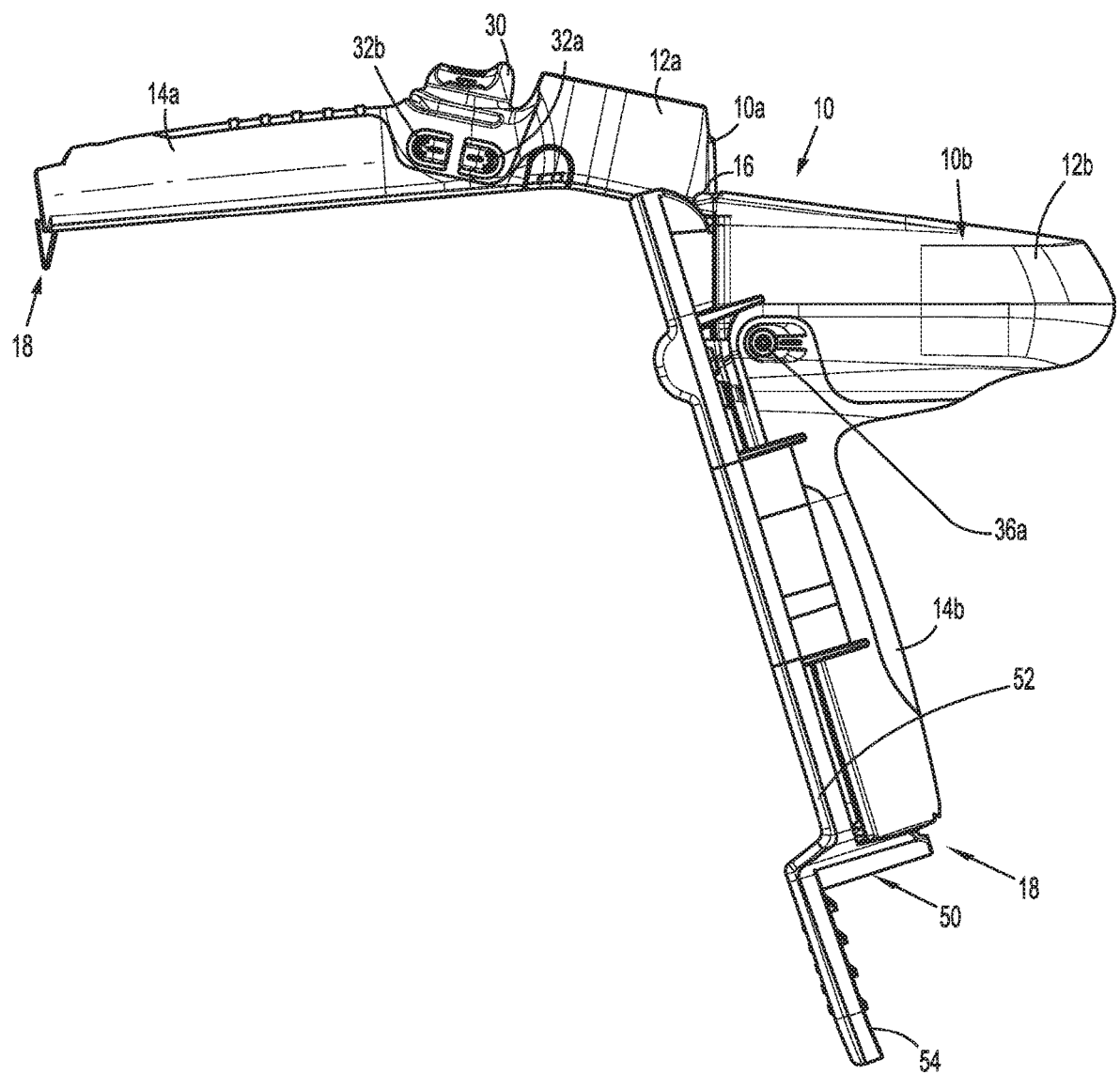
FIG. 7 is a side, elevational view of the outer shell housing, shown in an open condition.
Figure 10:
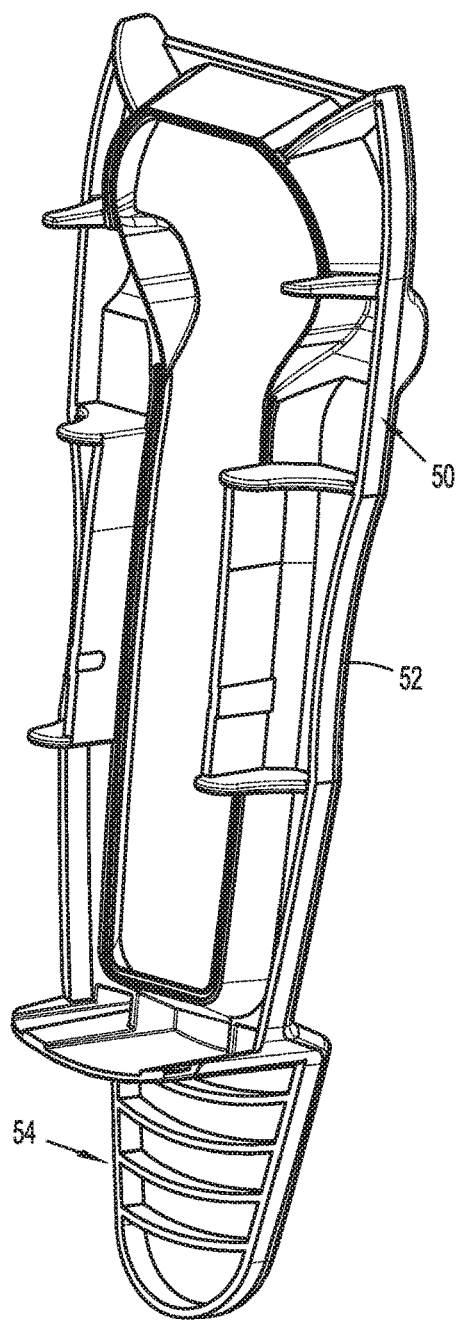
FIG. 10 is a rear, perspective view of the insertion guide.
Figure 11:
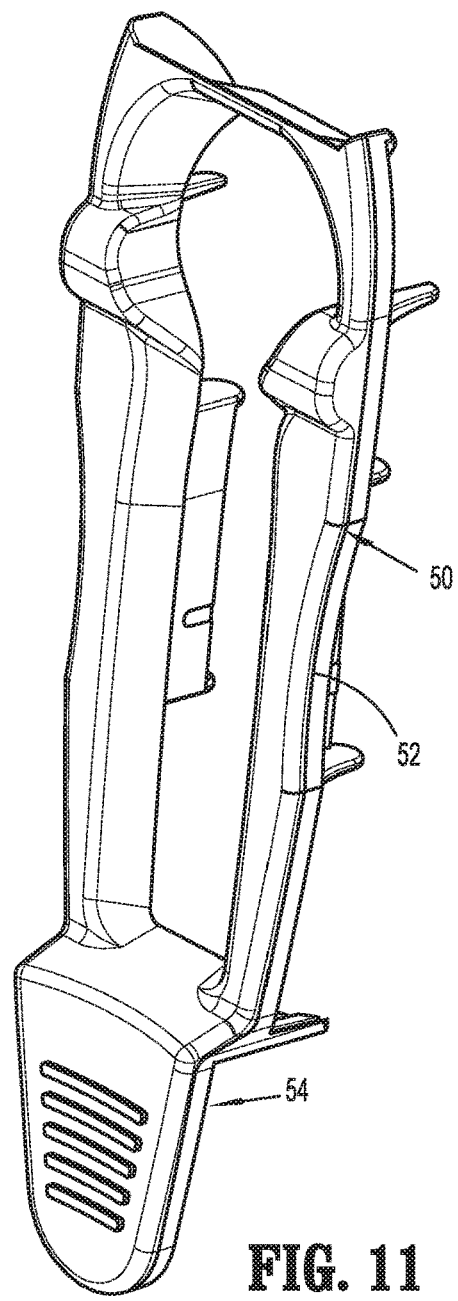
FIG. 11 is a front, perspective view of the insertion guide.

With reference to FIGS. 2-4, shell housing 10 includes a sterile barrier plate assembly 60 selectively supported in distal half-section 10a. Specifically, sterile barrier plate assembly 60 is disposed behind connecting portion 20 of distal half-section 10a and within shell cavity 10c of shell housing 10. Plate assembly 60 includes a plate 62 rotatably supporting three coupling shafts 64a, 64b, 64c. Each coupling shaft 64a, 64b, 64c extends from opposed sides of plate 62 and has a tri-lobe transverse cross-sectional profile. Each coupling shaft 64a, 64b, 64c extends through a respective aperture 22b, 22c, 22a of connecting portion 20 of distal half-section 10a when sterile barrier plate assembly 60 is disposed within shell cavity 10c of shell housing 10.

Plate assembly 60 further includes an electrical connector 66 supported on plate 62. Electrical connector 66 extends from opposed sides of plate 62. Each coupling shaft 64a, 64b, 64c extends through respective aperture 22a, 22b, 22c of connecting portion 20 of distal half-section 10a of shell housing 10 when sterile barrier plate assembly 60 is disposed within shell cavity 10c of shell housing 10. Electrical connector 66 includes a chip and defines a plurality of contact paths each including an electrical conduit for extending an electrical connection across plate 62.

When plate assembly 60 is disposed within shell cavity 10c of shell housing 10, distal ends of coupling shaft 64a, 64b, 64c and a distal end of pass-through connector 66 are disposed or situated within connecting portion 20 of distal half-section 10a of shell housing 10, and electrically and/or mechanically engage respective corresponding features of Adapter assembly 200, as will be described in greater detail below.

In operation, with a new and/or sterile shell housing 10 in an open configuration (e.g., distal half-section 10a separated from proximal half-section 10b, about hinge 16), and with the insertion guide 50 in place against the distal edge 10d of proximal half-section 10b of shell housing 10, power handle 101 is inserted through the central opening of insertion guide 50 and into shell cavity 10c of shell housing 10. With power handle 101 inserted into shell cavity 10c of shell housing 10, insertion guide 50 is removed from proximal half-section 10b and distal half-section 10a is pivoted, about hinge 16, to a closed configuration for shell housing 10. In the closed configuration, snap closure feature 18 of lower shell portion 14a of distal half-section 10a engages snap closure feature 18 of lower shell portion 14b of proximal half-section 10b. Also, right-side and left-side snap closure features 18a engage to further maintain shell housing 10 in the closed configuration.

In operation, following a surgical procedure, snap closure feature 18 of lower shell portion 14a of distal half-section 10a is disengaged from snap closure feature 18 of lower shell portion 14b of proximal half-section 10b, and right-side and left-side snap closure features 18a are disengaged, such that distal half-section 10a may be pivoted, about hinge 16, away from proximal half-section 10b to open shell housing 10. With shell housing 10 open, power handle 101 is removed from shell cavity 10c of shell housing 10 (specifically from proximal half-section 10b of shell housing 10), and shell housing 10 is discarded.

Power handle 101 is then disinfected and cleaned. Power handle 101 is not to be submerged and is not to be sterilized.

Referring to FIGS. 3-6 and FIGS. 12-19, handle assembly 100 includes a power handle 101. Power handle 101 includes an inner handle housing 110 having a lower housing portion 104 and an upper housing portion 108 extending from and/or supported on lower housing portion 104. Lower housing portion 104 and upper housing portion 108 are separated into a distal half-section 110a and a proximal half-section 110b connectable to distal half-section 110a by a plurality of fasteners. When joined, distal and proximal half-sections 110a, 110b define an inner handle housing 110 having an inner housing cavity 110c therein in which a power-pack core assembly 106 is situated.

Power-pack core assembly 106 is configured to control the various operations of handle assembly 100, as will be set forth in additional detail below.

Distal half-section 110a of inner handle housing 110 defines a distal opening 111a therein which is configured and adapted to support a control plate 160 of power-pack core assembly 106. Control plate 160 of power handle 101 abuts against a rear surface of plate 62 of sterile barrier plate assembly 60 of shell housing 10 when power handle 101 is disposed within shell housing 10.

Figure 12:
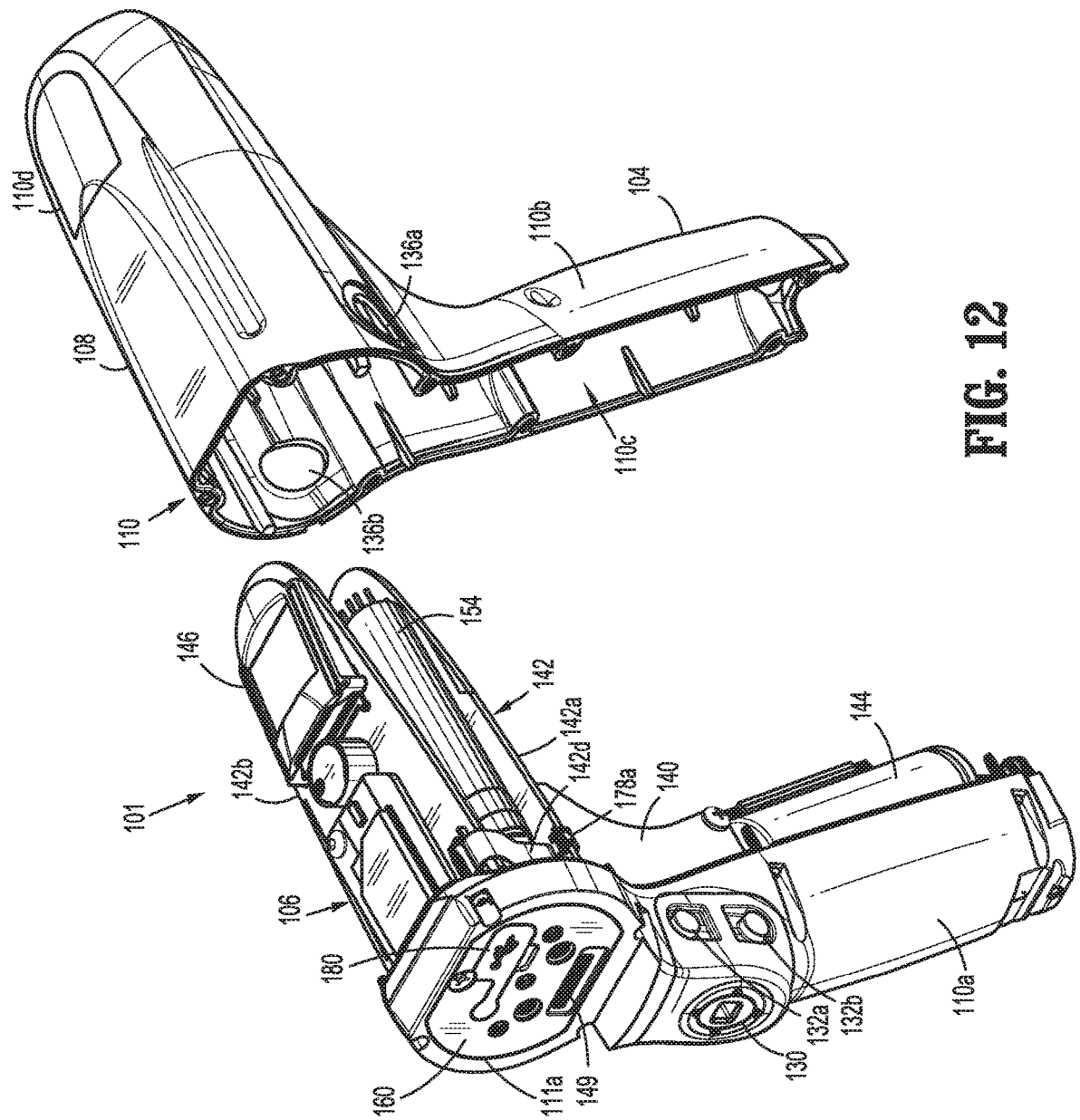
FIG. 12 is a front, perspective view of a power handle with an inner rear housing separated therefrom.
Figure 13:
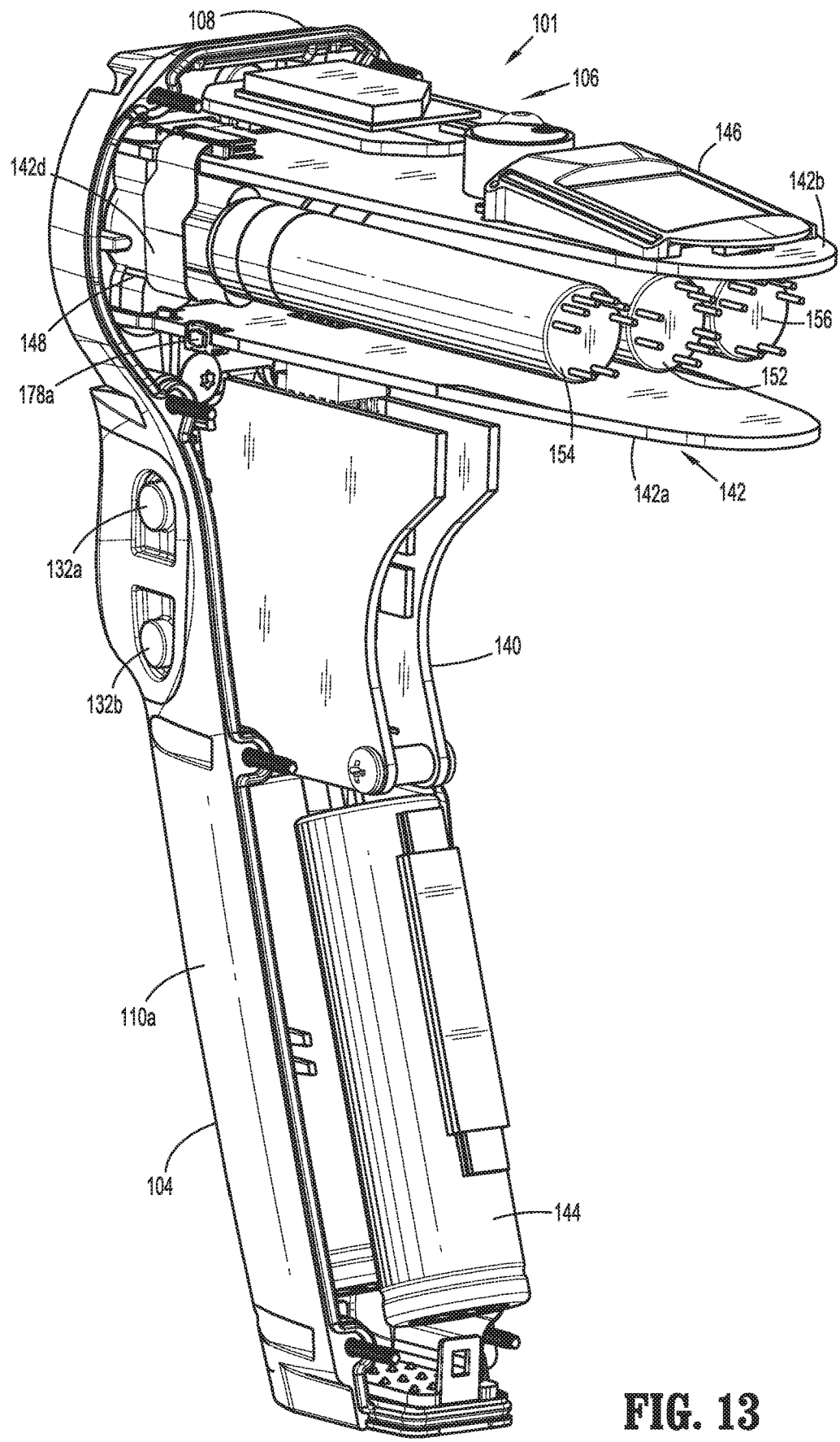
FIG. 13 is a rear, perspective view of the power handle with the inner rear housing removed therefrom.
Figure 15:
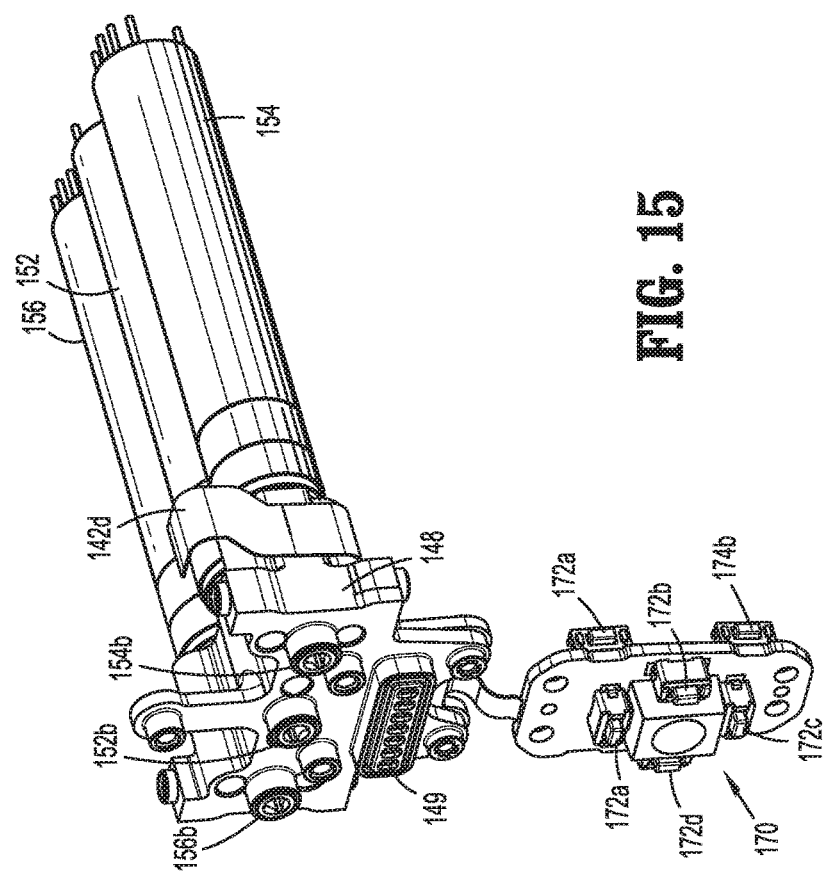
FIG. 15 is a front, perspective view of a motor assembly and a control assembly of the power handle core assembly of FIG. 14.

With reference to FIG. 12, distal half-section 110a of inner handle housing 110 supports a distal toggle control interface 130 that is in operative registration with distal toggle control button 30 of shell housing 10. In use, when power handle 101 is disposed within shell housing 10, actuation of toggle control button 30 exerts a force on toggle control interface 130.

Distal half-section 110a of inner handle housing 110 also supports a right-side pair of control interfaces 132a, 132b, and a left-side pair of control interfaces 134a, 134b. In use, when power handle 101 is disposed within shell housing 10, actuation of one of the right-side pair of control buttons 32a, 32b or the left-side pair of control button 34a, 34b of distal half-section 10a of shell housing 10 exerts a force on a respective one of the right-side pair of control interfaces 132a, 132b or the left-side pair of control interfaces 134a, 134b of distal half-section 110a of inner handle housing 110.

In use, control button 30, right-side fire button 36a or the left-side fire button 36b, the right-side pair of control interfaces 132a, 132b, and the left-side pair of control interfaces 134a, 134b of distal half-section 110a of inner handle housing 110 will be deactivated or fail to function unless shell housing 10 has been validated.

Proximal half-section 110b of inner handle housing 110 defines a right-side control aperture 136a and a left-side control aperture 136b. In use, when power handle 101 is disposed within shell housing 10, actuation of one of the right-side fire button 36a or the left-side fire button 36b of proximal half-section 10b of shell housing 10 extends the right-side fire button 36a or the left-side fire button 36b into and across the right-side control aperture 136a or the left-side control aperture 136b of the proximal half-section 110b of inner handle housing 110.

With reference to FIGS. 12-19, inner handle housing 110 provides a housing in which power-pack core assembly 106 is situated. Power-pack core assembly 106 includes a battery circuit 140, a controller circuit board 142 and a rechargeable battery 144 configured to supply power to any of the electrical components of handle assembly 100. Controller circuit board 142 includes a motor controller circuit board 142a, a main controller circuit board 142b, and a first ribbon cable 142c interconnecting motor controller circuit board 142a and main controller circuit board 142b.

Power-pack core assembly 106 further includes a display screen 146 supported on main controller circuit board 142b. Display screen 146 is visible through a clear or transparent window 110d (see FIGS. 12 and 17) provided in proximal half-section 110b of inner handle housing 110.

Power-pack core assembly 106 further includes a first motor 152, a second motor 154, and a third motor 156 each electrically connected to controller circuit board 142 and battery 144. Motors 152, 154, 156 are disposed between motor controller circuit board 142a and main controller circuit board 142b. Each motor 152, 154, 156 includes a respective motor shaft 152a, 154a, 156a extending therefrom. Each motor shaft 152a, 154a, 156a has a tri-lobe transverse cross-sectional profile for transmitting rotative forces or torque.

Each motor 152, 154, 156 is controlled by a respective motor controller. The motor controllers are disposed on motor controller circuit board 142a and are A3930/31K motor drivers from Allegro Microsystems, Inc. The A3930/31K motor drivers are designed to control a 3-phase brushless DC (BLDC) motor with N-channel external power MOSFETs, such as the motors 152, 154, 156. Each of the motor controllers is coupled to a main controller disposed on the main controller circuit board 142b. The main controller is also coupled to memory, which is also disposed on the main controller circuit board 142b. The main controller is an ARM Cortex M4 processor from Freescale Semiconductor, Inc, which includes 1024 kilobytes of internal flash memory. The main controller communicates with the motor controllers through an FPGA, which provides control logic signals (e.g., coast, brake, etc.). The control logic of the motor controllers then outputs corresponding energization signals to their respective motors 152, 154, 156 using fixed-frequency pulse width modulation (PWM).

Figure 16:
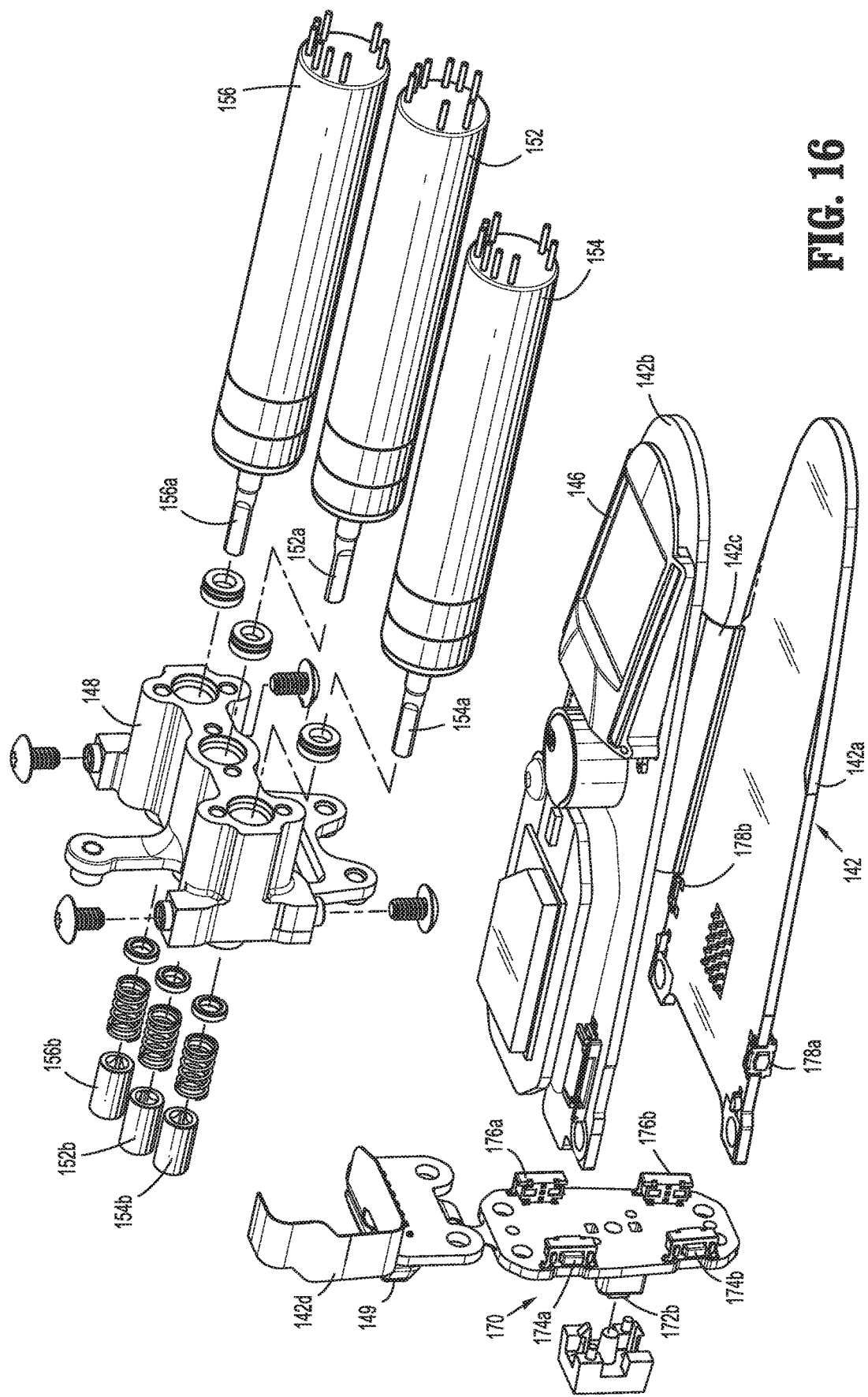
FIG. 16 is a rear, perspective view, with parts separated, of the motor assembly and the control assembly of FIG. 15.
Figure 17:
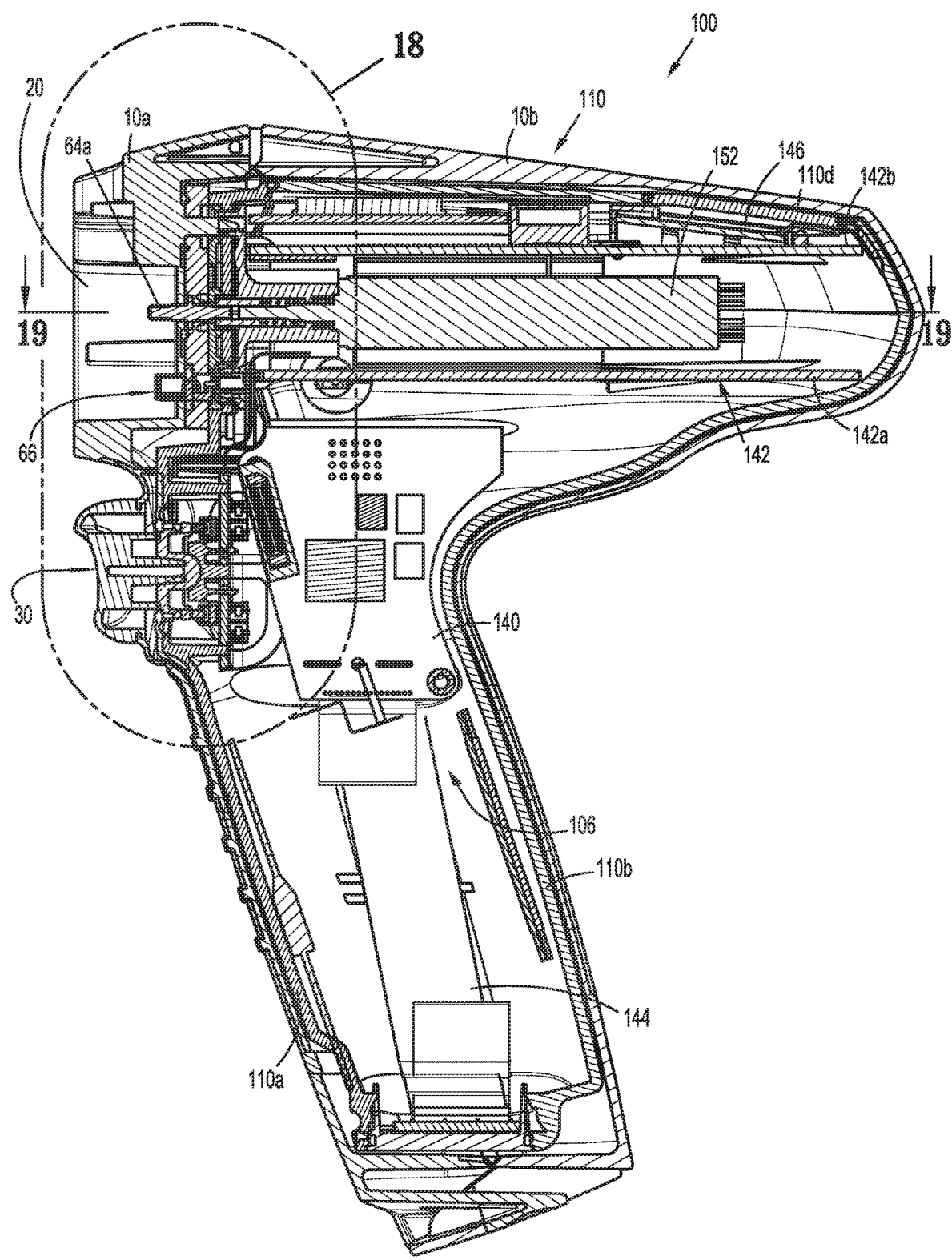
FIG. 17 is a longitudinal, cross-sectional view of the handle assembly of FIG. 2.
Figure 18:
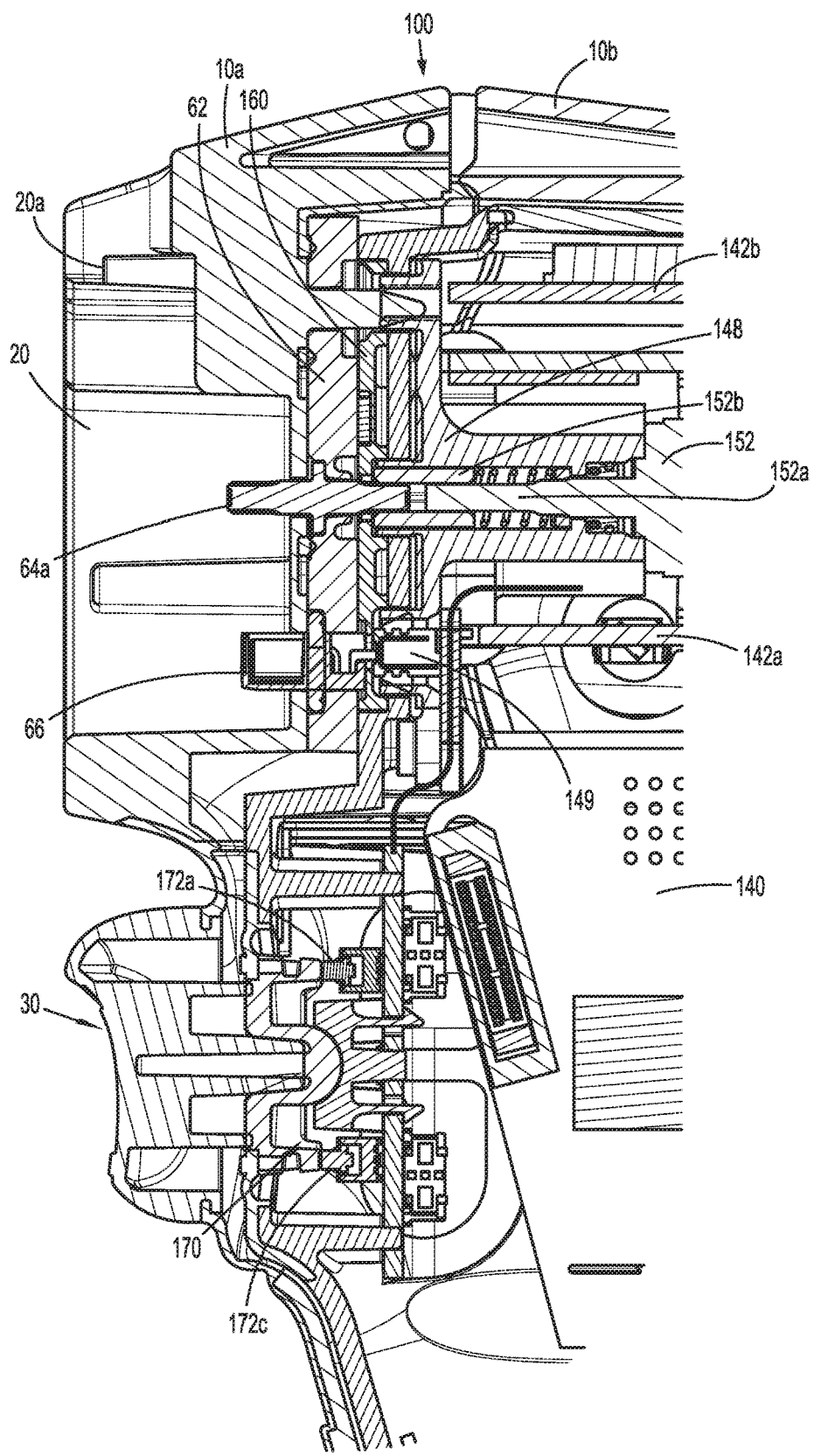
FIG. 18 is an enlarged view of the indicated area of detail of FIG. 17.
Figure 19:
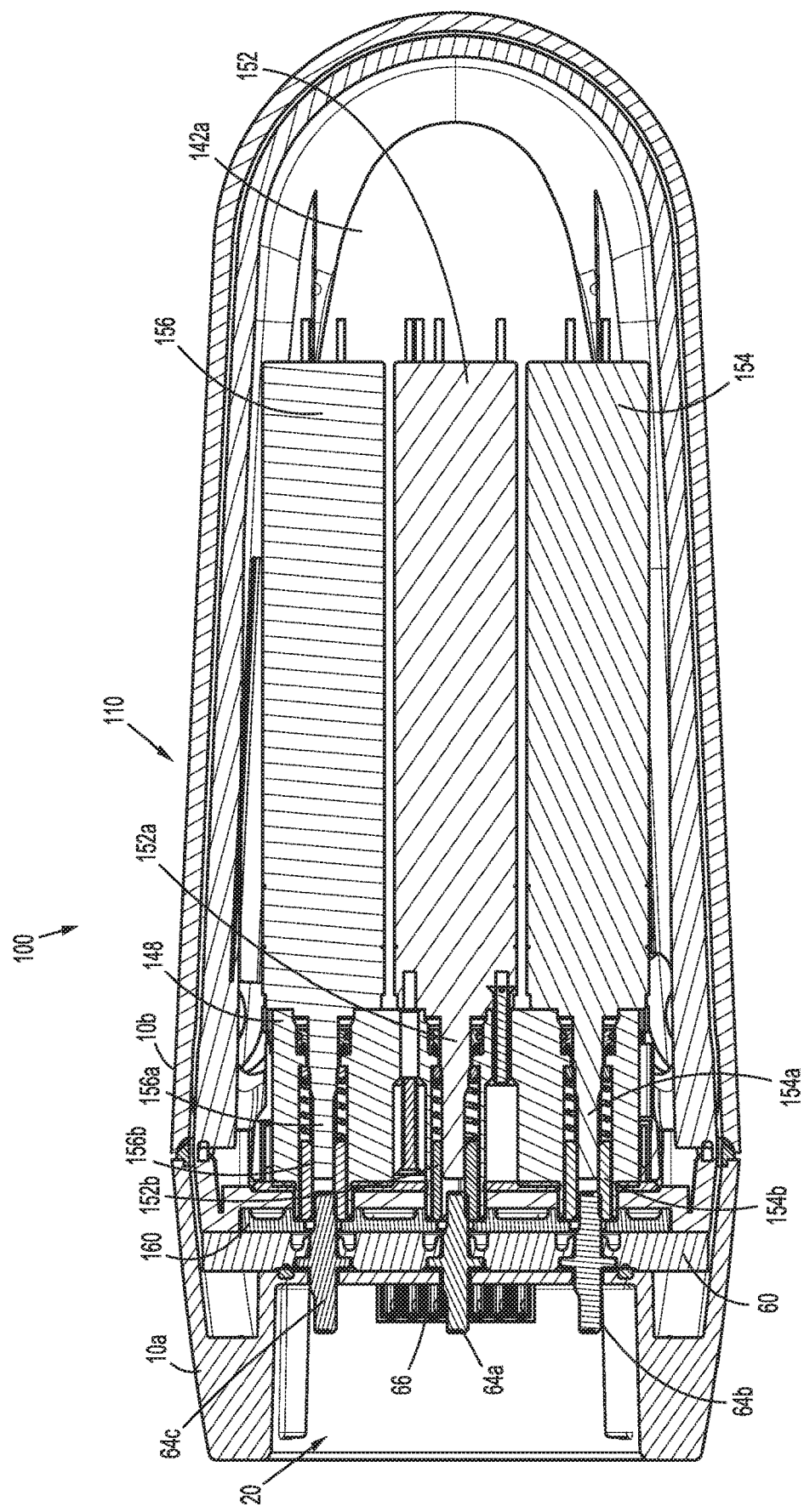
FIG. 19 is a cross-sectional view of the handle assembly as taken through 19-19 of FIG. 17.

Each motor 152, 154, 156 is supported on a motor bracket 148 such that motor shaft 152a, 154a, 156a are rotatably disposed within respective apertures of motor bracket 148. As illustrated in FIGS. 16 and 19, motor bracket 148 rotatably supports three rotatable drive connector sleeves 152b, 154b, 156b that are keyed to respective motor shafts 152a, 154a, 156a of motors 152, 154, 156. Drive connector sleeves 152b, 154b, 156b non-rotatably receive proximal ends of respective coupling shaft 64a, 64b, 64c of plate assembly 60 of shell housing 10, when power handle 101 is disposed within shell housing 10. Drive connector sleeves 152b, 154b, 156b are each spring biased away from respective motors 152, 154, 156.

Rotation of motor shafts 152a, 154a, 156a by respective motors 152, 154, 156 function to drive shafts and/or gear components of Adapter assembly 200 in order to perform the various operations of handle assembly 100. In particular, motors 152, 154, 156 of power-pack core assembly 106 are configured to drive shafts and/or gear components of adapter assembly 200 in order to selectively extend/retract a trocar member 274 of a trocar assembly 270 of adapter assembly 200; to, open/close reload 400 (when an anvil assembly 510 is connected to trocar member 274 of trocar assembly 270), to fire an annular array of staples of reload 400, and to fire an annular knife 444 of reload 400.

Motor bracket 148 also supports an electrical receptacle 149. Electrical receptacle 149 is in electrical connection with main controller circuit board 142b by a second ribbon cable 142d. Electrical receptacle 149 defines a plurality of electrical slots for receiving respective electrical contacts or blades extending from pass-through connector 66 of plate assembly 60 of shell housing 10.

Figure 22:
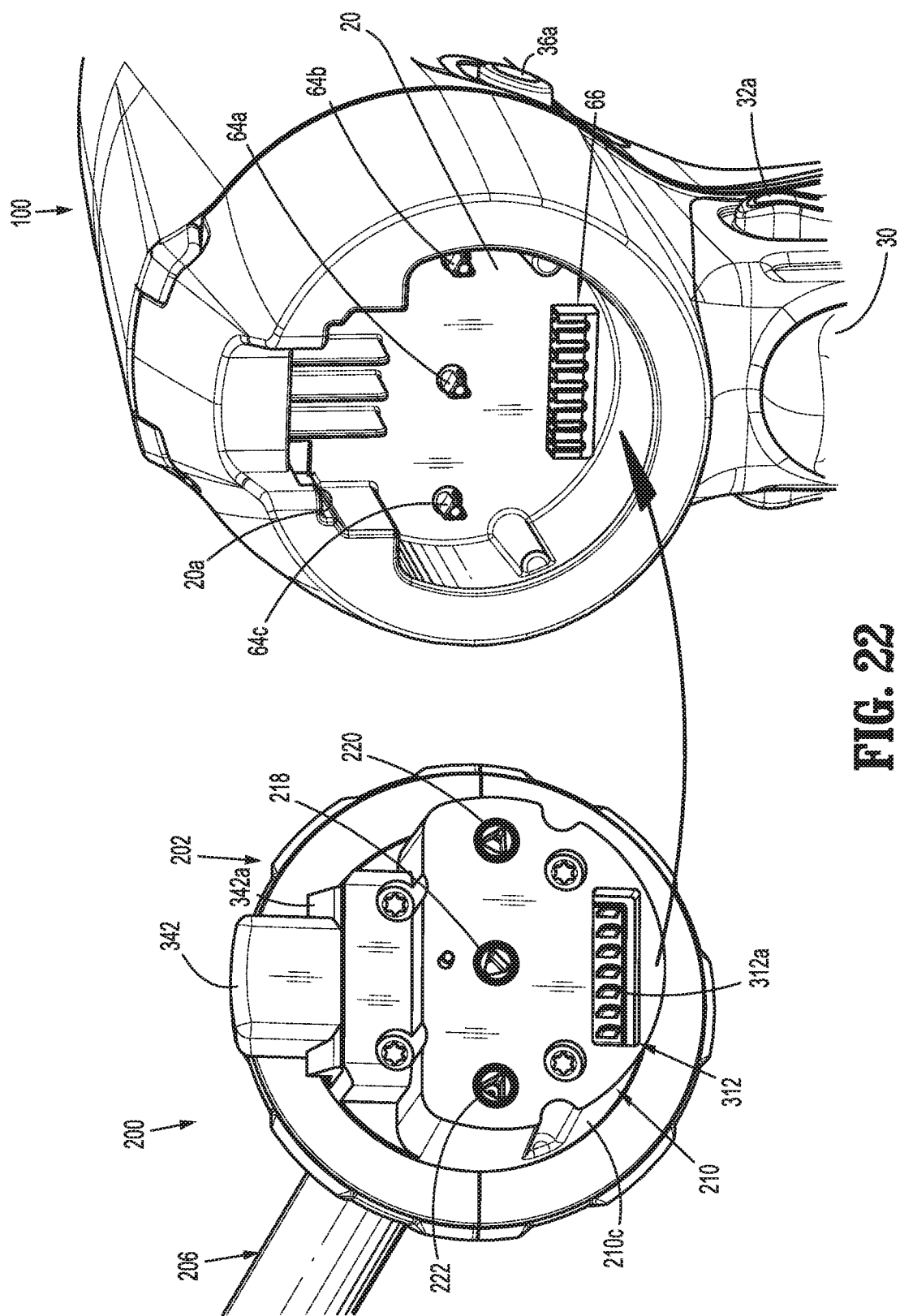
FIG. 22 is a perspective view illustrating a connection of the adapter assembly and the handle assembly.
Figure 23:
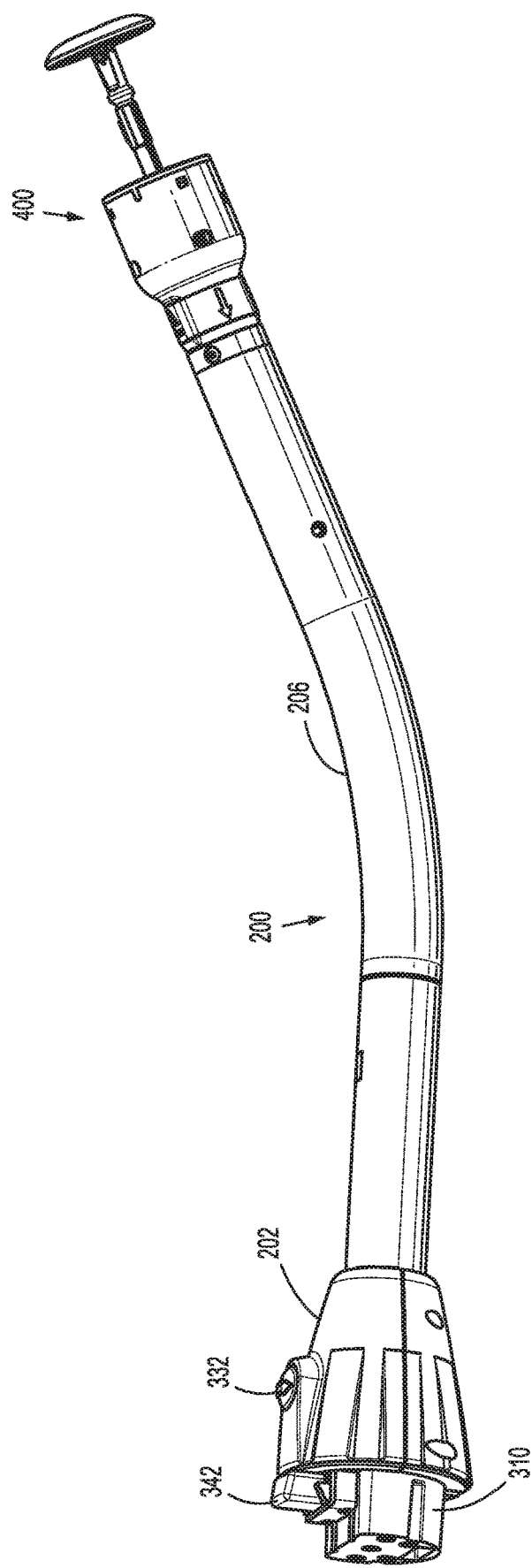
FIG. 23 is a perspective view of the adapter assembly, illustrating a reload secured to a distal end thereof.
Figure 24:
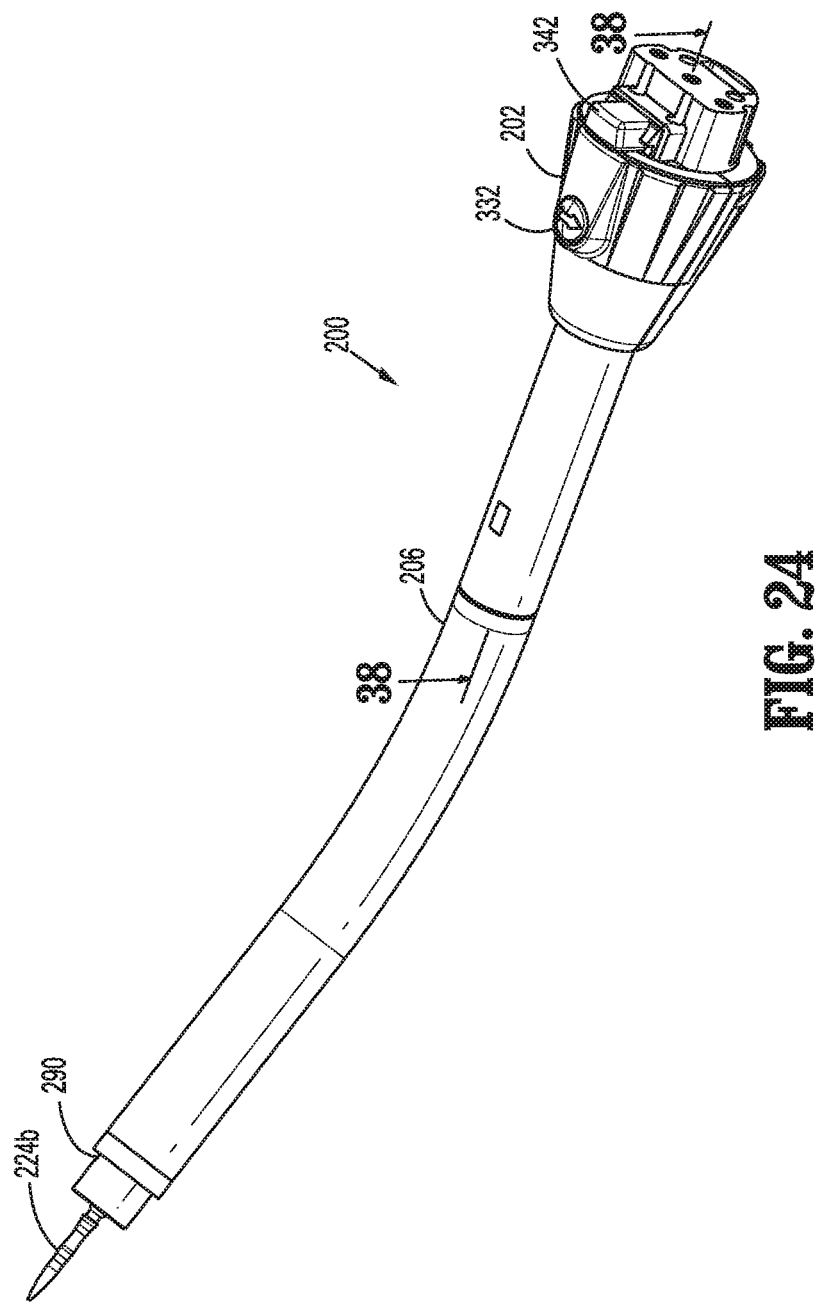
FIG. 24 is a perspective view of the adapter assembly without the reload secured to the distal end thereof.
Figure 25:
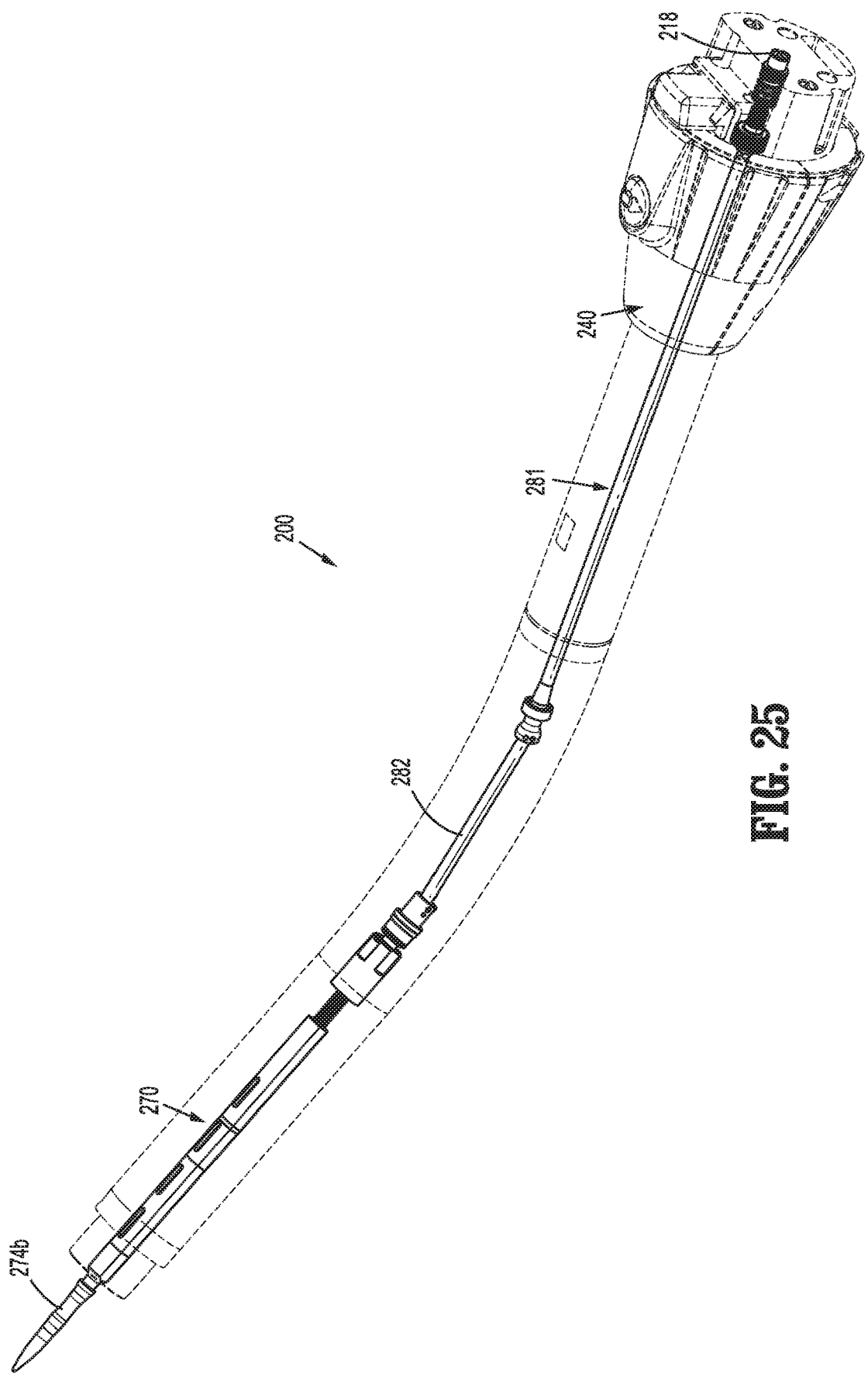
FIG. 25 is a perspective view of the adapter assembly, shown partially in phantom, illustrating a first force/rotation transmitting/converting assembly thereof.
Figure 26:
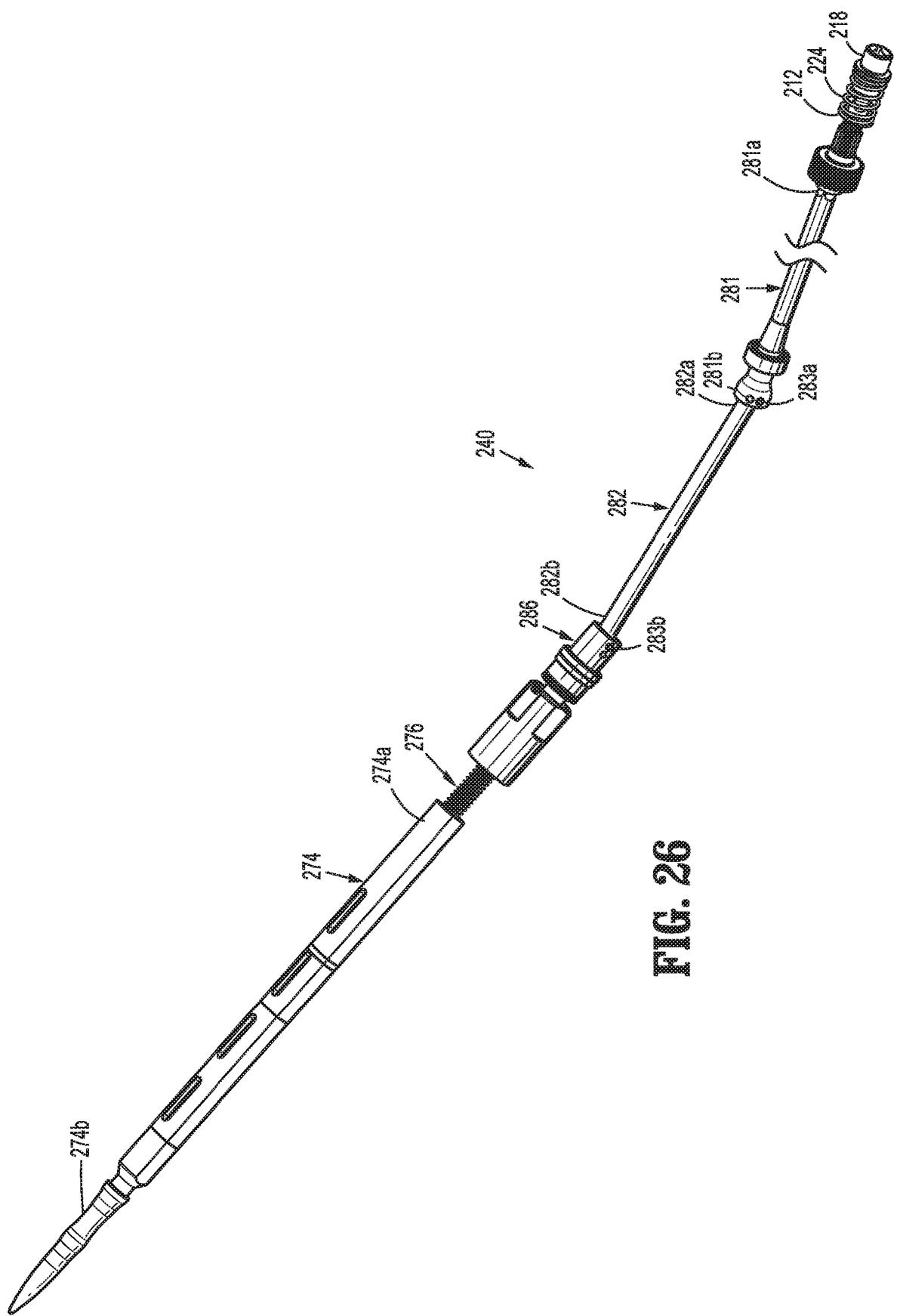
FIG. 26 is a perspective view of the first force/rotation transmitting/converting assembly of FIG. 25.
Figure 27:
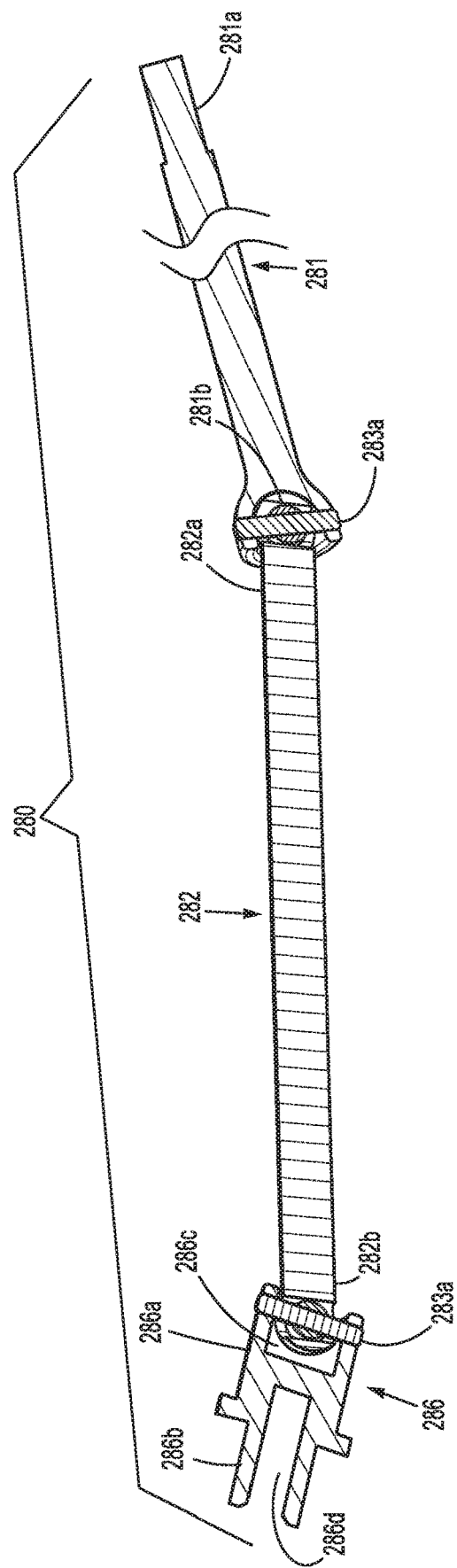
FIG. 27 is a longitudinal, cross-sectional view of a first rotatable proximal drive shaft, a first rotatable distal drive shaft and a coupling member of the first force/rotation transmitting/converting assembly of FIG. 25.
Figure 28:
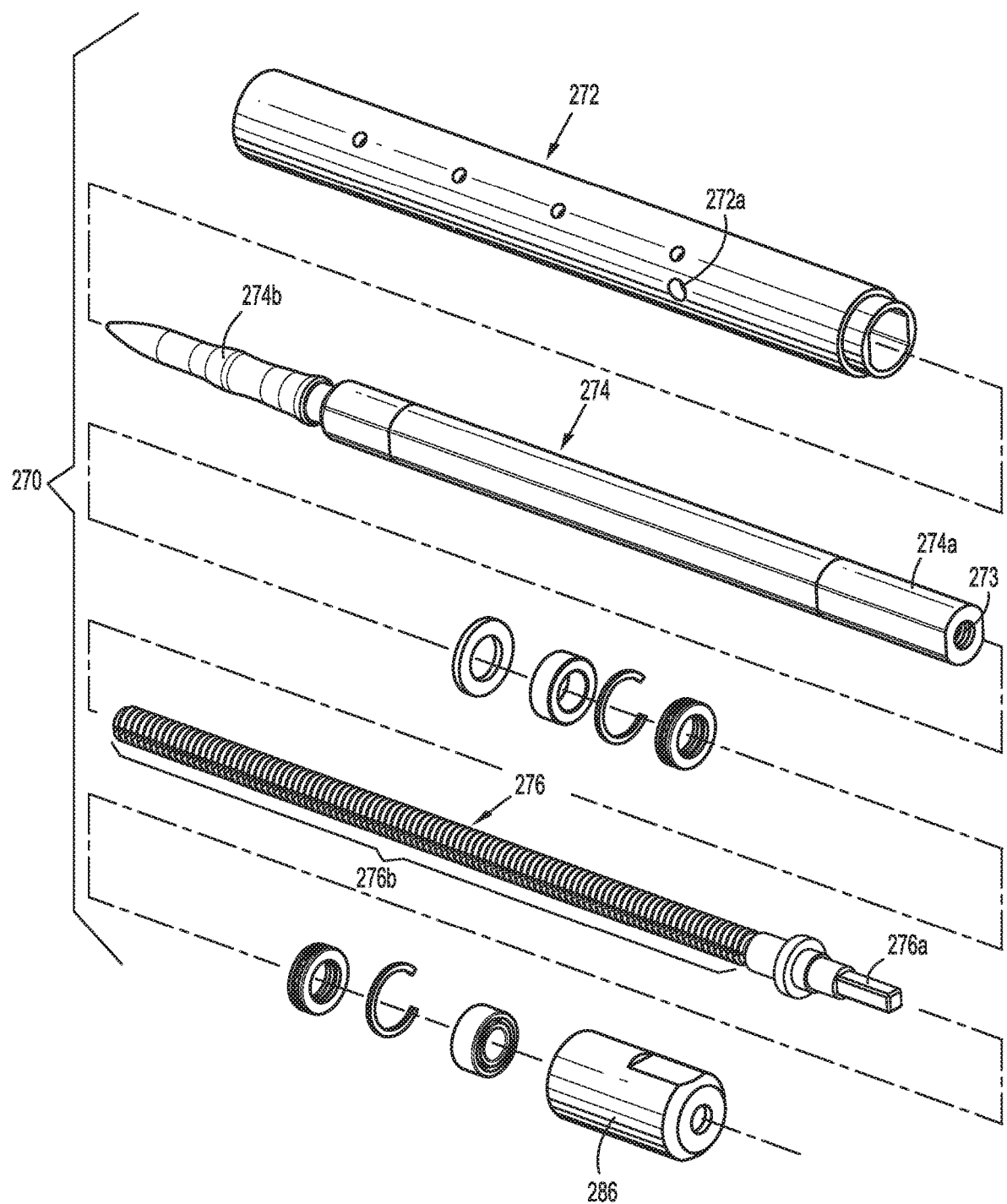
FIG. 28 is a perspective view, with parts separated, of a trocar assembly of the first force/rotation transmitting/converting assembly of FIG. 25.
Figure 34:
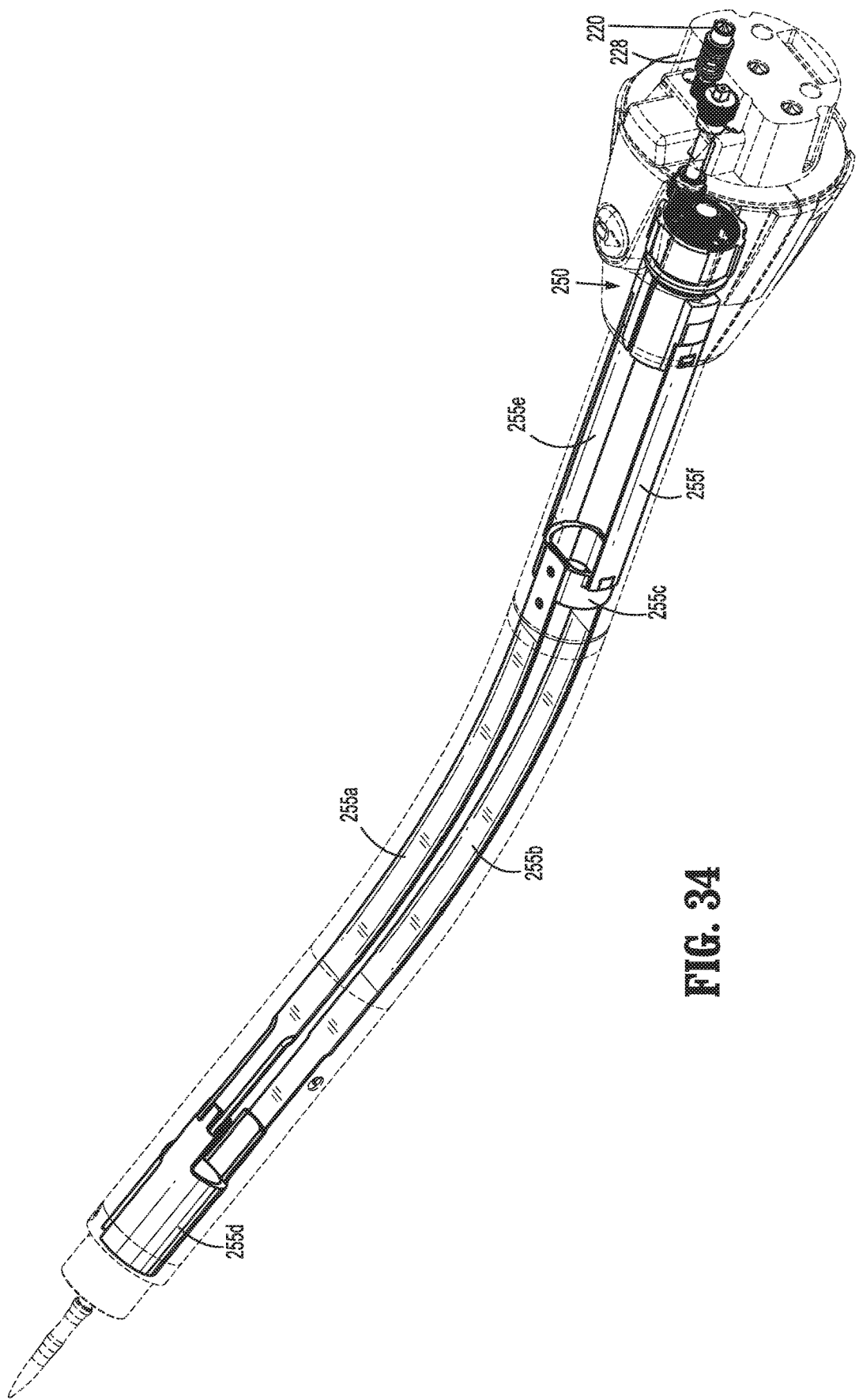
FIG. 34 is a perspective view of the adapter assembly, shown partially in phantom, illustrating a second force/rotation transmitting/converting assembly thereof.
Figure 37:
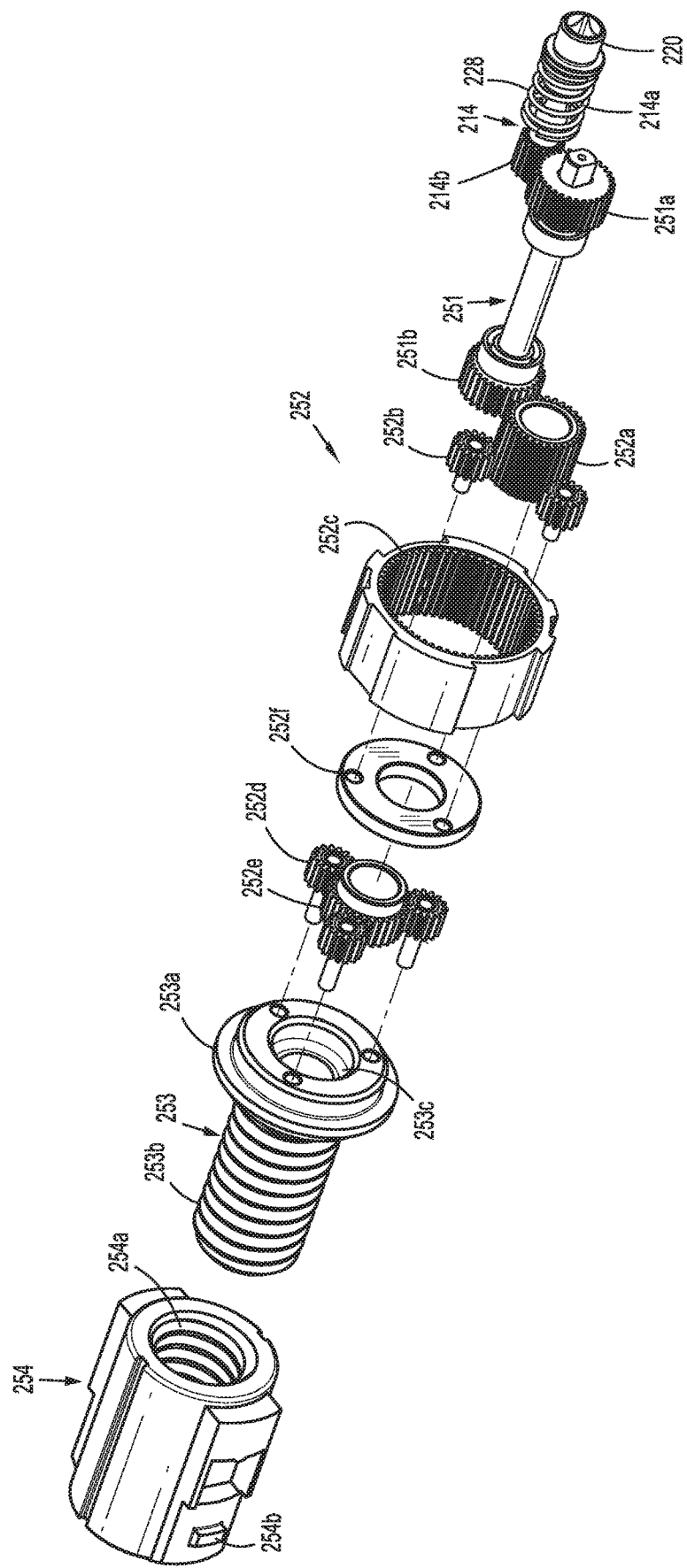
FIG. 37 is a perspective view, with parts separated, of a planetary gear set and staple driver, of the second force/rotation transmitting/converting assembly of FIG. 34.
Figure 38:
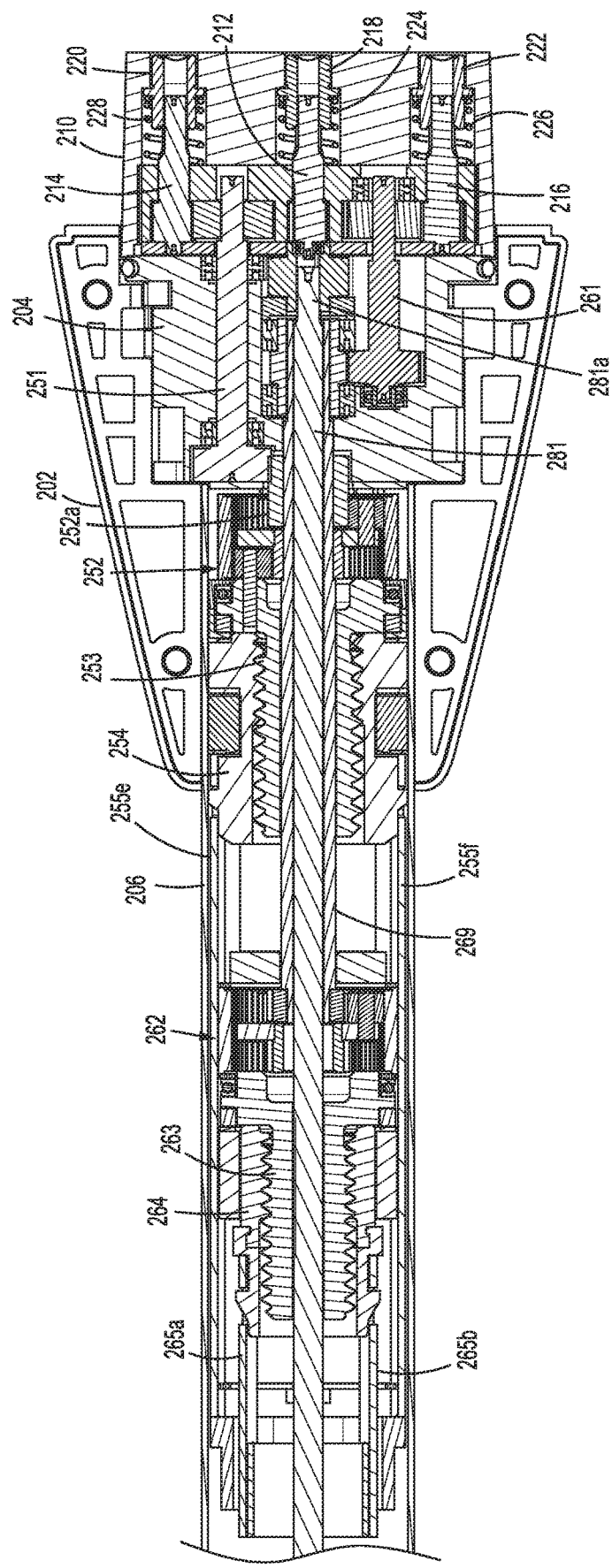
FIG. 38 is a cross-sectional view as taken through 38-38 of FIG. 24.
Figure 39:
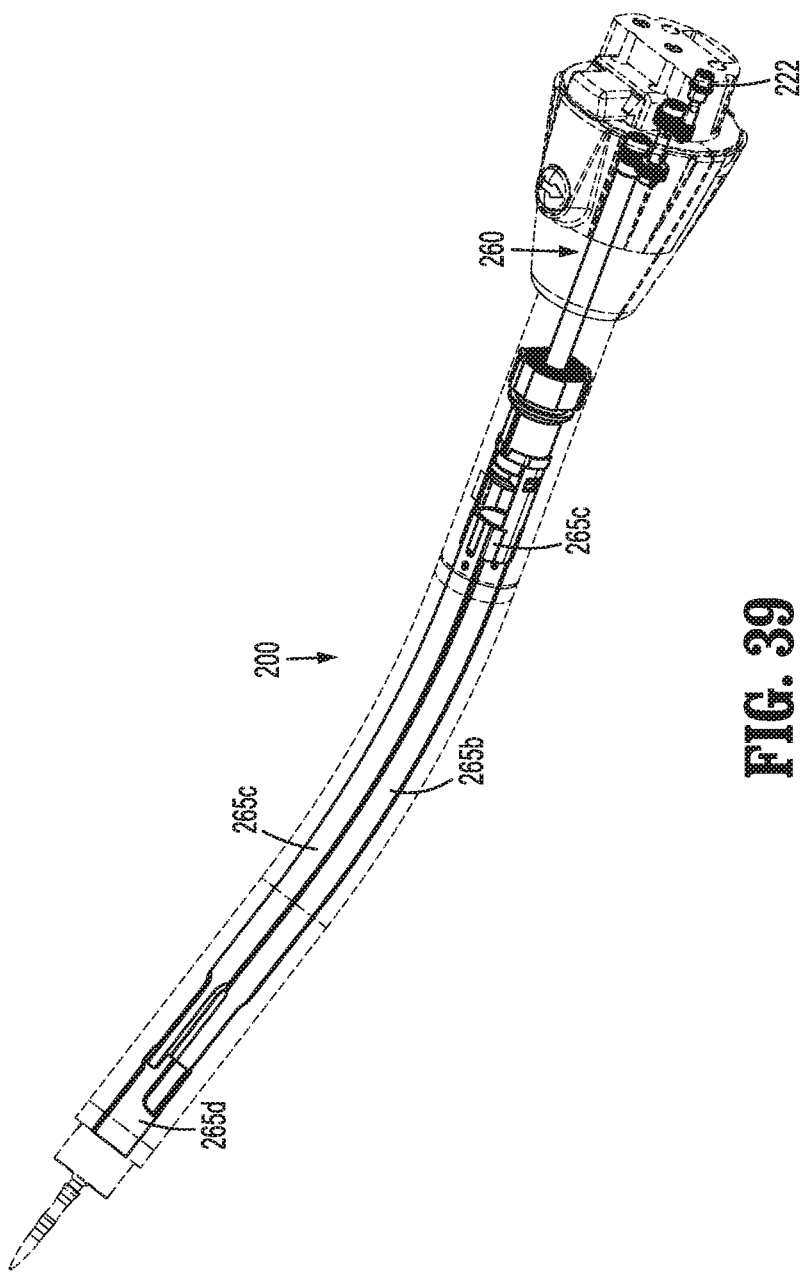
FIG. 39 is a perspective view of the adapter assembly, shown partially in phantom, illustrating a third force/rotation transmitting/converting assembly thereof.
Figure 42:
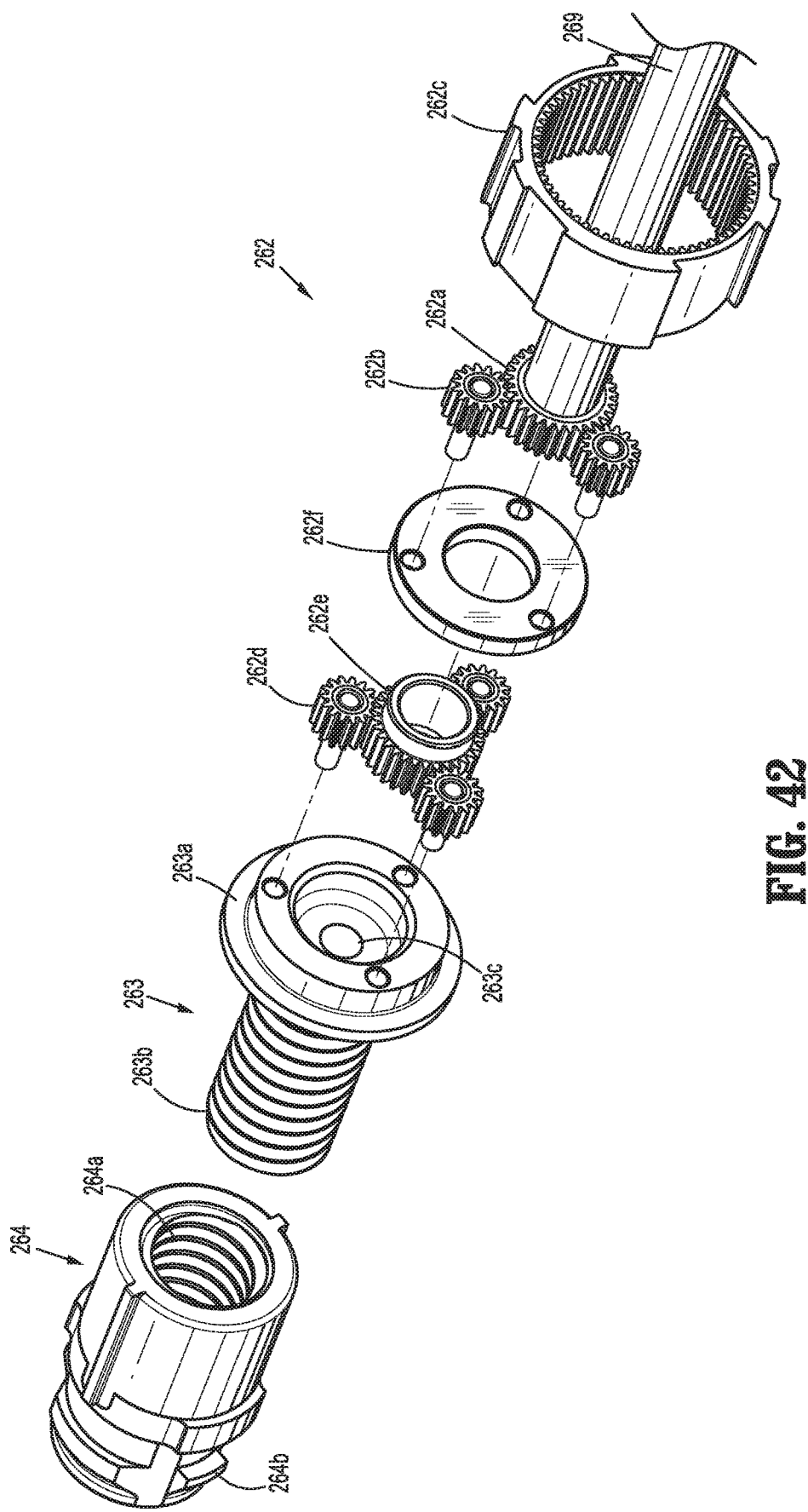
FIG. 42 is a perspective view, with parts separated, of a planetary gear set and knife driver, of the third force/rotation transmitting/converting assembly of FIG. 39.
Figure 43:
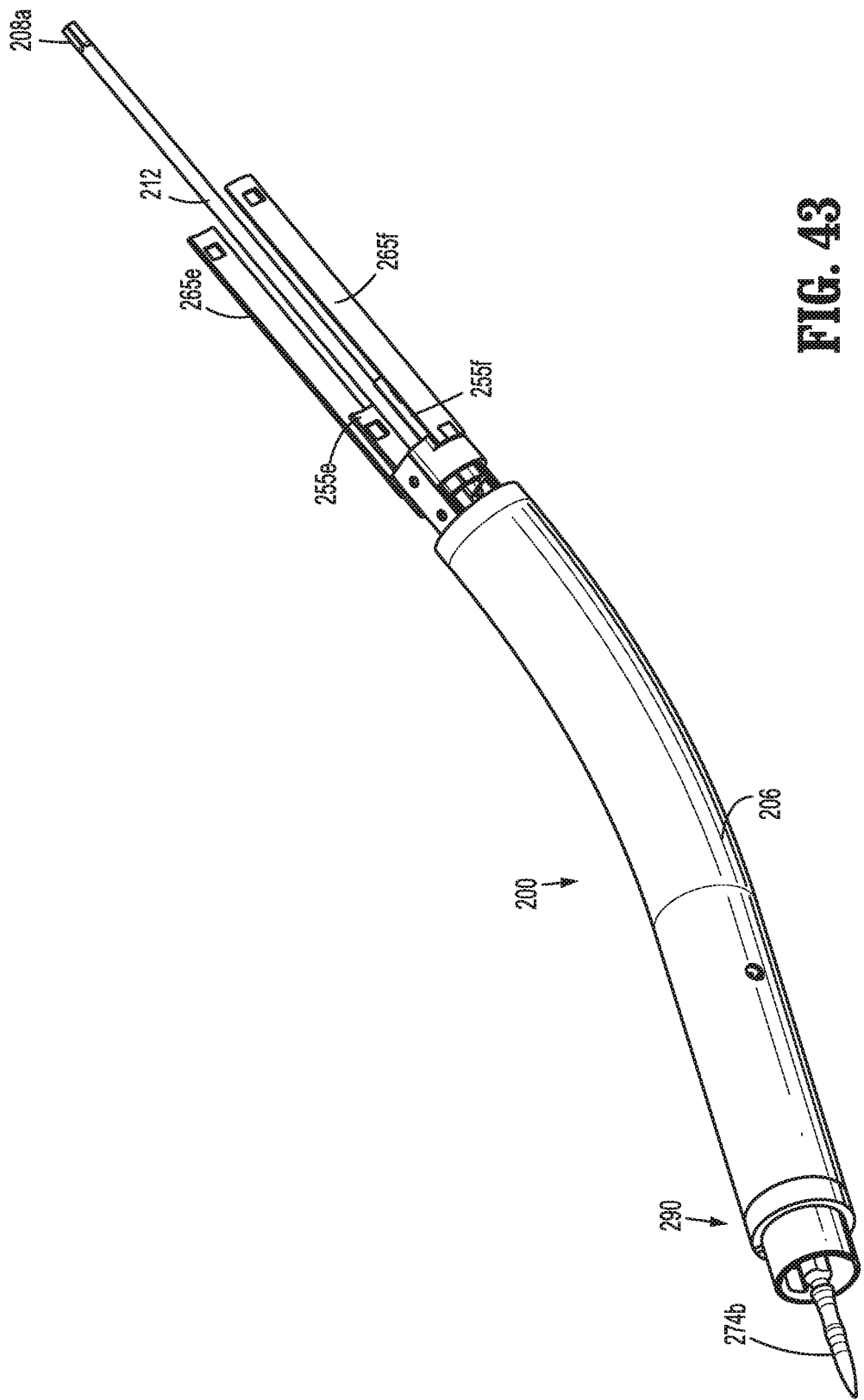
FIG. 43 is a perspective view of a distal portion of the adapter assembly.
Figure 44:
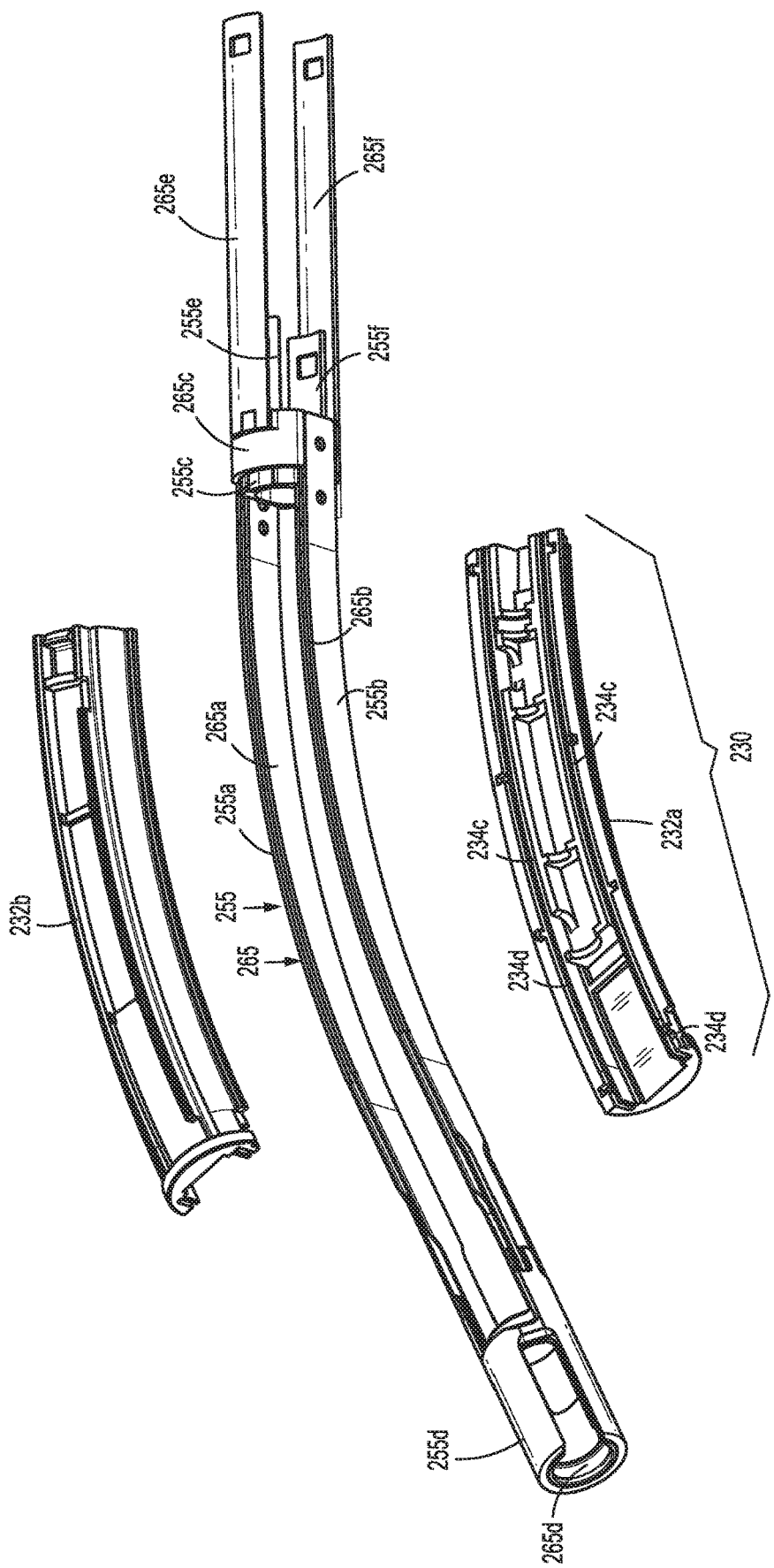
FIG. 44 is a further perspective view, with parts separated, of a distal portion of the adapter assembly.
Figure 45:
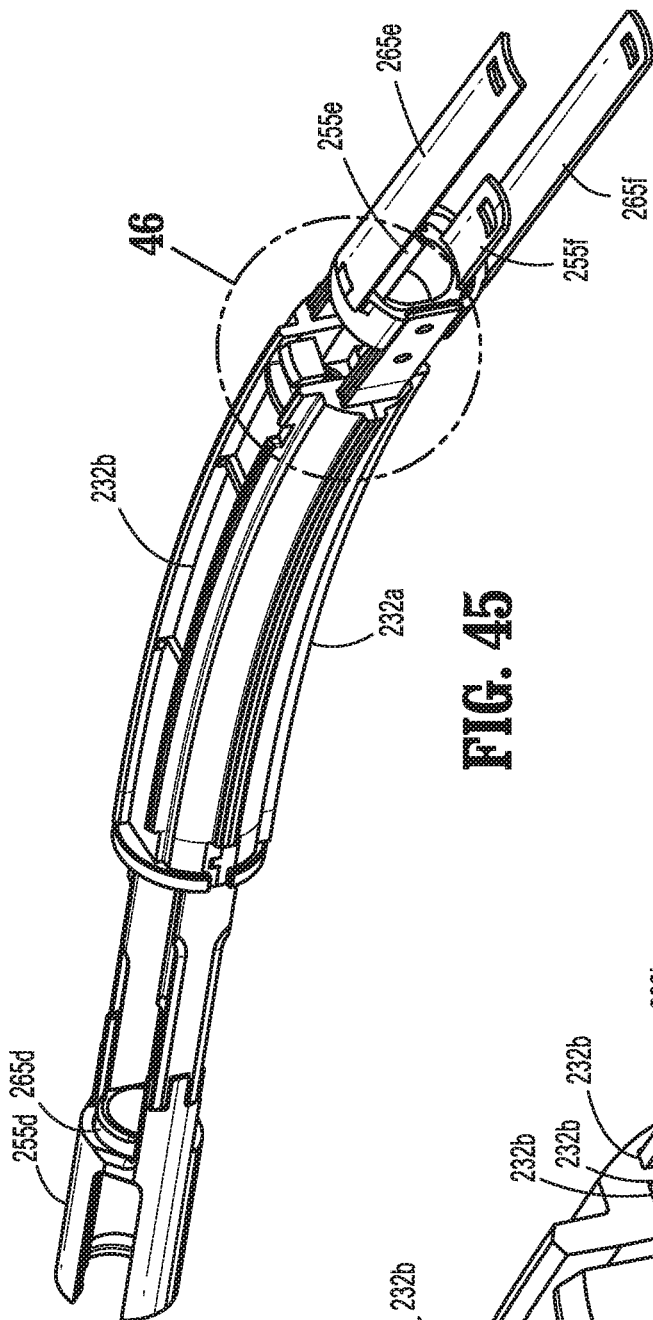
FIG. 45 is a rear, perspective view of the internal components of the distal end portion of the adapter assembly.
Figure 46:
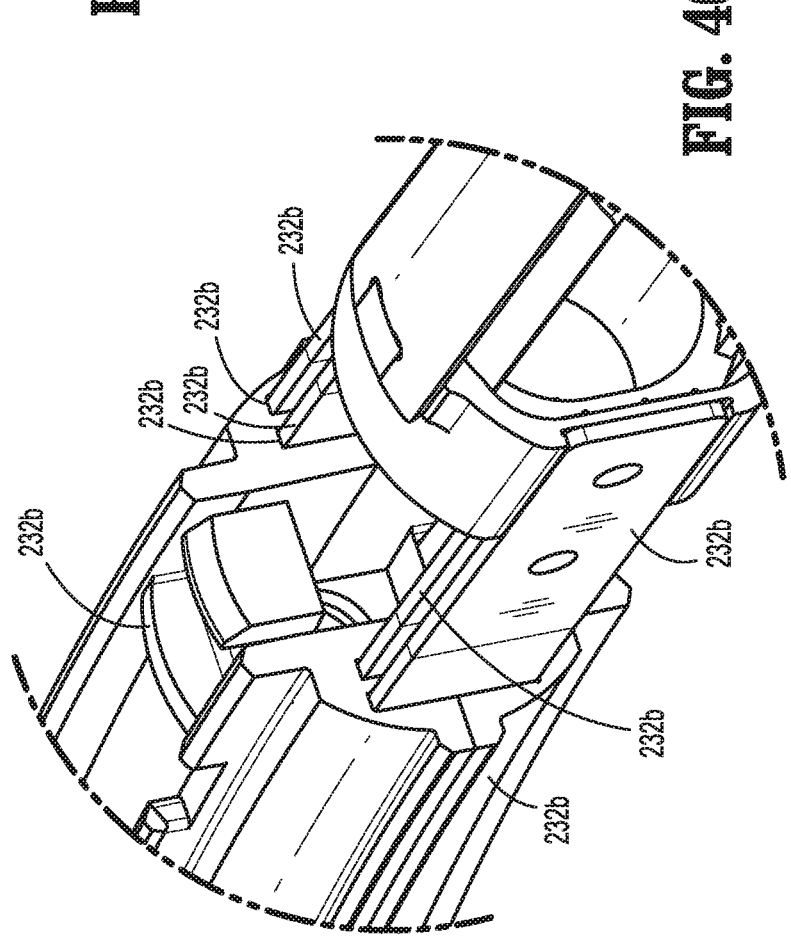
FIG. 46 is an enlarged view of the indicated area of detail of FIG. 45.
Figure 49:
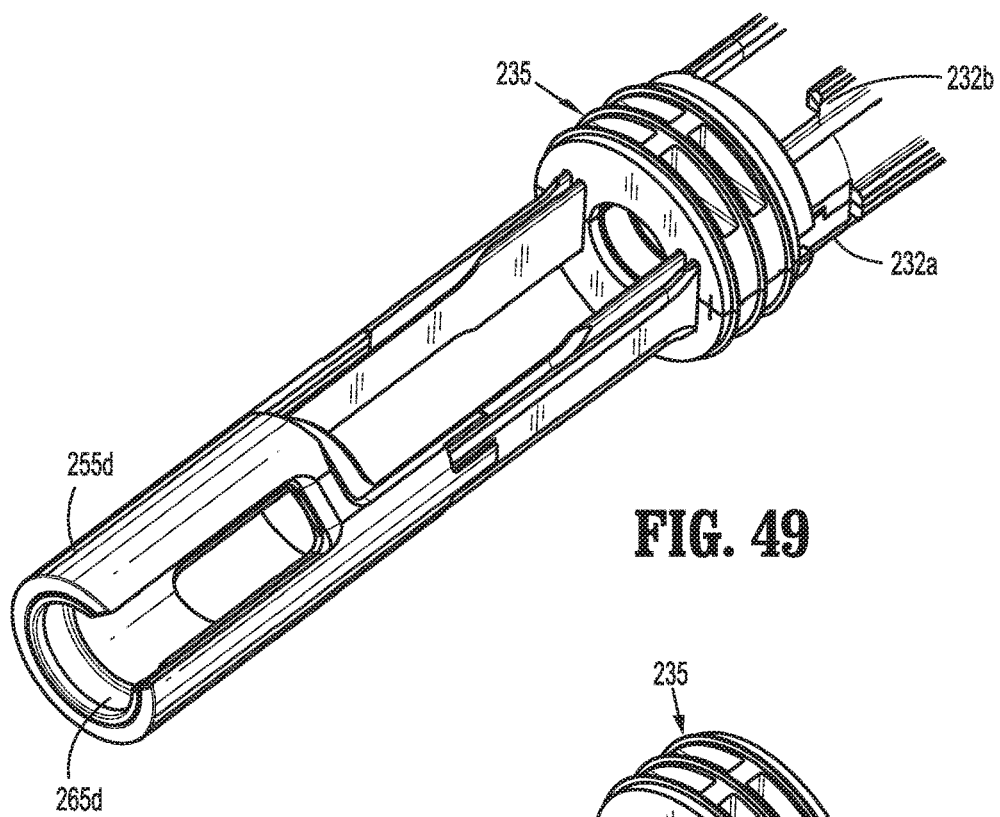
FIG. 49 is a front, perspective view of the internal components of a more distal end portion of the adapter assembly of FIGS. 45-48.
Figure 50:
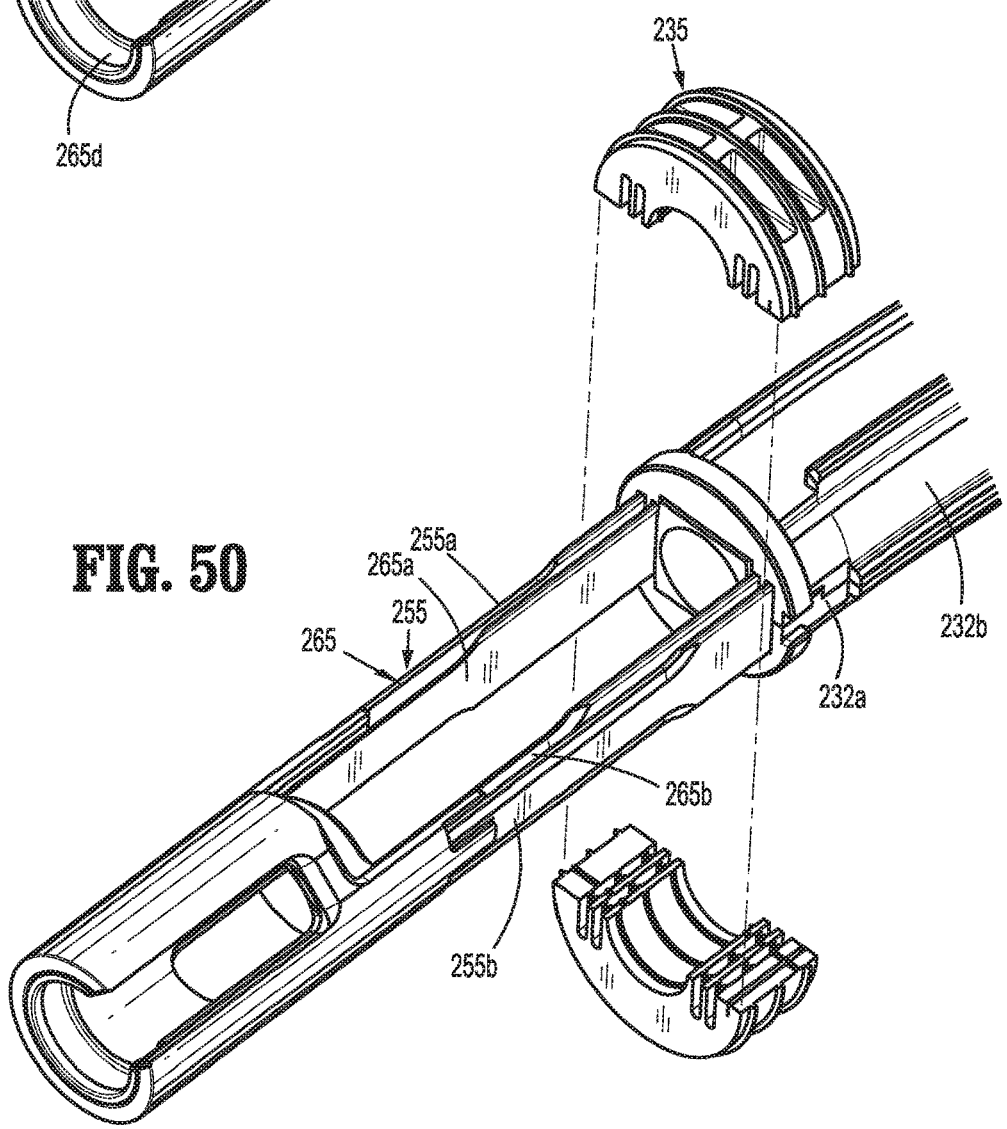
FIG. 50 is a front, perspective view, with parts separated, of the internal components of the more distal end portion of the adapter assembly of FIG. 49.
Figure 51:
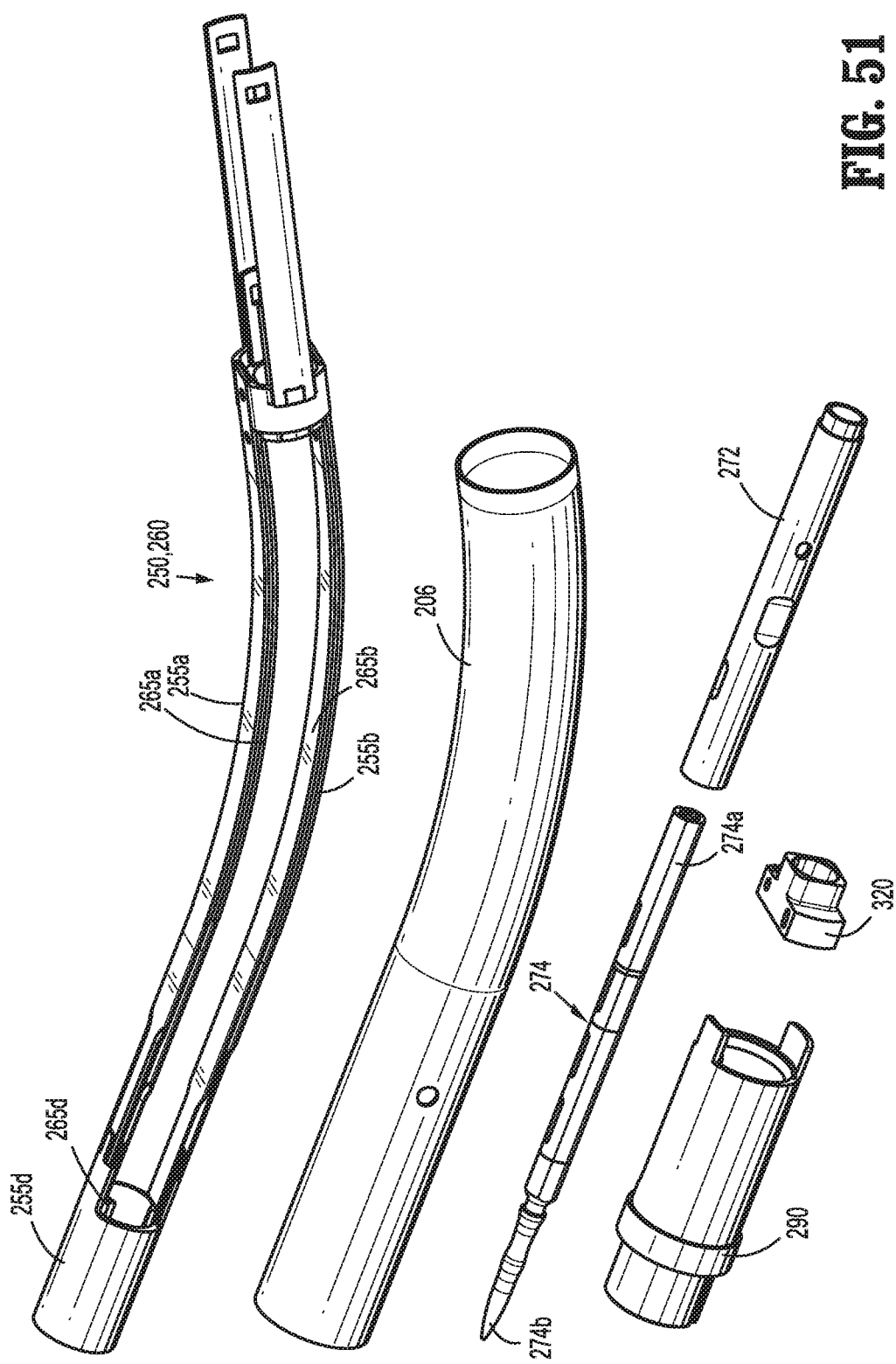
FIG. 51 is a perspective view, with parts separated, of the distal end portion of the adapter assembly of FIGS. 45-50.
Figure 52:
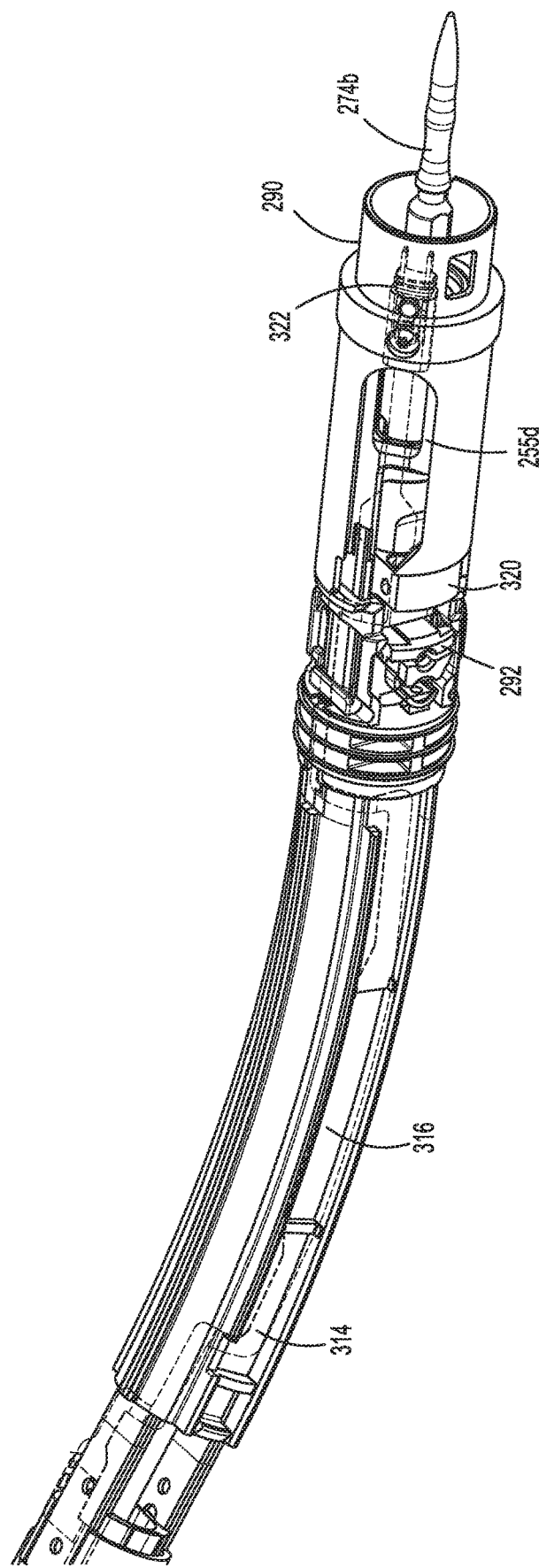
FIG. 52 is a perspective view of the distal end portion of the adapter assembly of FIGS. 45-51, illustrating an electrical assembly thereof.

In use, when adapter assembly 200 is mated to handle assembly 100, each of coupling shafts 64a, 64b, 64c of plate assembly 60 of shell housing 10 of handle assembly 100 couples with corresponding rotatable connector sleeves 218, 222, 220 of adapter assembly 200 (see FIG. 22). In this regard, the interface between corresponding first coupling shaft 64a and first connector sleeve 218, the interface between corresponding second coupling shaft 64b and second connector sleeve 222, and the interface between corresponding third coupling shaft 64c and third connector sleeve 220 are keyed such that rotation of each of coupling shafts 64a, 64b, 64c of handle assembly 100 causes a corresponding rotation of the corresponding connector sleeve 218, 222, 220 of adapter assembly 200.

The mating of coupling shafts 64a, 64b, 64c of handle assembly 100 with connector sleeves 218, 222, 220 of adapter assembly 200 allows rotational forces to be independently transmitted via each of the three respective connector interfaces. The coupling shafts 64a, 64b, 64c of handle assembly 100 are configured to be independently rotated by respective motors 152, 154, 156.

Since each of coupling shafts 64a, 64b, 64c of handle assembly 100 has a keyed and/or substantially non-rotatable interface with respective connector sleeves 218, 222, 220 of adapter assembly 200, when adapter assembly 200 is coupled to handle assembly 100, rotational force(s) are selectively transferred from motors 152, 154, 156 of handle assembly 100 to adapter assembly 200.

The selective rotation of coupling shaft(s) 64a, 64b, 64c of handle assembly 100 allows handle assembly 100 to selectively actuate different functions of reload 400. As will be discussed in greater detail below, selective and independent rotation of first coupling shaft 64a of handle assembly 100 corresponds to the selective and independent extending/retracting of trocar member 274 of adapter assembly 200 and/or the selective and independent opening/closing of reload 400 (when anvil assembly 510 is connected to trocar member 274). Also, the selective and independent rotation of third coupling shaft 64c of handle assembly 100 corresponds to the selective and independent firing of an annular array of staples of reload 400. Additionally, the selective and independent rotation of second coupling shaft 64b of handle assembly 100 corresponds to the selective and independent firing of an annular knife 444 of reload 400.

With reference to FIGS. 12-19, power-pack core assembly 106 further includes a switch assembly 170 supported within distal half-section 110a of inner handle housing 110, at a location beneath and in registration with toggle control interface 130, the right-side pair of control interfaces 132a, 132b, and the left-side pair of control interfaces 134a, 134b. Switch assembly 170 includes a first set of four push-button switches 172a-172d arranged around stem 30a of toggle control button 30 of outer shell housing 10 when power handle 101 is disposed within outer shell housing 10. Switch assembly 170 also includes a second pair of push-button switches 174a, 174b disposed beneath right-side pair of control interfaces 132a, 132b of distal half-section 110a of inner handle housing 110 when power handle 101 is disposed within outer shell housing 10. Switch assembly 170 further includes a third pair of push-button switches 176a, 176b disposed beneath left-side pair of control interfaces 134a, 134b of distal half-section 110a of inner handle housing 110 when power handle 101 is disposed within outer shell housing 10.

Power-pack core assembly 106 includes a single right-side push-button switch 178a disposed beneath right-side control aperture 136a of proximal half-section 110b of inner handle housing 110, and a single left-side push-button switch 178b disposed beneath left-side control aperture 136b of proximal half-section 110b of inner handle housing 110. Push-button switches 178a, 178b are supported on controller circuit board 142. Push-button switches 178a, 178b are disposed beneath right-side fire button 36a and left-side fire button 36b of proximal half-section 10b of shell housing 10 when power handle 101 is disposed within outer shell housing 10.

The actuation of push button switch 172c of switch assembly 170 of power handle 101, corresponding to a downward actuation of toggle control button 30, causes controller circuit board 142 to provide appropriate signals to motor 152 to activate, to retract a trocar member 274 of adapter assembly 200 and/or to close handle assembly 100 (e.g., approximate anvil assembly 510 relative to reload 400).

The actuation of push button switch 172a of switch assembly 170 of power handle 101, corresponding to an upward actuation of toggle control button 30, causes controller circuit board 142 to activate, to advance trocar member 274 of adapter assembly 200 and/or to open handle assembly 100 (e.g., separate anvil assembly 510 relative to reload 400).

The actuation of fire switch 178a or 178b of power handle 101, corresponding to an actuation of right-side or left-side control button 36a, 36b, causes controller circuit board 142 to provide appropriate signals to motors 154 and 156 to activate, as appropriate, to fire staples of reload 400, and then to advance (e.g., fire) and retract an annular knife 444 of reload 400.

The actuation of switches 174a, 174b (by right-hand thumb of user) or switches 176a, 176b (by left-hand thumb of user) of switch assembly 170, corresponding to respective actuation of right-side pair of control buttons 32a, 32b or left-side pair of control button 34a, 34b, causes controller circuit board 142 to provide appropriate signals to motor 152 to activate, to advance or retract trocar member 274 of adapter assembly 200.

Figure 14:
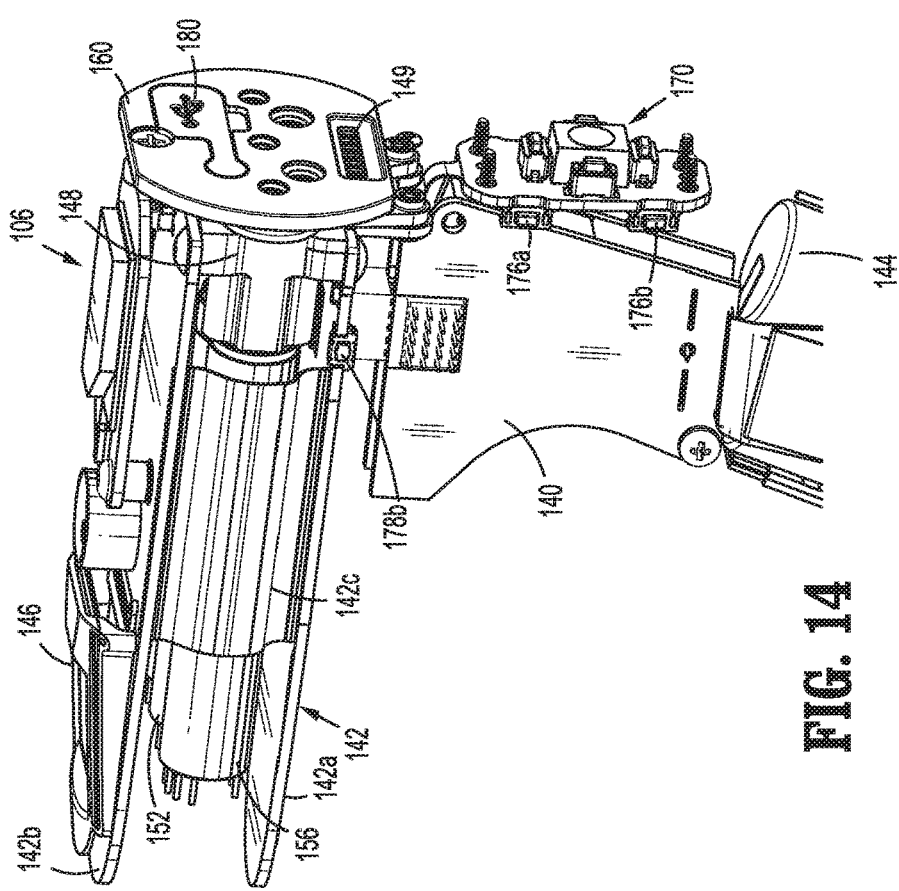
FIG. 14 is a perspective view of a power handle core assembly of the power handle.

With reference to FIGS. 12 and 14, power-pack core assembly 106 of handle assembly 100 includes a USB connector 180 supported on main controller circuit board 142b of controller circuit board 142. USB connector 180 is accessible through control plate 160 of power-pack core assembly 106. When power handle 101 is disposed within outer shell housing 10, USB connector 180 is covered by plate 62 of sterile barrier plate assembly 60 of shell housing 10.

As illustrated in FIG. 1 and FIGS. 20-65, handle assembly 100 is configured for selective connection with adapter assembly 200, and, in turn, adapter assembly 200 is configured for selective connection with reload 400.

Adapter assembly 200 is configured to convert a rotation of coupling shaft(s) 64a, 64b, 64c of handle assembly 100 into axial translation useful for advancing/retracting trocar member 274 of adapter assembly 200, for opening/closing handle assembly 100 (when anvil assembly 510 is connected to trocar member 274), for firing staples of reload 400, and for firing annular knife 444 of reload 400, as illustrated in FIG. 22, and as will be described in greater detail below.

Adapter assembly 200 includes a first drive transmitting/converting assembly for interconnecting first coupling shaft 64a of handle assembly 100 and an anvil assembly 510, wherein the first drive transmitting/converting assembly converts and transmits a rotation of first coupling shaft 64a of handle assembly 100 to an axial translation of trocar member 274 of trocar assembly 270, and in turn, the anvil assembly 510, which is connected to trocar member 274, to open/close handle assembly 100.

Adapter assembly 200 includes a second drive transmitting/converting assembly for interconnecting third coupling shaft 64c of handle assembly 100 and a second axially translatable drive member of reload 400, wherein the second drive transmitting/converting assembly converts and transmits a rotation of third coupling shaft 64c of handle assembly 100 to an axial translation of an outer flexible band assembly 255 of adapter assembly 200, and in turn, a driver adapter 432 of a staple driver assembly 430 of reload 400 to fire staples from a staple cartridge 420 of reload 400 and against anvil assembly 510.

Adapter assembly 200 includes a third drive transmitting/converting assembly for interconnecting second coupling shaft 64b of handle assembly 100 and a third axially translatable drive member of reload 400, wherein the third drive transmitting/converting assembly converts and transmits a rotation of second coupling shaft 64b of handle assembly 100 to an axial translation of an inner flexible band assembly 265 of adapter assembly 200, and in turn, a knife assembly 440 of reload 400 to fire annular knife 444 against anvil assembly 510.

Turning now to FIGS. 20-24, adapter assembly 200 includes an outer knob housing 202 and an outer tube 206 extending from a distal end of knob housing 202. Knob housing 202 and outer tube 206 are configured and dimensioned to house the components of adapter assembly 200. Knob housing 202 includes a drive coupling assembly 210 which is configured and adapted to connect to connecting portion 108 of handle housing 102 of handle assembly 100.

Adapter assembly 200 is configured to convert a rotation of either of first, second or third coupling shafts 64a, 64b, 64c, respectively, of handle assembly 100, into axial translations useful for operating trocar assembly 270 of adapter assembly 200, anvil assembly 510, and/or staple driver assembly 430 or knife assembly 440 of reload 400, as will be described in greater detail below.

As illustrated in FIGS. 57-61, adapter assembly 200 includes a proximal inner housing member 204 disposed within knob housing 202. Inner housing member 204 rotatably supports a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective coupling shafts 64a, 64c and 64b of handle assembly 100, as described in greater detail below.

As described briefly above, drive coupling assembly 210 of adapter assembly 200 is also configured to rotatably support first, second and third connector sleeves 218, 222 and 220, respectively, arranged in a common plane or line with one another. Each of connector sleeves 218, 220, 222 is configured to mate with respective first, second and third coupling shafts 64a, 64c and 64b of handle assembly 100, as described above. Each of connector sleeves 218, 220, 222 is further configured to mate with a proximal end of respective first, second and third proximal drive shafts 212, 214, 216 of adapter assembly 200.

Drive coupling assembly 210 of adapter assembly 200 also includes, as illustrated in FIGS. 26, 34, 35 and 40, a first, a second and a third biasing member 224, 226 and 228 disposed distally of respective first, second and third connector sleeves 218, 222, 220. Each of biasing members 224, 226 and 228 is disposed about respective first, second and third rotatable proximal drive shaft 212, 216 and 214. Biasing members 224, 226 and 228 act on respective connector sleeves 218, 222 and 220 to help maintain connector sleeves 218, 222 and 220 engaged with the distal end of respective coupling shafts 64a, 64b and 64c of handle assembly 100 when adapter assembly 200 is connected to handle assembly 100.

In particular, first, second and third biasing members 224, 226 and 228 function to bias respective connector sleeves 218, 222 and 220 in a proximal direction. In this manner, during connection of handle assembly 100 to adapter assembly 200, if first, second and or third connector sleeves 218, 222 and/or 220 is/are misaligned with coupling shafts 64a, 64b and 64c of handle assembly 100, first, second and/or third biasing member(s) 224, 226 and/or 228 are compressed. Thus, when handle assembly 100 is operated, coupling shafts 64a, 64c and 64b of handle assembly 100 will rotate and first, second and/or third biasing member(s) 224, 228 and/or 226 will cause respective first, second and/or third connector sleeve(s) 218, 220 and/or 222 to slide back proximally, effectively connecting coupling shafts 64a, 64c and 64b of handle assembly 100 to first, second and/or third proximal drive shaft(s) 212, 214 and 216 of drive coupling assembly 210.

As briefly mentioned above, adapter assembly 200 includes a first, a second and a third force/rotation transmitting/converting assembly 240, 250, 260, respectively, disposed within inner housing member 204 and outer tube 206. Each force/rotation transmitting/converting assembly 240, 250, 260 is configured and adapted to transmit or convert a rotation of a first, second and third coupling shafts 64a, 64c and 64b of handle assembly 100 into axial translations to effectuate operation of trocar assembly 270 of adapter assembly 200, and of staple driver assembly 430 or knife assembly 440 of reload 400.

As shown in FIGS. 25-28, first force/rotation transmitting/converting assembly 240 includes first rotatable proximal drive shaft 212, as described above, a second rotatable proximal drive shaft 281, a rotatable distal drive shaft 282, and a coupling member 286, each of which are supported within inner housing member 204, drive coupling assembly 210 and/or an outer tube 206 of adapter assembly 200. First force/rotation transmitting/converting assembly 240 functions to extend/retract trocar member 274 of trocar assembly 270 of adapter assembly 200, and to open/close handle assembly 100 (when anvil assembly 510 is connected to trocar member 274).

First rotatable proximal drive shaft 212 includes a non-circular or shaped proximal end portion configured for connection with first connector 218 which is connected to respective first coupling shaft 64a of handle assembly 100. First rotatable proximal drive shaft 212 includes a non-circular recess formed therein which is configured to key with a respective complimentarily shaped proximal end portion 281a of second rotatable proximal drive shaft 281. Second rotatable proximal drive shaft 281 includes a distal end portion 281b defining an oversized recess therein which is configured to receive a proximal end portion 282a of first rotatable distal drive shaft 282. Proximal end portion 282a of first rotatable distal drive shaft 282 is pivotally secured within the recess in distal end 281b of second rotatable proximal drive shaft 281 by a pin 283a received through the oversized recess in distal end portion 281b of second rotatable proximal drive shaft 281.

First rotatable distal drive shaft 282 includes a proximal end portion 282a, and a distal end portion 282b which is pivotally secured within a recess of coupling member 286. Distal end portion 282b of first rotatable distal drive shaft 282 is pivotally secured within a recess in a proximal end of coupling member 286 by a pin 283b received through the recess in the proximal end portion of coupling member 286. Proximal and distal end portions 282a, 282b of first rotatable distal drive shaft 282 define oversized openings for receiving pins 283a, 283b, respectively.

Coupling member 286 includes a proximal end 286a defining a recess 286c for receiving distal end portion 282b of first rotatable distal drive shaft 282, a distal end 286b defining a recess 286d for operably receiving a non-circular stem 276c on proximal end 276a of a drive screw 276 of trocar assembly 270.

Figure 73:
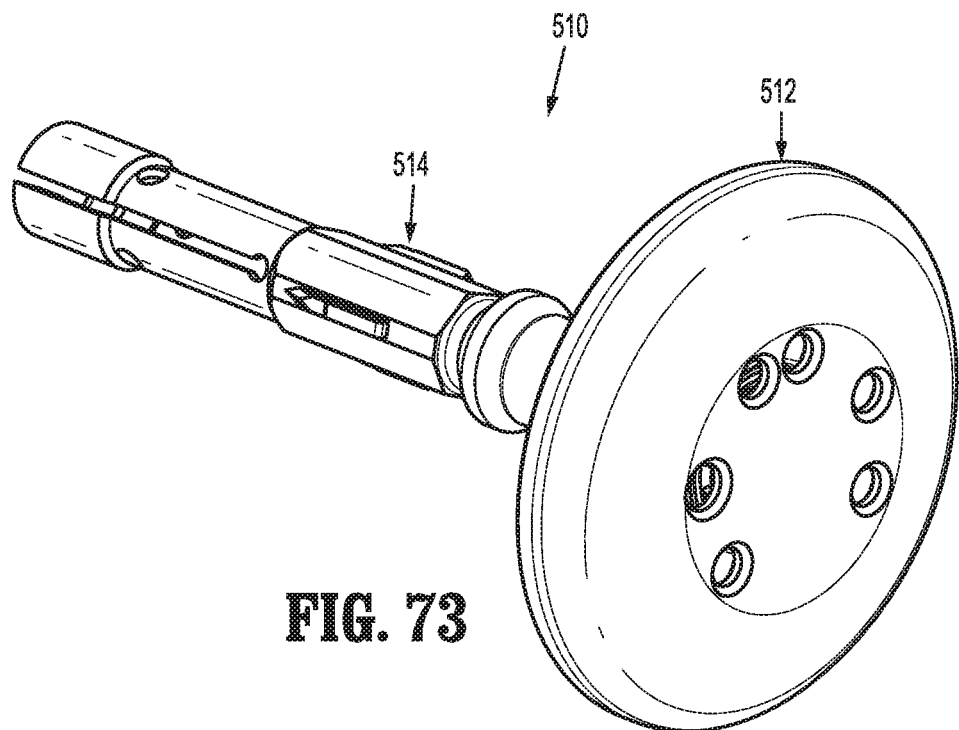
FIG. 73 is a front, perspective view of an anvil assembly of the present disclosure.
Figure 74:
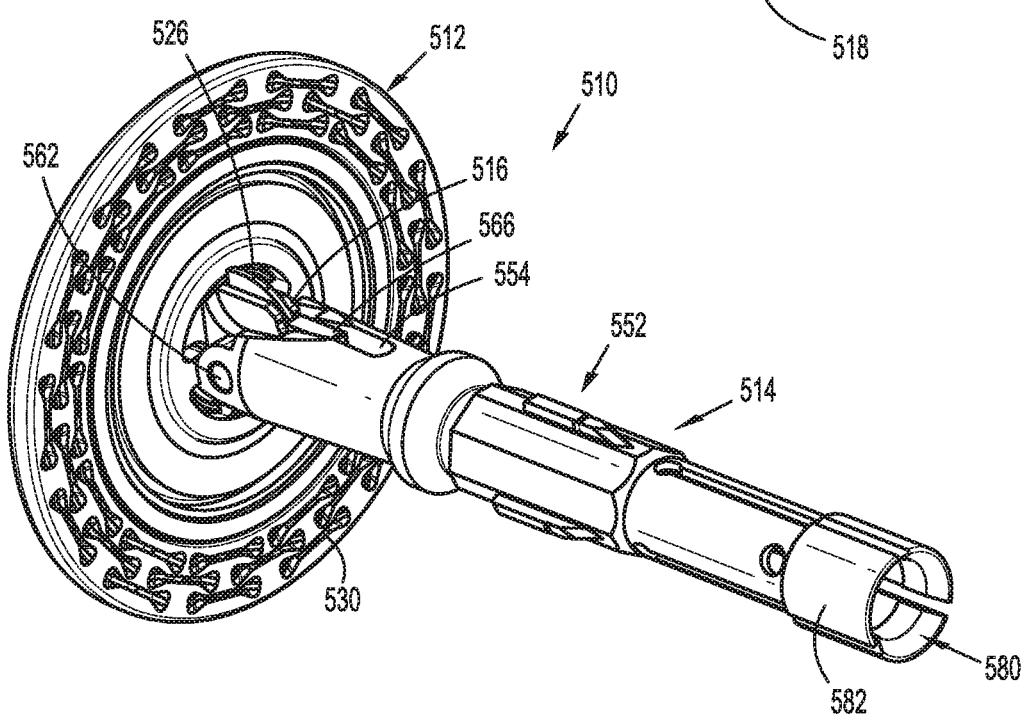
FIG. 74 is a rear, perspective view of the anvil assembly of FIG. 73.
Figure 75:
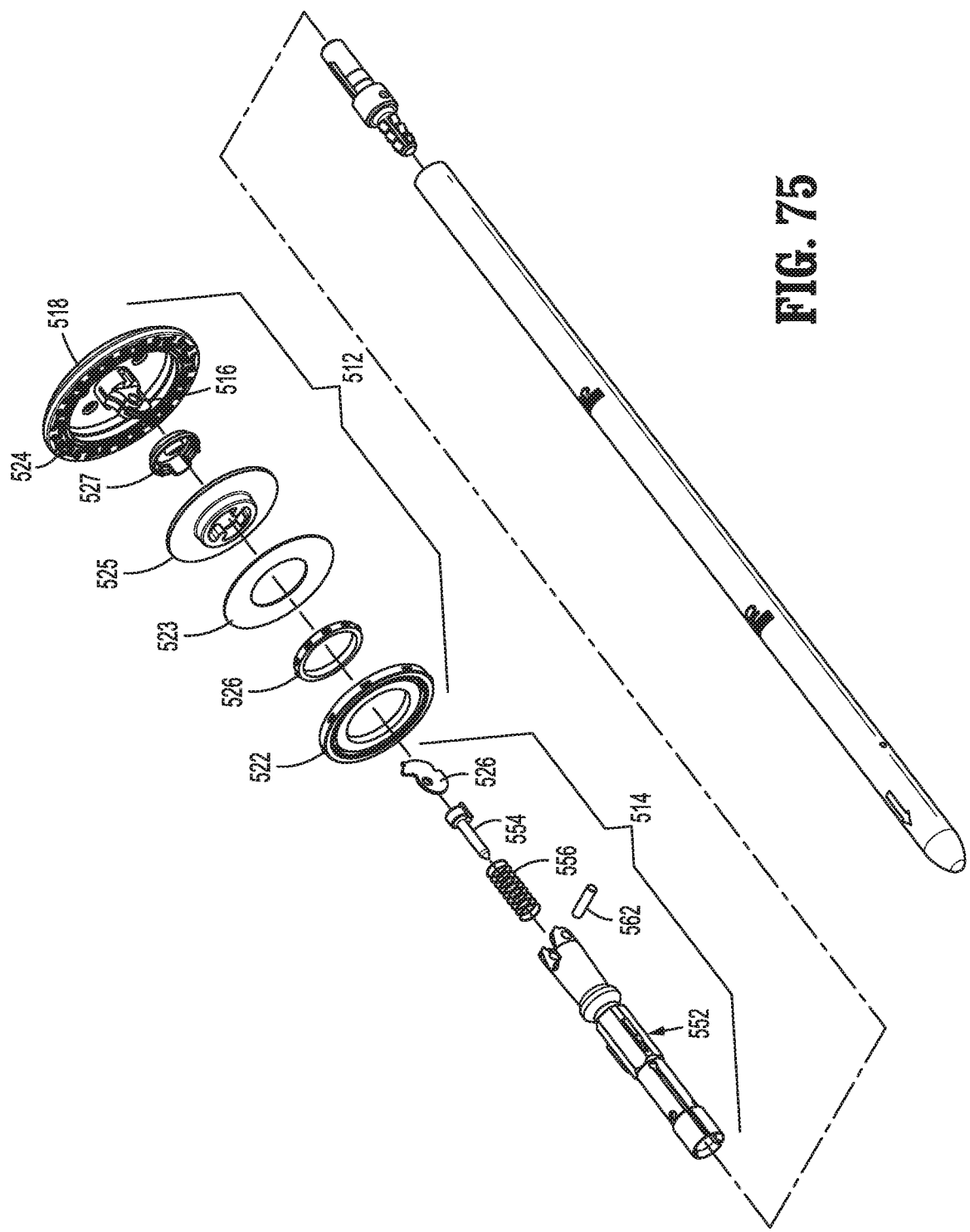
FIG. 75 is a perspective view, with parts separated, of the anvil assembly of FIGS. 73 and 74.
Figure 76:
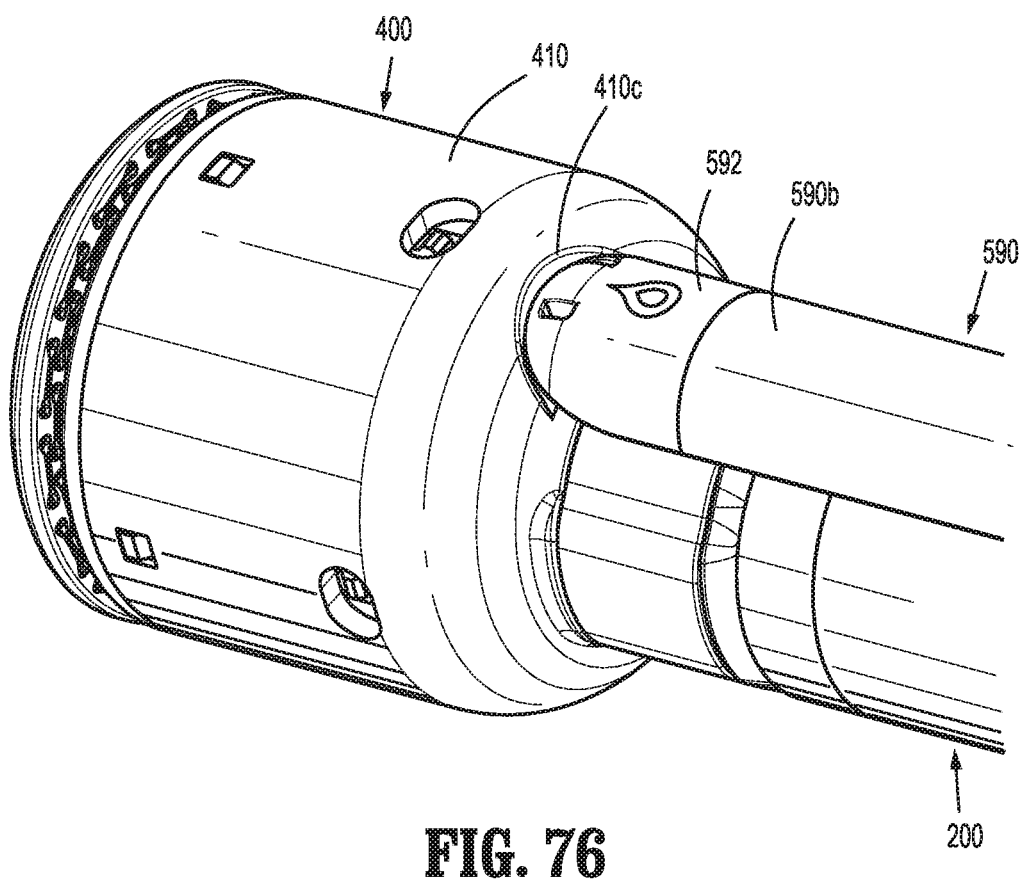
FIG. 76 is a rear, perspective view of the reload and more distal end portion of the adapter assembly, illustrating a connection of an irrigation tube thereto.
Figure 77:
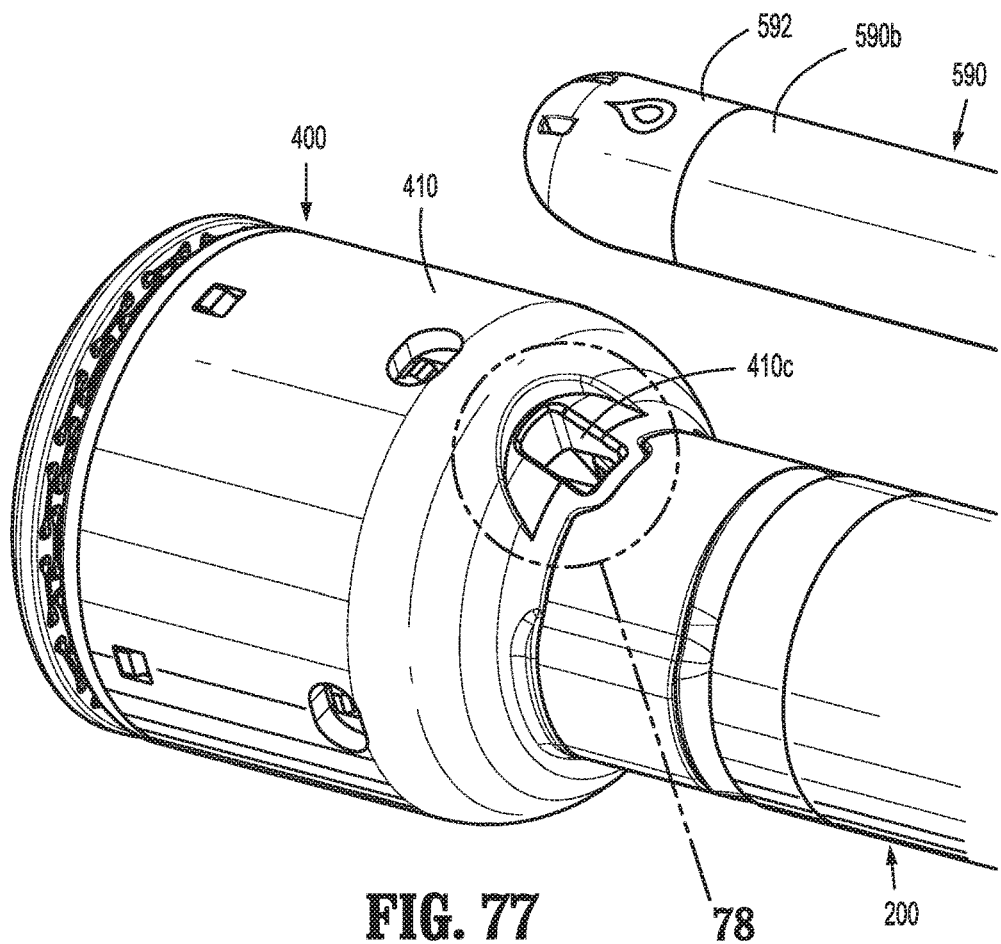
FIG. 77 is a rear, perspective view of the reload and more distal end portion of the adapter assembly, illustrating the irrigation tube separated therefrom.
Figure 78:
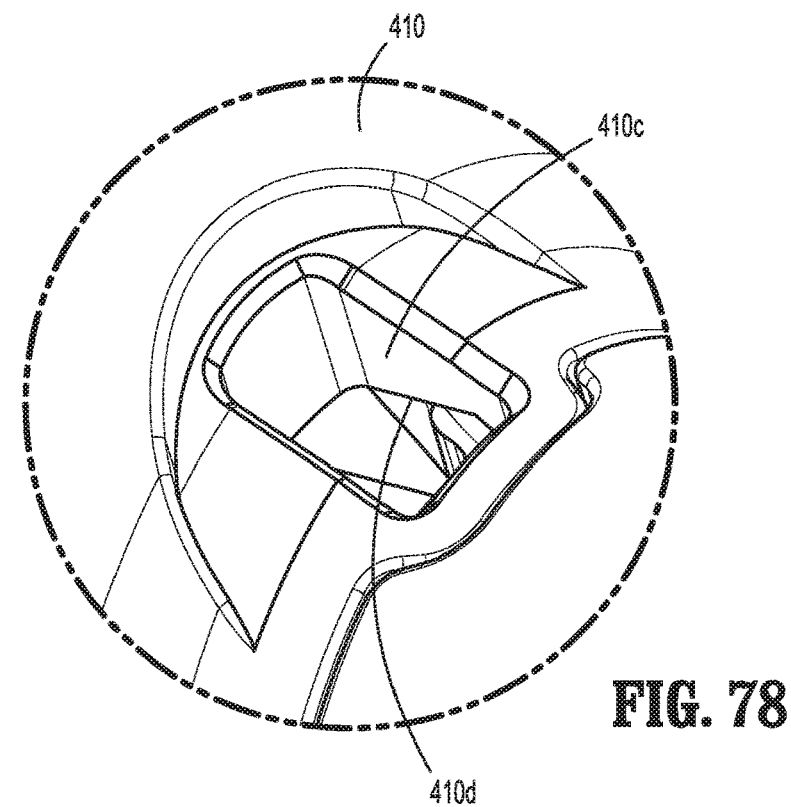
FIG. 78 is an enlarged view of the indicated area of detail of FIG. 77.

First force/rotation transmitting/converting assembly 240 further includes a trocar assembly 270 removably supported in a distal end of outer tube 206. Trocar assembly 270 includes an outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274a having an inner threaded portion which engages a threaded distal portion 276b of drive screw 276. Trocar member 274 further includes at least one longitudinally extending flat formed in an outer surface thereof which mates with a corresponding flat formed in tubular housing 272 thereby inhibiting rotation of trocar member 274 relative to tubular housing 272 as drive screw 276 is rotated. A distal end 274b of trocar member 274 is configured to selectively engage anvil assembly 510 (FIGS. 73-75).

Tubular housing 272 of trocar assembly 270 is axially and rotationally fixed within outer tube 206 of adapter assembly 200. Tubular housing 272 defines a pair of radially opposed, and radially oriented openings 272a which are configured and dimensioned to cooperate with a pair of lock pins 275c of a trocar assembly release mechanism 275. With reference to FIGS. 29-33, adapter assembly 200 includes a support block 292 fixedly disposed within outer tube 206. Support block 292 is disposed proximal of a connector sleeve 290 and proximal of a strain sensor 320a of a strain gauge assembly 320, as described in greater detail below. The pair of lock pins 275c extend through support block 292 and into tubular housing 272 of trocar assembly 270 to connect trocar assembly 270 to adapter assembly 200.

As illustrated in FIGS. 29-33, trocar assembly release mechanism 275 includes a release button 275a pivotally supported on support block 292 and in outer tube 206. Release button 275a is spring biased to a locked/extended condition. Trocar assembly release mechanism 275 further includes a spring clip 275b connected to release button 275a, wherein spring clip 275b includes a pair of legs that extend through support block 292 and transversely across trocar assembly 270. Each of the pair of legs of spring clip 275b extends through a respective lock pin 275c which is slidably disposed within a respective radial opening 272a of tubular housing 272 and radial opening 292a of support block 292 (see FIG. 31).

In use, when release button 275a is depressed (e.g., in a radially inward direction, FIG. 33), release button 275a moves spring clip 275b transversely relative to trocar assembly 270. As spring clip 275b is moved transversely relative to trocar assembly 270, the pair of legs of spring clip 275b translate through the pair of lock pins 275c such that a goose-neck in each leg acts to cam and urge the pair of lock pins 275c radially outward. Each of the pair of lock pins 275c is urged radially outward by a distance sufficient that each of the pair of lock pins 275c clears respective opening 272a of tubular housing 272. With the pair of lock pins 275c free and clear of tubular housing 272, trocar assembly 270 may be axially withdrawn from within the distal end of outer tube 206 of adapter assembly 200.

In operation, as first rotatable proximal drive shaft 212 is rotated, due to a rotation of first connector sleeve 218, as a result of the rotation of first coupling shaft 64a of handle assembly 100, second rotatable distal drive shaft 281 is caused to be rotated. Rotation of second rotatable distal drive shaft 281 results in contemporaneous rotation of first rotatable distal drive shaft 282. Rotation of first rotatable distal drive shaft 282 causes contemporaneous rotation of coupling member 286, which, in turn, causes contemporaneous rotation of drive screw 276 of trocar assembly 270. As drive screw 276 is rotated within and relative to trocar member 274, engagement of the inner threaded portion of trocar member 274 with threaded distal portion 276b of drive screw 276 causes axial translation of trocar member 274 within tubular housing 272 of trocar assembly 270. Specifically, rotation of drive screw 276 in a first direction causes axial translation of trocar member 274 in a first direction (e.g., extension of trocar assembly 270 of handle assembly 100), and rotation of drive screw 276 in a second direction causes axial translation of trocar member 274 in a second direction (e.g., retraction of trocar assembly 270 of handle assembly 100).

When anvil assembly 510 is connected to trocar member 274, as will be described in detail below, the axial translation of trocar member 274 in the first direction results in an opening of reload 400, and the axial translation of trocar member 274 in the second direction results in a closing of reload 400.

Forces during an actuation or trocar member 274 or a closing of reload 400 may be measured by strain sensor 320a of strain gauge assembly 320 in order to:
- determine a presence and proper engagement of trocar assembly 270 in adapter assembly 200;
- determine a presence of anvil assembly 510 during calibration;
- determine misalignment of the splines of trocar member 274 with longitudinally extending ridges 416 of reload 400;
- determine a re-clamping of a previously tiled anvil assembly 510;
- determine a presence of obstructions during clamping or closing of reload 400;
- determine a presence and connection of anvil assembly 510 with trocar member 274;
- monitor and control a compression of tissue disposed within reload 400;
- monitor a relaxation of tissue, over time, clamped within reload 400;
- monitor and control a firing of staples from reload 400;
- detect a presence of staples in reload 400;
- monitors forces during a firing and formation of the staples as the staples are being ejected from reload 400;
- optimize formation of the staples (e.g., staple crimp height) as the staples are being ejected from reload 400 for different indications of tissue;
- monitor and control a firing of annular knife 444 of reload 400;
- monitor and control a completion of the firing and cutting procedure; and
- monitor a maximum firing force and control the firing and cutting procedure to protect against exceeding a predetermined maximum firing force.

In operation, strain sensor 320a of strain gauge assembly 320 of adapter assembly 200 measures and monitors the retraction of trocar member 274, as described above. During the closing of reload 400, if and when head assembly 512 of anvil assembly 510 contacts tissue, an obstruction, staple cartridge 420 or the like, a reaction force is exerted on head assembly 512 which is in a generally distal direction. This distally directed reaction force is communicated from head assembly 512 to center rod assembly 514 of anvil assembly 510, which in turn is communicated to trocar assembly 270. Trocar assembly 270 then communicates the distally directed reaction force to the pair of pins 275c of trocar assembly release mechanism 275, which in turn then communicate the reaction force to support block 292. Support block 292 then communicates the distally directed reaction force to strain sensor 320a of strain gauge assembly 320.

Strain sensor 320a of strain gauge assembly 320 is a device configured to measure strain (a dimensionless quantity) on an object that it is adhered to (e.g., support block 292), such that, as the object deforms, a metallic foil of the strain sensor 320a is also deformed, causing an electrical resistance thereof to change, which change in resistance is then used to calculate loads experienced by trocar assembly 270.

Strain sensor 320a of strain gauge assembly 320 then communicates signals to main controller circuit board 142b of power-pack core assembly 106 of handle assembly 100. Graphics are then displayed on display screen 146 of power-pack core assembly 106 of handle assembly 100 to provide the user with real-time information related to the status of the firing of handle assembly 100.

With reference to FIGS. 34-38, second force/rotation transmitting/converting assembly 250 of adapter assembly 200 includes second proximal drive shaft 214, as described above, a first coupling shaft 251, a planetary gear set 252, a staple lead screw 253, and a staple driver 254, each of which are supported within inner housing member 204, drive coupling assembly 210 and/or an outer tube 206 of adapter assembly 200. Second force/rotation transmitting/converting assembly 250 functions to fire staples of reload 400 for formation against anvil assembly 510.

Second rotatable proximal drive shaft 214 includes a non-circular or shaped proximal end portion configured for connection with second connector or coupler 220 which is connected to respective second coupling shaft 64c of handle assembly 100. Second rotatable proximal drive shaft 214 further includes a distal end portion 214b having a spur gear non-rotatably connected thereto.

First coupling shaft 251 of second force/rotation transmitting/converting assembly 250 includes a proximal end portion 251a having a spur gear non-rotatably connected thereto, and a distal end portion 251b having a spur gear non-rotatably connected thereto. The spur gear at the proximal end portion 251a of first coupling shaft 251 is in meshing engagement with the spur gear at the distal end portion 214b of the second rotatable proximal drive shaft 214.

Planetary gear set 252 of second force/rotation transmitting/converting assembly 250 includes a first cannulated sun gear 252a, a first set of planet gears 252b, a ring gear 252c, a second set of planet gears 252d, and a second cannulated sun gear 252e. First sun gear 252a is in meshing engagement with the spur gear at the distal end portion 251b of first coupling shaft 251. The first set of planet gears 252b are interposed between, and are in meshing engagement with, first sun gear 252a and ring gear 252c. The second set of planet gears 252d are interposed between, and are in meshing engagement with, second sun gear 252e and ring gear 252c. Ring gear 252c is non-rotatably supported in outer tube 206 of adapter assembly 200.

Planetary gear set 252 of second force/rotation transmitting/converting assembly 250 includes a washer 252f disposed within ring gear 252c, and between the first set of planet gears 252b and the second set of planet gears 252d. The first set of planet gears 252b are rotatably supported radially about washer 252f, and second sun gear 252e is non-rotatably connected to a center of washer 252f.

Staple lead screw 253 of second force/rotation transmitting/converting assembly 250 includes a proximal flange 253a and a distal threaded portion 253b extending from flange 253a. Staple lead screw 253 defines a lumen 253c therethrough. The second set of planet gears 252d are rotatably supported radially about proximal flange 253a of staple lead screw 253.

Staple driver 254 of second force/rotation transmitting/converting assembly 250 includes a central threaded lumen 254a extending therethrough and is configured and dimensioned to support distal threaded portion 253b of staple lead screw 253 therein. Staple driver 254 includes a pair of tabs 254b projecting radially from an outer surface thereof, and which are configured for connection to outer flexible band assembly 255 of adapter assembly 200, as will be described in greater detail below.

With reference now to FIGS. 34, 35 and 43-51, second force/rotation transmitting/converting assembly 250 of adapter assembly 200 includes an outer flexible band assembly 255 secured to staple driver 254. Outer flexible band assembly 255 includes first and second flexible bands 255a, 255b laterally spaced and connected at proximal ends thereof to a support ring 255c and at distal ends thereof to a proximal end of a support base 255d. Each of first and second flexible bands 255a, 255b is attached to support ring 255c and support base 255d.

Outer flexible band assembly 255 further includes first and second connection extensions 255e, 255f extending proximally from support ring 255c. First and second connection extensions 255e, 255f are configured to operably connect outer flexible band assembly 255 to staple driver 254 of second force/rotation transmitting/converting assembly 250. In particular, each of first and second connection extensions 255e, 255f defines an opening configured to receive a respective tab 254b of staple driver 254. Receipt of tabs 254b of staple driver 254 within the openings of respective first and second connection extensions 255e, 255f secures outer flexible band assembly 255 to staple driver 254 of second force/rotation transmitting/converting assembly 250.

Support base 255d extends distally from flexible bands 255a, 255b and is configured to selectively contact driver adapter 432 of staple driver assembly 430 of reload 400. Flexible bands 255a, 255b are fabricated from stainless steel 301 half hard and are configured to transmit axial pushing forces along a curved path.

Second force/rotation transmitting/converting assembly 250 and outer flexible band assembly 255 are configured to receive first rotatable proximal drive shaft 212, first rotatable distal drive shaft 282, and trocar assembly 270 of first force/rotation transmitting/converting assembly 240 therethrough. Specifically, first rotatable proximal drive shaft 212 is non-rotatably connected to second rotatable proximal drive shaft 281 which in turn is rotatably disposed within and through first cannulated sun gear 252a of first planetary gear set 252, second cannulated sun gear 252e of planetary gear set 252, staple lead screw 253, and staple driver 254.

Second force/rotation transmitting/converting assembly 250 and outer flexible band assembly 255 are also configured to receive third force/rotation transmitting/converting assembly 260 therethrough. Specifically, as described below, inner flexible band assembly 265 is slidably disposed within and through outer flexible band assembly 255.

First rotatable distal drive shaft 282 of first force/rotation transmitting/converting assembly 240 is rotatably disposed within support base 255d of outer flexible band assembly 255, while trocar member 274 of trocar assembly 270 of first force/rotation transmitting/converting assembly 240 is slidably disposed within support base 255d of outer flexible band assembly 255.

Outer flexible band assembly 255 is also configured to receive inner flexible band assembly 265 therethrough.

Figure 67:
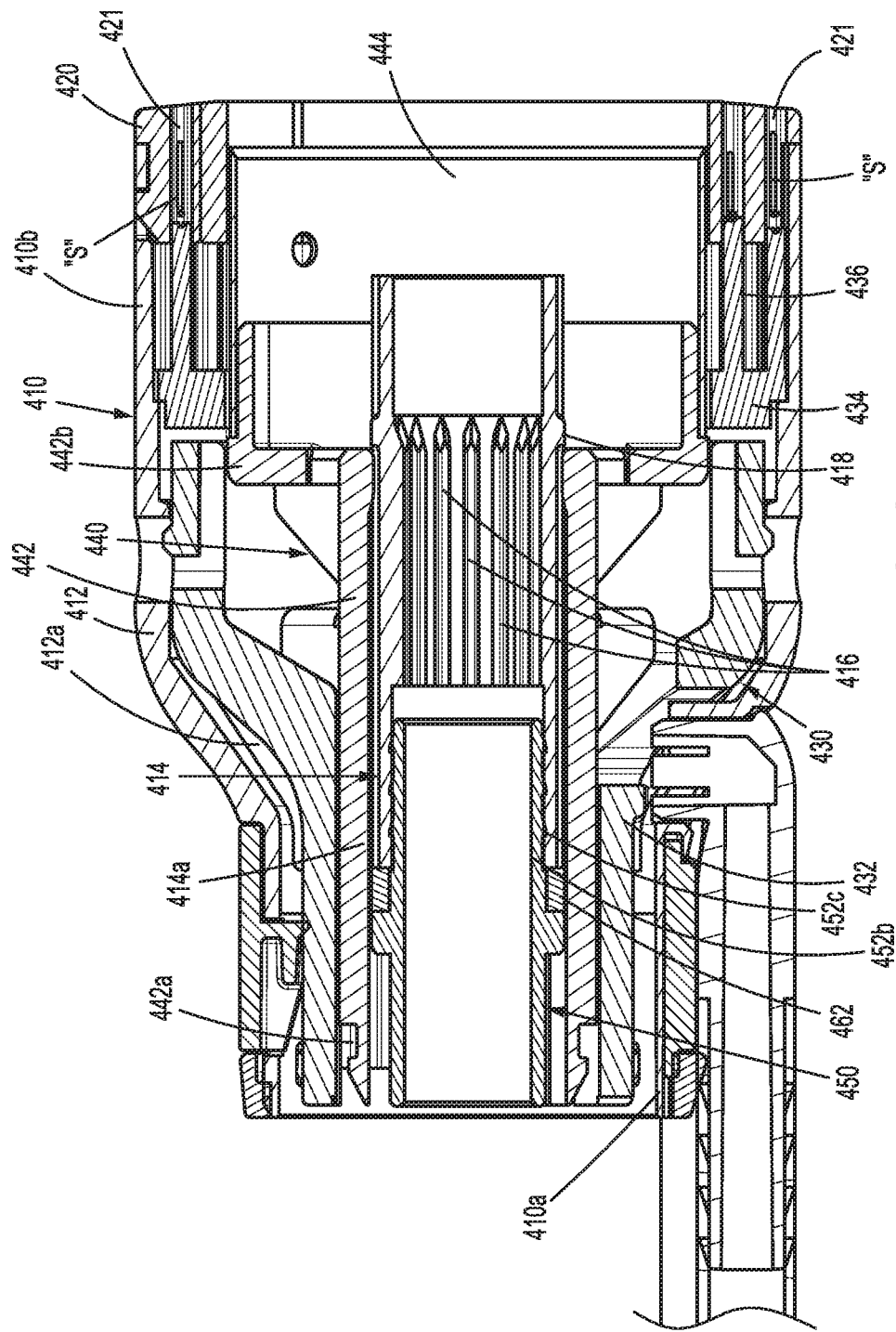
FIG. 67 is a longitudinal, cross-sectional view of the assembled reload of FIG. 66.

In operation, as second rotatable proximal drive shaft 214 is rotated due to a rotation of second connector sleeve 220, as a result of the rotation of the second coupling shaft 64c of handle assembly 100, first coupling shaft 251 is caused to be rotated, which in turn causes first cannulated sun gear 252a to rotate. Rotation of first cannulated sun gear 252a, results in contemporaneous rotation of the first set of planet gears 252b, which in turn causes washer 252f to contemporaneously rotate second cannulated sun gear 252e. Rotation of second cannulated sun gear 252e, results in contemporaneous rotation of the second set of planet gears 252d, which in turn causes contemporaneous rotation of staple lead screw 253. As staple lead screw 253 is rotated, staple driver 254 is caused to be axially translated, which in turn causes outer flexible band assembly 255 to be axially translated. As outer flexible band assembly 255 is axially translated, support base 255d presses against driver adapter 432 of staple driver assembly 430 of reload 400 to distally advance driver 434 and fire staples "S" (FIG. 67) of reload 400 against anvil assembly 510 for formation of staples "S" in underlying tissue.

With reference to FIGS. 39-42 and 45-51, third force/rotation transmitting/converting assembly 260 of adapter assembly 200 includes third proximal drive shaft 216, as described above, a second coupling shaft 261, a planetary gear set 262, a knife lead screw 263, and a knife driver 264, each of which are supported within inner housing member 204, drive coupling assembly 210 and/or an outer tube 206 of adapter assembly 200. Third force/rotation transmitting/converting assembly 260 functions to fire knife of reload 400.

Third rotatable proximal drive shaft 216 includes a non-circular or shaped proximal end portion configured for connection with third connector or coupler 222 which is connected to respective third coupling shaft 64b of handle assembly 100. Third rotatable proximal drive shaft 216 further includes a distal end portion 216b having a spur gear non-rotatably connected thereto.

Second coupling shaft 261 of third force/rotation transmitting/converting assembly 260 includes a proximal end portion 261a having a spur gear non-rotatably connected thereto, and a distal end portion 261b having a spur gear non-rotatably connected thereto. The spur gear at the proximal end portion 261a of second coupling shaft 261 is in meshing engagement with the spur gear at the distal end portion 216b of the third rotatable proximal drive shaft 216.

Planetary gear set 262 of third force/rotation transmitting/converting assembly 260 includes a first cannulated sun gear 262a, a first set of planet gears 262b, a ring gear 262c, a second set of planet gears 262d, and a second cannulated sun gear 262e. First sun gear 262a is non-rotatably supported on a distal end portion of a hollow shaft 269. Hollow shaft 269 includes a spur gear 269a non-rotatably supported on a proximal end thereof. Spur gear 269a of hollow shaft 269 is in meshing engagement with the spur gear at the distal end portion 261b of second coupling shaft 261. The first set of planet gears 262b are interposed between, and are in meshing engagement with, first sun gear 262a and ring gear 262c. The second set of planet gears 262d are interposed between, and are in meshing engagement with, second sun gear 262e and ring gear 262c. Ring gear 262c is non-rotatably supported in outer tube 206 of adapter assembly 200.

Planetary gear set 262 of third force/rotation transmitting/converting assembly 260 includes a washer 262f disposed within ring gear 262c, and between the first set of planet gears 262b and the second set of planet gears 262d. The first set of planet gears 262b are rotatably supported radially about washer 262f, and second sun gear 262e is non-rotatably connected to a center of washer 262f.

Knife lead screw 263 of second force/rotation transmitting/converting assembly 260 includes a proximal flange 263a and a distal threaded portion 263b extending from flange 263a. Knife lead screw 263 defines a lumen 263c therethrough. The second set of planet gears 262d are rotatably supported radially about proximal flange 263a of knife lead screw 263.

Knife driver 264 of second force/rotation transmitting/converting assembly 260 includes a central threaded lumen 264a extending therethrough and is configured and dimensioned to support distal threaded portion 263b of knife lead screw 263 therein. Knife driver 264 includes a pair of tabs 264b projecting radially from an outer surface thereof, and which are configured for connection to inner flexible band assembly 265 of adapter assembly 200, as will be described in greater detail below.

With reference now to FIGS. 39-42, third force/rotation transmitting/converting assembly 260 of adapter assembly 200 includes an inner flexible band assembly 265 secured to knife driver 264. Inner flexible band assembly 265 includes first and second flexible bands 265a, 265b laterally spaced and connected at proximal ends thereof to a support ring 265c and at distal ends thereof to a proximal end of a support base 265d. Each of first and second flexible bands 265a, 265b are attached to support ring 265c and support base 265d. Inner flexible band assembly 265 is configured to receive first rotatable proximal drive shaft 212, first rotatable distal drive shaft 282, and trocar assembly 270 of first force/rotation transmitting/converting assembly 240 therethrough.

Inner flexible band assembly 265 further includes first and second connection extensions 265e, 265f extending proximally from support ring 265c. First and second connection extensions 265e, 265f are configured to operably connect inner flexible band assembly 265 to knife driver 264 of third force/rotation transmitting/converting assembly 260. In particular, each of first and second connection extensions 265e, 265f defines an opening configured to receive a respective tab 264b of knife driver 264. Receipt of tabs 264b of knife driver 264 within the openings of respective first and second connection extensions 265e, 265f secures inner flexible band assembly 265 to knife driver 264 of third force/rotation transmitting/converting assembly 260.

Support base 265d extends distally from flexible bands 265a, 265b and is configured to connect with knife carrier 442 of knife assembly 440 of reload 400.

Flexible bands 265a, 265b are fabricated from stainless steel 301 half hard and are configured to transmit axial pushing forces along a curved path.

Third force/rotation transmitting/converting assembly 260 and inner flexible band assembly 265 are configured to receive first rotatable proximal drive shaft 212, first rotatable distal drive shaft 282, and trocar assembly 270 of first force/rotation transmitting/converting assembly 240 therethrough. Specifically, first rotatable proximal drive shaft 212 is rotatably disposed within and through hollow shaft 269, first cannulated sun gear 262a of first planetary gear set 262, second cannulated sun gear 262e of planetary gear set 262, knife lead screw 263, and knife driver 264.

First rotatable distal drive shaft 282 of first force/rotation transmitting/converting assembly 240 is also rotatably disposed within support base 265d of inner flexible band assembly 265, while trocar member 274 of trocar assembly 270 of first force/rotation transmitting/converting assembly 240 is slidably disposed within support base 265d of inner flexible band assembly 265.

In operation, as third rotatable proximal drive shaft 216 is rotated due to a rotation of third connector sleeve 222, as a result of the rotation of the third coupling shaft 64b of handle assembly 100, second coupling shaft 261 is caused to be rotated, which in turn causes hollow shaft 269 to rotate. Rotation of hollow shaft 269 results in contemporaneous rotation of the first set of planet gears 262b, which in turn causes washer 262f to rotate second cannulated sun gear 262e. Rotation of second cannulated sun gear 262e causes contemporaneous rotation of the second set of planet gears 262d, which in turn causes knife lead screw 263 to rotate. As knife lead screw 263 is rotated, knife driver 264 is caused to be axially translated, which in turn causes inner flexible band assembly 265 to be axially translated. As inner flexible band assembly 265 is axially translated, support base 265d presses against knife carrier 442 of reload 400 to distally advance knife carrier 442 and fire annular knife 444 of reload 400 against anvil assembly 510 for cutting of tissue clamped in reload 400.

Turning now to FIGS. 21-24, adapter assembly 200 includes an outer tube 206 extending from knob housing 202. As mentioned above, outer tube 206 is configured to support first, second and third force/rotation transmitting/converting assembly 240, 250, 260, respectively. Adapter assembly 200 further includes a frame assembly 230 supported in outer tube 206. Frame assembly 230 is configured to support and guide flexible bands 255a, 255b of outer flexible band assembly 255, and flexible bands 265a, 265b of inner flexible band assembly 265, as flexible bands 255a, 255b, 265a, 265b are axially translated through outer tube 206.

Frame assembly 230 includes first and second proximal spacer members 232a, 232b, and first and second distal spacer members 234a, 234b. When secured together, first and second proximal spacer members 232a, 232b define a pair of inner longitudinal slots 234c for slidably receiving first and second flexible bands 265a, 265b of inner flexible band assembly 265 and a pair of outer longitudinal slots 234d for slidably receiving first and second flexible bands 255a, 255b of outer flexible band assembly 255. First and second proximal spacer members 232a, 232b further define a longitudinal passage therethrough for receipt of first force/rotation transmitting/converting assembly 240 and trocar assembly 270.

First and second distal spacer members 234a, 234b define a pair of inner slots 234c for slidably receiving first and second flexible bands 265a, 265b of inner flexible band assembly 265 and a pair of outer slots 234d for slidably receiving first and second flexible bands 255a, 255b of outer flexible band assembly 255. First and second distal spacer members 234a, 234b further define a longitudinal passage therethrough for receipt of first force/rotation transmitting/converting assembly 240, and trocar assembly 270.

First and second proximal spacer members 232a, 232b and first and second distal spacer members 234a, 234b are formed of plastic to reduce friction with flexible bands 255a, 255b of outer flexible band assembly 255, and flexible bands 265a, 265b of inner flexible band assembly 265.

With reference now to FIGS. 44-50, frame assembly 230 further includes a seal member 235. Seal member 235 engages outer tube 206, inner and outer flexible bands 255a, 255b and 265a, 265b of respective inner and outer flexible band assemblies 255, 265 and trocar assembly 270, and wiring extending therethrough, in a sealing manner. In this manner, seal member 235 operates to provide a fluid tight seal through between the distal end and the proximal end of outer tube 206.

Adapter assembly 200 further includes a connector sleeve 290 fixedly supported at a distal end of outer tube 206. Connector sleeve 290 is configured to selectively secure securing reload 400 to adapter assembly 200, as will be described in greater detail below. Connector sleeve 290 is also configured to be disposed about distal ends of outer and inner flexible assemblies 255, 265 and trocar assembly 270. In particular, a proximal end of connector sleeve 290 is received within and securely attached to the distal end of outer tube 206 and is configured to engage a stain gauge assembly 320 of adapter assembly 200, and a distal end of connector sleeve 290 is configured to selectively engage a proximal end of reload 400.

With reference now to FIGS. 52-55, 60 and 69, adapter assembly 200 includes an electrical assembly 310 disposed therewithin, and configured for electrical connection with and between handle assembly 100 and reload 400. Electrical assembly 310 serves to allow for calibration and communication information (e.g., identifying information, life-cycle information, system information, force information) to the main controller circuit board 142b of power-pack core assembly 106 via electrical receptacle 149 of power-pack core assembly 106 of handle assembly 100.

Electrical assembly 310 includes a proximal pin connector assembly 312, a proximal harness assembly 314 in the form of a ribbon cable, a distal harness assembly 316 in the form of a ribbon cable, a strain gauge assembly 320, and a distal electrical connector 322.

Figure 53:
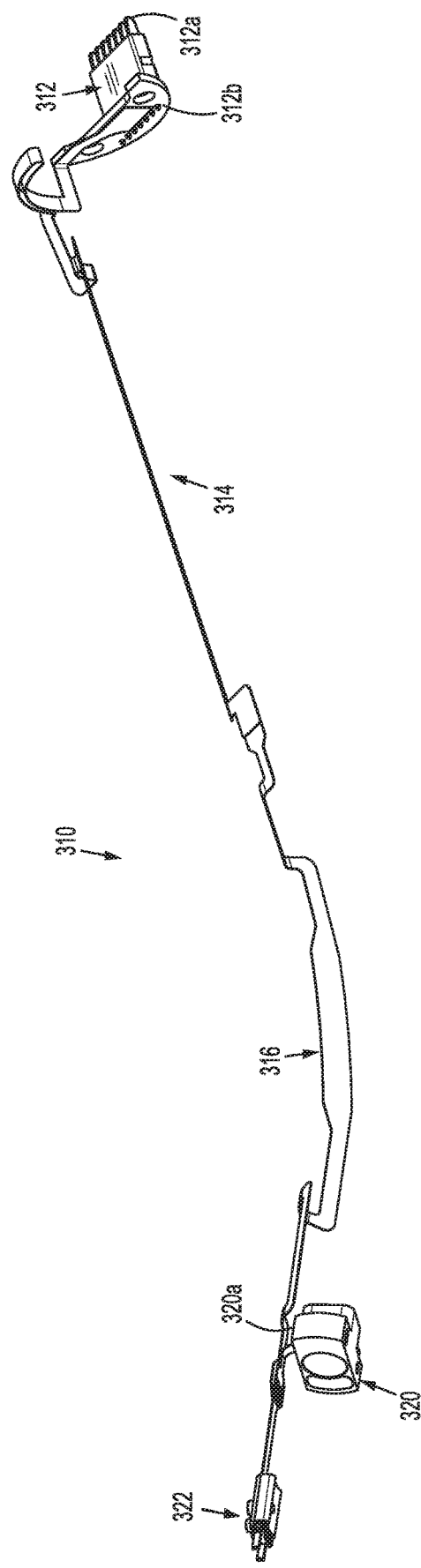
FIG. 53 is a perspective view of the electrical assembly of the adapter assembly of the present disclosure.
Figure 54:
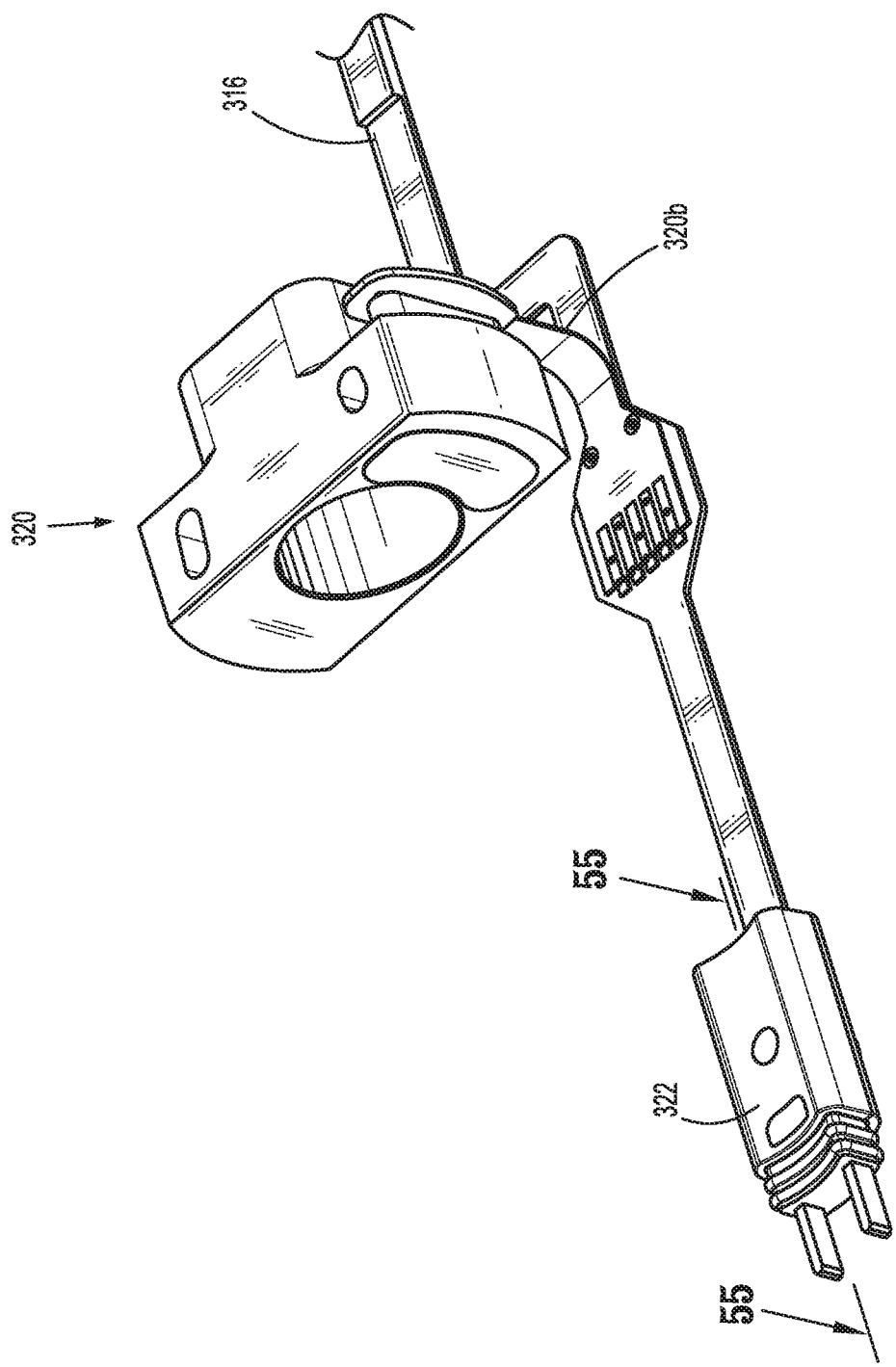
FIG. 54 is a perspective view of a strain gauge assembly of the electrical assembly of FIGS. 52-53.

Proximal pin connector assembly 312 of electrical assembly 310 is supported within inner housing member 204 and drive coupling assembly 210 of knob housing 202. Proximal pin connector assembly 312 includes a plurality of electrical contact blades 312a supported on a circuit board 312b and which enable electrical connection to pass-through connector 66 of plate assembly 60 of outer shell housing 10 of handle assembly 100. Proximal harness assembly 314 is electrically connected to circuit board 312b of proximal pin connector assembly 312 (FIGS. 53 and 54).

Strain gauge assembly 320 is electrically connected to proximal pin connector assembly 312 via proximal and distal harness assemblies 314, 316. Strain gauge assembly 320 includes a strain sensor 320a supported in outer tube 206 of adapter assembly 200. Strain sensor 320a is electrically connected to distal harness assembly 316 via a sensor flex cable 320b. Strain sensor 320a defines a lumen therethrough, through which trocar assembly 270 extends.

As illustrated in FIGS. 29-33, trocar assembly 270 of first force/rotation transmitting/converting assembly 240 extends through strain sensor 320a of strain gauge assembly 320. Strain gauge assembly 320 provides a closed-loop feedback to a firing/clamping load exhibited by first, second and third force/rotation transmitting/converting assembly 240, 250, 260, respectively.

Strain sensor 320a of strain gauge assembly 320 is supported in outer tube 206 and interposed between connector sleeve 290 and support block 292. Support block 292 includes a raised ledge 292b (see FIG. 29) which extends distally therefrom and which is in contact with strain sensor 320a.

Figure 55:
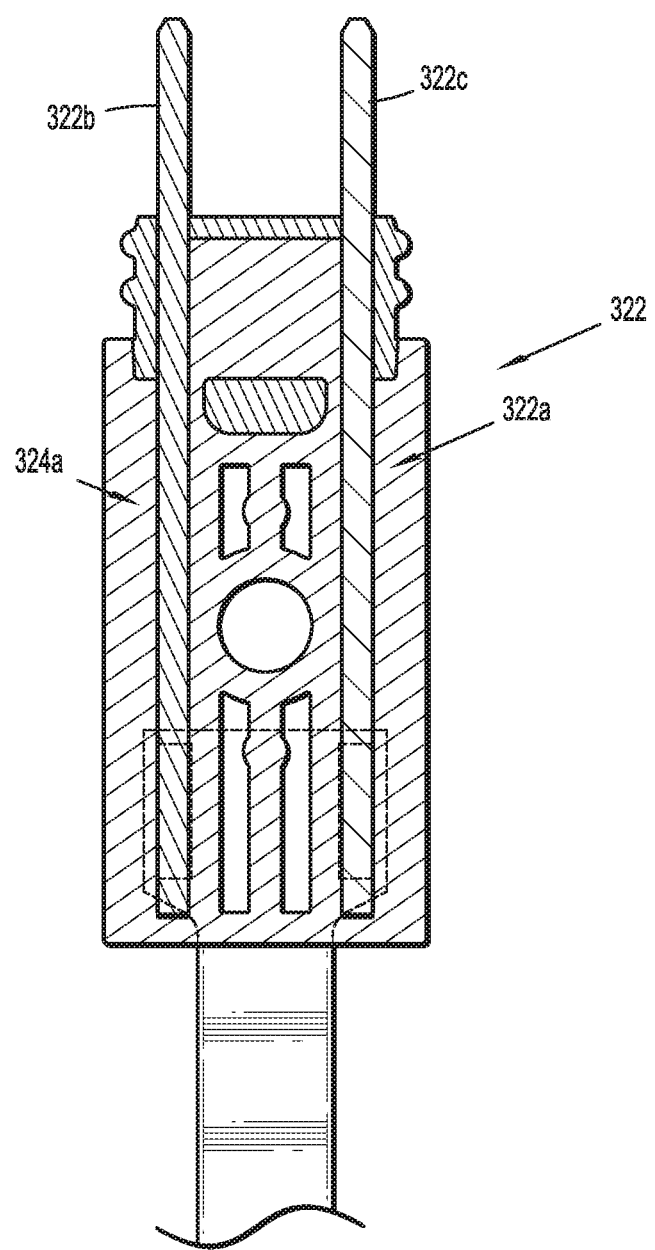
FIG. 55 is a cross-sectional view, as taken through 55-55 of FIG. 54.
Figure 56:
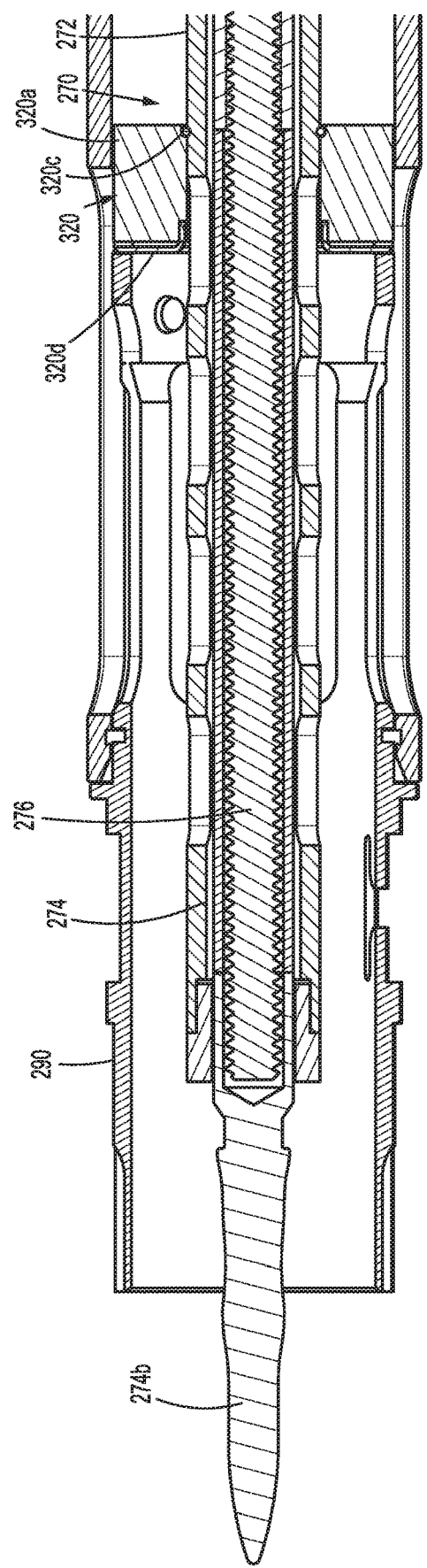
FIG. 56 is a longitudinal, cross-sectional view of the more distal end portion of the adapter assembly illustrated in FIGS. 49 and 50.

With reference now to FIGS. 53-55, electrical assembly 310 includes, as mentioned above, a distal electrical connector 322 which is supported in connector sleeve 290. Distal electrical connector 322 is configured to selectively mechanically and electrically connect to chip assembly 460 of reload 400 when reload 400 is connected to adapter assembly 200.

Distal electrical connector 322 includes a plug member 322a, first and second wires 323a, 323b, and first and second contact members 324a, 324b electrically connected to respective first and second wires 323a, 323b. Plug member 322a includes a pair of arms 322b, 322c supporting first and second contact members 324a, 324b, respectively. The pair of arms 322b, 322c are sized and dimensioned to be received within a cavity 461a of chip assembly 460 and about a circuit board assembly 464 of reload 400 when reload 400 is connected to adapter assembly 200.

First and second contact members 324a, 324b of distal electrical connector 322 are configured to engage respective contact members 464b of circuit board assembly 464 of chip assembly 460 of reload 400 when reload 400 is connected to adapter assembly 200.

With reference now to FIGS. 57-65, adapter assembly 200 includes a rotation assembly 330 configured to enable rotation of adapter assembly 200 relative to handle assembly 100. Specifically, outer knob housing 202 and an outer tube 206 of adapter assembly 200 are rotatable relative to drive coupling assembly 210 of adapter assembly 200.

Rotation assembly 330 includes a lock button 332 operably supported on outer knob housing 202. As will be described in further detail below, when rotation assembly 330 is in an unlocked configuration, outer knob housing 202 and an outer tube 206 are rotatable along a longitudinal axis of adapter assembly 200 relative to drive coupling assembly 210. When rotation assembly 330 is in a locked configuration, outer knob housing 202 and an outer tube 206 are rotationally secured relative to drive coupling assembly 210. In particular, being that outer tube 206 has a curved profile, rotation of outer knob housing 202 and an outer tube 206 about the longitudinal axis of adapter assembly 200 causes handle assembly 100 to be positioned in various orientations relative to adapter assembly 200 in order to provide the clinician with increased flexibility in manipulating the surgical instrument in the target surgical site.

Lock button 332 of rotation assembly 330 is configured to operatively engage inner housing member 204 of adapter assembly 200. Inner housing member 204 is a substantially cylindrical member defining a pair of longitudinal openings for receiving at least portions of first and second force/rotation transmitting/converting assemblies 240, 250 therethrough. Inner housing member 204 includes proximal and distal annular flanges 204a, 204b and further defines proximal and distal outer annular grooves. The proximal annular groove of inner housing member 204 accommodates an inner annular flange of outer knob housing 202 to rotatably secure outer knob housing 202 to inner housing member 204.

With reference still to FIGS. 57-65, distal annular flange 204b and the distal annular groove of inner housing member 204 operate in combination with rotation assembly 330 of adapter assembly 200 to secure outer knob housing 202 in fixed rotational orientations relative to inner housing member 204. In particular, distal annular flange 204b of inner housing member 204 defines first, second, and third radial cutouts 204c, 204d, 204e configured to selectively receive a lock shoe 334 of lock button 332 of rotation assembly 330. The first and third cutouts 204c, 204e are opposed to one another, and second cutout 204d is oriented perpendicular to the first and third cutouts 204c, 204e.

Figure 60:
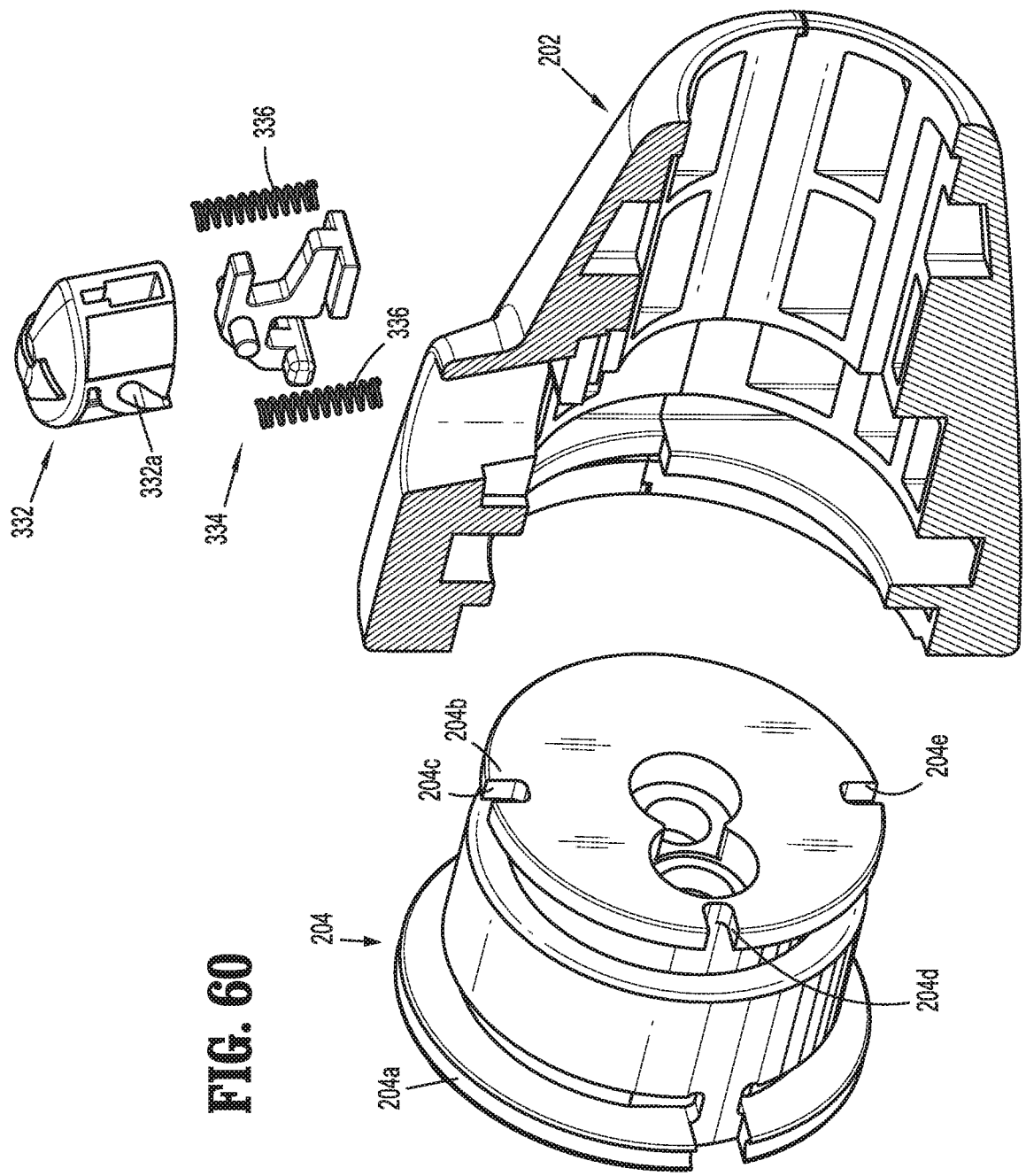
FIG. 60 is a perspective, partial cross-sectional view, with parts separated, of the rotation assembly of FIG. 58.
Figure 61:
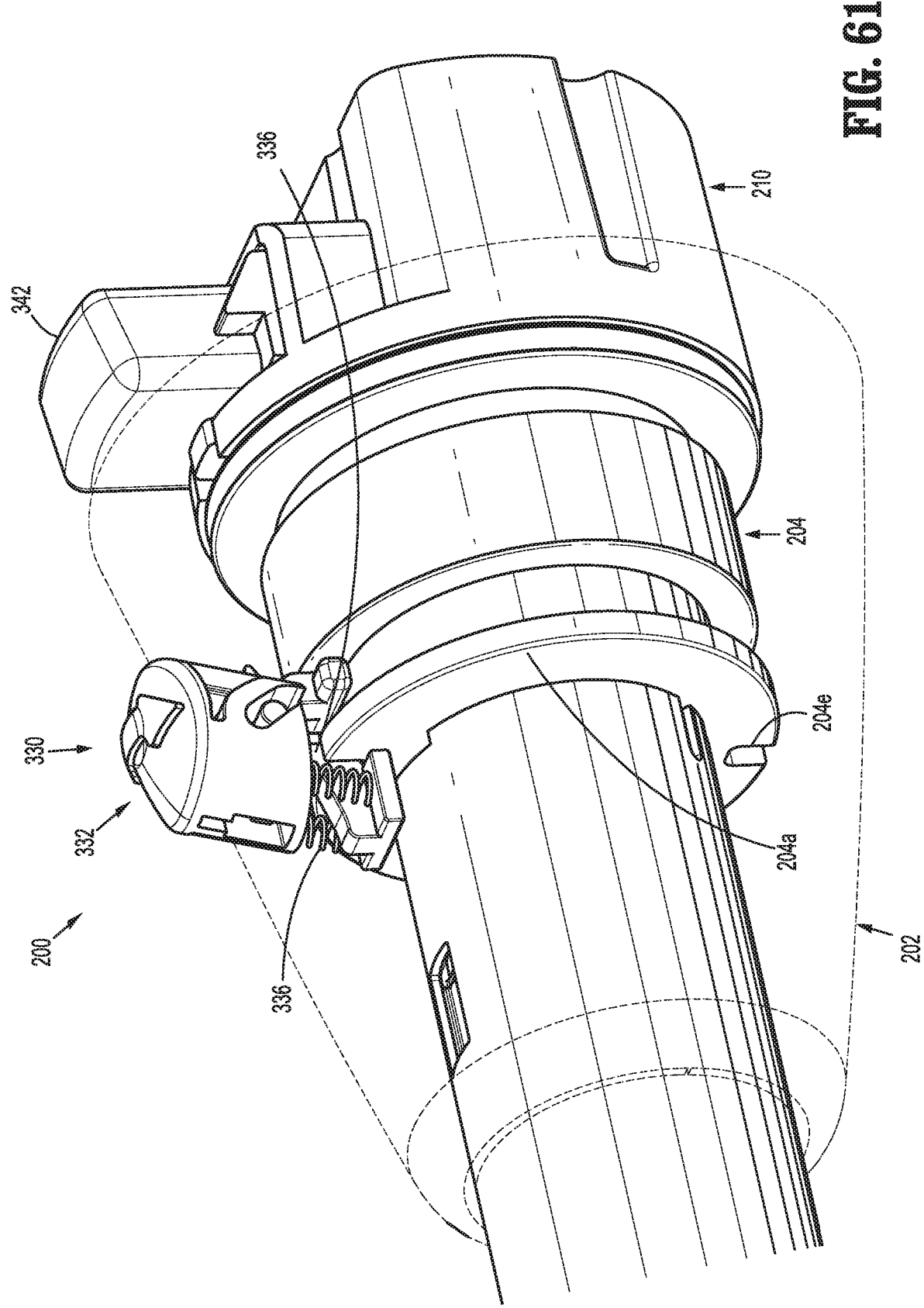
FIG. 61 is a perspective view of the rotation assembly, illustrating an operation thereof.

With reference to FIGS. 60-61, outer knob housing 202 has a frustoconical profile including a plurality of ridges configured for operable engagement by a clinician. Outer knob housing 202 defines a radial opening for operably supporting lock button 332. The opening in outer knob housing 202 is positioned in alignment or registration with the distal annular groove of inner housing member 204 such that lock button 332 of rotation assembly 330 is receivable with the distal annular groove and selectively receivable within each of the first, second, and third cutouts 204c, 204d, 204e in distal annular flange 204b of inner housing member 204.

As mentioned above, rotation assembly 330 of adapter assembly 200 includes a lock button 332 operably supported in an opening of outer knob housing 202 and configured for actuating rotation assembly 330. Rotation assembly 330 further includes a lock shoe 334 disposed between outer knob housing 202 and inner housing member 204 and axially slidable relative to lock button 332 and inner housing member 204. A biasing member 336 is interposed between lock button 332 and lock shoe 334 to urge lock button 332 to a locked position, wherein lock shoe 334 is disposed within one of first, second, and third cutouts 204c, 204d, 204e in distal annular flange 204b of inner housing member 204.

Lock button 332 is configured for operable engagement by a clinician. Lock button member 332 defines an angled cam slot 332a formed therein for receiving a cam pin or boss 334a of lock shoe 334. The biasing member 336 biases lock button 332 and lock shoe 334 away from one another, and urges lock shoe 334 into contact with distal annular flange 204b of inner housing member 204 and into one of first, second, and third cutouts 204c, 204d, 204e in distal annular flange 204b when lock shoe 334 is in registration with one of first, second, and third cutouts 204c, 204d, 204e.

As mentioned above, lock shoe 334 is configured to be selectively received within one of the first, second, and third radial cutouts 204c, 204d, 204e in distal annular flange 204b of inner housing member 204. Specifically, lock shoe 334 includes or defines a shoulder 334a projecting from a surface thereof for receipt in one of the first, second, and third radial cutouts 204c, 204d, 204e in distal annular flange 204b when shoulder 334a of lock shoe 334 is in registration with one of the first, second, and third radial cutouts 204c, 204d, 204e in distal annular flange 204b and lock button 332 is un-depressed. When shoulder 334a of lock shoe 334 is free of any of the first, second, and third radial cutouts 204c, 204d, 204e in distal annular flange 204b (e.g., rotation assembly 330 is in an unlocked condition), outer knob housing 202 is free to rotate relative to inner housing member 204, and thus adapter assembly 200 is free to rotate relative to handle assembly 100.

The operation of rotation assembly 330 will now be described with continued reference to FIGS. 57-65. Referring initially to FIGS. 58, 59, 61 and 64, rotation assembly 330 is shown in a locked condition. In particular, in the locked condition, shoulder 334a of lock shoe 334 is received within first cutout 204c in distal annular flange 204a of inner housing member 204. Also, in the locked condition, lock button 332 of rotation mechanism 330 is biased radially outward by biasing member 336.

Figure 64:
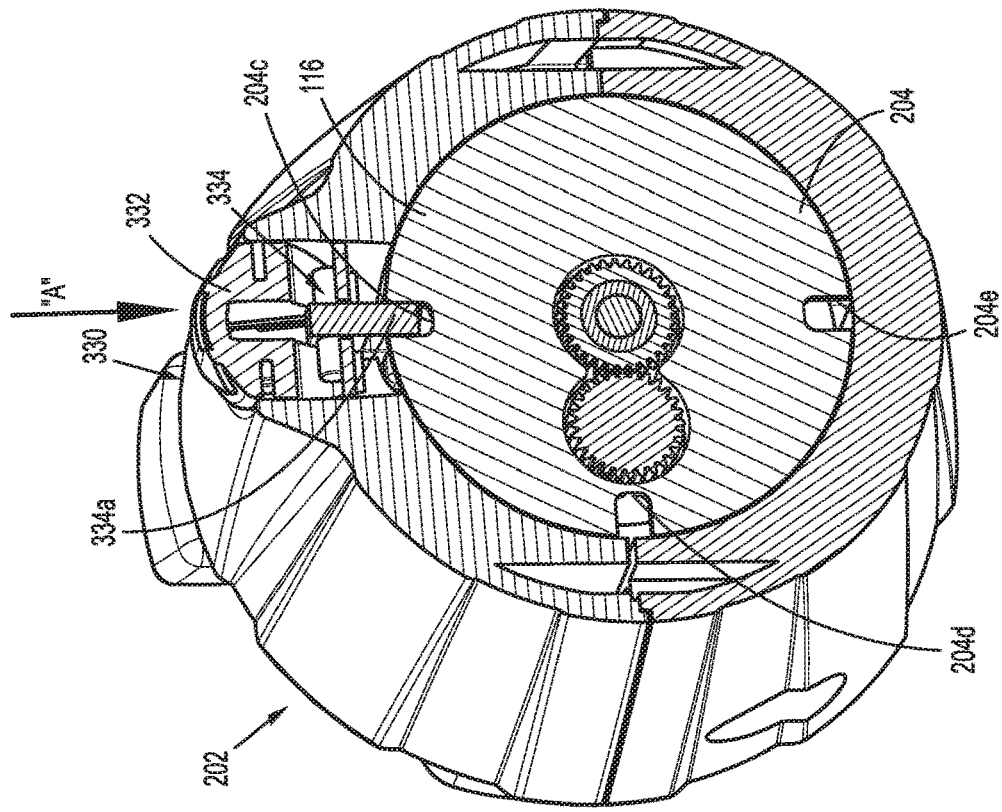
FIG. 64 is a cross-sectional view, as taken through 64-64 of FIG. 63.
Figure 66:
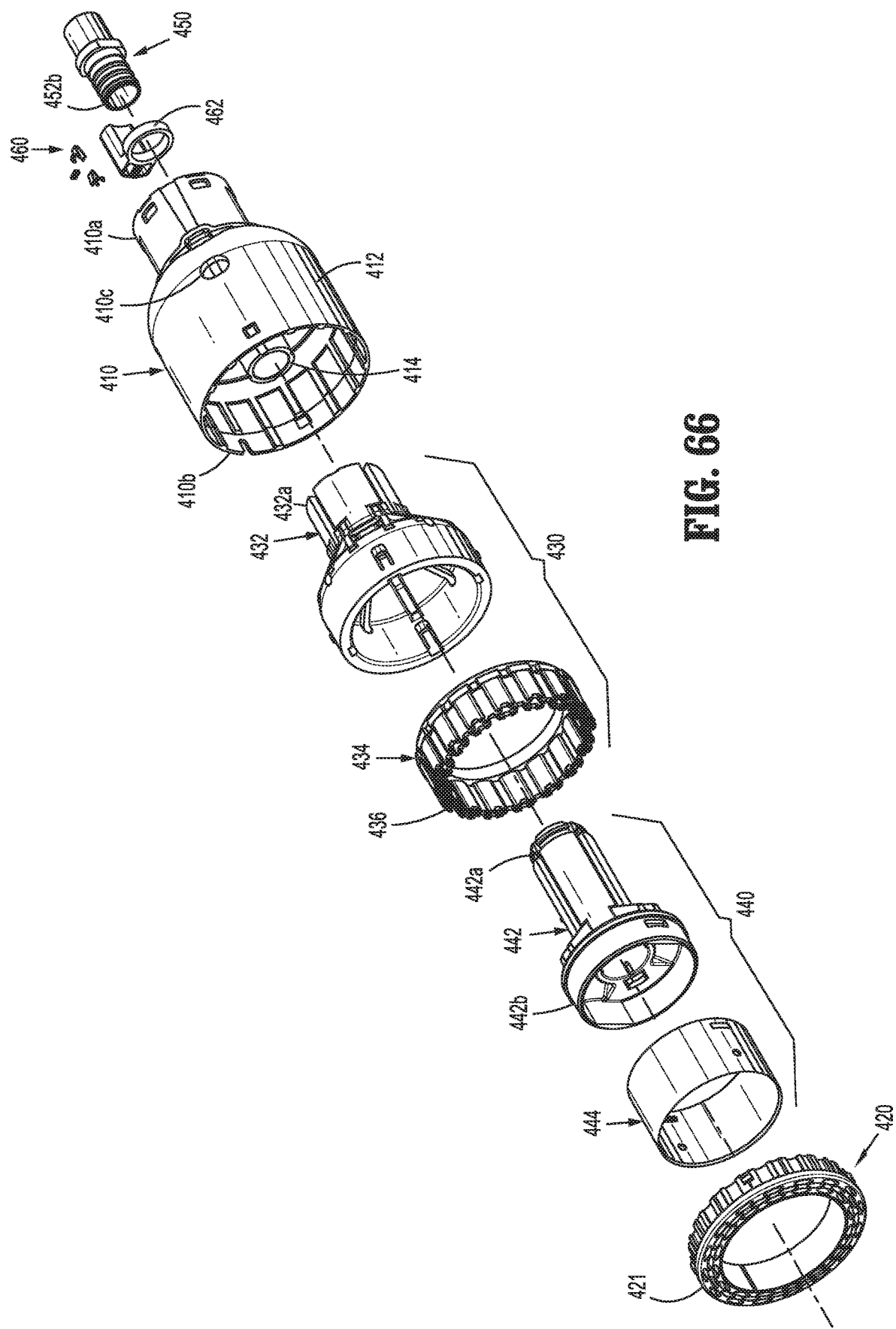
FIG. 66 is a perspective view, with parts separated, of a reload according to the present disclosure.

When lock button 332 of rotation assembly 330 is depressed, as indicated by arrow "A" in FIG. 64, lock button 332 moves radially inward against the bias of biasing member 336. As lock button 332 moves radially inward, lock shoe 334 slides axially in a distal direction, against the bias of biasing member 336. The axial sliding of lock shoe 334 moves shoulder 334a of lock shoe 334 from within the first radial cutout 204c of the distal annular flange 204b of inner housing member 204, thus placing rotation assembly 330 in an unlocked condition and freeing outer knob housing 202 to rotate, as indicated by arrow "B" in FIG. 62, relative to inner housing member 204.

Figure 65:
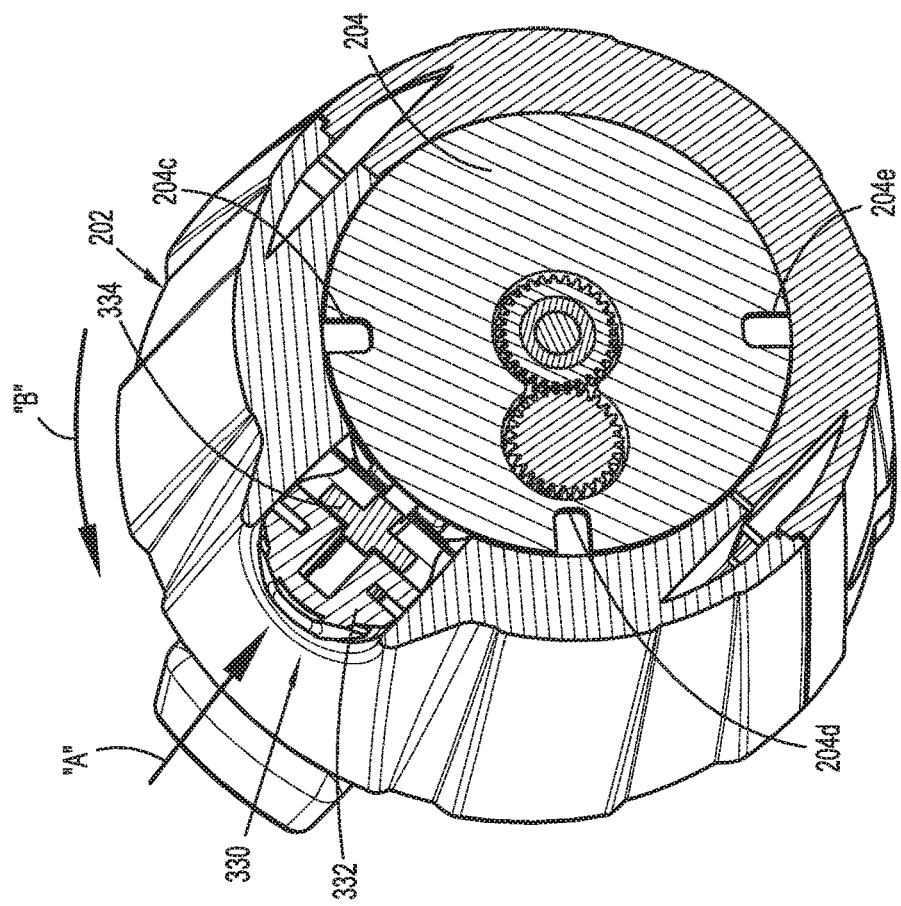
FIG. 65 is a cross-sectional view, as taken through 64-64 of FIG. 63, illustrating the rotation of the rotation assembly and the shaft assembly relative to the drive coupling assembly.

Turning now to FIG. 65, once rotation assembly 330 is in the unlocked condition, outer knob housing 202 may be rotated relative to inner housing member 204. The release of lock button 332 allows biasing member 336 to bias lock button 332 to its initial position. Similarly, biasing member 336 biases lock shoe 334 to its initial position. When lock shoe 334 is re-aligned with one of the first, second, and third radial cutouts 204c, 204d, 204e of distal annular flange 204b of inner housing member 204, as outer knob housing 202 is rotated relative to inner housing member 204, shoulder 334a of lock shoe 334 is free to be received within the respective first, second, and third cutout 204c, 204d, 204e and rotationally locks outer knob housing 202 relative to inner housing member 204 and drive coupling assembly 210 of adapter assembly 200.

Rotation assembly 330 may be used throughout the surgical procedure to rotate handle assembly 100 and adapter assembly 200 relative to one another.

During rotation of outer knob housing 202 relative to inner housing member 204 and drive coupling assembly 210 of adapter assembly 200, since proximal drive shafts 212, 214, 216 are supported in drive coupling assembly 210, and since first coupling shaft 251 of second force/rotation transmitting/converting assembly 250, second coupling shaft 261 of third force/rotation transmitting/converting assembly 260, and second rotatable proximal drive shaft 281 of first force/rotation transmitting/converting assembly 240 are supported in inner housing member 204, the respective angular orientations of proximal drive shaft 212 relative to second rotatable proximal drive shaft 281, proximal drive shaft 216 relative to second coupling shaft 261, and proximal drive shaft 214 relative to first coupling shaft 251, are changed relative to one another.

Figure 57:
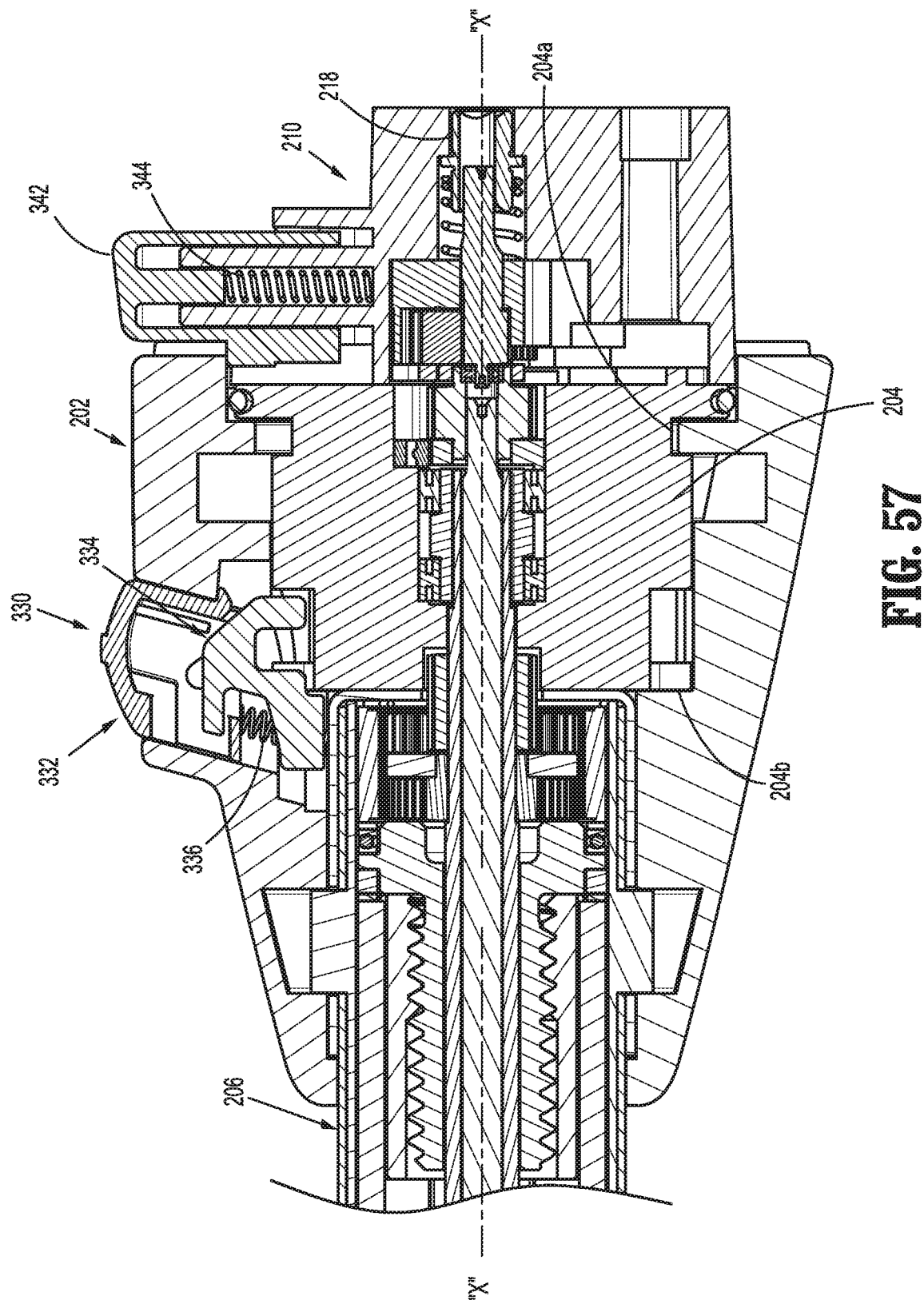
FIG. 57 is a longitudinal, cross-sectional view of a knob assembly of the adapter assembly of the present disclosure.
Figure 58:
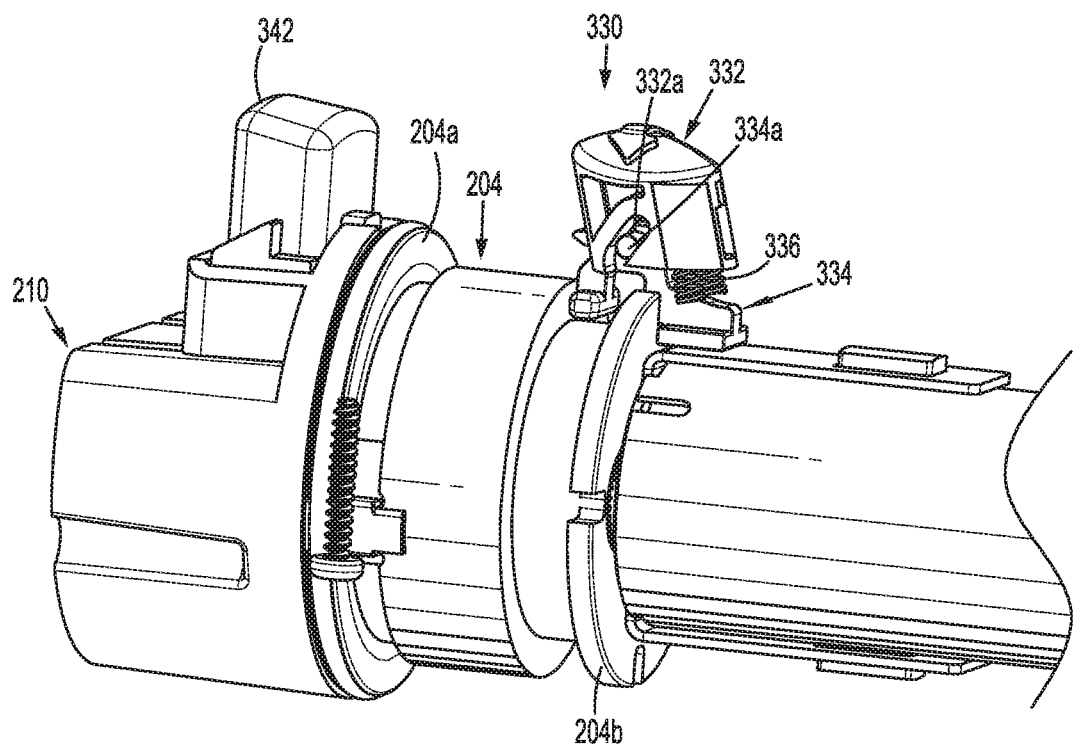
FIG. 58 is a perspective view of a rotation assembly of the knob assembly.
Figure 59:
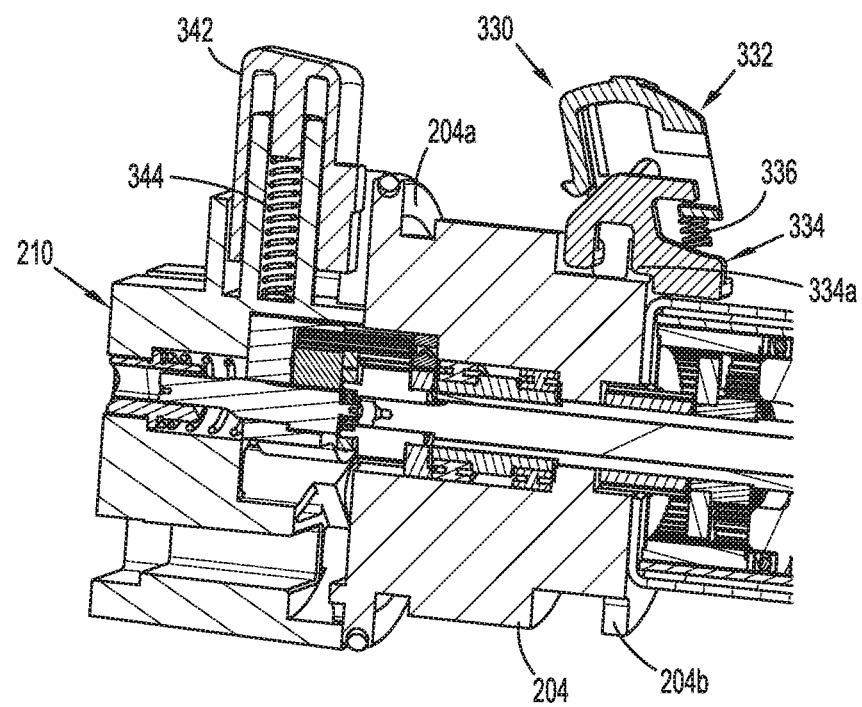
FIG. 59 is a longitudinal, cross-sectional view of the rotation assembly of FIG. 58.

Adapter assembly 200 further includes, as seen in FIGS. 57-59, an attachment/detachment button 342 supported thereon. Specifically, button 342 is supported on drive coupling assembly 210 of adapter assembly 200 and is biased by a biasing member 344 to an un-actuated condition. Button 342 includes a lip or ledge 342a formed therewith that is configured to snap behind a corresponding lip or ledge 20a (FIG. 18) defined along recess 20 of connecting portion 108 of handle housing 102 of handle assembly 100. In use, when adapter assembly 200 is connected to handle assembly 100, lip 342a of button 342 is disposed behind lip 108b of connecting portion 108 of handle housing 102 of handle assembly 100 to secure and retain adapter assembly 200 and handle assembly 100 with one another. In order to permit disconnection of adapter assembly 200 and handle assembly 100 from one another, button 342 is depressed or actuated, against the bias of biasing member 344, to disengage lip 342a of button 342 and lip 108b of connecting portion 108 of handle housing 102 of handle assembly 100.

As illustrated in FIGS. 1 and 66-80, reload 400 is configured for operable connection to adapter assembly 200 and is configured to fire and form an annular array of surgical staples, and to sever a ring of tissue.

Reload 400 includes a shipping cap assembly (not shown) that is selectively received on a distal end 402 of reload 400 and can function to facilitate insertion of reload 400 into a target surgical site and to maintain staples "S" (FIG. 67) within a staple cartridge 420 of reload 400. Shipping cap assembly 401 also functions to prevent premature advancement of a staple driver assembly 430 (FIG. 66) of reload 400 and of a knife assembly 440 (FIG. 66) of reload 400 prior to and during attachment of reload 400 to adapter assembly 200.

With reference now to FIGS. 66-72, reload 400 includes a housing 410 having a proximal end portion 410a and a distal end portion 410b, a staple cartridge 420 fixedly secured to distal end portion 410b of housing 410, a staple driver assembly 430 operably received within housing 410, a knife assembly 440 operably received within housing 410, a bushing member 450 received within proximal end 410a of housing 410, and a chip assembly 460 mounted about bushing member 450.

Housing 410 of reload 400 includes an outer cylindrical portion 412 and an inner cylindrical portion 414. A plurality of ribs (not shown) interconnects outer and inner cylindrical portions 412, 414. Outer cylindrical portion 412 and inner cylindrical portion 414 of reload 400 are coaxial and define a recess 412a (FIG. 67) therebetween configured to operably receive staple driver assembly 430 and knife assembly 440. Inner cylindrical portion 412 of reload 400 includes a plurality of longitudinally extending ridges 416 (FIG. 67) projecting from an inner surface thereof and configured for radially aligning (e.g., clocking) anvil assembly 510 with reload 400 during a stapling procedure. As will be described in further detail below, proximal ends 416a of longitudinal ridges 416 are configured to facilitate selective securement of shipping cap assembly 401 with reload 400. An annular ridge 418 (FIG. 67) is formed on an outer surface of inner cylindrical portion 412 and is configured to assist in maintaining knife assembly 440 in a retracted position.

Staple cartridge 420 of reload 400 is fixedly secured on distal end 410b of housing 410 and includes a plurality of staple pockets 421 formed therein which are configured to selectively retain staples "S".

With continued reference to FIGS. 66-72, staple driver assembly 430 of reload 400 includes a driver adapter 432 and a driver 434. A proximal end 432a of driver adapter 432 is configured for selective contact and abutment with support base 255d of outer flexible band assembly 255 of second force/rotation transmitting/converting assembly 250 of adapter assembly 200. In operation, during distal advancement of outer flexible band assembly 255, as described above, support base 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples "S". Accordingly, advancement of driver 434 relative to staple cartridge 420 causes ejection of the staples "S" from staple cartridge 420.

Still referring to FIGS. 66-72, knife assembly 440 of reload 400 includes a knife carrier 442 and a circular knife 444 secured about a distal end 442b of knife carrier 442. A proximal end 442a of knife carrier 442 is configured for operable connection with support base 265d of inner flexible band assembly 265 of third force/rotation transmitting/converting assembly 260 of adapter assembly 200. In operation, during distal advancement of inner flexible band assembly 265, as described above, support base 265d of inner flexible band assembly 265 connects with proximal end 442a of knife carrier 442 to advance knife carrier 442 and circular knife 444 from a first or proximal position to a second or advanced position to cause the cutting of tissue disposed between staple cartridge 420 and anvil assembly 510.

Distal end 452b of bushing member 450 is secured within a proximal end 414a of inner cylindrical portion 414 of housing 410 by a plurality of ridges 452c formed on distal end 452b of bushing member 450.

Chip assembly 460 includes a housing 461 from which annular flange 462 extends. Annular flange 462 extends perpendicular to a longitudinal axis of housing 461. Annular flange 462 is configured to be received about a distal end 452b of bushing member 450.

Chip assembly 460 includes a circuit board assembly 464 secured within a cavity 461a of housing 461. Circuit board assembly 464 includes a circuit board 464a, a pair of contact members 464b and a chip 464c. A first end of circuit board 464a supports chip 464c, and a second end of circuit board 464a supports first and second contact members 464b. Chip 464c is a writable/erasable memory chip. Chip 464c includes the following stored information: lot number, staple size, lumen size, fire count, manufacturing stroke offsets, excessive force index, shipping cap assembly presence, and demonstration modes. Chip 464c includes write capabilities which allow handle assembly 100 to encode to chip 464c that reload 400 has been used to prevent reuse of an empty, spent or fired reload.

Proximal end 410a of housing 410 is configured for selective connection to connector sleeve 290 of adapter assembly 200. Specifically, outer cylindrical portion 412 of housing 410 terminates in a proximal cylindrical flange 412a having an inner diameter which is larger than a diameter of a distal end portion 290a of connector sleeve 290 of adapter assembly 200. Further, proximal end 432a of driver adapter 432 has an outer diameter which is smaller than the diameter of distal end portion 290a of connector sleeve 290.

Reload 400 includes a compressible release ring 413 supported on flange 412a of outer cylindrical portion 412 of housing 410. Release ring 413 has a substantially ovoid profile including a relative long axis and a relative short axis. In operation, when radially inward directed forces act along the long axis of release ring 413 (as indicated by arrows "A1" of FIG. 70), release ring 413 flexes radially outwardly along the short axis thereof (as indicated by arrows "A2" of FIG. 70).

Release ring 413 includes a ramp feature 413a projecting radially inwardly and located substantially along the short axis of release ring 413. Ramp feature 413a of release ring 413 extends through a window 412b defined in flange 412a of outer cylindrical portion 412 of housing 410. Ramp feature 413a of release ring 413 projects sufficiently radially inwardly so as to be selectively received in a window 290b defined in distal end portion 290a of connector sleeve 290.

Reload 400 includes a retaining ring 415 connected to outer cylindrical portion 412 of housing 410 and configured to help retain release ring 413 on outer cylindrical portion 412 of housing 410.

For radial alignment and clocking of reload 400 with adapter assembly 200, reload 400 includes a longitudinally extending rib 412c projecting radially inwardly from outer cylindrical portion 412 of housing 410 which is configured for slidable receipt in a longitudinally extending slot 290c defined in distal end portion 290a of connector sleeve 290.

To connect reload 400 with adapter assembly 200, rib 412c of reload 400 is radially aligned with longitudinally extending slot 290c of connector sleeve 290 of adapter assembly 200, reload 400 and adapter assembly 200 are then axially approximated towards one another until distal end portion 290a of connector sleeve 290 is received within flange 412a of outer cylindrical portion 412 of housing 410 and until ramp feature 413a of release ring 413 is received in window 290b of connector sleeve 290, reload 400 and adapter assembly 200 are thus locked together.

When reload 400 is connected with adapter assembly 200, distal electrical connector 322 of adapter assembly 200 is mechanically and electrically connected to chip assembly 460 of reload 400.

To disconnect reload 400 and adapter assembly 200 from one another, release ring 413 is squeezed along the long axis thereof (in the direction of arrows "A1") to thereby remove ramp feature 413a of release ring 413 from within window 290b of connector sleeve 290, and thus allowing reload 400 and adapter assembly 200 to be axially separated from one another.

Referring now to FIGS. 71-75, an anvil assembly 510 is provided and is configured for selective connection to trocar member of adapter assembly 200 and for cooperation with reload 400.

Anvil assembly 510 includes a head assembly 512 and a center rod assembly 514. Head assembly 512 includes a post 516, a housing 518, a cutting ring 522, a cutting ring cover 523, an anvil plate 524, a spacer or washer 525, a cam latch member 526, and a retainer member 527. Post 516 is centrally positioned within housing 518.

With reference still to FIGS. 73-75, anvil plate 524 is supported in an outer annular recess 528 of housing 518 and includes a plurality of staple pockets 530 formed therein and configured to receive and form staples.

Cutting ring 522 includes a central opening which is positioned about post 516 within an inner annular recess of housing 518 between post 516 and outer annular recess 528. Cutting ring 522 is formed from polyethylene. Cutting ring cover 523 is secured to an outwardly facing or proximal surface of cutting ring 522.

Retainer member 527 is positioned in the inner annular recess between cutting ring 522 and a back wall of housing 518. Retainer member 527 is annular and includes a plurality of deformable tabs which engage a rear surface of cutting ring 522. Retainer member 527 prevents cutting ring 522 from moving or being pushed into the inner annular recess of housing 518 until a predetermined force sufficient to deform the tabs has been applied to cutting ring 522. When the predetermined force is reached, e.g., during cutting of tissue, cutting ring 522 is urged into the inner annular recess 536 and compresses the retainer members.

Turning back to FIG. 75, anvil center rod assembly 514 includes a center rod 552, a plunger 554 and a plunger spring 556. A first end of center rod 552 includes a pair of arms 159 which define a cavity 159a. A pivot member 562 is provided to pivotally secure post 516 to center rod 552 such that anvil head assembly 512 is pivotally mounted to anvil center rod assembly 514.

Cam latch member 526 is pivotally mounted within a transverse slot of post 516 of housing 518 and about pivot member 562. Cam latch member 526 has an outer cam profile which permits plunger 554 to move forward as cam latch member 526 rotates in a clockwise direction, and permits plunger 554 to be retracted as cam latch member 526 rotates in a counter-clockwise direction.

Plunger 554 is slidably positioned in a bore formed in the first end of center rod 552. Plunger 554 includes an engagement finger which is offset from the pivot axis of anvil head assembly 512 and biased into engagement with an edge of cam latch 526. Engagement of the finger of plunger 554 with the edge of cam latch 526 presses a leading portion of the edge of cam latch 526 against an inner periphery of cutting ring 522 to urge anvil head assembly 512 to an operative or non-tilted position on center rod 552.

Anvil head assembly 512 may be tilted relative to anvil center rod assembly 514 in a pre-fired tilted position. Tilting of anvil head assembly 512 relative to anvil center rod assembly 514 causes the body portion of cam latch member 526 to engage a finger 166 of plunger 554. As cam latch member 526 rotates with the tilting of anvil head assembly 512, plunger 554 is retracted with the bore of anvil center rod assembly 514, thereby compressing spring 556. In this manner, finger 566 of plunger 554 is distally biased against the body portion of cam latch member 526.

With reference to FIGS. 74-75, a second end of center rod 552 includes a bore 580 defined by a plurality of flexible arms 582. The proximal end of each of the flexible arms 582 includes an internal shoulder dimensioned to releasably engage a shoulder of trocar 274 of trocar assembly 270 of adapter assembly 200 to secure anvil assembly 510 to adapter assembly 200. A plurality of splines 586 are formed about center rod 552. Splines 586 function to align and/or clock anvil assembly 510 with staple cartridge 420 of reload 400.

With reference now to FIGS. 76-81, reload 400 is configured to selective optional connection with an external irrigation source via an irrigation tube 590. Irrigation tube 590 is configured to deliver air or saline to the anastomosis site for the purpose of leak testing, for improved insertion or for insulflating the rectal stump.

Irrigation tube 590 terminates at a proximal end 590a thereof with a proximal luer fitting 591 configured to connect to a syringe (not shown), and at a distal end 590b with a distal fitting 592 configured to selectively snap-fit connect to a port 410c of housing 410 of reload 400. Distal fitting 592 includes a pair of resilient fingers 592a configured to engage respective shoulders 410d defined in port 410c of housing 410.

Figure 89:
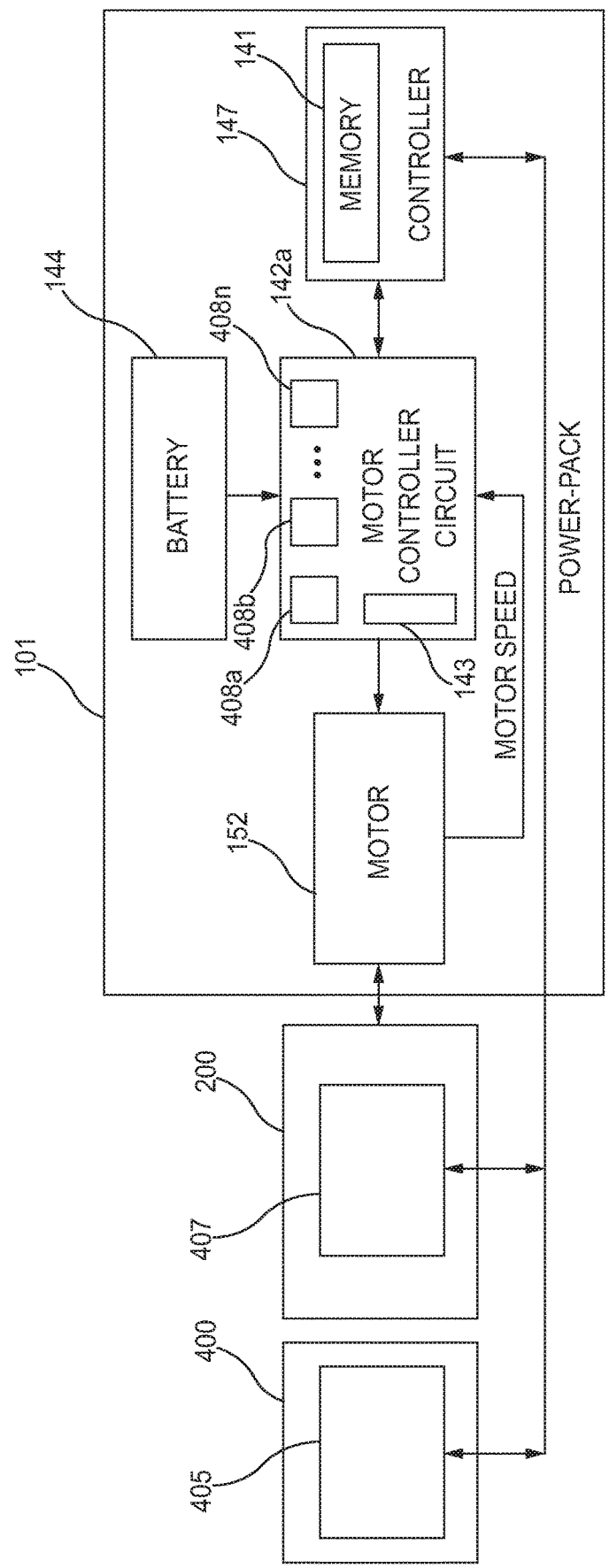
FIG. 89 is a schematic diagram of the the handheld surgical device, the adapter assembly, and the reload according to an embodiment of the present disclosure.

With reference to FIG. 89, a schematic diagram of the power handle 101, the circular adapter assembly 200, and the reload 400, is shown. For brevity, only one of the motors 152, 154, 156 is shown, namely, motor 152. The motor 152 is coupled to the battery 144. In embodiments, the motor 152 may be coupled to any suitable power source configured to provide electrical energy to the motor 152, such as an AC/DC transformer.

The battery 144 and the motor 152 are coupled to the motor controller circuit board 142a having a motor controller 143 which controls the operation of the motor 152 including the flow of electrical energy from the battery 144 to the motor 152. The main controller circuit board 142b (FIGS. 12 and 13) includes a main controller 147, which controls the power handle 101. The motor controller 143 includes a plurality of sensors 408a, 408b, 408n configured to measure operational states of the motor 152 and the battery 144. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152. Position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the circular adapter assembly 200 and/or the reload 400 by counting revolutions of the motors 152, 154, and 156.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions, which are discussed in more detail below. The main controller 147 is also configured to accept a plurality of user inputs from a user interface (e.g., switches, buttons, touch screen, etc. coupled to the main controller 147).

The main controller 147 is also coupled to a memory 141 that is disposed on the main controller circuit board 142b. The memory 141 may include volatile (e.g., RAM) and non-volatile storage configured to store data, including software instructions for operating the power handle 101. The main controller 147 is also coupled to the strain gauge 320 of the circular adapter assembly 200 using a wired or a wireless connection and is configured to receive strain measurements from the strain gauge 320 which are used during operation of the power handle 101.

The reload 400 includes a storage device 405 (e.g., chip 464c). The circular adapter assembly 200 also includes a storage device 407. The storage devices 405 and 407 include non-volatile storage medium (e.g., EEPROM) that is configured to store any data pertaining to the reload 400 and the circular adapter assembly 200, respectively, including but not limited to, usage count, identification information, model number, serial number, staple size, stroke length, maximum actuation force, minimum actuation force, factory calibration data, and the like. In embodiments, the data may be encrypted and is only decryptable by devices (e.g., main controller 147) have appropriate keys. The data may also be used by the main controller 147 to authenticate the circular adapter assembly 200 and/or the reload 400. The storage devices 405 and 407 may be configured in read only or read/write modes, allowing the main controller 147 to read as well as write data onto the storage device 405 and 407.

Figure 82A:
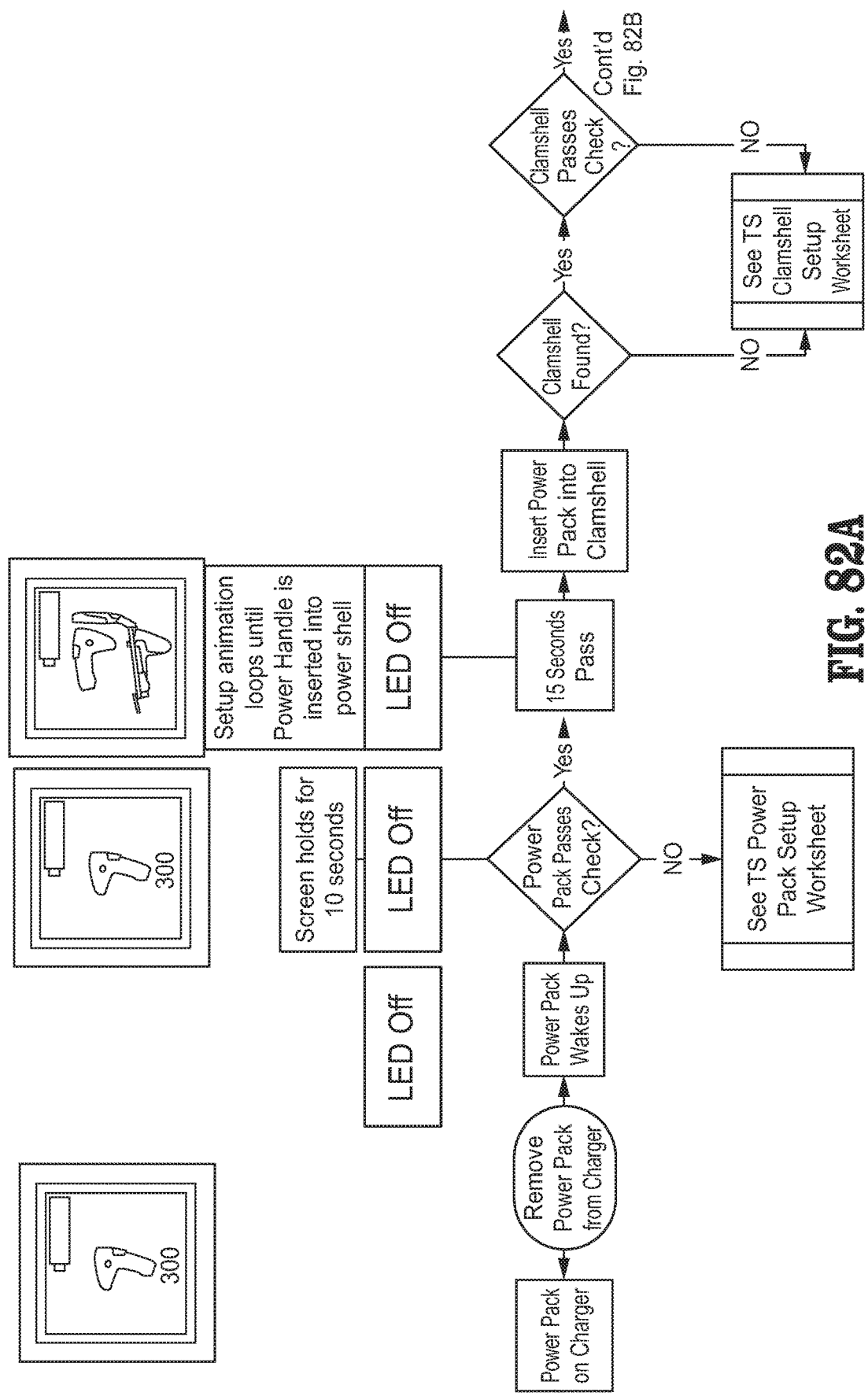
FIGS. 82A-F illustrate a flow chart of a method for operating the handheld surgical device of FIG. 1 according to an embodiment of the present disclosure.

Operation of the handle assembly 100, the circular adapter assembly 200, and the reload 400 is described below with reference to FIGS. 82A-F, which shows a flow chart of the operation process. With particular reference to FIG. 82A, the power handle 101 is removed from a charger (not shown) and is activated. The power handle 101 performs a self-check upon activation and if the self-check passes, the power handle 101 displays an animation on the display screen 146 illustrating how the power handle 101 should be inserted into shell housing 10.

After the power handle 101 is inserted into the shell housing 10, the power handle 101 verifies that it is properly inserted into the shell housing 10 by establishing communications with the electrical connector 66 of the shell housing 10, which has a chip (not shown) disposed therein. The chip within the electrical connector 66 stores a usage counter which the power handle 101 uses to confirm that the shell housing 10 has not been previously used. The data (e.g., usage count) stored on the chip is encrypted and is authenticated by the power handle 101 prior to determining whether the usage count stored on the chip exceeds the threshold (e.g., if the shell housing 10 has been previously used).

Figure 82B:
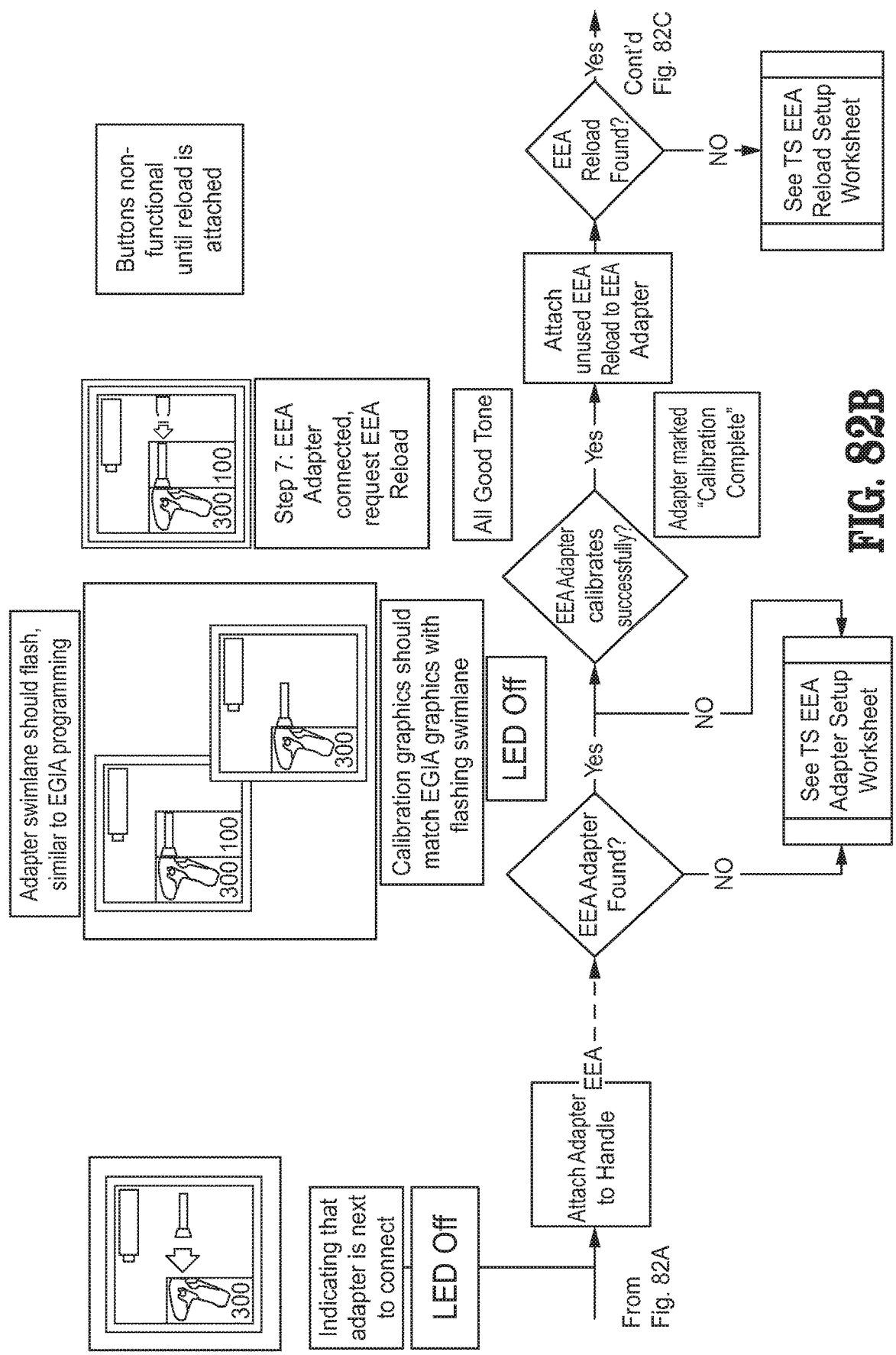

With reference to FIG. 82B, after the power handle 101 is enclosed within the shell housing 10 to form handle assembly 100, adapter assembly 200 is coupled to handle assembly 100. After attachment of circular adapter assembly 200, handle assembly 100 initially verifies that circular adapter assembly 200 is coupled thereto by establishing communications with the storage device 407 of the circular adapter assembly 200 and authenticates circular adapter assembly 200. The data (e.g., usage count) stored on the storage device 407 is encrypted and is authenticated by the power handle 101 prior to determining whether the usage count stored on the storage device 407 exceeds the threshold (e.g., if the adapter assembly 200 has been previously used). Power handle 101 then performs verification checks (e.g., end of life checks, trocar member 274 missing, etc.) and calibrates circular adapter assembly 200 after the handle assembly 100 confirms that the trocar member 274 is attached.

Figures 2, 82C:
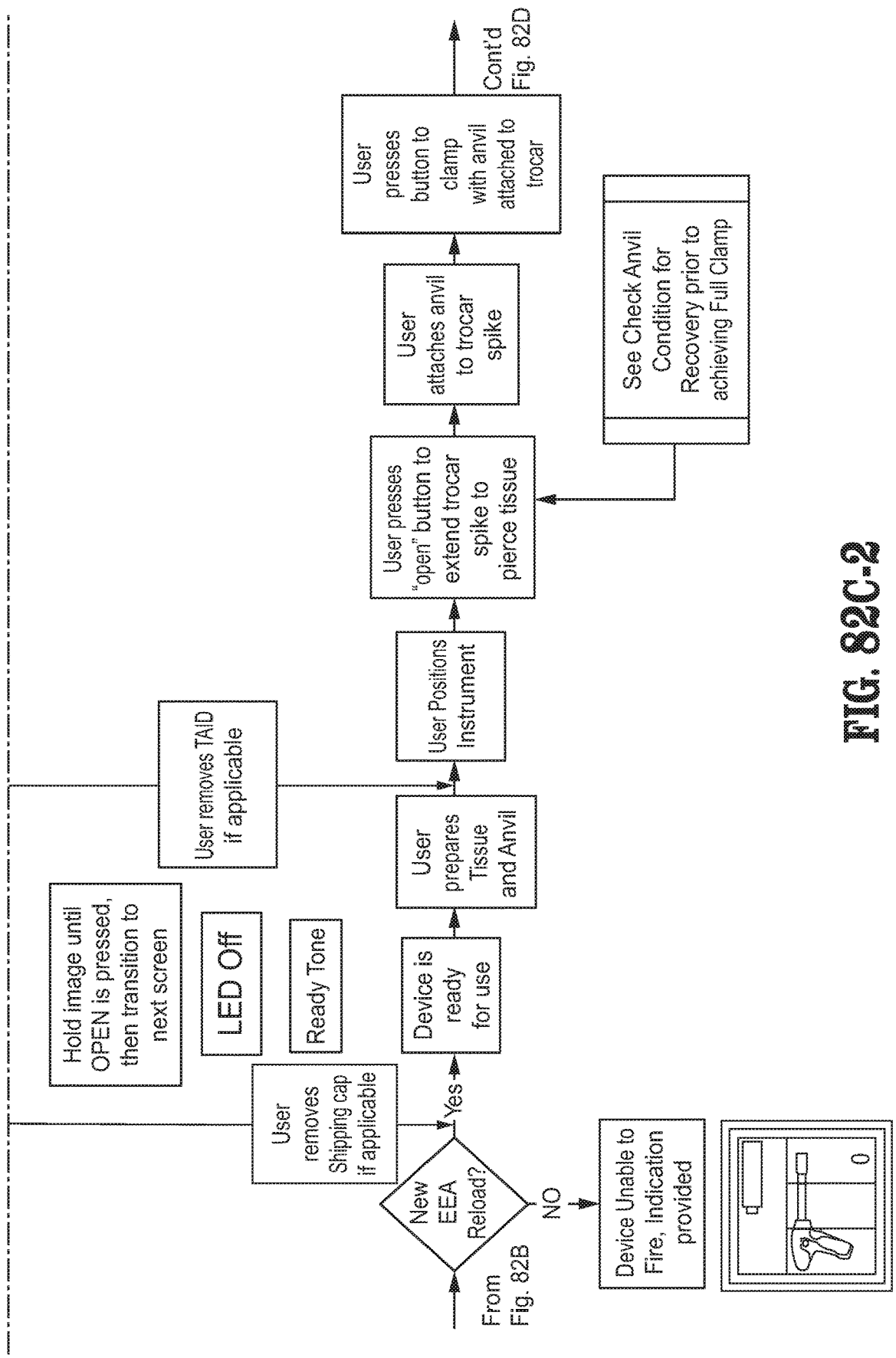

After circular adapter assembly 200 is calibrated, an unused reload 400, with the shipping cap assembly 401, is coupled to circular adapter assembly 200. The handle assembly 100 verifies that circular reload 400 is attached to circular adapter assembly 200 by establishing communications with the storage device 405 of circular reload 400. With reference to FIG. 82C, power handle 101 also authenticates the storage device 405 and confirms that circular reload 400 has not been previously fired by checking the usage count. The usage count is adjusted and encoded by handle assembly 100 after use of circular reload 400. If circular reload 400 has been previously used, handle assembly 100 displays an error indicating the same on the display screen 146.

The power handle 101 also performs calibration with the reload 400 attached to the circular adapter assembly 200 to determine a starting hard stop position. The main controller 147 calculates the distance travelled by the motors 152, 154, 156 to determine the hard stop. The main controller 147 also utilizes the traveled distance during calibration to confirm that the reload 400 is unused. Thus, if the traveled distance is determined to be above a predetermined hard stop threshold, then the main controller 147 confirms that the staples were previously ejected from the reload 400 and marks the reload 400 as used, if the reload 400 was not properly marked before. Once the anvil assembly 510 is attached, the main controller 147 performs another calibration.

With continued reference to FIG. 82C, upon attaching circular reload 400 and confirming that circular reload 400 is unused and has been authenticated, handle assembly 100 prompts the user to eject the shipping cap assembly 401 by prompting the user to press up on the toggle control button 30. The prompt is displayed as an animation on the display screen 146 with a flashing arrow pointing toward the toggle control button 30. The user depresses the upper portion of the toggle control button 30, which activates an automatic extension (and retraction) of trocar member 274 until the shipping cap assembly 401 is ejected, at which point the shipping cap ejection process is complete and the handle assembly 100 is now ready for use.

In embodiments, the circular adapter assembly 200 also operates with reloads 400 having disposable trans-anal/ abdominal introducers. Once the reload 400 with the introducer is attached, handle assembly 100 shows a ready screen. This allows the user to insert circular adapter assembly 200 along with the reload 400 more easily through intra-abdominal incisions. Thus, when the toggle control button 30 is pressed, a prompt for ejecting the introducer is displayed, which is similar to the animation for ejecting the shipping cap assembly 401. The user depresses the upper portion of the toggle control button 30, which activates an automatic extension (and retraction) of the trocar member 274 until the introducer is ejected, at which point the introducer ejection process is complete.

With continued reference to FIG. 82C, after the shipping cap assembly 401 or the introducer is removed, the user commences a surgical procedure which includes preparing the target tissue area and positioning circular adapter assembly 200 within the colorectal or upper gastrointestinal region or until trocar member 274 extends sufficiently to permit piercing of tissue. The user presses the toggle control button 30 to extend the trocar member 274 until it pierces tissue. While the trocar member 274 is extending, an animation illustrating the extension process is displayed on the display screen 146. In addition, distance traveled by the trocar member 274 is shown as a scale and the direction of the movement of the trocar member 274 is shown via an arrow. The trocar member 274 is extended until it reaches the maximum extension distance which is indicated on the display screen 146.

Figures 2, 82D:
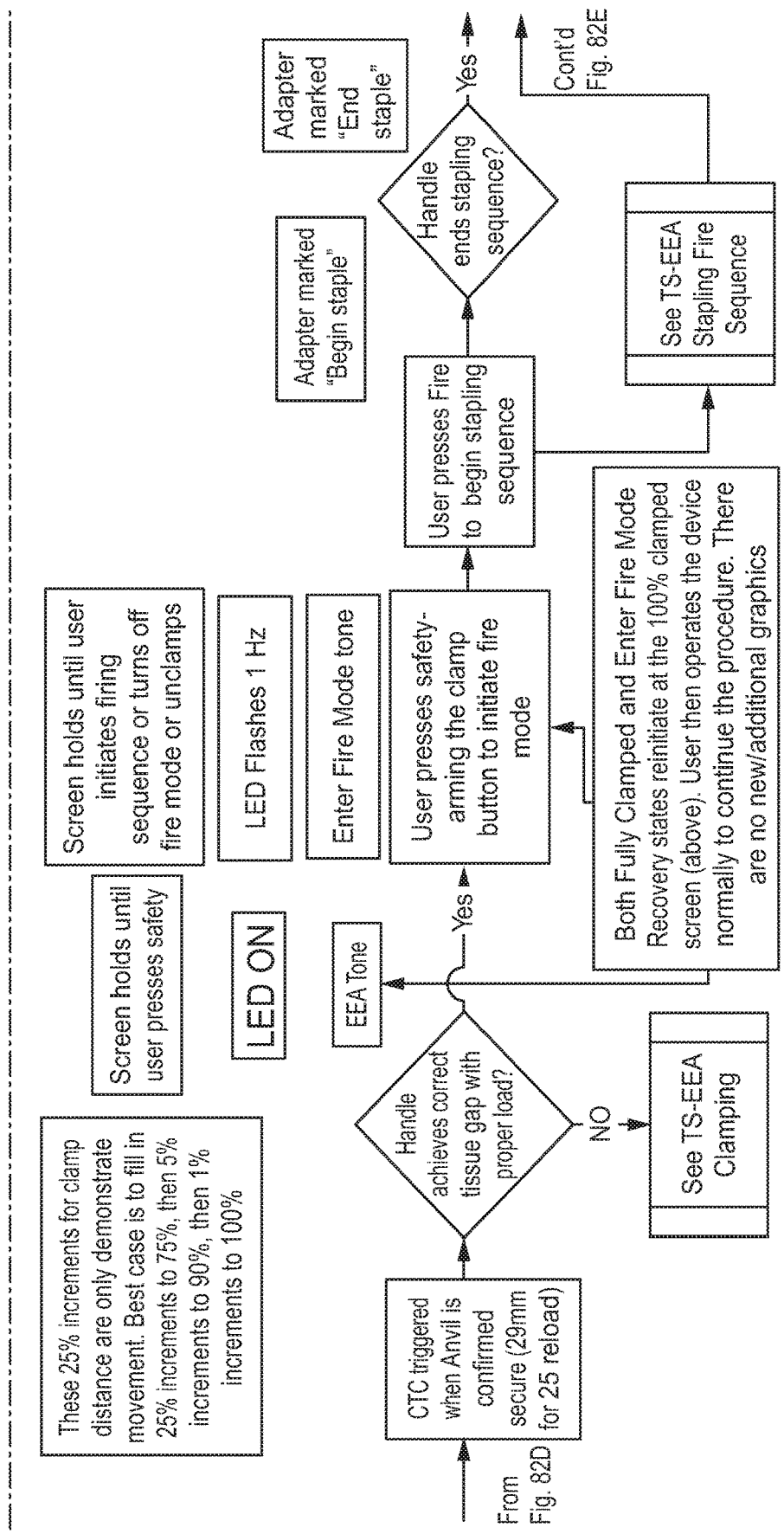
Figure 86:
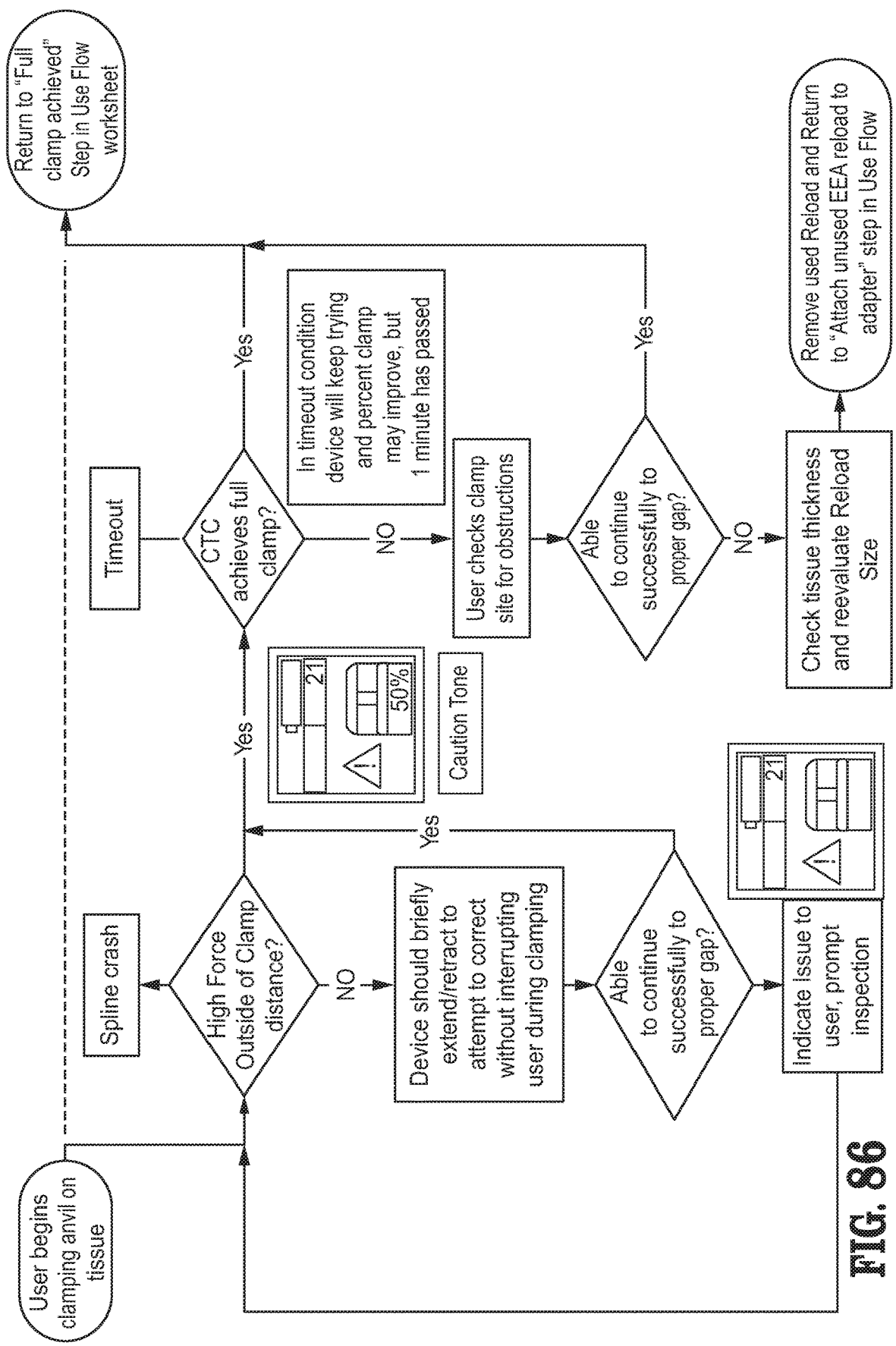
FIG. 86 illustrates a flow chart of a method for controlled tissue compression algorithm executed by the handheld surgical device of FIG. 1 according to an embodiment of the present disclosure.

With reference to FIGS. 82C-D and 86, which shows a flow chart of the clamping process, after extension of the trocar member 274, the anvil assembly 510 (already positioned by surgeon) is attached to the trocar member 274 and the user begins the clamping process on the tissue interposed between circular reload 400 and the anvil assembly 510 by pressing on the bottom of the toggle control button 30. The clamping process is also shown as an animation on the display screen 146, but as a reverse of the animation of the extension of the trocar member 274, e.g., an arrow is highlighted illustrating the retraction direction.

During clamping, the anvil assembly 510 is retracted toward the circular reload 400 until reaching a fully compressed position, namely position of the anvil assembly 510 at which the tissue is fully compressed between the anvil assembly 510 and the reload 400. Fully compressed distance varies for each of the different types of reloads (e.g., the distance is about 29 mm for 25 mm reloads). While clamping, the strain gauge assembly 320 continuously provides measurements to the main controller on the force imparted on the first rotation transmitting assembly 240 as it moves the anvil assembly 510.

Figure 83:
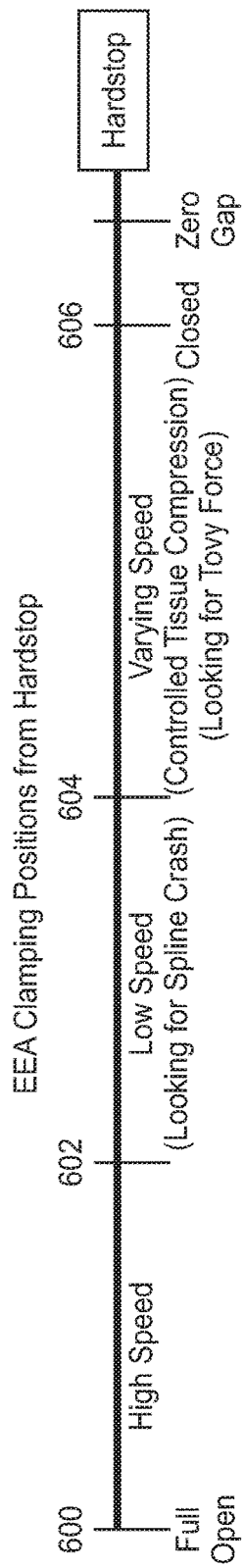
FIG. 83 is a schematic diagram illustrating travel distance and speed of the anvil assembly and a corresponding motor during a clamping sequence performed by the handheld surgical device of FIG. 1 according to an embodiment of the present disclosure.

With reference to FIG. 83, which schematically illustrates the travel distance and speed of the anvil assembly 510 as it is retracted by the first motor 152, the anvil assembly 510 is initially retracted from a full open position marker 600 at a first speed for a first segment from the full open position marker 600 to a first distance marker 602. Thereafter, the anvil assembly 510 traverses a second distance from the first distance marker 602 to a second distance marker 604 at the second speed, which is slower than the first speed. As the anvil assembly 510 is traversing the second segment, the main controller 147 continuously verifies whether the measured force is within predefined parameters to determine if the measured force exceeds a high force threshold limit prior to reaching a starting compression distance (FIGS. 83 and 86). This measurement is used to detect misalignment of the splines 586 of trocar member 274 with longitudinally extending ridges 416 of the reload 400. If the force is higher than the high force threshold, then the power handle 101 temporarily reverses the rotation transmitting assembly 240 to retract the anvil assembly in an attempt to correct the misalignment of the splines 586. The main controller 147 then reattempts to continue clamping until a third distance marker 604 is reached. If the third distance marker 604 is not reached within a predetermined period of time, the main controller 147 then issues an error, including an alarm on the display screen 146 prompting the user to inspect the anvil assembly 510. After inspection and clearance of any obstruction, the user may then restart the clamping process.

Once the anvil assembly 510 reaches the third distance marker 604 at the end of the second segment, the power handle 101 performs a rotation verification to check position of the anvil assembly 510. Then the main controller commences a controlled tissue compression ("CTC") algorithm which varies the clamping speed during tissue compression without exceeding a target compression force.

The CTC accounts for slow-changing and rapid-changing forces imparted on the tissue during compression with a second-order predictive force filter. As the predicted force approaches the target force, the clamping speed is slowed to prevent over-shoot. When the measured force reaches the target force and the clamp gap has not yet been achieved, clamping is stopped to allow for tissue relaxation. During tissue relaxation, after the measured force falls below the target clamping force, the CTC recommences. The force exerted on tissue is derived from the strain measurements by the main controller 147 from the strain gauge assembly 320.

During CTC, the user continues to press down on the toggle control button 30 to continue operation of handle assembly 100. The third distance marker 604, at which the controller commences the CTC, corresponds to the distance at which the anvil assembly 510 begins to compress the tissue against the staple guide of the circular reload 400 for the remainder of the clamping process. CTC controls the movement of the anvil assembly 510 during a third segment, from the third distance marker 604 to a fourth distance marker 606, which corresponds to the fully compressed position of the anvil assembly 510. CTC continues until the anvil assembly 510 reaches the fourth distance marker 606. During clamping, if no forces are detected, the handle assembly 100 identifies that the anvil assembly 510 is missing and the handle assembly 100 issues an error.

The CTC is run for a predetermined time period, namely, a first time period, and an optional second time period. During execution of the CTC, the main controller monitors force based on strain as measured by the strain gauge assembly 320 that is imparted on the first rotation transmitting assembly 240 as it moves the anvil assembly 510 until the measured force approaches the target clamping force.

During execution of the CTC, the main controller 147 determines whether the measured forces approaches the target clamping force by calculating a predicted clamping force using a second-order predictive filter. Target clamping force may be any suitable threshold from about 100 pounds to about 200 pounds, in embodiments, the target clamping force may be approximately 150 pounds. The CTC calculates a predicted clamping force and compares it to the target clamping force. The main controller samples a plurality of strain gauge values at predetermined frequency (e.g., every 1 millisecond) during a predetermined sampling time period. The main controller 147 then uses a first plurality of strain gauge samples obtained during the sampling time period to calculate a filtered strain gauge value. The main controller 147 stores a plurality of filtered strain gauge values and uses three strain gauge samples to predict the target clamping force. In particular, the main controller 147 initially calculates a first difference between the first two (e.g., first and second) filtered strain gauge values, which provides a first-order comparison. More specifically, the main controller 147 then calculates a second difference between subsequent two filtered strain gauge values (e.g., second and third values). In embodiments, the subsequent filtered strain gauge values may be any other subsequent values, rather than encompassing the second value used to calculate the first difference. The first difference is then divided by the second difference, to obtain a percentage of the difference. The main controller determines the target clamping force based on a predicted strain change, which is calculated by multiplying the first difference by the percentage of the difference and a value representing future periods of strain extrapolation. The predicted strain change is then added to the current filtered strain gauge value to determine a predicted strain value, which corresponds to the predicted clamping force.

If the predicted clamping force is above the target force, the PWM voltage driving the motor 152, which is driving the first rotation transmitting assembly 240 is set to zero. The force is continued to be monitored, and once the force drops below a target threshold, the speed of the motor 152 is set to an updated speed to continue the clamping process. This process repeats until the fourth distance marker 606 is reached.

The target speed is calculated by the main controller 147 based on a strain ratio. The strain ratio is calculated by subtracting the predicated strain value from the target clamping force and dividing the difference by the target clamping force. The strain ratio is then used to determine a speed offset by multiplying a difference between maximum and minimum speeds of the motor 152 by the strain ratio. The speed offset is then added to the minimum speed of the motor 152 to determine the target speed. The target speed is used to control the motor 152 in response to the motor deviating by a predetermined amount from currently set speed (e.g., if the motor 152 deviates by about 50 revolutions per minute). In addition, the motor 152 is set to a newly calculated target speed, if the current speed of the motor 152 is zero, e.g., following the predicted clamping force approaching the target force. This allows for varying the speed of the motor 152 while maintaining the desired force on the tissue during clamping.

The target clamping force is fixed for the first time period. When thick tissue is encountered, the clamp gap may not be attained within the first time period (e.g., reaching the fourth distance marker 606), clamping is stopped and the operator is notified via the display screen. If the operator chooses to continue the clamping operation, CTC continues to operate for the second time period, during which the target clamping force is incremented until the maximum force is reached. During the second period, clamping movement distance is monitored to determine if the anvil assembly 510 is moved in response to incremental force increases. Thereafter, the clamp distance is periodically monitored for any minimal movement. If no minimal movement is detected, the target force is dynamically incremented by a proportional amount based on a difference between the current clamp position and the fourth distance marker 606. If a maximum force, which is higher than the target clamping force, is detected, all clamping is stopped. In addition, if clamping is not achieved within the second time period, then the CTC issues an alarm. This may include instructing the user on the display screen 146 to check the clamp site for obstructions. If none are found, the user may continue the clamping process. If the clamping is not complete, e.g., second time period expires and/or the maximum force limit is reached, another alarm is triggered, instructing the user to check tissue thickness and to use a larger reload 400 to restart the clamping process.

With reference to FIGS. 82C-D and 86, once CTC is commenced, the display screen 146 displays a CTC user interface after the main controller 147 confirms that the anvil assembly 510 is present based on detection of a minimum force. In particular, the distance scale on the display screen 146 is replaced with a gauge illustrating the force being imparted on the tissue, and the trocar is replaced with the anvil and tissue being compressed. Also displayed is the progress of the clamping until the fourth distance marker 606 is reached. Thus, as the anvil assembly 510 is being moved to compress the tissue under the CTC, the gauge, the anvil animation, and the distance traveled by the anvil assembly 510 are updated continuously to provide real time feedback regarding the CTC progress.

During CTC, the strain gauge assembly 320 continuously provides measurements to the main controller on the force imparted on the first rotation transmitting assembly 240 as it moves the anvil assembly 510. The force measured by the strain gauge assembly 320 is represented by the gauge on the display screen 146, which is separated into three zones, zone I shows the force from 0% to 50% of the target clamp force, zone II shows the force from 51% to 100%, and zone III shows the maximum force above the target clamp force. High force caution graphic is displayed on screen for zone III, the user is required to perform a second activation of the toggle to confirm clamping despite zone III high forces.

The user can then press the toggle control button 30 to re-clamp, which would move the anvil assembly 510 until the force reaches the maximum force limit of zone III. This allows for further compression of the tissue in certain circumstances where the user deems it necessary, e.g., based on tissue thickness. Once the CTC algorithm is complete and tissue is compressed, handle assembly 100 activates an LED and issues a tone indicating the same and the CTC screen indicating 100% compression is continuously displayed on the display screen 146 until the stapling sequence is started. A pre-fire calibration is performed prior to commencement of the stapling sequence.

Figure 87A:
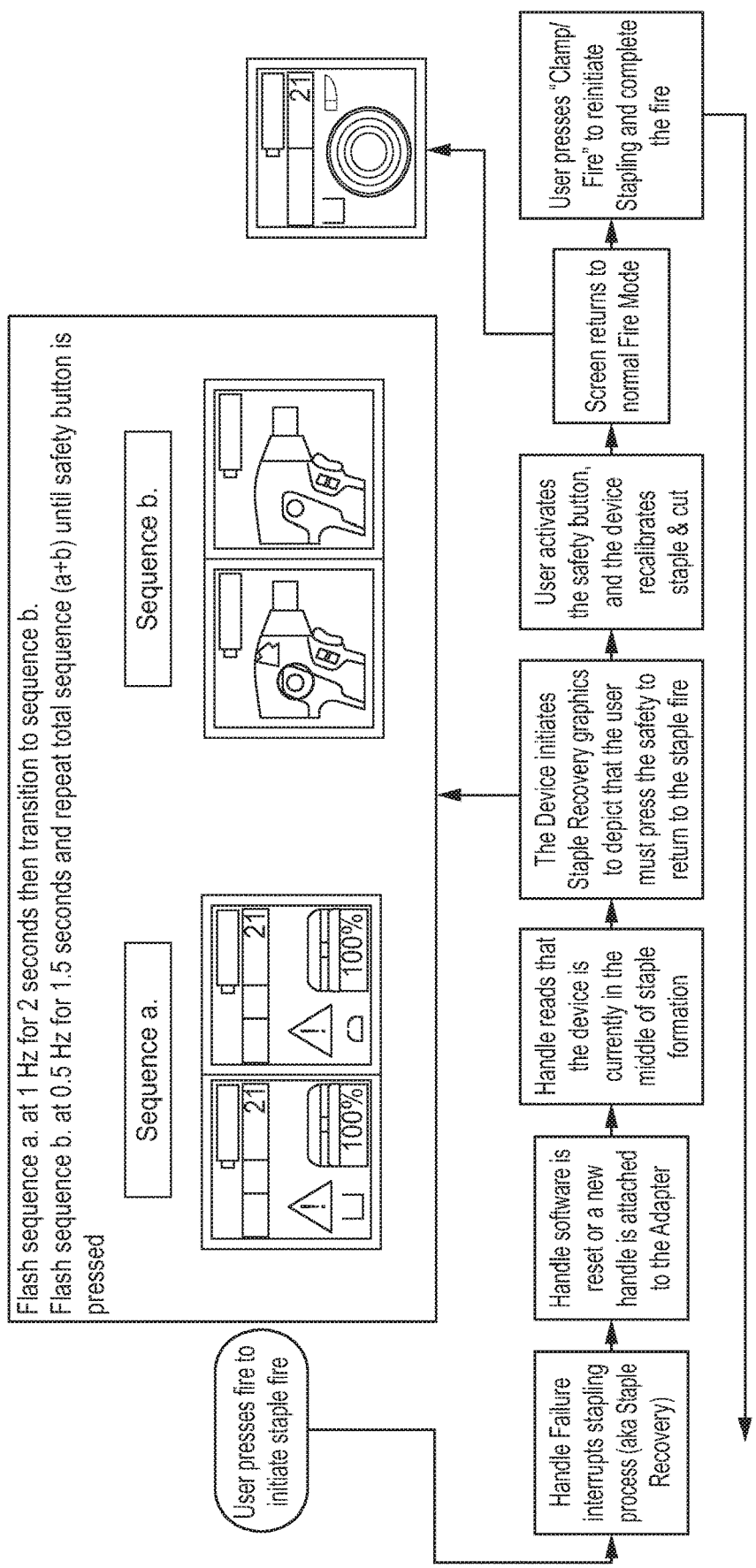
FIGS. 87A-B illustrate a flow chart of a method for a stapling algorithm executed by the handheld surgical device of FIG. 1 according to an embodiment of the present disclosure.
Figure 87B:
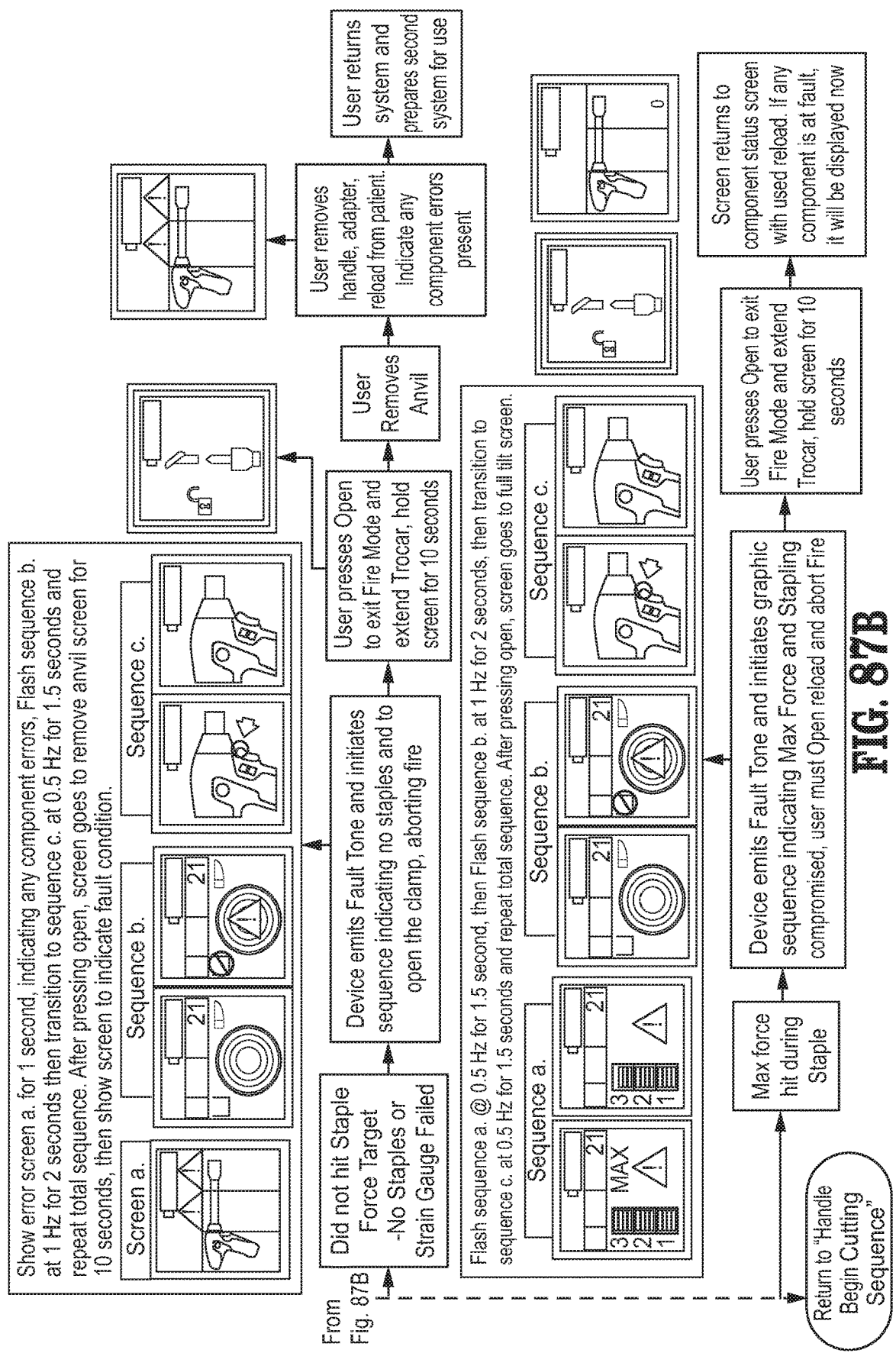

With reference to FIGS. 82D and 87A-B, to initiate stapling sequence, the user presses one of the safety buttons 36a or 36b of the power handle 101, which acts as a safety and arms the toggle control button 30, allowing it to commence stapling. Upon activation of the safety button 36a or 36b, a second rotation verification calibration check is performed. The display screen 146 transitions to the stapling sequence display, which includes a circle illustrating an animated view of a circular anastomosis, a progress bar, and a staple icon. The stapling sequence screen is displayed until user initiates the stapling sequence, exits the stapling sequence, or unclamps. At the start of the stapling sequence, the LED begins to flash and an audio tone is played. The LED continues to flash throughout the duration of the stapling and cutting sequences.

To commence the stapling sequence, the user presses down on the toggle control button 30, which moves the second rotation transmitting assembly 250 to convert rotation to linear motion and to eject and form staples from circular reload 400. In particular, during the firing sequence, the second motor 152 advances the driver 434 using the second rotation transmitting assembly 250. The force imparted on the second rotation transmitting assembly 250 is monitored by the strain gauge assembly 320. The process is deemed complete once the second rotation transmitting assembly 250 reaches a hard stop corresponding to a force threshold and detected by the strain gauge assembly 320. This indicates that the staples have been successfully ejected and deformed against the anvil assembly 510.

Figure 84:
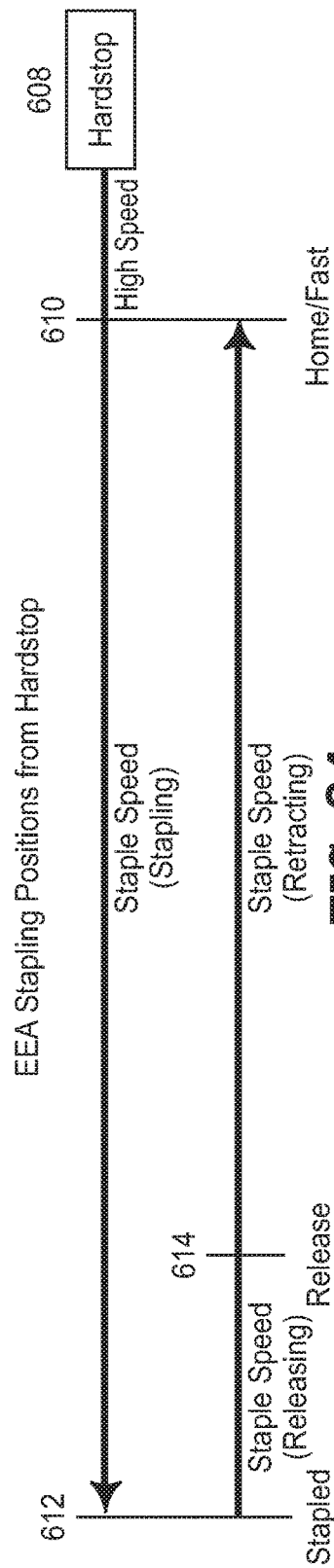
FIG. 84 is a schematic diagram illustrating travel distance and speed of the driver and a corresponding motor during a stapling sequence performed by the handheld surgical device of FIG. 1 according to an embodiment of the present disclosure.

With reference to FIG. 84, which schematically illustrates the travel distance and speed of the second motor 154 as it advances the driver 434, driver 434 is initially advanced from a first position marker 608 (e.g., hardstop) at a first speed for a first segment from the first distance marker 608 to a second distance marker 610. From the second distance marker 610, the driver 434 is advanced at a second speed, slower than the first speed, until it reaches a third distance marker 612, to eject the staples.

During the first segment, the second motor 154 advances the driver 434 until the driver 434 contacts the staples to commence firing. The main controller 147 also writes to the storage devices 405 and 407 of the reload 400 and the circular adapter assembly 200. In particular, main controller 147 marks the reload 400 as "used" in the storage device 405 and increments the usage count in the storage device 407 of the circular adapter assembly 200.

After reaching the second distance marker 610, the second motor 154 is operated at the second, slower speed to eject the staples from the reload 400. With reference to FIG. 87B, during the second segment, as the staples are ejected from the reload 400 to staple tissue, the main controller 147 continually monitors the strain measured by the strain gauge assembly 320 and determines whether the force corresponding to the measured strain is between a minimum stapling force and a maximum stapling force. The stapling force range may be stored in the storage device 405 of the reload 400 and used by the main controller 147 during the stapling sequence. Determination whether the measured force is below the minimum stapling force is used to verify that the staples are present in the reload 400. In addition, a low force may be also indicative of a failure of the strain gauge 320. If the measured force is below the minimum stapling force, then the main controller 147 signals the second motor 154 to retract the driver 434 to the second distance marker 610. The main controller 147 also displays a sequence on the display 146 instructing the user the steps to exit stapling sequence and retract the anvil assembly 510. After removing the anvil assembly 510, the user may replace the circular adapter assembly 200 and the reload 400 and restart the stapling process.

If the measured force is above the maximum stapling force, which may be about 500 lbs., the main controller 147 stops the second motor 154 and displays a sequence on the display 146 instructing the user the steps to exit the stapling sequence. However, the user may still continue the stapling process without force limit detection by pressing on toggle control button 30.

The main controller 147 determines that the stapling process is completed successfully, if the second motor 154 reached a third distance marker 612 associated with stapled tissue and during this movement the measured strain was within the minimum and maximum stapling force limits. Thereafter, the second motor 154 retracts the driver 434 to a fourth distance marker 614 to release pressure on the tissue and subsequently to the second distance marker 610 prior to starting the cutting sequence.

The main controller 147 is also configured to account for band compression of outer flexible band assembly 255 during the stapling process which may result in a non-linear relationship between motor position as determined by the main controller 147 and position of components of the circular adapter assembly 200. The main controller 147 is configured to resolve the discrepancy between the calculated position of the motors 152, 154, 156 and the actual position of the components of the circular adapter assembly 200 using a second order mapping of force changes that result in the discrepancies. The force changes are based on the strain measurements from the strain gauge assembly 320. In particular, the main controller 147 maintains a count of lost turns by the motors 152, 154, 156, namely, turns that did not result in movement of the components of the circular adapter assembly 200, e.g., due to compression, based on the force imparted on the components of the circular adapter assembly 200. The main controller 147 accumulates the total lost turns each time the imparted force changes by a predetermined amount, e.g., about 5 lbs. The motor position is then adjusted by the total accumulated lost-turns value to determine whether the target position has been attained.

With reference to FIG. 82D, progress of staple firing is illustrated by an animation of the anastomosis, the firing progress bar, and staple formation. In particular, the animation illustrates staple legs penetrating tissue and then forming to create concentric staple lines. Once the stapling sequence is complete, the outer circumference is displayed in green. The staple icon also shows initially unformed staples, and then shows the legs of the staples being curled inward. The progress bar is separated into two segments, the first segment being indicative of the stapling process and the second segment being indicative of the cutting process. Thus, as the stapling sequence is ongoing the progress bar continues to fill until it reaches its midpoint.

Figure 82E:
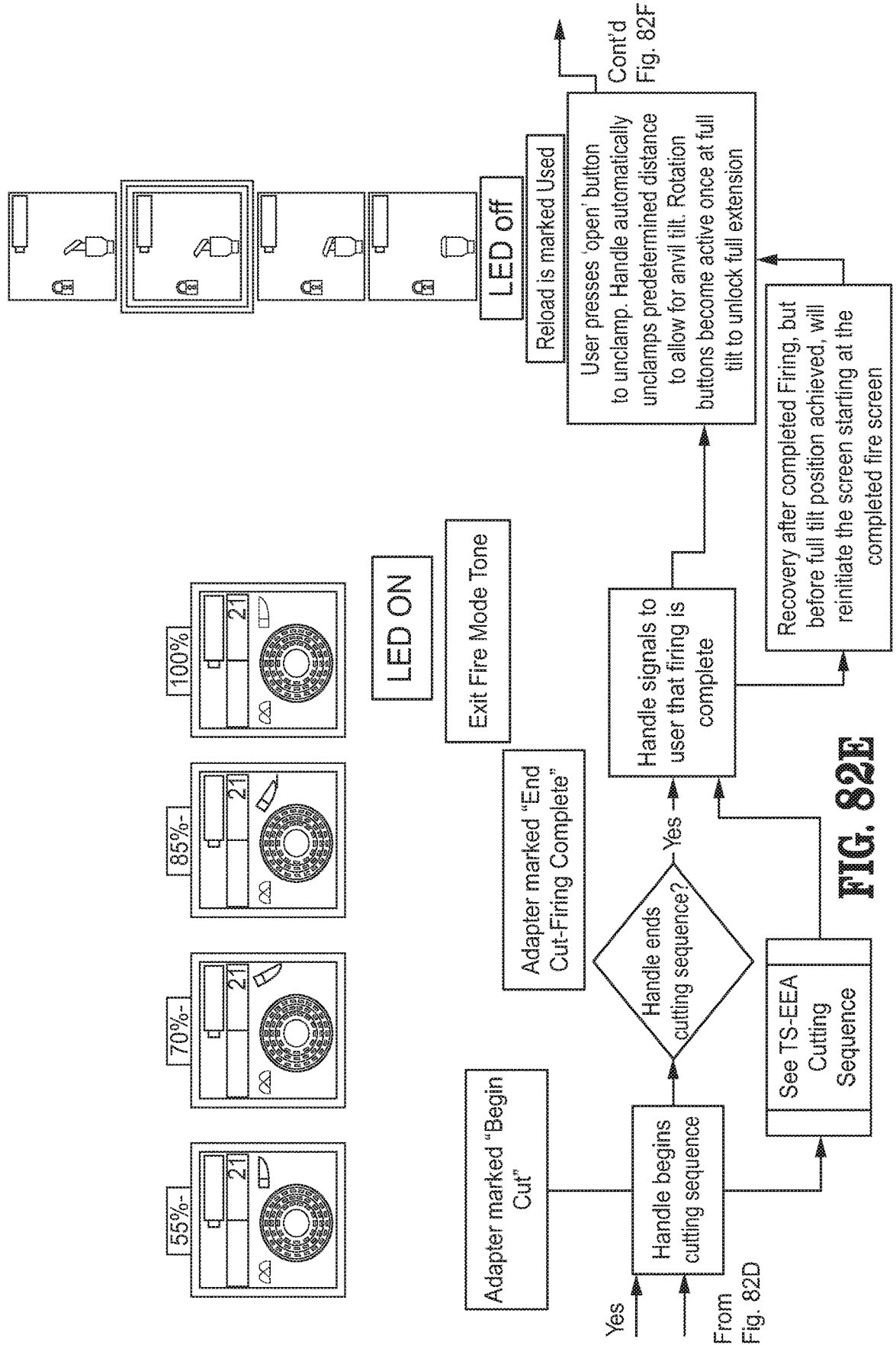
Figure 88A:
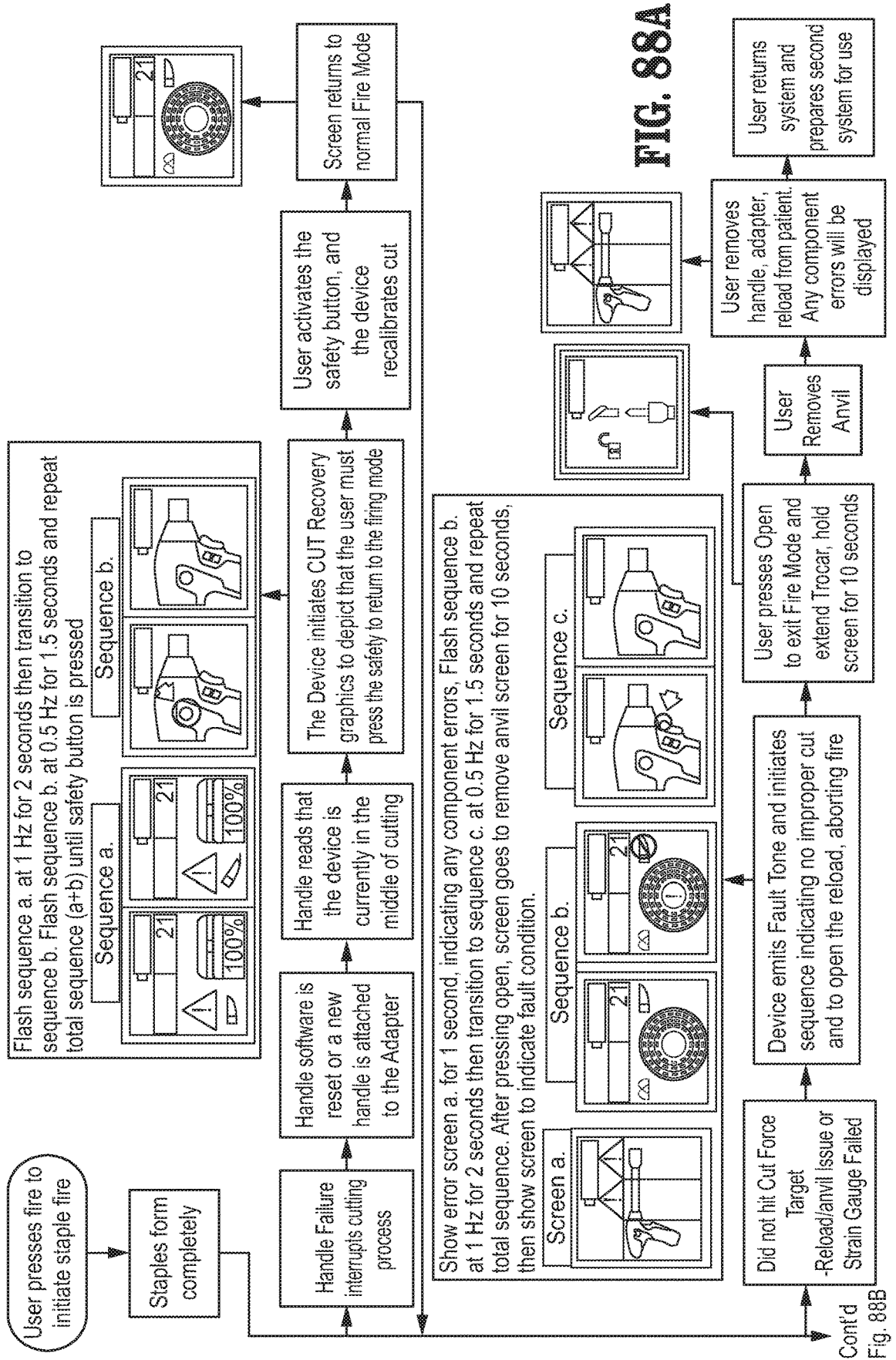
FIGS. 88A-B illustrate a flow chart of a method for a cutting algorithm executed by the handheld surgical device of FIG. 1 according to an embodiment of the present disclosure.
Figure 88B:
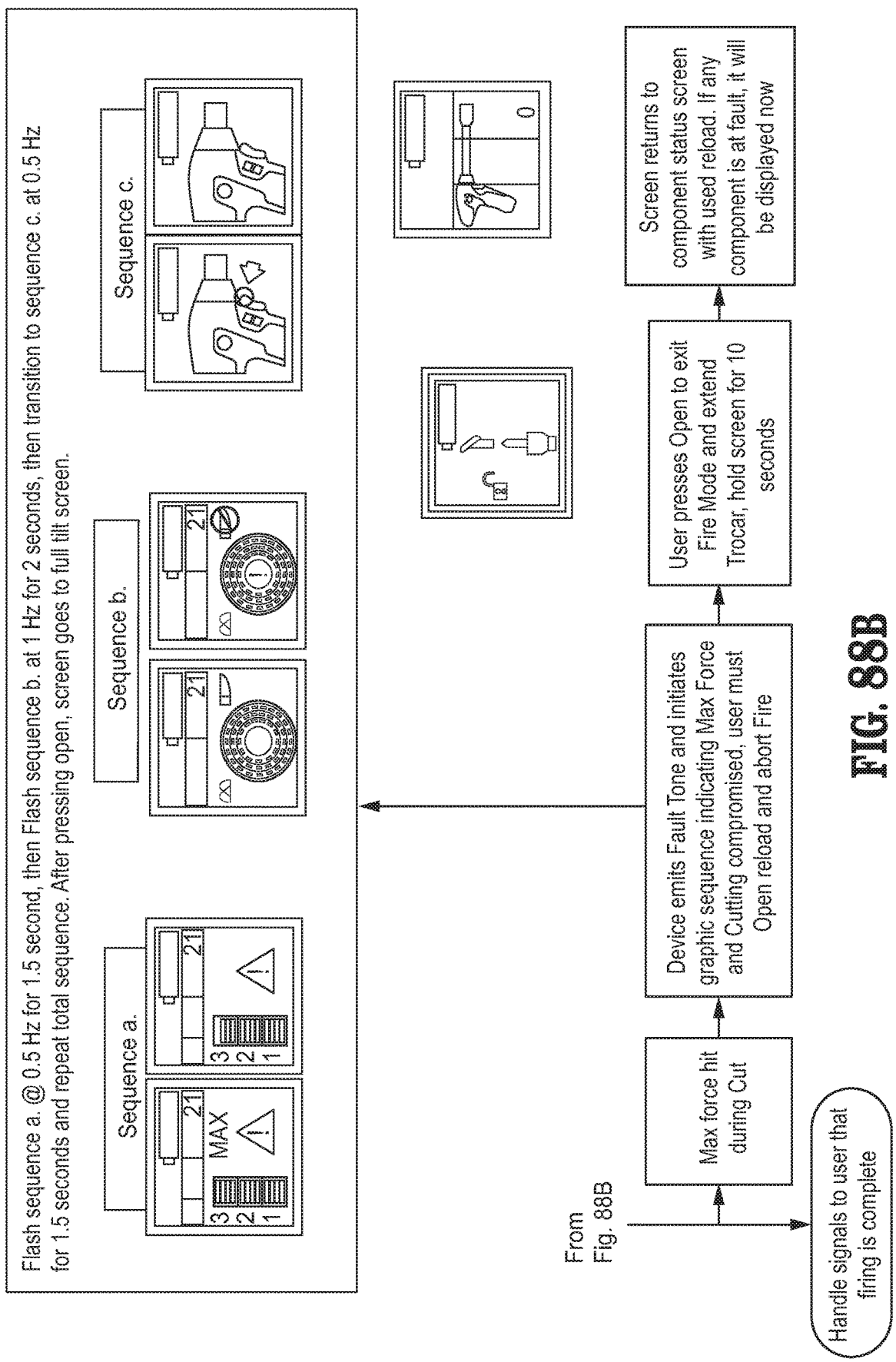

With reference to FIGS. 82E and 88A-B, after the stapling sequence is complete, the power handle 101 automatically commences the cutting sequence. During the cutting sequence, the third motor 154 advances the knife assembly 440 using the third rotation transmitting assembly 260. The force imparted on the third rotation transmitting assembly 260 is monitored by the strain gauge assembly 320. The process is deemed complete once the third rotation transmitting assembly 260 reaches a hard stop corresponding to a force threshold and detected by the strain gauge assembly 320 or a maximum position is reached. This indicates that the knife assembly 320 has cut through the stapled tissue.

Figure 85:
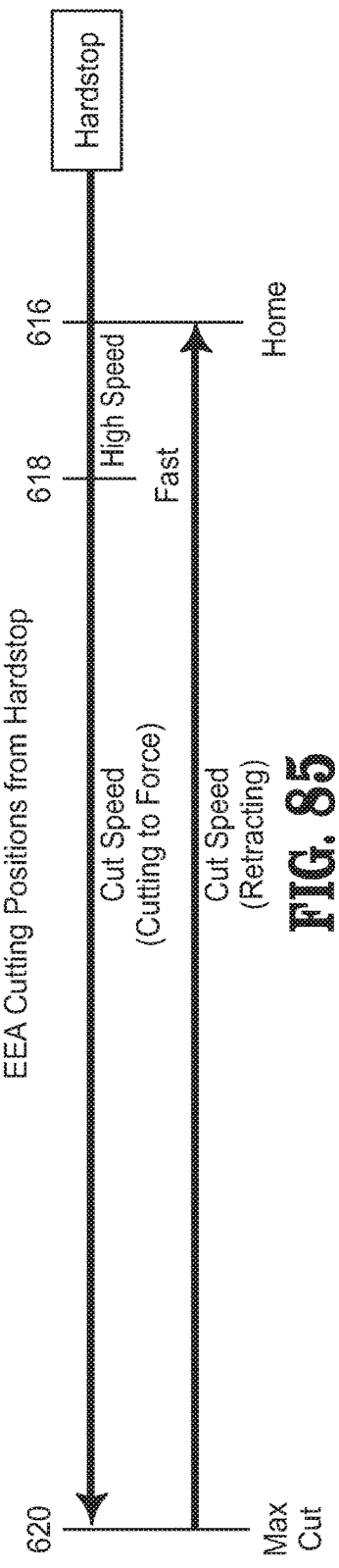
FIG. 85 is a schematic diagram illustrating travel distance and speed of the knife assembly and a corresponding motor during a cutting sequence performed by the handheld surgical device of FIG. 1 according to an embodiment of the present disclosure.

With reference to FIG. 85, which schematically illustrates the travel distance and speed of the third motor 156 as it advances the knife assembly 440. The knife assembly 440 is initially advanced from a first position marker 616 at a first speed for a first segment from the first distance marker 616 until a second distance marker 618. From the second distance marker 618, the knife assembly 440 is advanced at a second speed, slower than the first speed, until it reaches a third distance marker 620, to cut the stapled tissue.

During the first segment, the third motor 156 advances the knife assembly 440 until the knife assembly 440 contacts the stapled tissue. After reaching the second distance marker 618, the third motor 154 is operated at the second, slower speed to cut the stapled tissue. With reference to FIGS. 88A-B, during the second segment, as the knife assembly 440 is advanced to cut tissue, the main controller 147 continually monitors the strain measured by the strain gauge assembly 320 and determines whether the force corresponding to the measured strain is between a target cutting force and a maximum cutting force. The target cutting force and the maximum cutting force may be stored in the storage device 405 of the reload 400 and used by the main controller 147 during cutting sequence. If the target cutting force is not reached during the cutting sequence, which is indicative of improper cutting, then the main controller 147 signals the third motor 156 retract the knife assembly 440 allowing the user to open the reload 400 and abort the cutting sequence.

The main controller 147 also displays a sequence on the display 146 indicating to the user the steps to exit the cutting sequence and retract the anvil assembly 510. After removing the anvil assembly 510, the user may replace the circular adapter assembly 200 and the reload 400 and restart the stapling process. If the measured force is above the maximum cutting force, the main controller 147 stops the third motor 156 and displays a sequence on the display 146 instructing the user to exit the cutting sequence.

The main controller 147 determines that the stapling process is completed successfully, if the knife assembly 440 being moved by the third motor 156 reached a third distance marker 620 associated with cut tissue and during this movement the measured strain was within the target and maximum cutting force limits. Thereafter, the third motor 154 retracts the knife assembly 440 back to the first distance marker 616.

Each of the distance markers 600-620 are stored in the memory 141 and/or the storage device 405 and are used by the main controller 147 to control the operation of the power handle 101 to actuate various components of the circular adapter assembly 200 based thereon. As noted above the distance markers 600-620 may be different for different type of reloads accounting for variations in staple size, diameter of the reload, etc. In addition, the distance markers 600-620 are set from the hard stop as determined during the calibration process described above.

With reference to FIG. 82E, the cutting sequence is illustrated by the same user interface, except the staple icon is grayed out and a knife icon is highlighted. During the cutting sequence, the knife icon is animated with motion and the progress bar moves from its midpoint to the right. In addition, the inner circumference of the circle is displayed in green once the cutting sequence is complete. During the cutting sequence the force imparted on the third rotation transmitting assembly 260 is monitored by the strain gauge assembly 320 to ensure that maximum force limit is not exceeded. The process is deemed complete once the third rotation transmitting assembly 260 reaches a hard stop or a force threshold as detected by the strain gauge assembly 320. This indicates that the knife has successfully dissected the tissue. Completion of the cutting sequence is indicated by another tone and the LED stops flashing and remains lit.

Figure 82F:
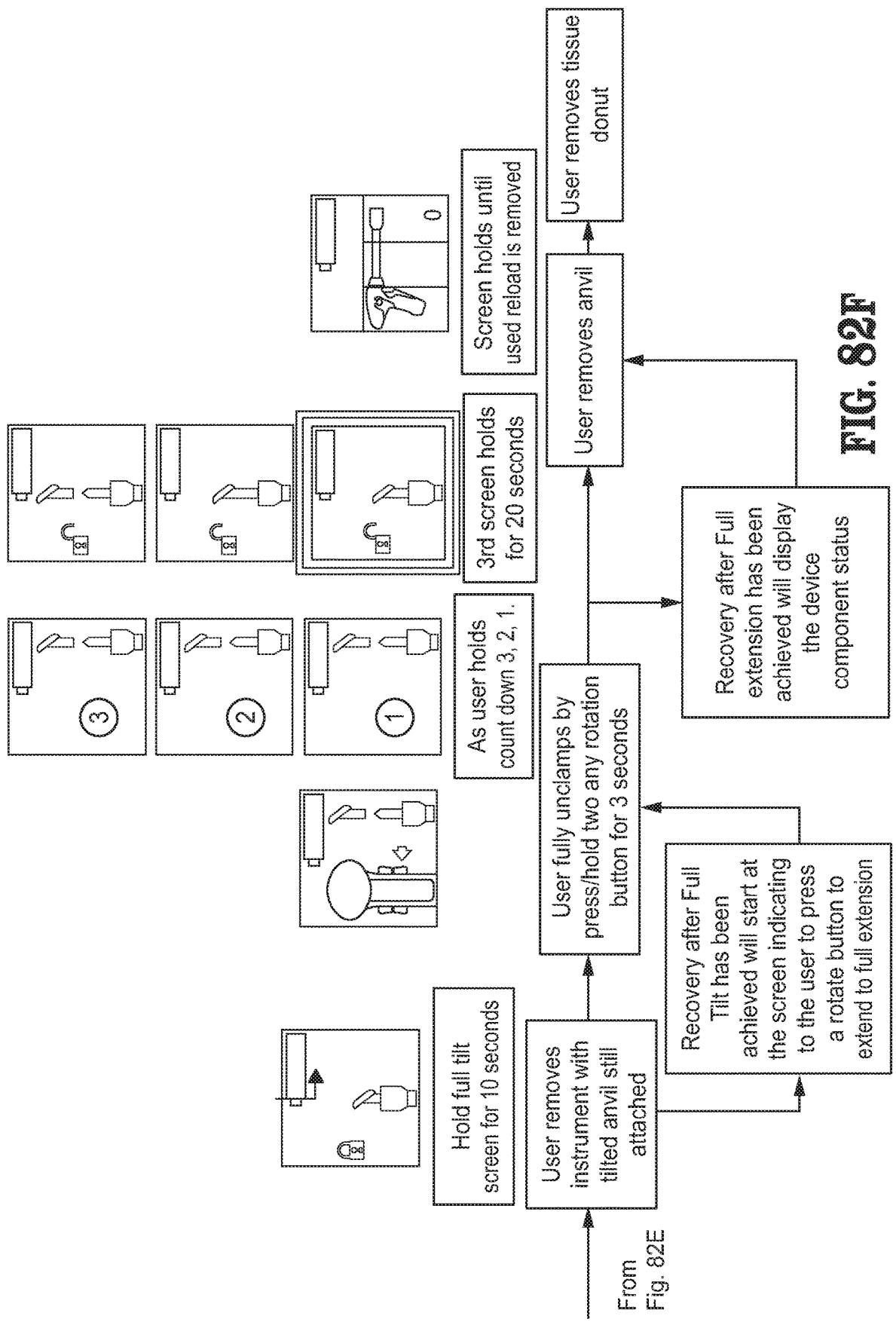

With reference to FIG. 82F, after the stapling and cutting sequences are complete, the user begins an unclamping sequence to release the anvil assembly 510 from the trocar member 274 by pressing on the top of the toggle control button 30. As the toggle control button 30 is pressed up, the trocar member 274 is automatically extended distally, thereby moving the anvil assembly 510 away from circular reload 400 and unclamping the tissue to the preset anvil tilt distance. The unclamping sequence is illustrated on the display screen 146. In particular, an unclamping animation shows the anvil assembly 510 moving distally and the head assembly 512 being tilted. In addition, the display screen 146 also shows a lock icon to show that the anvil assembly 510 is secured to the trocar member 274. Once the anvil assembly 510 is moved away from circular reload 400 to its tilt distance, the display screen 146 shows the anvil assembly 510 in the extended state with the head assembly 512 in the tilted state. This indicates that the user may remove the circular adapter assembly 200 from the patient. The LED then turns off. Once circular adapter assembly 200 is removed, the user then may unlock the anvil assembly 510 from the trocar member 274 by pressing one of the left-side or right-side control buttons 32a, 32b, 34a, 34b of the of the power handle 101 for a predetermined period of time (e.g., 3 seconds or more). The display screen 146 shows which button needs to be pressed on the power handle 101 to unlock the anvil assembly 510. As the user is pressing one of the control buttons 32a, 32b, 34a, 34b, the display screen 146 displays a countdown (e.g., 3, 2, 1) and the lock icon is shown to be in the unlocked state. At this point, the anvil assembly 510 is unlocked and may be removed. The user may then remove reload 400 as well as the severed tissue from the resection procedure. Circular adapter assembly 200 is also detached from handle assembly 100 and is cleaned and sterilized for later reuse. The shell housing 10 is opened and discarded, with the power handle 101 being removed therefrom for reuse.

The surgical device 1 according to the present disclosure is also configured to enter recovery states during the clamping, stapling, and cutting sequences if any of the components, e.g., the power handle 101, circular adapter assembly 200, circular reload 400, and/or the anvil assembly 510, encounters errors. The recovery states are software states executed by main controller 147 that guide the user through correcting and/or troubleshooting the errors and allow the user to resume any of the clamping, stapling, and cutting sequences once the error is corrected.

At the start of each operational sequence (e.g, clamping, stapling, firing, etc.), the main controller 147 writes to the storage device 407 of the circular adapter assembly 200 a recovery code associated with the operational sequence. Thus, at the start of the procedure the storage device 407 stores an initialization recovery code indicating that the circular adapter assembly 200 has not yet been used. However, as the circular adapter assembly 200 is used throughout the procedure, namely, progressing through the different sequences described above, corresponding recovery codes are written to the storage device 407. In addition, the main controller 147 writes corresponding recovery states to the memory 141. In either instance, this allows for replacement of either of the adapter assembly 200 and/or the power handle 101 depending on the error state as both of the components store the last recovery state locally, namely, in the storage device 407 or the memory 141, respectively.

With reference to FIG. 87A, which shows a recovery procedure during the stapling sequence and FIG. 88A, which shows a recovery procedure during the cutting sequence, during the procedure there may be instances that the power handle 101 identifies a flaw with one or more of the components of the power handle 101, the circular adapter assembly 200, and/or the reload 400. These recovery procedures are illustrative and similar procedures are also envisioned to be implemented in other operational sequences of the power handle 101, e.g., clamping sequence. The recovery procedures may include, but are not limited to, attaching a new power handle 101 to an adapter assembly 200 that is inserted into the patient, replacing the adapter assembly 200 and/or the reload 400.

When an adapter assembly 200 is attached to the power handle 101, the power handle 101 reads the recovery code from the storage device 407 to determine the state of the adapter assembly 200. The recovery code was written when the adapter assembly 200 was previously detached from the power handle 101. As noted above, at the start of the procedure, the recovery code indicates the initial state, which directs the power handle 101 to transition into start-up sequence, e.g., calibration. If the adapter assembly 200 was detached in the middle of the procedure, e.g., clamping, stapling, cutting, etc., the corresponding recovery code provides the entry point back into the mainline flow after performing a recovery procedure. This allows the operator to continue the surgical procedure at the point where the adapter assembly 200 was originally detached.

Similarly, in situations where the power handle 101 is being replaced, a new power handle 101 is configured to read the recovery state from the adapter assembly 200. This allows the new power handle 101 to resume operation of the previous power handle 101. Thus, during any of the operational sequences, e.g., clamping, stapling, and cutting, the adapter assembly 200 may be left in the corresponding configuration, e.g., clamped, stapled, etc., and after the new power handle 101 is attached, operation may be resumed.

To facilitate replacement of the power handle 101 in response to various failures of the power handle 101 the storage device 407 is used to store recovery codes associated with each of the operational sequences, e.g., calibration, clamping, stapling, cutting, and unclamping. In particular, the storage device 407 may be erased after every use of the adapter assembly 200 such that the storage device 407 only maintains the recovery codes for a single procedure. In embodiments, the storage device 407 may store a separate database of recovery codes for each procedure.

At the beginning of each of the operational sequences, the power handle 101 writes an initial recovery code. Similarly, at the end of each of the operational sequences the power handle 101 writes an ending recovery code. This provides for a recovery point whether the power handle 101 fails during one of the operational sequences or in between switching from one operational sequence to another (e.g., clamping has completed and stapling is commencing). Recovery codes may include the stage of the operational sequence (e.g., initial recovery code or an ending recovery code), distance traveled by components of the reload 400 (e.g., anvil assembly 510, knife assembly 440, etc.).

After a replacement power handle 101 is attached to the adapter assembly 200, the power handle 101 reads the recovery code from the adapter assembly 200. The power handle 101 then proceeds with recalibration of the adapter assembly 200 and the reload 400 as described above. After calibration is completed, the calibration data is stored in the storage device 405 of the power handle 101. The power handle 101 then resumes the operational sequence based on the recovery code read from the storage device 407 and the calibration data.

Figure 72:
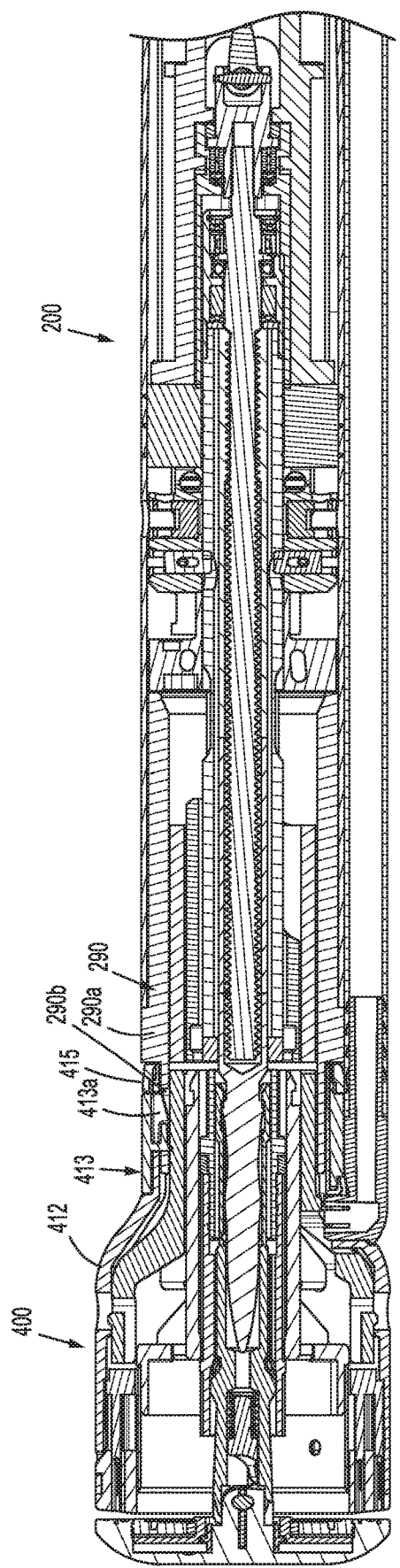
FIG. 72 is a longitudinal, cross-sectional view, illustrating the reload aligned and connected with the more distal end portion of the adapter assembly.
Figure 90:
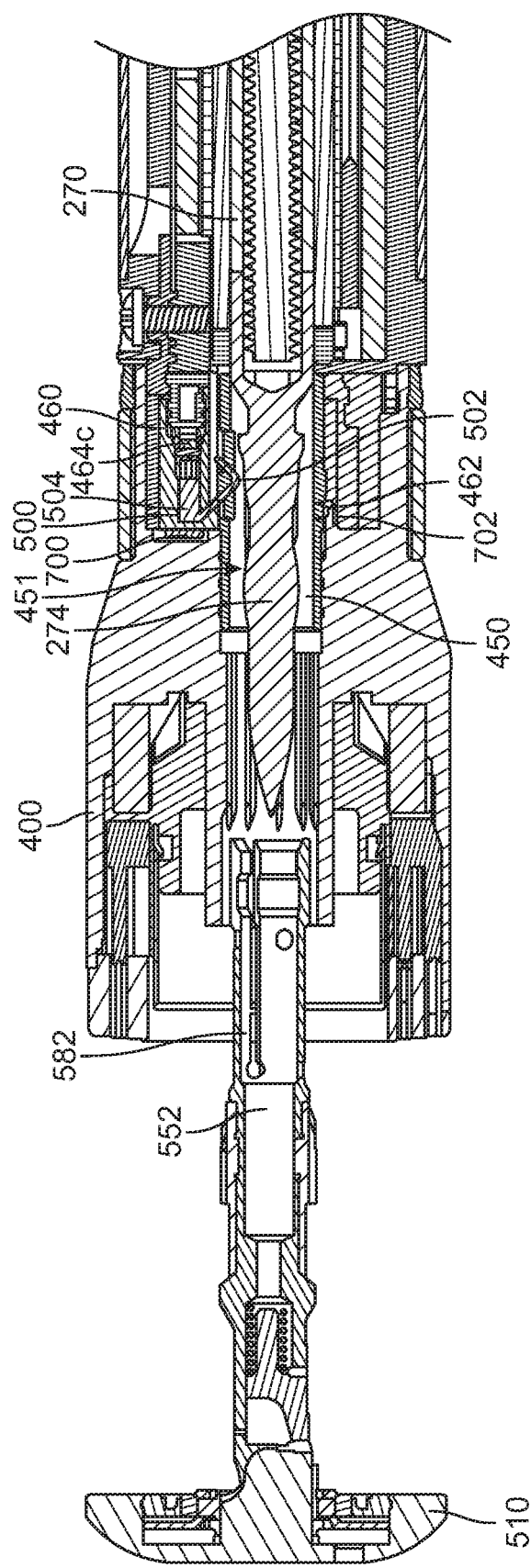
FIG. 90 is a longitudinal, cross-sectional view, illustrating a reload including one or more anvil sensors and the anvil assembly separated from the trocar of the adapter assembly according to an embodiment of the present disclosure.
Figure 91:
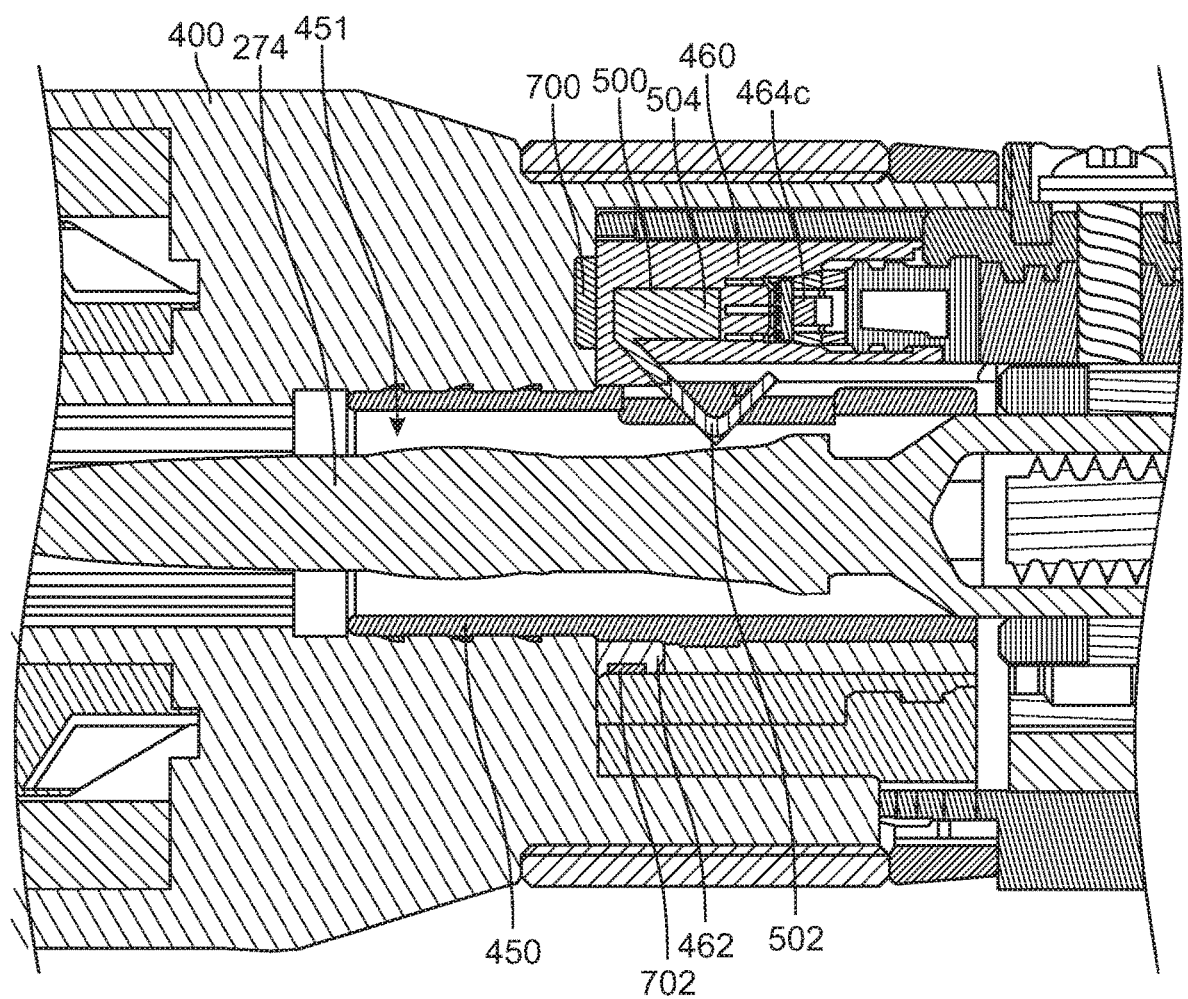
FIG. 91 is an enlarged view of the reload of FIG. 90.

The surgical device 1 (FIG. 1) according to the present disclosure is configured to determine whether the anvil assembly 510 is fully engaged to the trocar member 274 of trocar assembly 270 (FIG. 72). With reference to FIGS. 90 and 91, the reload 400 includes a sensor (e.g., an electromechanical anvil sensor 500 or a magnetic anvil sensor 700) configured to measure a mechanical or magnetic property indicative of the anvil assembly 510 being fully seated on the trocar member 274. The sensor is in electrical communication with the chip assembly 460, which is in turn, in communication with the main controller circuit board 142*b* of the handle assembly 100 (FIG. 16). Thus, the sensor communicates the measured mechanical or magnetic property to the main controller circuit board 142*b* (FIG. 16), which then determines based on the measurement signal whether the anvil assembly 510 is fully engaged to the trocar member 274. The determination may be utilized as a safety check prior to actuating the anvil assembly 510 to prevent improper operation of the surgical device 1. The sensor may be operating continuously to provide for safety verification that the anvil assembly 510 has not detached from the trocar member 274 for any period of time during use. In particular, this prevents situations where the anvil assembly 510 has disengaged from the trocar member 274, which would result in improper clamping, stapling, and/or cutting of the tissue.

Figure 69:
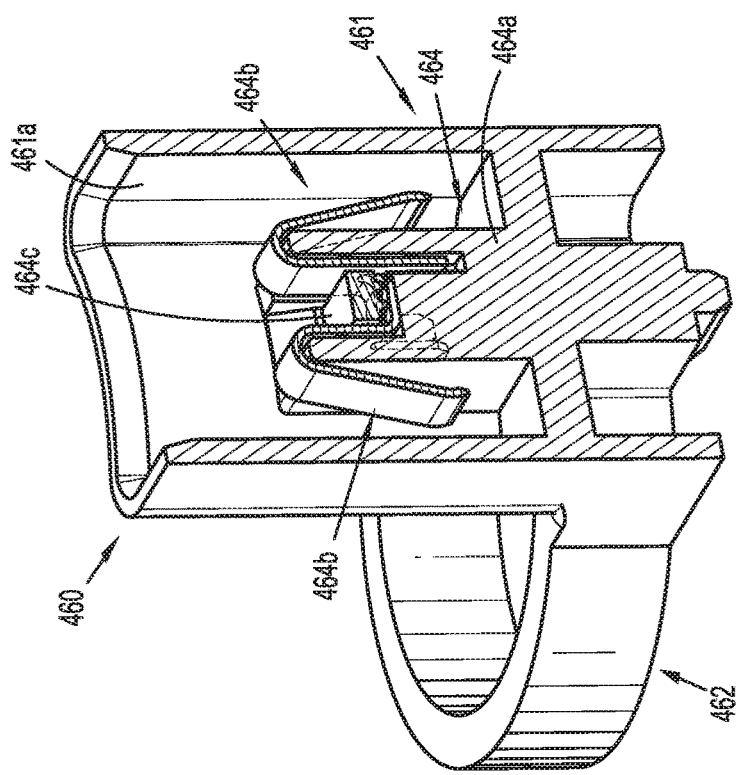
FIG. 69 is a cross-sectional view, as taken through 69-69 of FIG. 68.
Figure 68:
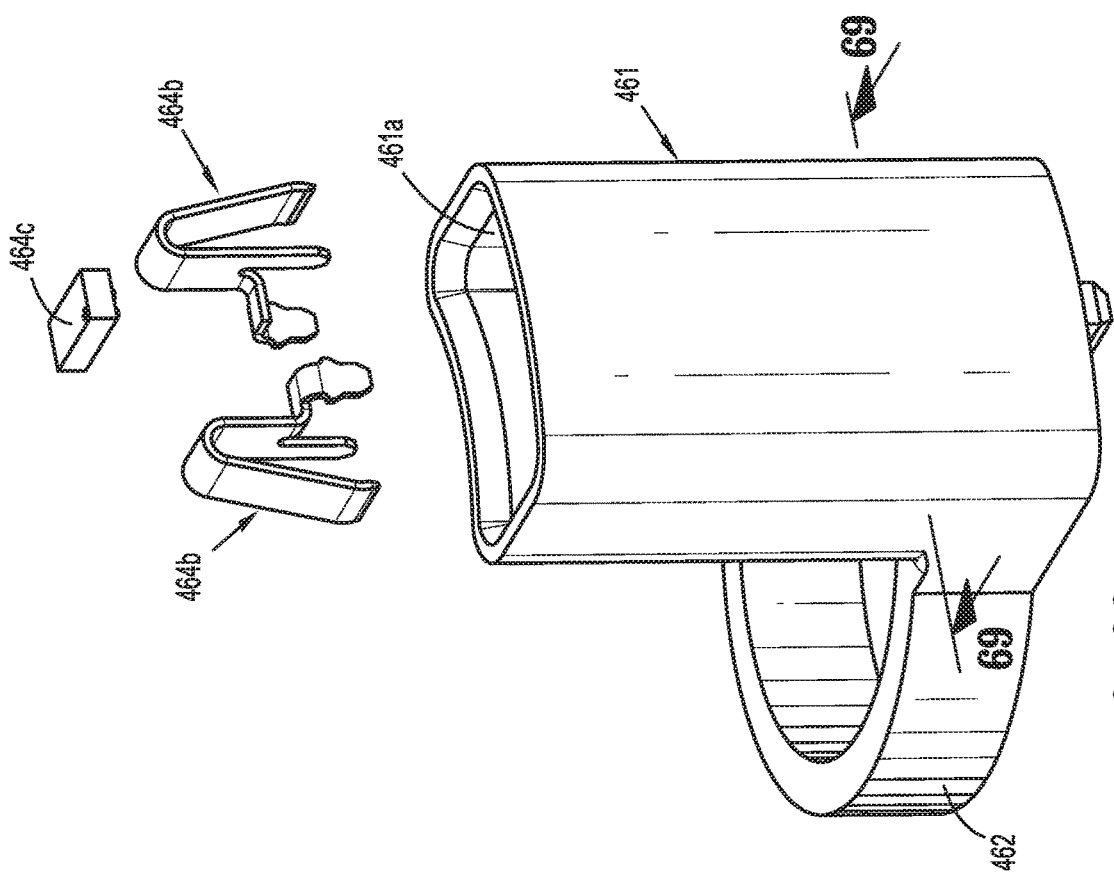
FIG. 68 is a perspective view of an electrical connector of the reload of FIGS. 66-67.
Figure 70:
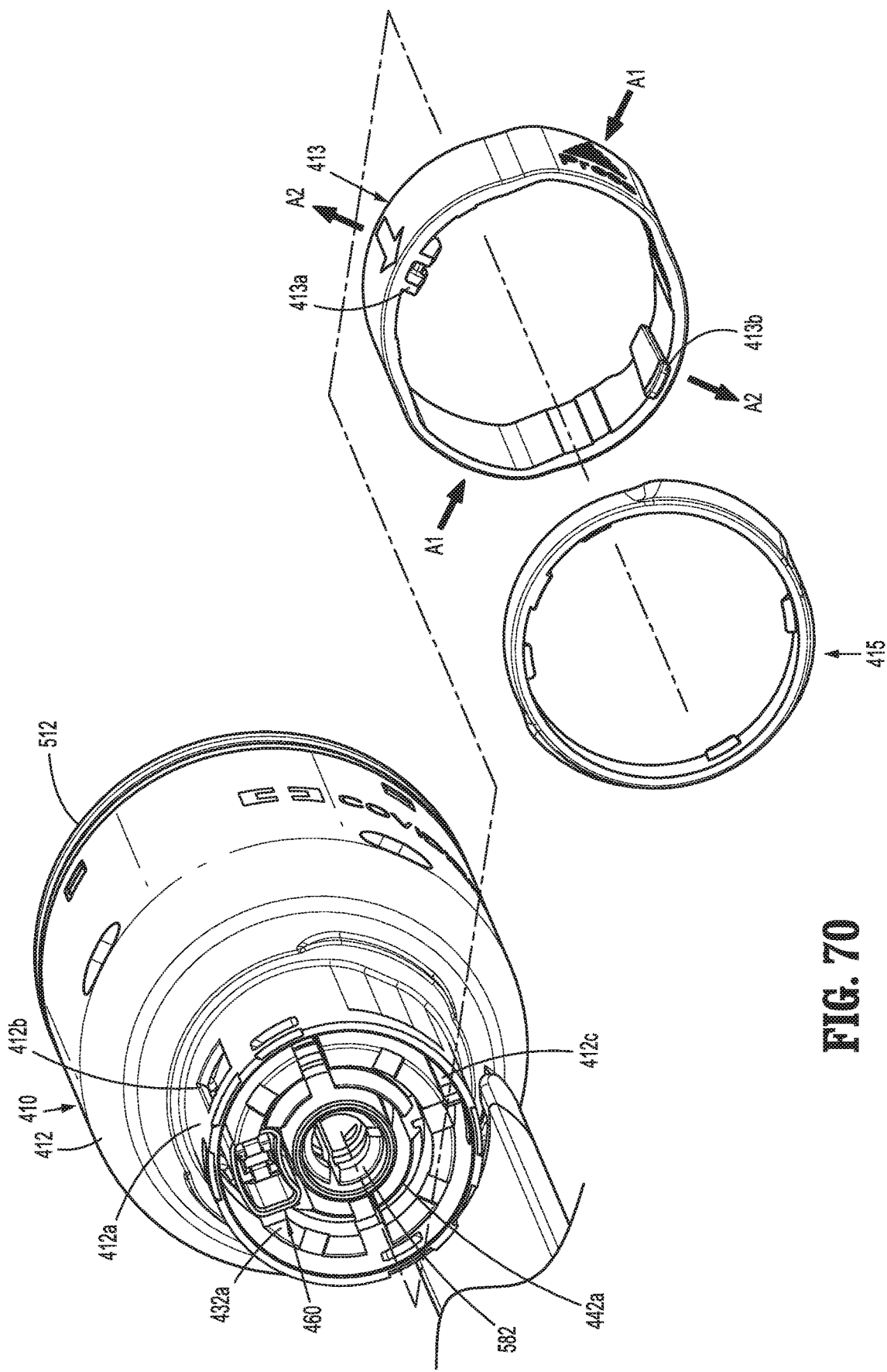
FIG. 70 is a rear, perspective view of the reload of FIGS. 66-69, with a release ring and a retaining ring illustrated separated therefrom.
Figure 71:
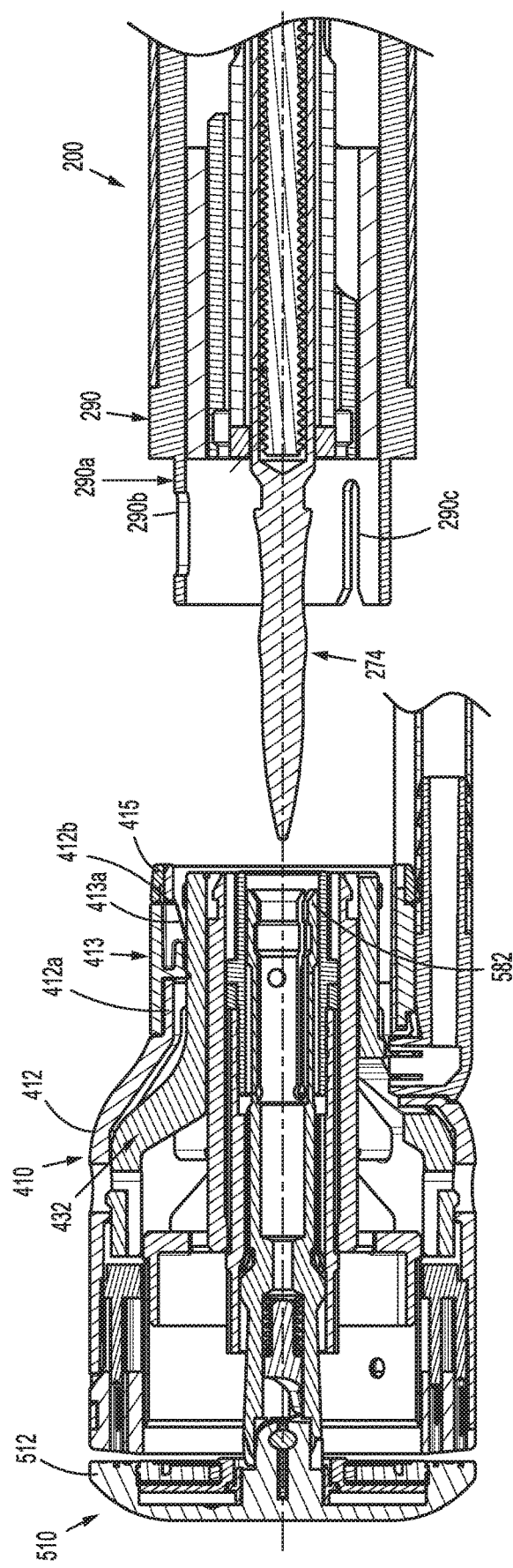
FIG. 71 is a longitudinal, cross-sectional view, illustrating the reload aligned with and separated from the more distal end portion of the adapter assembly.

With reference to FIGS. 90 and 91, the reload 400 includes an electromechanical anvil sensor 500, which in embodiments may be a limit switch. In further embodiments, the switching element 504 may be any single-pole switch. The electromechanical anvil sensor 500 includes a leg 502 that is coupled to a switching element 504. The leg 502 may be formed from any resilient material, such as thermoplastics or metals. The electromechanical anvil sensor 500 may be disposed within the chip assembly 460 (FIG. 69.) The leg 502 is disposed within the reload 400 such that the leg 502 comes in contact with the anvil assembly 510. In embodiments, the leg 502 extends through the bushing member 450 and is disposed within a central lumen 451 of the bushing member 450. This configuration allows the anvil center rod assembly 514 to engage the leg 502 of the electromechanical anvil sensor 500 as the anvil assembly 510 is inserted into the reload 400 and to engage the trocar member 274 as shown in FIGS. 92 and 93.

The leg 502 may be disposed along any longitudinal position of the reload 400 such that the leg 502 is engageable by the anvil assembly 510 or any component thereof as the anvil assembly 510 is being coupled to the reload 400 and the trocar member 274. In further embodiments, the leg 502 may be disposed at a proximal portion of the central lumen 451 such that a proximal portion of the anvil assembly 510, e.g., the center rod 552 and/or the flexible arms 582 (FIG. 74), engage the leg 502 thereby actuating the switching element 504. This configuration of the leg 502 ensures that the leg 502 is engaged upon the anvil assembly 510 being fully inserted into the reload 400 and coupled to the trocar member 274.

Figure 92:
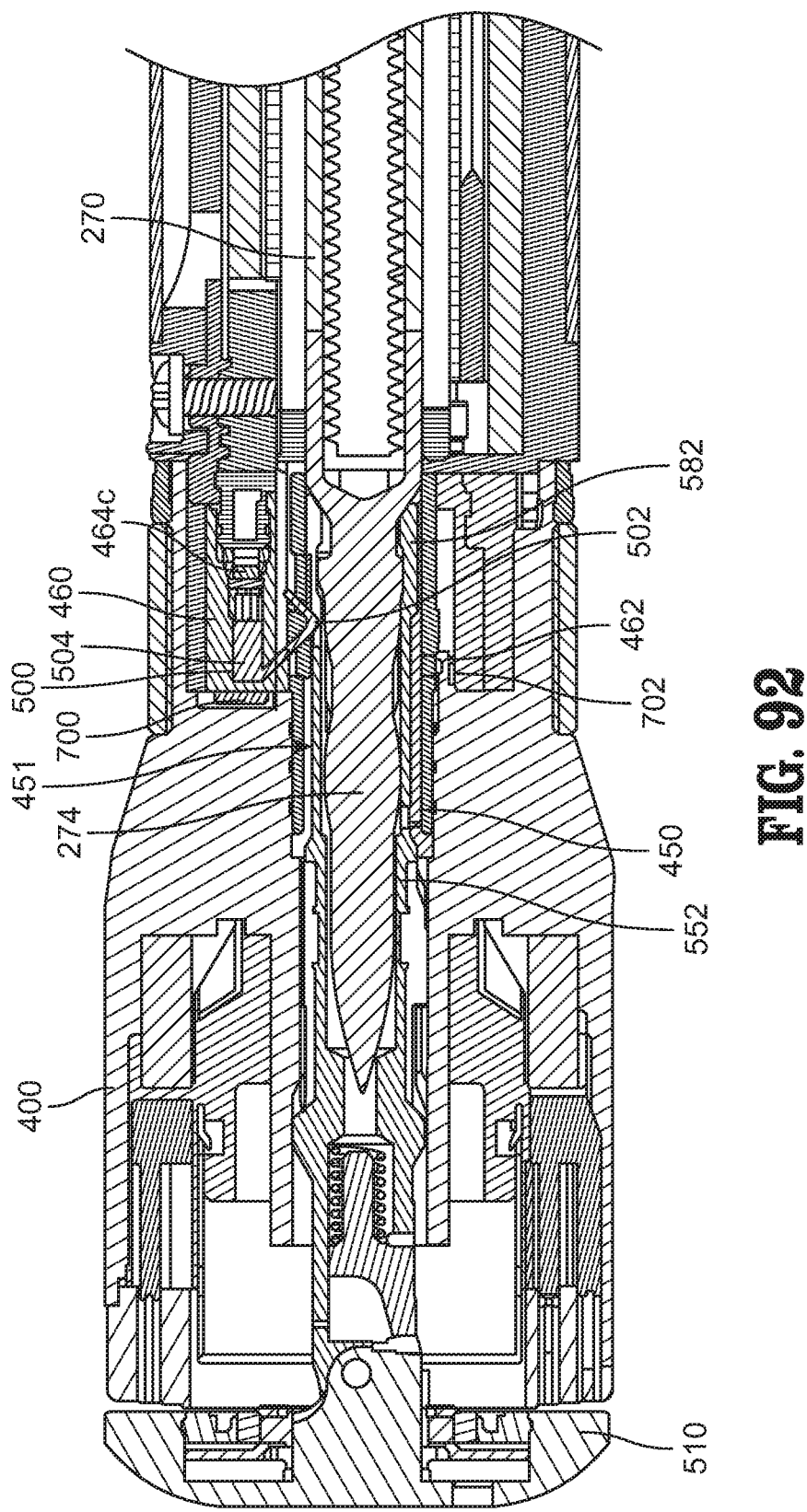
FIG. 92 is a longitudinal, cross-sectional view, illustrating the reload and the anvil assembly of FIG. 90 aligned with and coupled to the trocar of the adapter assembly according to an embodiment of the present disclosure.
Figure 93:
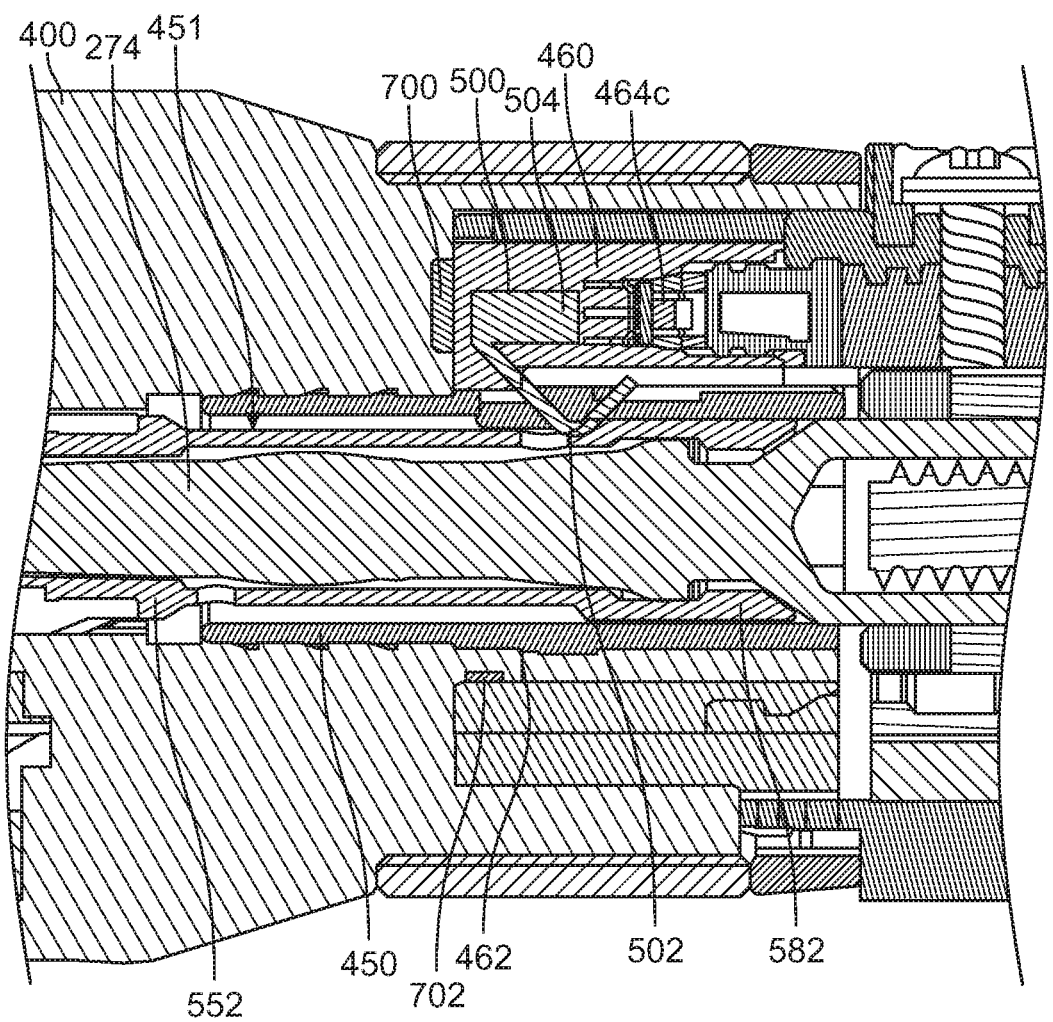
FIG. 93 is an enlarged view of the reload of FIG. 92.

After the leg 502 is engaged by the center rod 552 of the anvil assembly 510 as shown in FIGS. 92 and 93, the switching element 504 is activated and outputs a signal to the chip assembly 460. Conversely, once the leg 502 is disengaged by the anvil assembly 510, the switching element 504 is deactivated since the leg 502 would be is into a disengaged position.

The switching element 504 is coupled to the chip assembly 460 and transmits a signal to the chip 464*c*, which is in communication with the main controller circuit board 142*b*. The main controller of the main controller circuit board 142*b* utilizes the signal from the switching element 504 to control the operation of the surgical device 1. In particular, after the anvil assembly 510 is attached to the reload 400 and the trocar member 274 (FIG. 82C), the main controller may prevent subsequent operation of the surgical device 1, e.g., clamping, unless a signal is received from the switching element 504 of the electromechanical anvil sensor 500 indicating that the anvil assembly 510 is properly coupled to the trocar member 274. The main controller may utilize the signal from the electromechanical anvil sensor 500 throughout any or every operation of the surgical device 1 that involves the anvil assembly 510, namely, from the initial clamping as shown in FIG. 82C until detachment of the anvil assembly 510 after the procedure is complete as shown in FIG. 82F.

With continued reference to FIGS. 90 and 91, the reload 400 also includes a magnetic anvil sensor 700. In embodiments, the reload 400 may include one or both of the electromechanical anvil sensor 500 and the magnetic anvil sensor 700. The magnetic anvil sensor 700 may be any magnetic field sensing device, such as a tunneling magnetoresistance sensor or a Hall Effect sensor that is configured to detect changes in magnetic fields. The magnetic field may be produced by a magnet 702 disposed within the reload 400, and in particular within the annular flange 462 of the chip assembly 460 (FIG. 69). The magnetic anvil sensor 700 may also be disposed within the chip assembly 460. In embodiments, the magnetic anvil sensor 700 may be diametrically opposed relative to the magnet 702 such that the magnetic field produced by the magnet 702 is affected by the anvil assembly 510, and in particular, by the center rod 552 and/or the flexible arms 582, as the anvil assembly 510 is inserted into the reload 400. The center rod 552 is formed from a ferromagnetic material such that the center rod 552 modifies the magnetic field. The trocar member 274 may be formed from a non-magnetic material that does not affect the magnetic field. In further embodiments, the magnet 702 may be disposed on or within the center rod 552 at a proximal portion thereof.

The magnet 702 and the magnetic anvil sensor 700 may be disposed along any longitudinal position of the reload 400 such that the magnetic anvil sensor 700 can detect changes in the magnetic field as the anvil assembly 510 is being coupled to the reload 400 and the trocar member 274 as shown in FIGS. 92 and 93. In particular, the magnetic anvil sensor 700 is configured to detect the disruption in the magnetic field generated by the magnet 702, if the magnet 702 is disposed within the reload 400, or presence of the magnetic field, if the magnet 702 is disposed on or within the anvil assembly 510. In further embodiments, the magnetic anvil sensor 700 may be disposed at a proximal portion of the central lumen 451 such that a proximal portion of the anvil assembly 510, e.g., the center rod 552 and/or the flexible arms 582 (FIG. 74), modify the magnetic field. This placement of the magnetic anvil sensor 700 ensures that the magnetic anvil sensor 700 detects the changes in the magnetic field upon the anvil assembly 510 being fully inserted into the reload 400 and coupled to the trocar member 274 as shown in FIGS. 92 and 93.

The magnetic anvil sensor 700 is coupled to the chip assembly 460 and transmits a signal in response to the change in the magnetic field to the chip 464c, which is in communication with the main controller circuit board 142b. The main controller of the main controller circuit board 142b utilizes the signal from the magnetic anvil sensor 700 to control the operation of the surgical device 1. In particular, after the anvil assembly 510 is attached to the reload 400 and the trocar member 274 (FIG. 82C), the main controller is configured to prevent subsequent steps in the process, e.g., clamping, unless a signal is received from the magnetic anvil sensor 700 indicating that the anvil assembly 510 is properly coupled to the trocar member 274. The main controller may utilize the signal from the magnetic anvil sensor 700 throughout any or every operation of the surgical device 1 that involves the anvil assembly 510, namely, from the initial clamping as shown in FIG. 82C until detachment of the anvil assembly 510 after the procedure is complete as shown in FIG. 82F.

Figure 94:
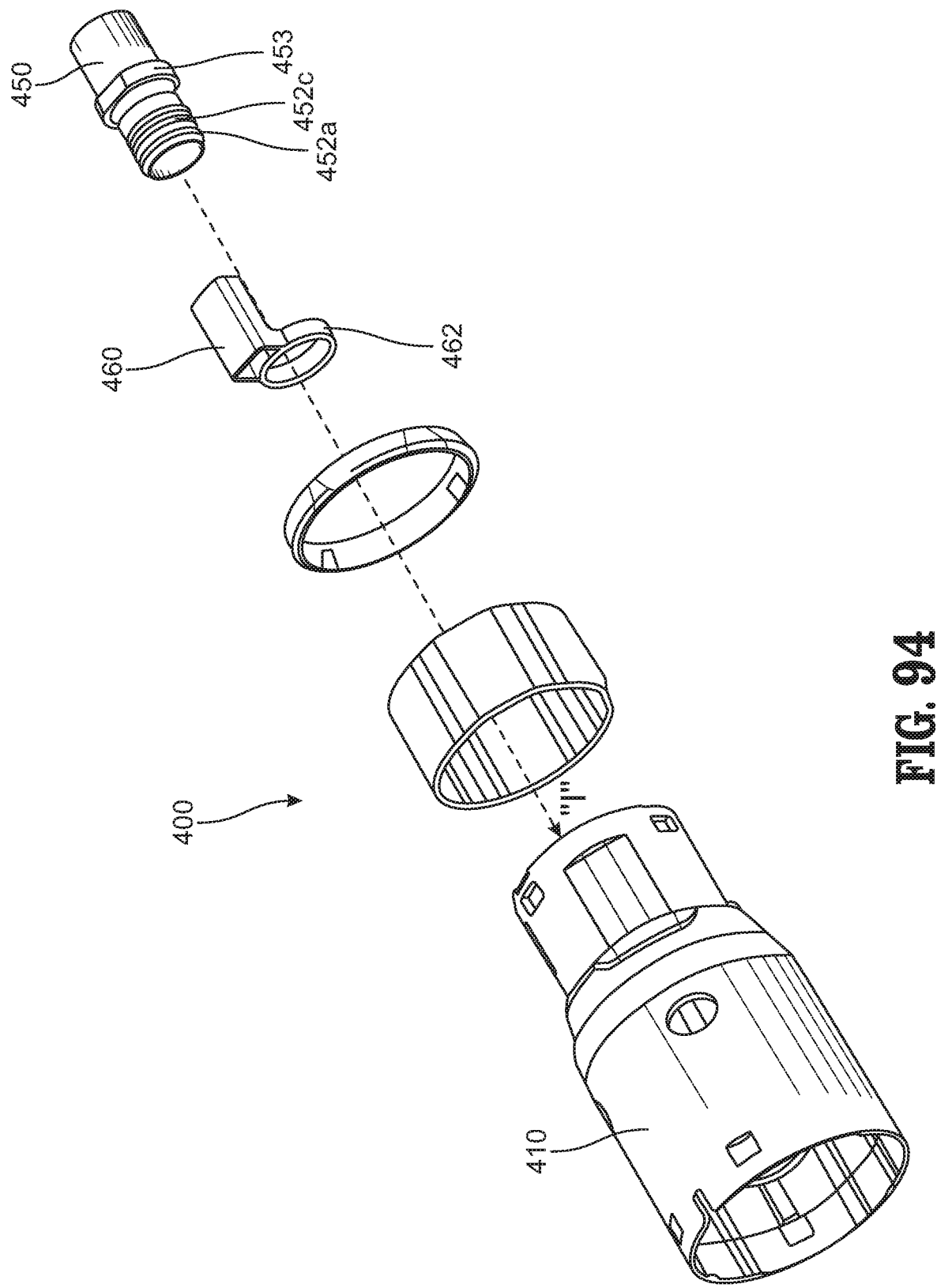
FIG. 94 is a perspective view of the reload with parts separated.
Figure 95:
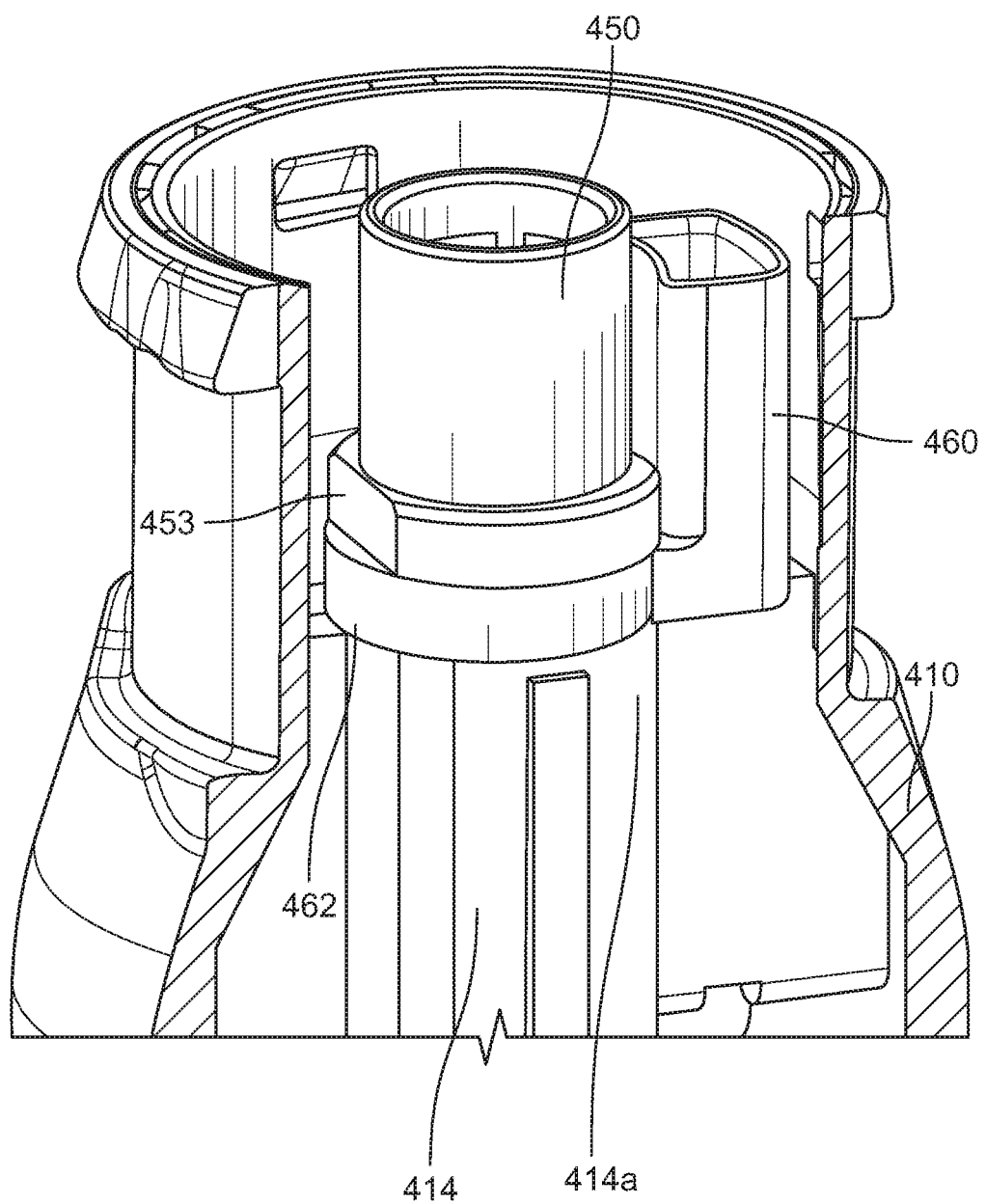
FIG. 95 is a partially cross-sectional view of the reload.

With reference to FIGS. 94 and 95, during assembly of the reload 400 the chip assembly 460 is coupled to the housing 410 of the reload 400. The chip assembly 460 is initially placed onto the proximal end 414a of inner cylindrical portion 414. Thereafter, the distal end 452a of the bushing member 450 is inserted through the annular flange 462 of the chip assembly 460 to secure the bushing member 450 to the inner cylindrical portion 414. In particular, the bushing member 450 is press-fitted within the proximal end 414a of inner cylindrical portion 414 using the plurality of ridges 452c, which provide frictional contact with the inner cylindrical portion 414. The bushing member 452 also includes an annular ridge 453 which contacts the annular flange 462, thereby securing the chip assembly 460 to the inner cylindrical portion 414.

As the bushing member 450 is inserted in a direction "I" into the inner cylindrical portion 414, the annular ridge 453 compresses the annular flange 462 between itself and the proximal end 414a of inner cylindrical portion 414. The compression force may exceed the structural integrity of the annular flange 462, especially if the annular flange 462 is formed from a thermopolymer or other moldable material. The present disclosure provides for a modified design of the annular flange 462 and the annular ridge 453. The design according to the present disclosure distributes the compression forces imparted on the annular flange 462 by the annular ridge 453 during assembly due to press fitting of the bushing member 450 into the inner cylindrical portion 414.

Figure 96:
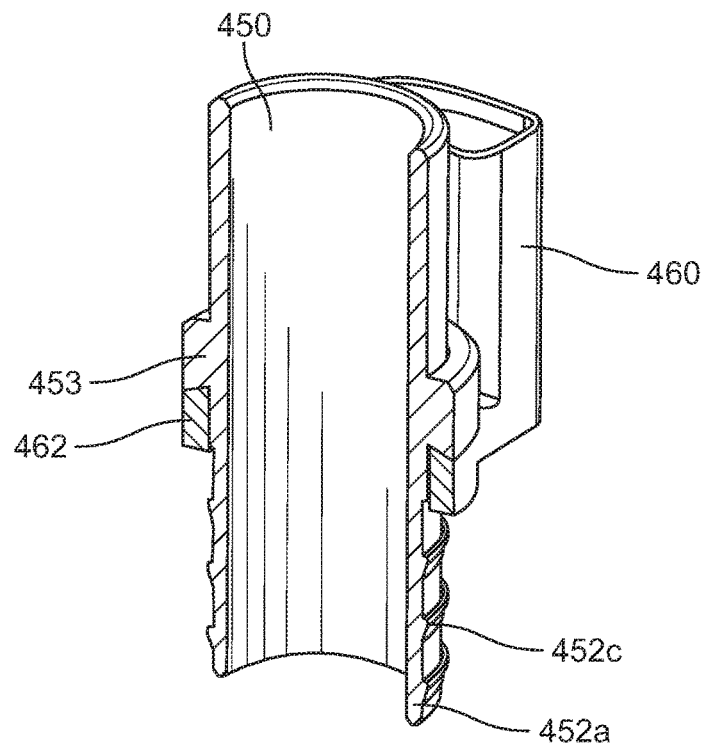
FIG. 96 is a partially cross-sectional view of the chip assembly and a bushing member of the reload with complementary tapered surfaces.
Figure 97:
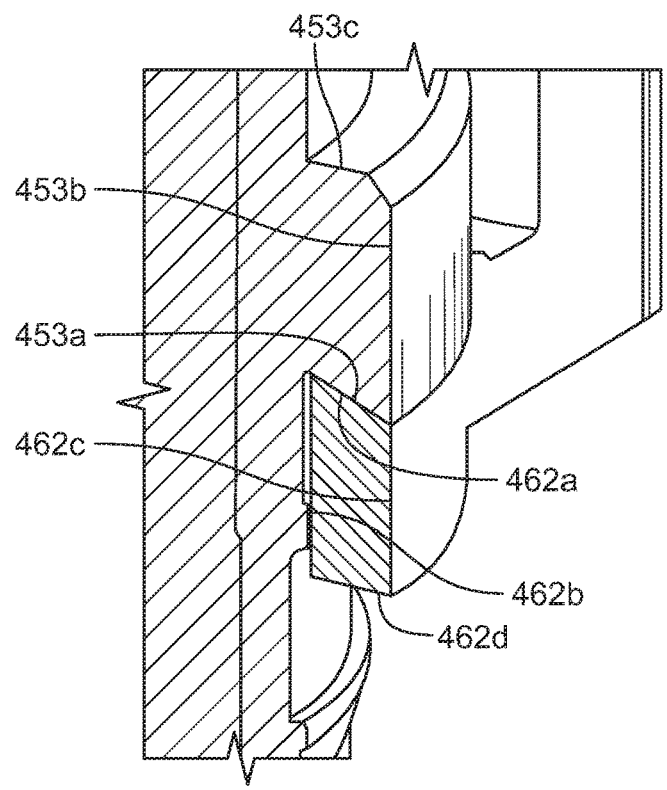
FIG. 97 is an enlarged, partially cross-sectional view of the chip assembly and the bushing member with complementary tapered surfaces.

With reference to FIGS. 96 and 97, each of the annular flange 462 and the annular ridge 453 includes a complementary tapered surface 462a and 453a, respectively. The annular flange 462 includes an inner surface 462b and an outer surface 462c, which are interconnected by the tapered surface 462a and a side surface 462d. The tapered surface 462a of the annular flange 462 forms an acute angle with the inner surface 462b providing for the sloping of the tapered surface 462a outward from the inner cylindrical portion 414 in the direction "I" of the insertion of the bushing member 450. In embodiments, the side surface 462d may also be tapered either at an acute or an obtuse angle relative to the outer surface 462c.

The tapered surface 453a of the annular ridge 453 is complementary to the tapered surface 462a. In particular, the annular ridge 453 includes an outer surface 453b and a side surface 453c. The tapered surface 453a of the annular ridge 453 forms an acute angle with the outer surface 453b, which is the same as the acute angle of the tapered surface 462a. Thus, the tapered surface 453a also slopes outwardly from the inner cylindrical portion 414 in the direction "I" of the insertion of the bushing member 450.

Due to the combination of the tapered surface 453a and the tapered surface 462a, the compression force imparted on the annular flange 462 is directed inward, namely, toward the inner cylindrical portion 414. As a result, the annular flange 462 is constrained by the inner cylindrical portion 414, thereby preventing damage to the annular flange 462 (e.g., shearing, fracturing, and/or splaying) due to the compression force.

During use of the surgical device 1, the trocar member 274 may become electrostatically charged. As a result, the electrostatic charge may discharge uncontrollably, thereby damaging the power handle 101 and/or affecting transmission of sensor signals to the power handle 101. The present disclosure provides for an apparatus to prevent formation of electrostatic charges by providing for a conductive pathway (e.g., lead) to dissipate and/or discharge the electrostatic charge which may accumulate at the trocar member 274.

Figure 98:
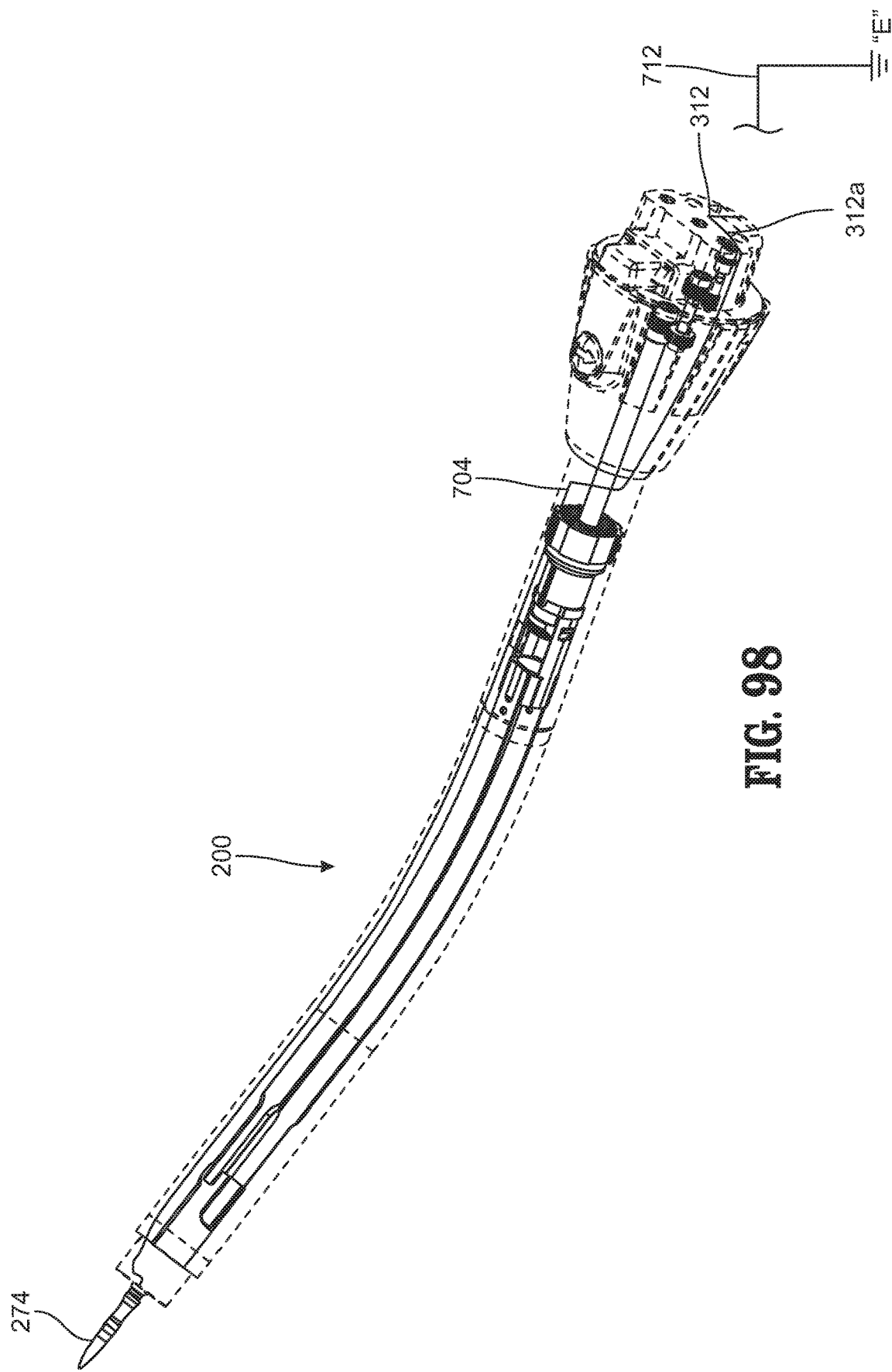
FIG. 98 is a perspective view of the adapter assembly, shown partially in phantom, illustrating a grounded trocar according to an embodiment of the present disclosure.

With reference to FIG. 98, the adapter assembly includes a conductive lead 704, which is electrically coupled to the trocar member 274. The conductive lead 704 may be any wire or electrical lead. In embodiments, the conductive lead 704 may be a lead disposed within the flexible circuits of the proximal harness assembly 314 and the distal harness assembly 316 (FIG. 53). The conductive lead 704 is coupled to one of the electrical contact blades 312a (FIG. 53) of the proximal pin connector assembly 312. Thus, one of the electrical contact blades 312a may serve as a grounding connector, which in turn may be coupled to a grounding wire 712 that is in turn connected to an earth ground "E." In embodiments, the power handle 101 may be coupled to the grounding wire 712, allowing the conductive lead 704 to be coupled to the grounding wire 712 through the proximal pin connector assembly 312 and the pass-through connector 66. Since the trocar member 274 is grounded through the conductive lead 704 and other intervening electrical connectors (e.g., proximal pin connector assembly 312) to the earth ground "E," electrostatic charges would dissipate.

As described with reference to FIGS. 1, 71, 82C, and 89, the surgical device 1 includes the handle assembly 100, the adapter assembly 200 configured to selectively couple to the handle assembly 100, an annular surgical reload 400 configured to selectively couple to a distal portion of the adapter assembly 200 (e.g., connector sleeve 290), and a shipping cap 401 (FIG. 82C) coupled to the annular reload 400 and configured to detach from the annular reload 401 in response to a movement of the trocar member 274 (FIG. 71) of the adapter assembly 200. The handle assembly 100 has the outer housing shell 101 and the power pack-core assembly 106 disposed therein. The power pack-core assembly 106 has the main controller 147 (FIG. 89), which is coupled to the memory 141.

The memory 141 may include volatile (e.g., RAM) and non-volatile storage configured to store data, including software instructions for operating the power handle 101. The memory 141 of the power pack-core assembly 106 has stored therein instructions to write to the memory 464c (FIGS. 68 and 69) of the annular reload 400 an occurrence of a detachment of the shipping cap 401 (FIG. 82C) from the annular reload 400. The occurrence of the detachment of the shipping cap 400 is encoded into the chip 464c to prevent a second occurrence of a shipping cap removal process when another handle assembly (or power pack assembly) is coupled to the annular reload 400 and after a shipping cap 401 was already removed, as will be described in greater detail herein.

The annular reload 400 has a memory, such as, for example, the EEPROM memory chip 464c (FIGS. 68 and 69) having stored therein information about the annular reload 400. For example, the memory 464c may include the following stored information: lot number, staple size, lumen size, fire count, manufacturing stroke offsets, excessive force index, shipping cap assembly presence, and demonstration modes. The memory 464c includes write capabilities which allow the main controller 147 of the handle assembly 100 to encode or otherwise mark chip 464c that the shipping cap 401 has been detached from the annular reload 400. The controller 147 may be configured to read the memory 464c of the annular reload 400 to determine whether the shipping cap 400 is detached from the annular reload 400.

As mentioned above, the circular adapter assembly 200 also includes a storage device 407. The storage device includes non-volatile storage medium (e.g., EEPROM) that is configured to store any data pertaining to the circular adapter assembly 200, including but not limited to, usage count, identification information, model number, serial number, staple size, stroke length, maximum actuation force, minimum actuation force, factory calibration data, and the like. The storage device 407 may be configured in read only or read/write modes, allowing the main controller 147 of the handle assembly 100 to read as well as write data onto the storage device 407. That is, the controller 147 of the handle assembly 100 may be configured to encode in the storage device 407 of the adapter assembly 200 that the shipping cap 401 was detached from the annular reload 400. Instead of or in addition to the controller 147 of the handle assembly 100 encoding to the memory 464c of the annular reload 400 that the shipping cap 401 is detached, the adapter assembly 200 may include a controller (not explicitly shown) configured to encode to the memory 464c of the annular reload 400 and/or the memory 407 thereof that the shipping cap 401 is detached from the annular reload 400.

Figure 99:
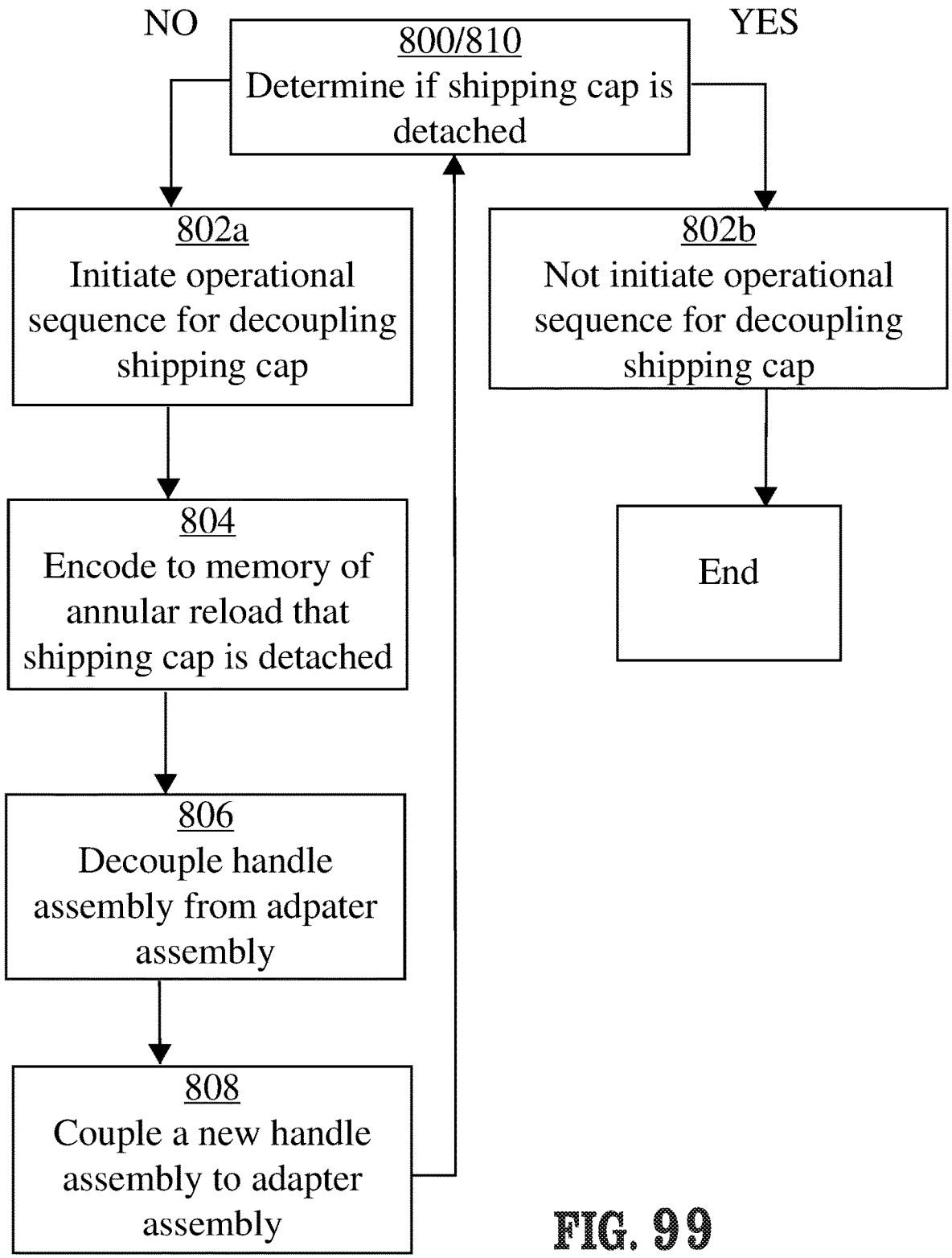
FIG. 99 is a flow chart of a method for operating the handheld surgical device of FIG. 1 according to an embodiment of the present disclosure.

With reference to FIG. 99, a method of using the surgical device 1 will be described. Initially, in step 800, during a surgical procedure, the controller 147 of the handle assembly 100 may read the memory 464c of the annular reload 400 to determine whether the shipping cap 401 is detached from the annular reload 400. In step 802a, if the controller 147 determines, based on the information stored in memory 464c of the annular reload 400, that the shipping cap 401 is not detached from the annular reload 400 (e.g., the annular reload 400 did not yet undergo a shipping cap removal process), the controller 147 may initiate an operational sequence for decoupling the shipping cap 4001 from the annular reload 400. In particular, the controller 147 may activate one or more motors 152, 154, 156 of the power-pack core assembly 106 to extend/retract the trocar member 274 of the adapter assembly 200 to detach the shipping cap 401 from the annular reload 400. In aspects, the operational sequence may further include the controller 147 prompting a user to actuate a toggle (e.g., toggle control button 30, FIG. 2) of the surgical device 1, thereby activating the one or more motors 152, 154, 156.

In step, 804, during or immediately after the controller 147 initiates the operational sequence for detaching the shipping cap 401, the controller 147 encodes/write to the memory 464c of the annular reload 400 that the shipping cap 401 is detached from the annular reload 400. As such, the memory 464c of the annular reload 400 has stored therein information that the shipping cap 401 is detached from the annular reload 400.

During the surgical procedure, in step 806, it may become desirable or otherwise necessary to decouple the handle assembly 100 from the adapter assembly 200 due to either a mechanical or electrical failure in the handle assembly 100. In aspects, rather than decoupling the entire handle assembly 100, including the outer shell housing 101 and the power pack-core assembly 106), only the power pack-core assembly 106 may be removed from the outer shell housing 101 while leaving the outer shell housing 101 attached to the adapter assembly 200.

In step 808, to continue performing the surgical procedure, a new handle assembly (not explicitly shown, but identical or similar to the original handle assembly 100) may be coupled to the adapter assembly 200. Upon coupling the new handle assembly, in step 810, the controller 147 of the new handle assembly reads the memory 464c of the annular reload 400 to determine whether the shipping cap 401 is detached from the annular reload 400. In aspects, reading the memory 464c may include the controller 147 of the new handle assembly searching for the encoding in the memory 464c of the annular reload 400. When the controller 147 reads the encoding in the memory 464c of the annular reload 400 that the shipping cap 401 is detached from the annular reload 400, in step 802b, the controller 147 is programmed to not initiate the operational sequence for detaching the shipping cap 401. Alternatively, in circumstances where the shipping cap 401 was not detached from the annular reload 400 during use of the original handle assembly 100, and therefore the memory 464c of the annular reload 400 is devoid of the corresponding encoding, the controller 147 is configured to initiate the operational sequence for detaching the shipping cap 401 from the annular reload 400.

In aspects, rather than having a shipping cap 401 attached thereto, the reload 400 may have a disposable trans-anal/abdominal introducer ("TAID") attached thereto. It is contemplated that the method of FIG. 99 may be used to prevent a redundant occurrence of a removal process of the TAID.

Figure 100:
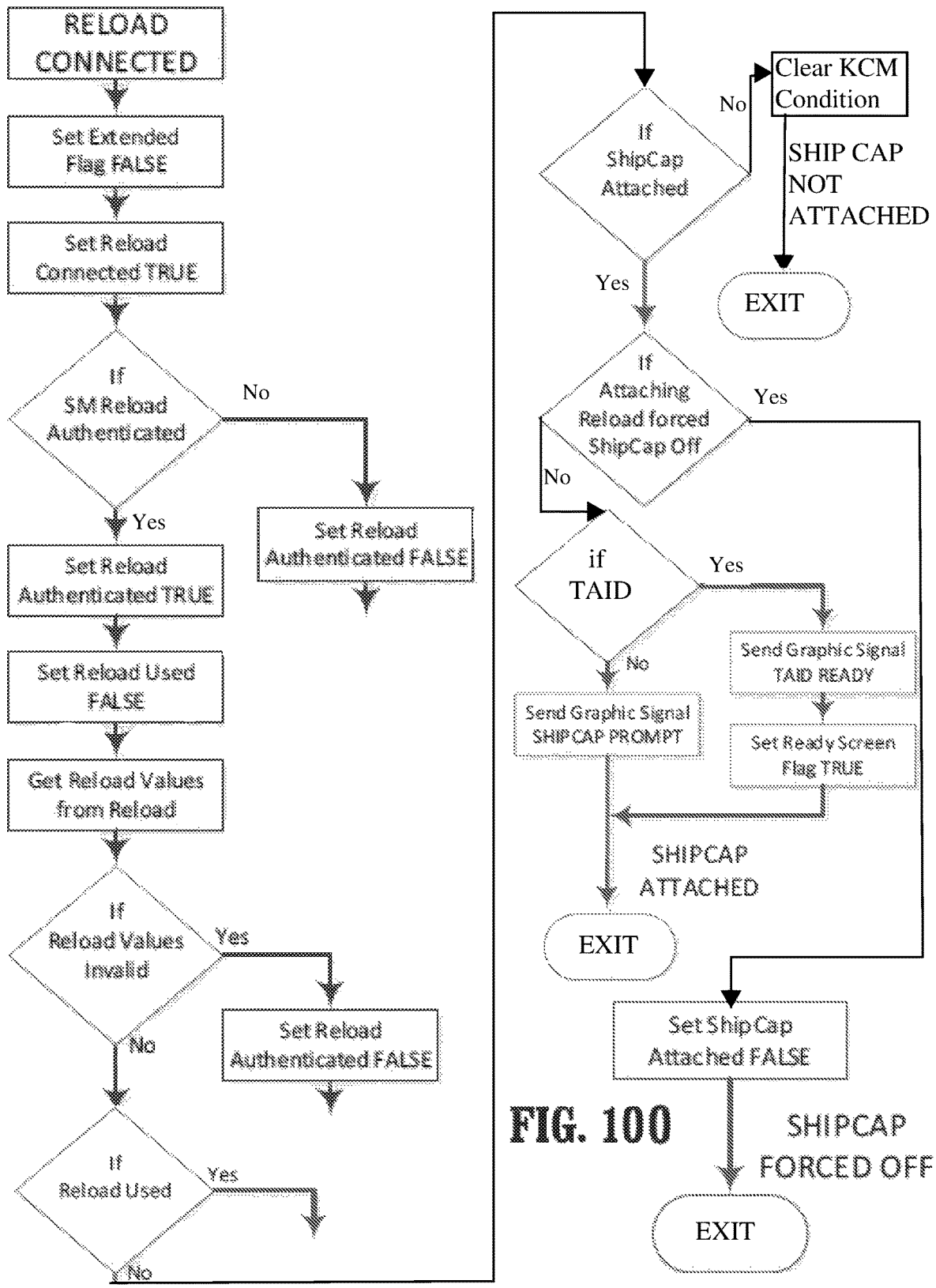
FIG. 100 is a flow chart of a method for operating the handheld surgical device of FIG. 1 according to an embodiment of the present disclosure.

With reference to FIG. 100, a flow chart is illustrated that portrays various steps for assembling and operating surgical device 1. The annular reload 400 is connected to the adapter assembly 200 and the surgical device 1 performs a protocol to authenticate the annular reload 400 and receive operating parameters of the reload 400.

In particular, the reload 400 is connected and if surgical device 1 authenticates reload 400, the operational parameters or values of the reload 400 are received by the surgical device 1 and determined to be valid. If the operational parameters or values of the reload 400 are determined to be valid, it is then determined whether reload 400 is used, and if not reload 400 is used, the surgical device 1 then determines if a shipping cap 401 is attached and whether attaching the reload 400 forced the shipping cap 401 off or to become removed.

If it is determined that a TAID is present, then a graphic of the TAID is displayed and the graphic is indicated as being ready for use. If it is determined that no TAID is present, then the shipping cap 401 is detached in the manner described above.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of using a surgical device, the method comprising:
decoupling a first handle assembly from an adapter assembly, the adapter assembly supporting an annular reload having a memory;
coupling a second handle assembly to the adapter assembly;
reading the memory of the annular reload to determine whether a shipping cap is detached from the annular reload, the shipping cap being configured to maintain staples within the reload and to prevent inadvertent advancement of a staple driver assembly or a knife assembly of the reload;
at least one of proximally or distally moving a trocar of the adapter assembly, thereby engaging the shipping cap to detach the shipping cap from the annular reload when the first or second handle assembly is coupled to the adapter assembly and the reload is connected to the adapter assembly;
encoding to the memory an occurrence of the at least one of the proximal or distal movement of the trocar, the at least one of the proximal or distal movement of the trocar being indicative of the shipping cap being detached from the reload; and
attaching an anvil to the trocar after the shipping cap is detached.

2. The method according to claim 1, wherein reading the memory includes a controller of the second handle assembly searching for the encoding in the memory.

3. The method according to claim 2, wherein the controller of the second handle assembly is configured to not initiate an operational sequence for detaching the shipping cap from the annular reload in response to finding the encoding in the memory.

4. The method according to claim 1, further comprising initiating, by a controller of the second handle assembly, an operational sequence for detaching the shipping cap from the annular reload in response to determining that the shipping cap is attached to the annular reload.

5. The method according to claim 4, wherein the operational sequence includes activating a motor of the second handle assembly to move the trocar of the adapter assembly to detach the shipping cap from the annular reload.

6. The method according to claim 5, wherein the operational sequence further includes the controller prompting a user to actuate a toggle of the surgical device, thereby activating the motor.

* * * * *